(12) United States Patent
Mita et al.

(10) Patent No.: US 8,268,754 B2
(45) Date of Patent: Sep. 18, 2012

(54) SUBSTITUTED DIHYDROAZOLE COMPOUND AND PEST CONTROL AGENT

(75) Inventors: Takeshi Mita, Funabashi (JP); Eitatsu Ikeda, Funabashi (JP); Hiroaki Takahashi, Funabashi (JP); Mitsuaki Komoda, Minami Saitama-gun (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 63 days.

(21) Appl. No.: 12/746,230

(22) PCT Filed: Dec. 5, 2008

(86) PCT No.: PCT/JP2008/072182
§ 371 (c)(1),
(2), (4) Date: Jul. 15, 2010

(87) PCT Pub. No.: WO2009/072621
PCT Pub. Date: Jun. 11, 2009

(65) Prior Publication Data
US 2010/0298558 A1    Nov. 25, 2010

(30) Foreign Application Priority Data
Dec. 7, 2007    (JP) ................. 2007-316833

(51) Int. Cl.
*A01N 43/36* (2006.01)
*C07D 207/18* (2006.01)
(52) U.S. Cl. ..... 504/283; 548/250; 548/255; 548/262.2; 548/364.1; 548/565; 544/63; 544/88; 544/224
(58) Field of Classification Search ............... 548/400, 548/565, 250, 255, 262.2, 304.7, 364.1; 504/283; 544/63, 88, 224
See application file for complete search history.

(56) References Cited

U.S. PATENT DOCUMENTS
2007/0066617 A1    3/2007    Mita et al.

FOREIGN PATENT DOCUMENTS
| JP | A-2007-016017 | 1/2007 |
|---|---|---|
| JP | A-2007-091708 | 4/2007 |
| WO | WO 2004/018410 A1 | 3/2004 |
| WO | WO 2005/085216 A1 | 9/2005 |
| WO | WO 2007/105814 A1 | 9/2007 |
| WO | WO 2008/122375 A2 | 10/2008 |
| WO | WO 2009/097992 A1 | 8/2009 |

OTHER PUBLICATIONS

Murata et al (2010): STN International HCAPLUS database, (Columbus, Ohio), Accession No. 2010:1465393.*
Iwata et al (2008): STN International HCAPLUS database, (Columbus, Ohio), Accession No. 2008:699408.*
Supplementary European Search Report issued in European Application No. EP 08 85 7288 dated Feb. 8, 2011.
Tsuge et al., "Regioselective Cycloadditions of N-Protonated Azomethine Ylides and 2-Azaallyl Anions Generated from N-(Silylmethyl) Thioimidates, Synthetic Equivalents of Nonstabilized Nitrile Ylides," *Journal of Organic Chemistry*, 1987, pp. 2523-2530, vol. 52.
Bellos et al., "Reactions of a Tertiary Carbon Carrying a *tert*-Butyl Group: Acid-Catalyzed Alcoholyses of Activated Aziridines without and with Solvent Assistance," *Journal of Organic Chemistry*, 1995, pp. 5661-5666, vol. 60.
Kopczynski, T., "Isoquinoline Syntheses Via 2-Oxazolines. Part V. Syntheses of 4-Alkyl-1-Phenylisoquinolines by Pictet-Gams Reaction," *Polish Journal of Chemistry*, 1985, pp. 375-386, vol. 59.
Fitton et al., "Cyclisation of 1-Aryl-1-benzamidopropan-2-ols. Formation of Rearranged 4,5-Dihydro-oxazoles, and Isoquinolines," *Journal of Chemical Research, Synopses*, 1988, pp. 352-353.
Kopczynski, T., "Isoquinoline Syntheses Via $\Delta^2$-Oxazolines. Part III. New Methods of Synthesizing Isoquinoline Derivatives," *Polish Journal of Chemistry*, 1982, pp. 867-869, vol. 56.
Lee et al., "*N*-(3-Acyloxy-2-benzylpropyl)-*N*'-[4-(methylsulfonylamino)benzyl]thiourea Analogues: Novel Potent and High Affinity Antagonists and Partial Antagonists of the Vanilloid Receptor," *Journal of Medicinal Chemistry*, 2003, pp. 3116-3126, vol. 46, No. 14.
Hanafusa et al., "Useful Synthesis of $\alpha$-Aminonitriles by Means of Alumina and Ultrasound," *Chemistry Letters*, 1987, pp. 687-690.
Kung et al., "Synthesis of New Bis(aminoethanethiol) (BAT) Derivatives: Possible Ligands for $^{99m}$Tc Brain Imaging Agents," *Journal of Medicinal Chemistry*, 1985, pp. 1280-1284, vol. 28.
Bertus et al., "A Direct Synthesis of 1-Aryl- and 1-Alkenylcyclopropylamines from Aryl and Alkenyl Nitriles," *Journal of Organic Chemistry*, 2003, pp. 7133-7136, vol. 68.
International Search Report issued in International Patent Application No. PCT/JP2008/072182 mailed on Jan. 20, 2009.

* cited by examiner

*Primary Examiner* — Golam M M Shameem
(74) *Attorney, Agent, or Firm* — Oliff & Berridge, PLC

(57) ABSTRACT

There is provided a novel pest control agent, particularly an insecticide or miticide. A substituted dihydroazole compound of General Formula (1) or a salt thereof:

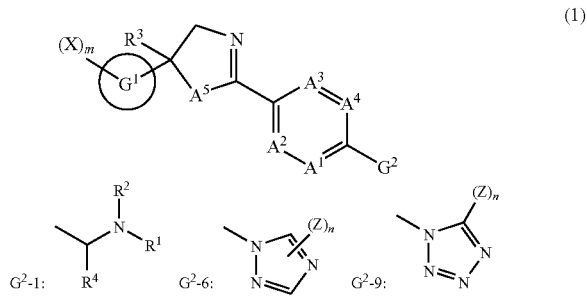

where $A^1$, $A^2$, $A^3$ and $A^4$ are independently C—Y or N, $A^5$ is —$CH_2$—, etc., $G^1$ is a benzene ring, etc., $G^2$ is $G^2$-1, $G^2$-6, $G^2$-9, etc., X is a halogen atom, $C_{1-2}$haloalkyl, etc., Z is methyl, —$NH_2$, etc., $R^1$ is —$C(O)R^{1a}$, etc., $R^{1a}$ is $C_{1-4}$alkyl, etc., $R^2$ is H, $C_{1-4}$alkyl, etc., $R^3$ is $C_{1-2}$haloalkyl, etc., $R^4$ is H, cyano, methyl, etc., m is an integer of 1, 2, 3, etc., n is an integer of 0 or 1; and a pest control agent comprising the compound or the salt thereof.

6 Claims, No Drawings

SUBSTITUTED DIHYDROAZOLE COMPOUND AND PEST CONTROL AGENT

TECHNICAL FIELD

The present invention relates to a novel substituted dihydroazole compound and a salt thereof, and a pest control agent containing the compound as an active ingredient. The pest control agent in the present invention means insect pest control agents aimed at harmful arthropods in the agricultural and horticultural fields, in the livestock and sanitation fields (internal or external parasites of mammals or birds as domestic animals or pet animals and sanitary insects and discomfort insects at home and at business sites), or the like. In addition, the agricultural chemicals in the present invention mean insecticides and miticides, nematicides, herbicides, fungicides and the like in the agricultural and horticultural fields.

BACKGROUND ART

In the related art, with respect to bis(substituted aryl)-substituted dihydroazole compounds, 4-dihydroazole-substituted benzoic acid amide compounds (see Patent Document 1) such as 4-[4-(3,5-dichlorophenyl)-4-trifluoromethyl-4,5-dihydro-3H-pyrrole-2-yl]-2-methyl-N-(2,2,2-trifluoroethyl) benzoic acid amide, N-acyl-1-(4-dihydroisoxazole-substituted phenyl) alkylamine compounds (see Patent Document 2) such as 2-chloro-N-cyclopropylcarbonyl-4-[5-[3,5-bis(trifluoromethyl)phenyl]-5-trifluoromethyl-4,5-dihydroisoxazole-3-yl]benzyl amine, and 3,5-bis(substituted aryl)-substituted dihydroisoxazole compounds (see Patent Document 3) such as 5-(3,5-dichlorophenyl)-3-[4-(1,2,4-triazole-1-yl) phenyl]-5-trifluoromethyl-4,5-dihydroisoxazole are known to exhibit pest control activity, particularly insecticidal and miticidal activity. However, nothing is disclosed with respect to an N-acyl-1-(4-dihydroazole-substituted phenyl) alkylamine compound and a bis(substituted aryl)-substituted dihydroazole compound according to the present invention.

In addition, it is known that a 4-(4-aminophenyl)-4-trifluoromethyl-2-substituted phenyl-4,5-dihydro-3H-pyrrole derivative, a 5-(4-aminophenyl)-5-trifluoromethyl-2-substituted phenyl-4,5-dihydroisoxazole derivative and a 5-(4-aminophenyl)-5-trifluoromethyl-2-substituted phenyl-4,5-dihydrothiazole derivative are used as an intermediate for producing an insecticide (see Patent Document 4), and further, there are also known a report of synthesizing a 2,5-bis(substituted phenyl)-5-alkyl-4,5-dihydroxazole derivative (for example, see Non-patent Document 1 to Non-patent Document 4) and a report of synthesizing a 2,5,5-tris(substituted phenyl)-4,5-dihydroxazole derivative (for example, see Non-patent Document 5). However, nothing is disclosed with respect to an N-acyl-1-(4-dihydroazole-substituted phenyl) alkylamine compound and a bis(substituted aryl)-substituted dihydroazole compound according to the present invention, and further, nothing is known with respect to the usefulness of these compounds as a pest control agent.

Patent Document 1: Japanese Patent Application Publication No. JP-A-2007-091708 specification
Patent Document 2: International Publication No. WO 2007/105814 pamphlet
Patent Document 3: Japanese Patent Application Publication No. JP-A-2007-016017 specification
Patent Document 4: International Publication No. WO 2004/018410 pamphlet
Non-patent Document 1: The Journal of Organic Chemistry (J. Org. Chem.), vol. 52, p. 2523 (1987)
Non-patent Document 2: The Journal of Organic Chemistry (J. Org. Chem.), vol. 60, p. 5661 (1995)
Non-patent Document 3: Polish Journal of Chemistry (Polish J. Chem.), vol. 59, p. 375 (1985)
Non-patent Document 4: Journal of Chemical Research, Synopses (J. Chem. Research, Synopses), p. 352 (1988)
Non-patent Document 5: Polish Journal of Chemistry (Polish J. Chem.), vol. 56, p. 867-869 (1982)

DISCLOSURE OF THE INVENTION

Problem to be Solved by the Invention

The development of pest control agents for the purpose of controlling various pests such as agricultural and horticultural pests, forest pests or sanitary pests has been progressed, and until today, various agents have been practically applied.

However, due to the use of such agents for a long period, recently, pests have acquired drug resistance, and there has been increased the number of situations in which the control with conventional insecticides and fungicides becomes difficult. In addition, a part of the conventional pest control agents has high toxicity or some of them remain in the environment for a long period to disturb the ecosystem, which is becoming a significant problem. Under such a situation, the development of a novel pest control agent having not only high pest control activity, but also low toxicity and a low residual property is constantly expected.

Means for Solving the Problem

As a result of assiduous research intended to overcome these disadvantages, the inventors of the present invention have found that a novel N-acyl-1-(4-dihydroazole-substituted phenyl) alkylamine compound and a novel bis(substituted aryl)-substituted dihydroazole compound of the following General Formula (1) according to the present invention are extremely useful compounds that exhibit excellent pest control activity, particularly excellent insecticidal and miticidal activity and have substantially no adverse effect on non-target organisms such as mammals, fish and beneficial insects to complete the present invention.

That is, the present invention relates to [1] to [10].

[1] A substituted dihydroazole compound of General Formula (1) or a salt of the substituted dihydroazole compound:

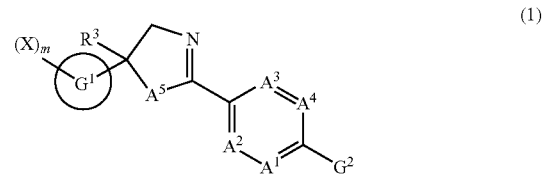

(1)

[where $A^1$, $A^2$, $A^3$ and $A^4$ are independently C—Y or N, $A^5$ is —CH($R^{3a}$)—, O or S, $G^1$ is a benzene ring, a nitrogen-containing 6-membered aromatic heterocycle, a furan ring, a thiophene ring or a 5-membered aromatic heterocycle containing two or more hetero atoms selected from an oxygen atom, a sulfur atom and a nitrogen atom, $G^2$ is a structure of $G^2$-1 to $G^2$-10:

$G^2$-1:

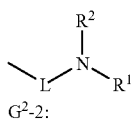

$G^2$-2:

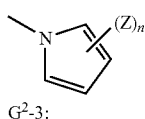

$G^2$-3:

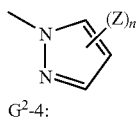

$G^2$-4:

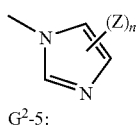

$G^2$-5:

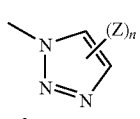

$G^2$-6:

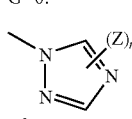

$G^2$-7:

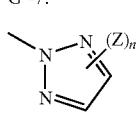

$G^2$-8:

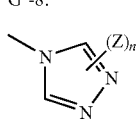

$G^2$-9:

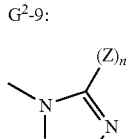

$G^2$-10:

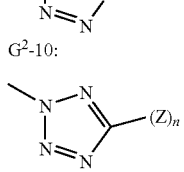

L is —C($R^4$)($R^{4a}$)—, —C($R^4$)($R^{4a}$)CH$_2$—, —CH$_2$C($R^4$)($R^{4a}$)—, —N($R^{4b}$)—, —C($R^4$)($R^{4a}$)N($R^{4b}$)— or a single bond, X is a halogen atom, cyano, nitro, azide, —SCN, —SF$_5$, C$_{1-6}$ alkyl, (C$_{1-6}$) alkyl optionally substituted with $R^5$, C$_{3-8}$ cycloalkyl, (C$_{3-8}$) cycloalkyl optionally substituted with $R^5$, E1 to E19, C$_{2-6}$ alkenyl, (C$_{2-6}$) alkenyl optionally substituted with $R^5$, C$_{5-10}$ cycloalkenyl, C$_{5-10}$halocycloalkenyl, C$_{2-6}$ alkynyl, (C$_{2-6}$) alkynyl optionally substituted with $R^5$, —OH, —OR$^6$, —OS(O)$_2$R$^6$, —SH, —S(O)$_r$R$^6$, —N(R$^8$)R$^7$, —N=C(R$^{8a}$)R$^{7a}$, —C(O)R$^9$, —C(R$^9$)=NOH, —C(R$^9$)=NOR$^{10}$, M3, M13, M30, —C(O)OR$^{10}$, —C(O)SR$^{10}$, —C(O)N(R$^{12}$)R$^{11}$, —C(S)OR$^{10}$, —C(S)SR$^{10}$, —C(S)N(R$^{12}$)R$^{11}$, M23 to M26, M28, M29, —S(O)$_2$OR$^{10}$, —S(O)$_2$N(R$^{12}$)R$^{11}$, —Si(R$^{13a}$)(R$^{13b}$)R$^{13}$, phenyl, phenyl substituted with (Z$^a$)$_{p1}$ or D1 to D38, when m is an integer of 2 or more, Xs may be the same as or different from each other, and further, when two Xs are adjacent to each other, the two adjacent Xs may form —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —CH$_2$CH$_2$N(R$^{14}$)—, —CH$_2$N(R$^{14}$)CH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —CH$_2$CH=CH—, —OCH=CH—, —SCH=CH—, —N(R$^{14}$)CH=CH—, —OCH=N—, —SCH=N—, —N(R$^{14}$)CH=N—, —N(R$^{14}$)N=CH—, —CH=CHCH=CH—, —OCH$_2$CH=CH—, —N=CHCH=CH—, —N=CHCH=N— or —N=CHN=CH— to form together with carbon atoms to which each of the two Xs is bonded, a 5-membered ring or a 6-membered ring, and in this case, hydrogen atoms bonded to each carbon atom forming the ring may be optionally substituted with $Z^a$s, further when hydrogen atoms are substituted simultaneously with 2 or more $Z^a$s, such $Z^a$s may be the same as or different from each other, Y is a hydrogen atom, a halogen atom, cyano, nitro, azide, —SCN, —SF$_5$, C$_{1-6}$ alkyl, (C$_{1-6}$) alkyl optionally substituted with $R^5$, C$_{3-8}$ cycloalkyl, (C$_{3-8}$) cycloalkyl optionally substituted with $R^5$, E1 to E19, C$_{2-6}$ alkenyl, (C$_{2-6}$) alkenyl optionally substituted with $R^5$, C$_{2-6}$ alkynyl, (C$_{2-6}$) alkynyl optionally substituted with $R^5$, —OH, —OR$^6$, —OS(O)$_2$R$^6$, —SH, —S(O)$_r$R$^6$, —N(R$^8$)R$^7$, —N(R$^8$)C(O)R$^{9a}$, —N=C(R$^{8a}$)R$^{7a}$, —C(O)N(R$^{12}$)R$^{11}$, —C(S)N(R$^{12}$)R$^{11}$, —Si(R$^{13a}$)(R$^{13b}$)R$^{13}$, phenyl, phenyl substituted with (Z$^a$)$_{p1}$ or D1 to D38, when two or more Ys exist simultaneously, the Ys may be the same as or different from each other, and further, when two Ys are adjacent to each other, the two adjacent Ys may form —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —SCH$_2$S—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —SCH$_2$CH$_2$S—, —OCH=N—, —SCH=N—, —CH=CHCH=CH—, —CH=CHCH=N—, —CH=CHN=CH—, —CH=NCH=CH— or —N=CHCH=CH— to form together with carbon atoms to which each of the two Ys is bonded, a 5-membered ring or a 6-membered ring, and in this case, hydrogen atoms bonded to each carbon atom forming the ring may be optionally substituted with $Z^a$s, and further when hydrogen atoms are substituted simultaneously with two or more $Z^a$s, such $Z^a$s may be the same as or different from each other, Z is a halogen atom, cyano, nitro, C$_{1-6}$ alkyl, (C$_{1-6}$) alkyl optionally substituted with $R^5$, —OH, —OR$^6$, —OS(O)$_2$R$^6$, —SH, —S(O)$_r$R$^6$, —N(R$^8$)R$^7$, —C(O)R$^9$, —C(R$^9$)=NOH, —C(R$^9$)=NOR$^{10}$, M3, M13, M30, —C(O)OR$^{10}$, —C(O)SR$^{10}$, —C(O)N(R$^{11s}$, —C(S)OR$^{10}$, —C(S)SR$^{10}$, —C(S)N(R$^{12a}$)R$^{11a}$, M23 to M26, M28, M29, —S(O)$_2$OR$^{10}$, —S(O)$_2$N(R$^{12}$)R$^{11}$, —Si(R$^{13a}$)(R$^{13b}$)R$^{13}$, phenyl or phenyl substituted with (Z$^a$)$_{p1}$, when n is an integer of 2 or more, Zs may be the same as or different from each other, and further, when two Zs are adjacent to each other, the two adjacent Zs may form —CH=CH—CH=CH— to form a condensed ring, and in this case, hydrogen atoms bonded to each carbon atom forming the ring may be optionally substituted with a halogen atom, a cyano group, a nitro group, a $C_{1-4}$ alkyl group, a $C_{1-4}$ haloalkyl group, a $C_{1-4}$ alkoxy group or a $C_{1-4}$ alkylthio group, $Z^a$ is a halogen atom, cyano, nitro, $C_{1-6}$ alkyl, $C_{1-6}$ haloalkyl, $C_{1-4}$ alkoxy($C_{1-4}$) alkyl, $C_{1-4}$ haloalkoxy($C_{1-4}$) alkyl, $C_{1-4}$ alkylthio($C_{1-4}$) alkyl, $C_{1-4}$ haloalkylthio($C_{1-4}$) alkyl, $C_{1-4}$ alkylsulfinyl($C_{1-4}$) alkyl, $C_{1-4}$ haloalkylsulfinyl($C_{1-4}$) alkyl, $C_{1-4}$ alkylsulfonyl($C_{1-4}$) alkyl, $C_{1-4}$ haloalkylsulfonyl($C_{1-4}$) alkyl, $C_{3-6}$ cycloalkyl, $C_{3-6}$ halocycloalkyl, —OH, $C_{1-6}$ alkoxy, $C_{1-6}$ haloalkoxy, $C_{1-6}$ alkyl sulfonyloxy, $C_{1-6}$ haloalkylsulfonyloxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, —NH$_2$, $C_{1-6}$ alkylamino, di($C_{1-6}$ alkyl)amino, $C_{1-6}$ alkoxycarbonyl, $C_{1-6}$ haloalkoxycarbonyl, —C(O)NH$_2$, $C_{1-6}$ alkylaminocarbonyl, $C_{1-6}$ haloalkylaminocarbonyl, di($C_{1-6}$ alkyl)aminocarbonyl, —C(S)NH$_2$, —S(O)$_2$NH$_2$, $C_{1-6}$ alkylaminosulfonyl, di($C_{1-6}$ alkyl)aminosulfonyl or phenyl, when p or p1 is an integer of 2 or more, $Z^a$s may be the same as or different from each other, and further, when two $Z^a$s are adjacent to each other, the two adjacent $Z^a$s may form —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —CH$_2$CH$_2$CH$_2$S—, —OCH$_2$CH$_2$S— or —CH=CH—CH=CH— to form together with carbon atoms to which each of the two $Z^a$s is bonded, a 5-membered ring or a 6-membered ring, and in this case, hydrogen atoms bonded to each carbon atom forming the ring may be optionally substituted with a halogen atom, a cyano group, a nitro group, a $C_{1-4}$ alkyl group, a $C_{1-4}$ haloalkyl group, a $C_{1-4}$ alkoxy group or a $C_{1-4}$ alkylthio group, $R^1$ is a hydrogen atom, —C(O)R$^{1a}$, —C(O)OR$^{1b}$, —C(O)SR$^{1b}$, —C(O)N(R$^{1d}$)R$^{1c}$, —C(S)R$^{1a}$, —C(S)OR$^{1b}$, —C(S)SR$^{1b}$, —C(S)N(R$^{1d}$)R$^{1c}$, —S(O)$_2$R$^{1b}$ or —S(O)$_2$N(R$^{1d}$)R$^{1c}$, $R^{1a}$ is a hydrogen atom, $C_{1-12}$ alkyl, ($C_{1-12}$) alkyl optionally substituted with R$^{15}$, $C_{3-12}$ cycloalkyl, ($C_{3-12}$) cycloalkyl optionally substituted with R$^{15}$, E1 to E21, $C_{2-12}$ alkenyl, ($C_{2-12}$) alkenyl optionally substituted with R$^{15}$, $C_{5-12}$ cycloalkenyl, $C_{5-12}$ halocycloalkenyl, $C_{2-12}$ alkynyl, ($C_{2-12}$) alkynyl optionally substituted with R$^{15}$, —C(O)R$^9$, —C(O)R$^{9a}$, —C(R$^9$)=NOH, —C(R$^9$)=NOR$^{10}$, —C(R$^9$)=NN(R$^{17}$)R$^{16}$, —C(O)OR$^{10}$, —C(O)N(R$^{12}$)R$^{11}$, M4, phenyl, phenyl substituted with $(Z^a)_{p1}$ or D-1 to D-38, $R^{1b}$ is $C_{1-12}$ alkyl, ($C_{1-12}$) alkyl optionally substituted with R$^{15}$, $C_{3-12}$ cycloalkyl, ($C_{3-12}$) cycloalkyl optionally substituted with R$^{15}$, E2 to E6, E12 to E19, $C_{2-12}$ alkenyl, $C_{2-12}$ haloalkenyl, $C_{3-12}$ alkynyl, $C_{3-12}$ haloalkynyl, phenyl, phenyl substituted with $(Z^a)_{p1}$, D1, D2, D4 to D6, D8 to D10, D12 to D19, D21, D23, D25, D27 or D30 to D38, $R^{1c}$ is a hydrogen atom, $C_{1-12}$ alkyl, ($C_{1-12}$) alkyl optionally substituted with R$^{15}$, $C_{3-12}$ cycloalkyl, ($C_{3-12}$) cycloalkyl optionally substituted with R$^{15}$, E2 to E6, E12 to E19, $C_{2-12}$ alkenyl, $C_{2-12}$ haloalkenyl, $C_{3-12}$ alkynyl, $C_{3-12}$ haloalkynyl, —C(O)R$^9$, —C(O)R$^{9a}$, —C(R$^9$)=NOR$^{10}$, C(O)OR$^{10}$, —C(O)SR$^{10}$, —C(O)N(R$^{12}$)R$^{11}$, M7, M17, —C(S)R$^9$, —C(S)OR$^{10}$, —C(S)SR$^{10}$, —C(S)N(R$^{12}$)R$^{11}$, M9, M19, —OR$^{10}$, —S(O)$_2$R$^{10}$, —S(O)$_2$N(R$^{12}$)R$^{11}$, —N(R$^{17}$)R$^{16}$, phenyl, phenyl substituted with $(Z^a)_{p1}$, D1 to D25 or D27 to D38, $R^{1d}$ is a hydrogen atom, $C_{1-6}$ alkyl, $C_{1-6}$ haloalkyl, $C_{3-6}$ cycloalkyl($C_{1-4}$) alkyl, $C_{1-6}$ alkoxy($C_{1-4}$) alkyl, $C_{1-6}$ alkylthio($C_{1-4}$) alkyl, cyano($C_{1-6}$) alkyl, phenyl($C_{1-4}$) alkyl, $C_{3-6}$ alkenyl or $C_{3-6}$ alkynyl, or R$^{1d}$ together with R$^{1c}$ may form a $C_{2-6}$ alkylene chain to form together with a nitrogen atom to which R$^{1c}$ and R$^{1d}$ are bonded, a 3- to 7-membered ring, and in this case, the alkylene chain may contain one oxygen atom, sulfur atom or nitrogen atom and may be optionally substituted with a $C_{1-6}$ alkyl group, a —CHO group, a $C_{1-6}$ alkylcarbonyl group, a $C_{1-6}$ alkoxycarbonyl group, a $C_{1-6}$ alkylaminocarbonyl group, a $C_{1-6}$ haloalkylaminocarbonyl group, a di($C_{1-6}$ alkyl)aminocarbonyl group, an oxo group or a thioxo group, $R^2$ is a hydrogen atom, cyano, $C_{1-12}$ alkyl, ($C_{1-12}$) alkyl optionally substituted with R$^{15a}$, $C_{3-12}$ cycloalkyl, $C_{3-12}$ alkenyl, $C_{3-12}$ haloalkenyl, $C_{3-12}$ alkynyl, $C_{3-12}$ haloalkynyl, —C(O)R$^9$, —C(O)R$^{9a}$, —C(O)OR$^{10}$, —C(O)SR$^{10}$, —C(O)N(R$^{12}$)R$^{11}$, —C(O)C(O)OR$^{10}$, —C(S)OR$^{10}$, —C(S)SR$^{10}$, —C(S)N(R$^{12}$)R$^{11}$, $C_{1-12}$alkoxy, $C_{1-12}$ haloalkoxy, —SR$^{10}$, —S(O)$_2$R$^{10}$, —SN(R$^{17a}$)R$^{16a}$, phenyl, phenyl substituted with $(Z^a)_{p1}$ or D32, or $R^2$ together with $R^1$ may form a $C_{4-6}$ alkylene chain to form together with a nitrogen atom to which $R^1$ and $R^2$ are bonded, a 5- to 7-membered ring, and in this case, the alkylene chain may contain one oxygen atom, sulfur atom or nitrogen atom and may be optionally substituted with a $C_{1-6}$ alkyl group, a $C_{1-6}$ alkylidene group, a —CHO group, a $C_{1-6}$ alkylcarbonyl group, a $C_{1-6}$ haloalkylcarbonyl group, a $C_{1-6}$ alkoxycarbonyl group, a $C_{1-6}$ haloalkoxycarbonyl group, a $C_{1-6}$ alkylaminocarbonyl group, a $C_{1-6}$ haloalkylaminocarbonyl group, a di($C_{1-6}$ alkyl)aminocarbonyl group, a phenyl group, a D32 group, a D34 group, an oxo group or a thioxo group, $R^3$ is a halogen atom, cyano, $C_{1-6}$ alkyl, ($C_{1-6}$) alkyl optionally substituted with R$^5$, $C_{3-8}$ cycloalkyl, ($C_{3-8}$) cycloalkyl optionally substituted with R$^5$, E1 to E19, $C_{3-6}$ alkenyl, ($C_{2-6}$) alkenyl optionally substituted with R$^5$, $C_{3-6}$ alkynyl, ($C_{2-6}$) alkynyl optionally substituted with R$^5$, —OR$^6$, —S(O)$_r$R$^6$, —N(R$^{12}$)R$^{11}$, —C(O)R$^9$, —C(R$^9$)=NOH, —C(R$^9$)=NOR$^{10}$, M3, M13, M30, —C(O)OR$^{10}$, —C(O)SR$^{10}$, —C(O)N(R$^{12}$)R$^{11}$, —C(S)OR$^{10}$, —C(S)SR$^{10}$, —C(S)N(R$^{12}$)R$^{11}$, —Si(R$^{13a}$)(R$^{13a}$)R$^{13}$, —P(O)(OR$^{18}$)$_2$, phenyl, phenyl substituted with $(Z^a)_{p1}$ or D1 to D38, $R^{3a}$ is a hydrogen atom, $C_{1-6}$ alkyl or $C_{1-6}$ haloalkyl, $R^4$ is a hydrogen atom, cyano, $C_{1-6}$ alkyl, $C_{1-6}$ haloalkyl, $C_{3-6}$ cycloalkyl, $C_{2-6}$ alkenyl, $C_{2-6}$ alkynyl, $C_{1-6}$ alkoxycarbonyl, —C(O)NH$_2$, —C(S)NH$_2$, phenyl, phenyl substituted with $(Z^a)_{p1}$, D1, D2, D9, D10 or D32, $R^{4a}$ is a hydrogen atom or $C_{1-6}$ alkyl, or $R^{4a}$ together with $R^4$ may form a $C_{2-5}$ alkylene chain to form together with a carbon atom to which $R^4$ and $R^{4a}$ are bonded, a 3- to 6-membered ring, and in this case, the alkylene chain may contain one oxygen atom, sulfur atom or nitrogen atom and may be optionally substituted with a $C_{1-4}$ alkyl group, a —CHO group, a $C_{1-4}$ alkylcarbonyl group, a $C_{1-4}$ alkoxycarbonyl group, a $C_{1-4}$ alkylaminocarbonyl group, a $C_{1-4}$ haloalkylaminocarbonyl group, a di($C_{1-4}$ alkyl)aminocarbonyl group or a phenyl group, $R^{4b}$ is a hydrogen atom, $C_{1-6}$ alkyl, $C_{1-6}$ haloalkyl, $C_{1-6}$ alkylcarbonyl, $C_{1-6}$ haloalkylcarbonyl, $C_{3-6}$ cycloalkylcarbonyl, $C_{3-6}$ halocycloalkylcarbonyl, $C_{1-6}$ alkoxycarbonyl or $C_{1-6}$ haloalkoxycarbonyl, D1 to D38 are individually an aromatic heterocycle of Structural Formulae below:

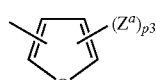

D1

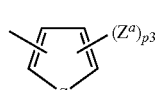

D2

|  |  |
|---|---|
| 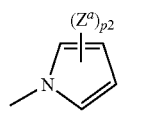 D3 | 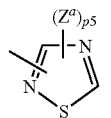 D15 |
| 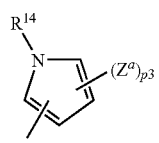 D4 | 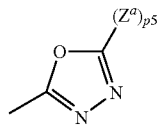 D16 |
| 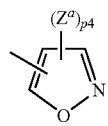 D5 | 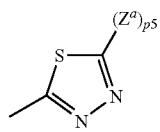 D17 |
| 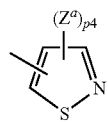 D6 | 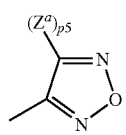 D18 |
| 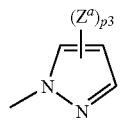 D7 | 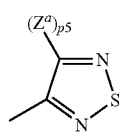 D19 |
| 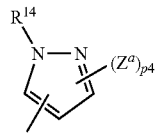 D8 | 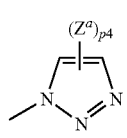 D20 |
| 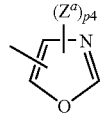 D9 | 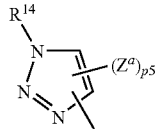 D21 |
| 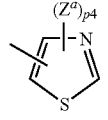 D10 | 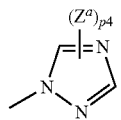 D22 |
| 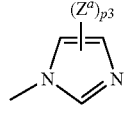 D11 | 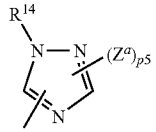 D23 |
| 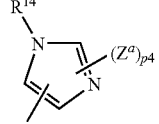 D12 | 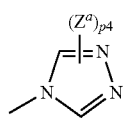 D24 |
| 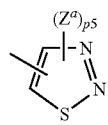 D13 | 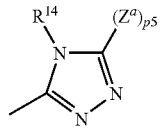 D25 |
| 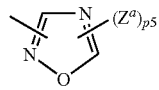 D14 | 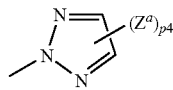 D26 |

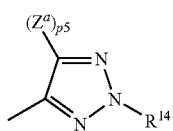 D27
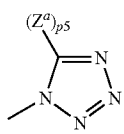 D28
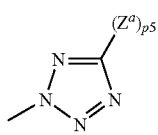 D29
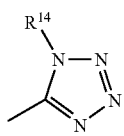 D30
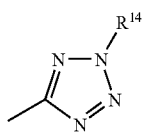 D31
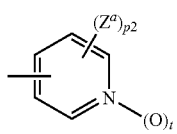 D32
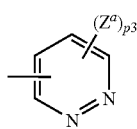 D33
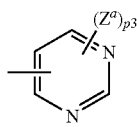 D34
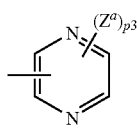 D35
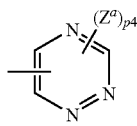 36
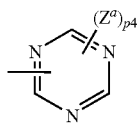 37
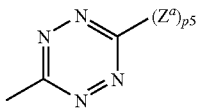 38
E1 to E21 are individually a saturated heterocycle of Structural Formulae below:
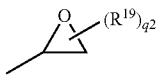 E1
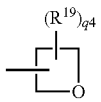 E2
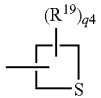 E3
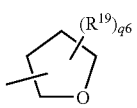 E4
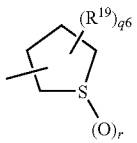 E5
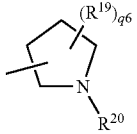 E6
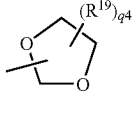 E7
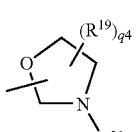 E8
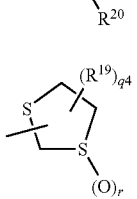 E9
E10

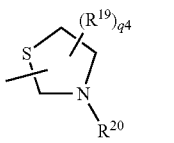

E11

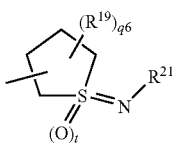

E20

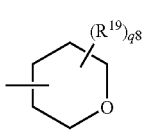

E12

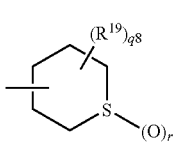

E13

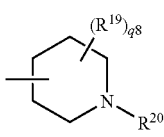

E14

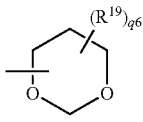

E15

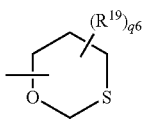

E16

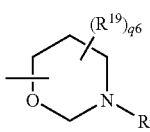

E17

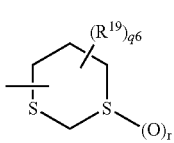

E18

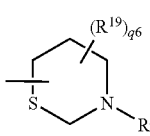

E19

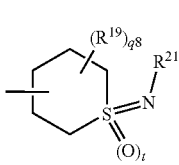

E21

$R^5$ is a halogen atom, cyano, $C_{3-8}$ cycloalkyl, $C_{3-8}$ halocycloalkyl, E1 to E19, —OH, —OR$^6$, —SH, —S(O)$_r$R$^6$, —N(R$^8$)R$^7$, —N(R$^8$)C(O)R$^{9a}$, —C(O)OR$^{10}$, —C(O)N(R$^{12}$)R$^{11}$, —Si(R$^{13a}$)(R$^{13b}$)R$^{13}$, phenyl, phenyl substituted with $(Z^a)_{p1}$ or D1 to D38, $R^6$ is $C_{1-6}$ alkyl, $(C_{1-6})$ alkyl optionally substituted with $R^{22}$, $C_{3-8}$ cycloalkyl, $(C_{3-8})$ cycloalkyl optionally substituted with $R^{22}$, E2 to E6, E12 to E15, E18, $C_{2-6}$ alkenyl, $(C_{2-6})$ alkenyl optionally substituted with $R^{22}$, $C_{5-10}$ cycloalkenyl, $C_{5-10}$ halocycloalkenyl, $C_{3-6}$ alkynyl, $(C_{3-6})$ alkynyl optionally substituted with $R^{22}$, $C_{1-6}$ alkylcarbonyl, $C_{1-6}$ alkoxycarbonyl, phenyl, phenyl substituted with $(Z^a)_{p1}$, D1, D2, D4 to D6, D8 to D10, D12 to D19, D21, D23, D25, D27 or D30 to D38, $R^7$ is a hydrogen atom, $C_{1-6}$ alkyl, $(C_{1-6})$ alkyl optionally substituted with $R^{22}$, $C_{3-8}$ cycloalkyl, $C_{3-8}$ halocycloalkyl, $C_{3-6}$ alkenyl, $C_{3-6}$ haloalkenyl, $C_{3-6}$ alkynyl, $C_{3-6}$ haloalkynyl, —C(O)R$^9$, —C(O)OR$^{10}$, —C(O)SR$^{10}$, —C(O)N(R$^{12}$)R$^{11}$, —C(S)OR$^{10}$, —C(S)SR$^{10}$, —C(S)N(R$^{12}$)R$^{11}$, —C(O)C(O)R$^{10}$, —C(O)C(O)OR$^{10}$, —OH, —S(O)$_2$R$^{10}$, —S(O)$_2$N(R$^{12}$)R$^{11}$, —P(O)(OR$^{18}$)$_2$ or —P(S)(OR$^{18}$)$_2$, $R^8$ is a hydrogen atom, $C_{1-6}$ alkyl, $(C_{1-6})$ alkyl optionally substituted with $R^{22}$, $C_{3-8}$ cycloalkyl, $C_{3-6}$ alkenyl, $C_{3-6}$ haloalkenyl, $C_{3-6}$ alkynyl, $C_{3-6}$ haloalkynyl, —CHO, $C_{1-6}$ alkylcarbonyl, $C_{1-6}$ haloalkylcarbonyl or $C_{1-6}$ alkoxycarbonyl, or R$^8$ together with R$^7$ may form a $C_{2-6}$ alkylene chain to form together with a nitrogen atom to which R$^7$ and R$^8$ are bonded, a 3- to 7-membered ring, and in this case, the alkylene chain may contain one oxygen atom, sulfur atom or nitrogen atom and may be optionally substituted with a halogen atom, a $C_{1-4}$ alkyl group, a $C_{1-4}$ haloalkyl group, an oxo group or a thioxo group, $R^{7a}$ is $C_{1-6}$ alkyl, $C_{1-6}$ alkoxy, $C_{1-6}$ haloalkoxy, $C_{3-6}$ alkenyloxy, phenoxy or phenoxy substituted with $(Z^a)_{p1}$, $R^{8a}$ is a hydrogen atom, $C_{1-6}$ alkyl, $C_{1-6}$ haloalkyl, $C_{3-6}$ alkenyl, phenyl, phenyl substituted with $(Z^a)_{p1}$, or R$^{8a}$ together with R$^{7a}$ may form a $C_{4-6}$ alkylene chain to form together with a carbon atom to which R$^{7a}$ and R$^{8a}$ are bonded, a 5- to 7-membered ring, and in this case, the alkylene chain may contain one oxygen atom or sulfur atom, $R^9$ is a hydrogen atom, $C_{1-6}$ alkyl, $(C_{1-6})$ alkyl optionally substituted with $R^{22}$, $C_{3-8}$ cycloalkyl, $C_{3-8}$ halocycloalkyl, E4 to E6, E12 to E14, $C_{2-6}$ alkenyl, $C_{2-6}$ haloalkenyl, $C_{5-10}$ cycloalkenyl, $C_{5-10}$ halocycloalkenyl, $C_{2-6}$ alkynyl or $C_{2-6}$ haloalkynyl, $R^{9a}$ is phenyl, phenyl substituted with $(Z^a)_{p1}$, naphthyl or D1 to D38, $R^{10}$ is $C_{1-6}$ alkyl, $(C_{1-6})$ alkyl optionally substituted with $R^{22}$, $C_{3-8}$ cycloalkyl, $C_{3-8}$ halocycloalkyl, E2 to E6, E12 to E19, $C_{2-6}$ alkenyl, $C_{2-6}$ haloalkenyl, $C_{5-10}$ cycloalkenyl, $C_{5-10}$ halocycloalkenyl, $C_{3-6}$ alkynyl, $C_{3-6}$ haloalkynyl, phenyl, phenyl substituted with $(Z^a)_{p1}$, D1, D2, D4 to D6, D8 to D10, D12 to D19, D21, D23, D25, D27 or D30 to D38, $R^{11}$ is a hydrogen atom, $C_{1-6}$ alkyl, $(C_{1-6})$ alkyl optionally substituted with $R^{22}$, $C_{3-8}$ cycloalkyl, $C_{3-8}$ halocycloalkyl, E2 to E6, E12 to E19, $C_{2-6}$ alkenyl, $C_{2-6}$ haloalkenyl, $C_{3-6}$ alkynyl, $C_{3-6}$ haloalkynyl, phenyl, phenyl substituted with $(Z^a)_{p1}$, D1 to D25 or D27 to D38, $R^{12}$ is a hydrogen atom, $C_{1-6}$ alkyl, $C_{1-6}$ haloalkyl, $C_{3-6}$ cycloalkyl($C_{1-4}$)alkyl, $C_{1-4}$ alkoxy($C_{1-4}$)alkyl, $C_{1-4}$ alkylthio($C_{1-4}$)alkyl, cyano($C_{1-4}$)alkyl, $C_{3-6}$ alkenyl or $C_{3-6}$ alkynyl, or R$^{12}$ together with R$^{11}$ may form a $C_{2-6}$ alkylene chain to form together with a nitrogen atom to which R$^{11}$ and R$^{12}$ are bonded, a 3- to 7-membered ring, and in this case, the alkylene chain may contain one oxygen atom, sulfur atom or nitrogen atom and may be optionally substituted with a halogen atom, a $C_{1-4}$ alkyl group, a $C_{1-4}$ alkoxy group, a —CHO group, a $C_{1-4}$ alkylcarbonyl group or a $C_{1-4}$ alkoxycarbonyl group, $R^{11a}$ is a hydrogen atom, $C_{1-6}$ alkyl, $(C_{1-6})$ alkyl optionally substituted with $R^{22}$, $C_{3-4}$ cycloalkyl, cyclopropyl substituted with $R^{22}$, E4, E5, $C_{3-6}$ alkenyl, $C_{3-6}$ haloalkenyl, —CH=NOR$^{10}$, —C(O)OR$^{10}$, —C(O)N(R$^{12}$)R$^{11}$, —C(S)OR$^{10}$, —N(R$^{12b}$)R$^{11b}$, D34 or D35, $R^{12a}$ is a hydrogen atom, $C_{1-6}$ alkyl, $(C_{1-4})$ alkyl substituted with $R^{22a}$, $C_{3-6}$ alkynyl, —C(O)R$^9$, —C(O)OR$^{10}$ or $C_{1-6}$ haloalkylthio, or R$^{12a}$ together with R$^{11a}$ may form =C(R$^{12c}$)R$^{11c}$, $R^{11b}$ is phenyl, D32 or D34, $R^{12b}$ is a hydrogen atom, $C_{1-4}$ alkyl, $C_{3-4}$ alkenyl or $C_{3-4}$ alkynyl, $R^{11c}$ is $C_{1-4}$ alkoxy or $C_{1-4}$ alkylthio, $R^{12c}$ is —NH$_2$ or $C_{1-4}$ alkylamino, $R^{13}$ is $C_{1-6}$ alkyl, $C_{1-6}$ haloalkyl, $C_{1-6}$ alkoxy, phenyl, phenyl substituted with $(Z^a)_{p1}$, $R^{13a}$ and $R^{13b}$ are independently $C_{1-6}$ alkyl, $C_{1-6}$ haloalkyl or $C_{1-6}$ alkoxy, $R^{14}$ is a hydrogen atom, $C_{1-6}$ alkyl, $C_{1-6}$ haloalkyl, $C_{1-4}$ alkoxycarbonyl($C_{1-4}$) alkyl, $C_{1-4}$ haloalkoxycarbonyl($C_{1-4}$) alkyl, phenyl($C_{1-4}$) alkyl, phenyl($C_{1-4}$) alkyl substituted with $(Z^a)_{p1}$, $C_{2-6}$ alkenyl, $C_{2-6}$ haloalkenyl, $C_{3-6}$ alkynyl, $C_{3-6}$ haloalkynyl, $C_{1-6}$ alkoxy, $C_{1-6}$ alkoxycarbonyl, $C_{1-6}$ haloalkoxycarbonyl, phenyl or phenyl substituted with $(Z^a)_{p1}$, and further, when $Z^a$ is present adjacent to $R^{14}$, $R^{14}$ and $Z^a$ adjacent to each other may form —CH$_2$CH$_2$CH$_2$CH$_2$—, —CH=CH—CH=CH—, —N=CH—CH=CH—, —CH=N—CH=CH—, —CH=CH—N=CH— or —CH=CH—CH=N— to form together with atoms to which each of R$^{14}$ and Z$^a$ is bonded, a 6-membered ring, and in this case, hydrogen atoms bonded to each carbon atom forming the ring may be optionally substituted with a halogen atom, a $C_{1-4}$ alkyl group or a $C_{1-4}$ haloalkyl group, $R^{15}$ is a halogen atom, cyano, nitro, $C_{3-8}$ cycloalkyl, $C_{3-8}$ halocycloalkyl, hydroxy($C_{3-8}$) cycloalkyl, $C_{1-4}$ alkoxy($C_{3-8}$) cycloalkyl, E1 to E 21, $C_{5-10}$ cycloalkenyl, $C_{5-10}$ halocycloalkenyl, —OR$^{23}$, —N(R$^{24}$)R$^{23}$, —SH, —S(O)$_r$R$^{25}$, —S(O)$_t$(R$^{25}$)=NR$^{21}$, —C(O)R$^{26}$, —C(R$^{26}$)=NOH, —C(R$^{26}$)=NOR$^{27}$, —C(O)OH, —C(O)OR$^{27}$, —C(O)SR$^{27}$, —C(O)N(R$^{29}$)R$^{28}$, —C(O)N(R$^{29}$)OR$^{27}$, —C(O)N(R$^{29}$)N(R$^{28a}$)R$^{28}$, —C(O)C(O)OR$^{27}$, —C(S)OR$^{27}$, —C(S)SR$^{27}$, —C(S)N(R$^{29}$)R$^{28}$, —C(=NR$^{28}$)OR$^{27}$, —C(=NR$^{28}$)SR$^{27}$, —C(=NR$^{29}$)N(R$^{28a}$)R$^{28}$, —C(=NOR$^{27}$)N(R$^{29}$)R$^{28}$, —S(O)$_2$OH, —S(O)$_2$OR$^{27}$, —S(O)$_2$N(R$^{29}$)R$^{28}$, —Si(R$^{13a}$)(R$^{13b}$)R$^{13}$, —P(O)(OR$^{18}$)$_2$, —P(S)(OR$^{18}$)$_2$, —P(phenyl)$_2$, —P(O)(phenyl)$_2$, M1 to M30, phenyl, phenyl substituted with $(Z^a)_{p1}$, naphthyl or D1 to D38, M1 to M30 are individually a partially saturated heterocycle of Structural Formulae below:

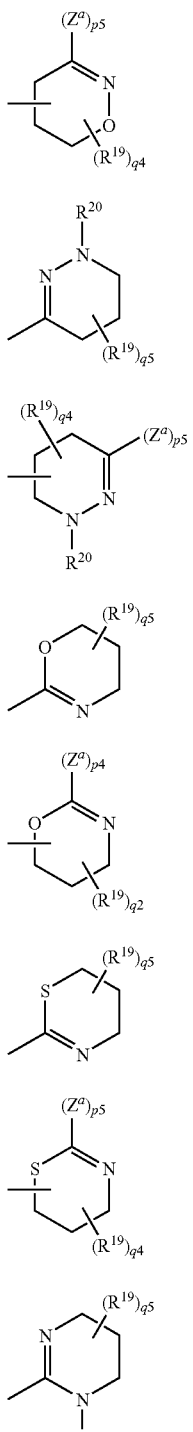

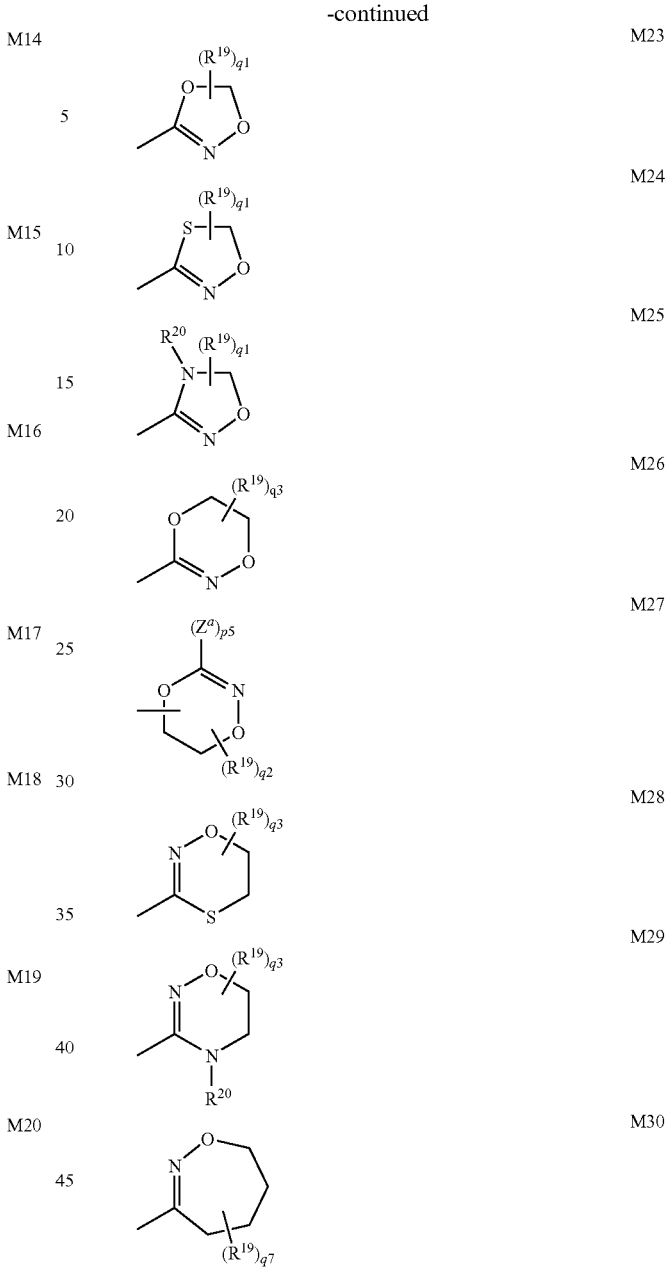

R$^{15a}$ is a halogen atom, cyano, nitro, C$_{3-8}$ cycloalkyl, E4, E5, E12, E13, C$_{5-10}$ cycloalkenyl, —OR$^{23}$, —N(R$^{24}$)R$^{23}$, —S(O)$_r$R$^{25}$, —C(O)R$^{26}$, —C(R$^{26}$)=NOH, —C(R$^{26}$)=NOR$^{27}$, M3, —C(O)OR$^{27}$, —C(O)N(R$^{29}$)R$^{28}$, M7, M17, —C(S)OR$^{27}$, —C(S)SR$^{27}$, —C(S)N(R$^{29}$)R$^{28}$, M9, M19, —C(O)C(O)OR$^{27}$, —S(O)$_2$N(R$^{29}$)R$^{28}$, —Si(R$^{13a}$)(R$^{13b}$)R$^{13}$, —P(O)(OR$^{18}$)$_2$, —P(S)(OR$^{18}$)$_2$, phenyl, phenyl substituted with (Z$^a$)$_{p1}$, D1 to D3, D7, D10, D11, D22 or D32 to D35, R$^{16}$ is a hydrogen atom, C$_{1-6}$ alkyl, (C$_{1-6}$) alkyl optionally substituted with R$^{30}$, C$_{3-8}$ cycloalkyl, C$_{3-8}$ halocycloalkyl, E2 to E6, E12 to E19, C$_{2-6}$ alkenyl, C$_{2-6}$ haloalkenyl, C$_{5-10}$ cycloalkenyl, C$_{5-10}$ halocycloalkenyl, C$_{3-6}$ alkynyl, C$_{3-6}$ haloalkynyl, —C(O)R$^{26}$, —C(O)OR$^{27}$, —C(O)SR$^{27}$, —C(O)N(R$^{29}$)R$^{28}$, —C(S)R$^{26}$, —C(S)OR$^{27}$, —C(S)SR$^{27}$, —C(S)N(R$^{29}$)R$^{28}$, —S(O)$_2$OR$^{27}$, —S(O)$_2$N(R$^{29}$)R$^{28}$, —P(O)(OR$^{18}$)$_2$, —P(S)(OR$^{18}$)$_2$, phenyl, phenyl substituted with (Z$^a$)$_{p1}$, D1 to D25 or D27 to D38, $R^{17}$ is a hydrogen atom, $C_{1-6}$ alkyl, $C_{1-6}$ haloalkyl, $C_{3-6}$ cycloalkyl($C_{1-4}$) alkyl, $C_{1-4}$ alkoxy($C_{1-4}$) alkyl, $C_{1-4}$ haloalkoxy($C_{1-4}$) alkyl, $C_{1-4}$ alkylthio($C_{1-4}$) alkyl, $C_{1-4}$ haloalkylthio($C_{1-4}$) alkyl, $C_{1-4}$ alkylsulfonyl($C_{1-4}$) alkyl, $C_{1-4}$ haloalkylsulfonyl($C_{1-4}$) alkyl, cyano($C_{1-4}$) alkyl, $C_{1-4}$ alkoxycarbonyl($C_{1-4}$) alkyl, phenyl($C_{1-4}$) alkyl, $C_{2-6}$ alkenyl, $C_{2-6}$ haloalkenyl, $C_{3-6}$ alkynyl or $C_{3-6}$ haloalkynyl, or $R^{17}$ together with $R^{16}$ may form a $C_{2-6}$ alkylene chain to form together with a nitrogen atom to which $R^{16}$ and $R^{17}$ are bonded, a 3- to 7-membered ring, and in this case, the alkylene chain may contain one oxygen atom, sulfur atom or nitrogen atom and may be optionally substituted with a halogen atom, a $C_{1-4}$ alkyl group, a $C_{1-2}$ alkoxy($C_{1-2}$) alkyl group, a $C_{1-4}$ alkoxy group, a —CHO group, a $C_{1-4}$ alkylcarbonyl group or a $C_{1-4}$ alkoxycarbonyl group, $R^{16a}$ is $C_{1-12}$ alkyl, $C_{1-12}$ haloalkyl, $C_{1-12}$ alkoxy($C_{1-12}$) alkyl, cyano($C_{1-12}$) alkyl, $C_{1-12}$ alkoxycarbonyl($C_{1-12}$) alkyl, phenyl($C_{1-4}$) alkyl, phenyl ($C_{1-4}$) alkyl substituted with $(Z^a)_{p1}$, $C_{3-12}$ alkenyl, $C_{3-12}$ haloalkenyl, $C_{3-12}$ alkynyl, $C_{3-12}$ haloalkynyl, $C_{1-12}$ alkylcarbonyl, $C_{1-12}$ alkoxycarbonyl, —C(O)ON=C(CH$_3$)SCH$_3$, —C(O)ON=C(SCH$_3$)C(O)N(CH$_3$)$_2$, phenyl or phenyl substituted with $(Z^a)_{p1}$, $R^{17a}$ is $C_{1-12}$ alkyl, $C_{1-12}$ haloalkyl, $C_{1-12}$ alkoxy($C_{1-12}$) alkyl, cyano($C_{1-12}$) alkyl, $C_{1-12}$ alkoxycarbonyl($C_{1-12}$) alkyl, phenyl($C_{1-4}$) alkyl, phenyl ($C_{1-4}$) alkyl substituted with $(Z^a)_{p1}$, $C_{3-12}$ alkenyl, $C_{3-12}$ haloalkenyl, $C_{3-12}$ alkynyl, $C_{3-12}$ haloalkynyl, phenyl or phenyl substituted with $(Z^a)_{p1}$, or $R^{17a}$ together with $R^{16a}$ may form a $C_{4-7}$ alkylene chain to form together with a nitrogen atom to which $R^{16a}$ and $R^{17a}$ are bonded, a 5- to 8-membered ring, and in this case, the alkylene chain may contain one oxygen atom or sulfur atom and may be optionally substituted with a $C_{1-4}$ alkyl group or a $C_{1-4}$ alkoxy group, $R^{18}$ is $C_{1-6}$ alkyl or $C_{1-6}$ haloalkyl, $R^{19}$ is a halogen atom, cyano, $C_{1-6}$ alkyl, $C_{1-6}$ haloalkyl, hydroxy($C_{1-4}$) alkyl, $C_{1-4}$ alkoxy($C_{1-4}$) alkyl, $C_{1-4}$ alkoxycarbonyl($C_{1-4}$)alkyl, $C_{1-6}$ alkoxy, $C_{1-6}$ alkylthio, $C_{1-6}$ alkylamino, di($C_{1-6}$ alkyl)amino, $C_{1-6}$ alkoxycarbonyl, phenyl or phenyl substituted with $(Z^a)_{p1}$, when q1 to q8 are an integer of 2 or more, $R^{19}$s may be the same as or different from each other, and further when two $R^{19}$s are substituents on the same carbon atom, the two $R^{19}$s together may form oxo, thioxo, imino, $C_{1-4}$ alkylimino, $C_{1-4}$ alkoxyimino or $C_{1-4}$ alkylidene, $R^{20}$ is a hydrogen atom, $C_{1-6}$ alkyl, ($C_{1-6}$) alkyl optionally substituted with $R^{30}$, $C_{3-6}$ cycloalkyl, $C_{3-6}$ alkenyl, $C_{3-6}$ haloalkenyl, $C_{3-6}$ alkynyl, —OH, benzyloxy, —C(O)$R^{31}$, —C(O)O$R^{32}$, —C(O)S$R^{32}$, —C(O)N($R^{34}$)$R^{33}$, —C(S)N($R^{34}$)$R^{33}$, —S(O)$_2R^{32}$, —P(O)(O$R^{18}$)$_2$, —P(S)(O$R^{18}$)$_2$, phenyl, phenyl substituted with $(Z^a)_{p1}$ or D3, $R^{21}$ is a hydrogen atom, cyano, nitro, $C_{1-6}$ alkyl, $C_{1-6}$ haloalkyl, $C_{1-6}$ alkylcarbonyl, $C_{1-6}$ haloalkylcarbonyl, $C_{1-6}$ alkoxycarbonyl, $C_{1-6}$ haloalkoxycarbonyl, $C_{1-6}$ alkylsulfonyl or $C_{1-6}$ haloalkylsulfonyl, $R^{22}$ is a halogen atom, cyano, $C_{3-8}$ cycloalkyl, $C_{3-8}$ halocycloalkyl, E1 to E19, —O$R^{23}$, $C_{1-6}$ alkylthio, $C_{1-6}$ haloalkylthio, $C_{1-6}$ alkylsulfonyl, $C_{1-6}$ haloalkylsulfonyl, —N($R^{24}$)$R^{23}$, —C(O)$R^{26}$, —C($R^{26}$)=NO$R^{27}$, —C(O)O$R^{27}$, —C(O)N($R^{29}$)$R^{28}$, phenyl, phenyl substituted with $(Z^a)_{p1}$ or D1 to D38, $R^{22a}$ is cyano, $C_{3-6}$ cycloalkyl, —O$R^{23}$ or $C_{1-6}$ alkylthio, $R^{23}$ is a hydrogen atom, $C_{1-8}$ alkyl, ($C_{1-8}$) alkyl optionally substituted with $R^{30}$, $C_{3-8}$ cycloalkyl, ($C_{3-8}$) cycloalkyl optionally substituted with $R^{30}$, E2 to E6, E12 to E19, $C_{3-8}$ alkenyl, ($C_{3-8}$) alkenyl optionally substituted with $R^{30}$, $C_{3-8}$ alkynyl, ($C_{3-8}$) alkynyl optionally substituted with $R^{30}$, —C(O)$R^{31}$, —C(O)O$R^{32}$, —C(O)S$R^{32}$, —C(O)N($R^{34}$)$R^{33}$, —C(O)C(O)$R^{32}$, —C(O)C(O)O$R^{32}$, —C(S)$R^{31}$, —C(S)O$R^{32}$, —C(S)S$R^{32}$, —C(S)N($R^{34}$)$R^{33}$, —S(O)$_2R^{32}$, —S(O)$_2$N($R^{34}$)$R^{33}$, —Si($R^{13a}$)($R^{13b}$)$R^{13}$, —P(O)(O$R^{18}$)$_2$, —P(S)(O$R^{18}$)$_2$, phenyl, phenyl substituted with $(Z^a)_{p1}$, D1, D2, D4 to D6, D8 to D10, D12 to D19, D21, D23, D25, D27 or D30 to D38, $R^{24}$ is a hydrogen atom, $C_{1-6}$ alkyl, $C_{1-6}$ haloalkyl, $C_{3-4}$ cycloalkyl($C_{1-4}$) alkyl, $C_{1-4}$ alkoxy($C_{1-4}$) alkyl, $C_{1-4}$ alkylthio($C_{1-4}$) alkyl, cyano($C_{1-4}$) alkyl, $C_{3-6}$ cycloalkyl, $C_{3-6}$ alkenyl, $C_{3-6}$ alkynyl, $C_{1-6}$ alkoxy, $C_{1-6}$ haloalkylcarbonyl, $C_{1-6}$ alkoxycarbonyl, $C_{1-6}$ alkylsulfonyl, phenyl or phenyl substituted with $(Z^a)_{p1}$, or $R^{24}$ together with $R^{23}$ may form a $C_{2-5}$ alkylene chain to form together with a nitrogen atom to which $R^{23}$ and $R^{24}$ are bonded, a 3- to 6-membered ring, and in this case, the alkylene chain may contain one oxygen atom, sulfur atom or nitrogen atom and may be substituted with a halogen atom, a $C_{1-4}$ alkyl group, a $C_{1-4}$ haloalkyl group, a $C_{1-4}$ alkoxy group, a —CHO group, a $C_{1-4}$ alkylcarbonyl group, a $C_{1-4}$ alkoxycarbonyl group, a phenyl group, a phenyl group substituted with $(Z^a)_{p1}$, an oxo group or a thioxo group, $R^{25}$ is $C_{1-8}$ alkyl, ($C_{1-8}$) alkyl optionally substituted with $R^{30}$, $C_{3-8}$ cycloalkyl, ($C_{3-8}$) cycloalkyl optionally substituted with $R^{30}$, E2 to E6, E12 to E19, $C_{3-8}$ alkenyl, ($C_{3-8}$) alkenyl optionally substituted with $R^{30}$, $C_{3-8}$ alkynyl, ($C_{3-8}$) alkynyl optionally substituted with $R^{30}$, —C(O)$R^{31}$, —C(O)O$R^{32}$, —C(O)S$R^{32}$, —C(O)N($R^{34}$)$R^{33}$, —C(O)C(O)$R^{32}$, —C(O)C(O)O$R^{32}$, —C(S)$R^{31}$, —C(S)O$R^{32}$, —C(S)S$R^{32}$, —C(S)N($R^{34}$)$R^{33}$, —SH, $C_{1-6}$ alkylthio, $C_{1-6}$ haloalkylthio, phenylthio, phenylthio substituted with $(Z^a)_{p1}$, —P(O)(O$R^{18}$)$_2$, —P(S)(O$R^{18}$)$_2$, phenyl, phenyl substituted with $(Z^a)_{p1}$, D9, D10, D12, D14 to D17, D30 or D32 to D35, $R^{26}$ is a hydrogen atom, $C_{1-6}$ alkyl, $C_{1-6}$ haloalkyl, $C_{3-6}$ cycloalkyl($C_{1-4}$) alkyl, $C_{1-6}$ alkoxy($C_{1-4}$) alkyl, $C_{1-6}$ haloalkoxy($C_{1-4}$) alkyl, $C_{1-6}$ alkylthio($C_{1-4}$) alkyl, $C_{1-6}$ haloalkylthio($C_{1-4}$) alkyl, $C_{1-6}$ alkylsulfonyl($C_{1-4}$) alkyl, $C_{1-6}$ haloalkylsulfonyl($C_{1-4}$) alkyl, phenyl($C_{1-4}$) alkyl, phenyl ($C_{1-4}$) alkyl substituted with $(Z^a)_{p1}$, $C_{3-6}$ cycloalkyl, phenyl or phenyl substituted with $(Z^a)_{p1}$, $R^{27}$ is $C_{1-6}$ alkyl, ($C_{1-6}$) alkyl optionally substituted with $R^{30}$, $C_{3-8}$ cycloalkyl, ($C_{3-8}$) cycloalkyl optionally substituted with $R^{30}$, E2 to E6, E12 to E19, $C_{2-6}$ alkenyl, ($C_{2-4}$ alkenyl optionally substituted with $R^{30}$, $C_{3-6}$ alkynyl, ($C_{3-6}$) alkynyl optionally substituted with $R^{30}$, phenyl, phenyl substituted with $(Z^a)_{p1}$, D1, D2, D4 to D6, D8 to D10, D12 to D19, D21, D23, D25, D27 or D30 to D38, $R^{28}$ is a hydrogen atom, $C_{1-6}$ alkyl, ($C_{1-4}$ alkyl optionally substituted with $R^{30}$, $C_{3-8}$ cycloalkyl, ($C_{3-8}$) cycloalkyl optionally substituted with $R^{30}$, E1 to E6, E12 to E19, $C_{2-6}$ alkenyl, ($C_{2-6}$) alkenyl optionally substituted with $R^{30}$, $C_{3-8}$ alkynyl, ($C_{3-4}$ alkynyl optionally substituted with $R^{30}$, phenyl, phenyl substituted with $(Z^a)_{p1}$, D1 to D25 or D27 to D38, $R^{28a}$ is a hydrogen atom or $C_{1-4}$ alkyl, $R^{29}$ is a hydrogen atom, $C_{1-6}$ alkyl, ($C_{1-6}$) alkyl optionally substituted with $R^{30}$, $C_{3-6}$ alkenyl, $C_{3-6}$ haloalkenyl, $C_{3-6}$ alkynyl, $C_{3-6}$ haloalkynyl, phenyl or phenyl substituted with $(Z^a)_{p1}$, or $R^{29}$ together with $R^{28}$ may form a $C_{2-5}$ alkylene chain to form together with a nitrogen atom to which $R^{28}$ and $R^{29}$ are bonded, a 3- to 6-membered ring, and in this case, the alkylene chain may contain one oxygen atom, sulfur atom or nitrogen atom and may be optionally substituted with a halogen atom, a $C_{1-4}$ alkyl group, a $C_{1-4}$ alkoxy group, a —CHO group, a $C_{1-4}$ alkylcarbonyl group, a $C_{1-4}$ alkoxycarbonyl group, a phenyl group, a phenyl group substituted with $(Z^a)_{p1}$ or an oxo group, $R^{30}$ is a halogen atom, cyano, nitro, $C_{3-8}$ cycloalkyl, $C_{3-8}$ halocycloalkyl, E4, E5, E7, E8, E10, E12, E13, E15, E16, E18, $C_{2-6}$ alkenyl, $C_{2-6}$ haloalkenyl, —OH, —O$R^{32}$, —OC(O)$R^{31}$, —OC(O)O$R^{32}$, —OC(O)N($R^{34}$)$R^{33}$, —OC(S)N $(R^{34})R^{33}$, —SH, —S(O)$_r$R$^{32}$, —SC(O)R$^{31}$, —SC(O)OR$^{32}$, —SC(O)N(R$^{34}$)R$^{33}$, —SC(S)N(R$^{34}$)R$^{33}$, —N(R$^{34}$)R$^{33}$, —N(R$^{34}$)CHO, —N(R$^{34}$)C(O)R$^{31}$, —N(R$^{34}$)C(O)OR$^{32}$, —N(R$^{34}$)C(O)N(R$^{34}$)R$^{33}$, —N(R$^{34}$)C(S)N(R$^{34}$)R$^{33}$, —N(R$^{34}$)S(O)$_2$R$^{32}$, —C(O)R$^{31}$, —C(O)OH, —C(O)OR$^{32}$, —C(O)SR$^{32}$, —C(O)N(R$^{34}$)R$^{33}$, —C(O)C(O)OR$^{32}$, —Si(R$^{13a}$)(R$^{13b}$)R$^{13}$, —P(O)(OR$^{18}$)$_2$, —P(S)(OR$^{18}$)$_2$, —P(phenyl)$_2$, —P(O)(phenyl)$_2$, phenyl, phenyl substituted with $(Z^a)_{g1}$ or D1 to D38, R$^{31}$ is a hydrogen atom, C$_{1-6}$ alkyl, C$_{1-6}$ haloalkyl, (C$_{1-4}$) alkyl optionally substituted with R$^{35}$, C$_{3-6}$ cycloalkyl, C$_{3-6}$ halocycloalkyl, E4, E5, E12, E13, C$_{2-8}$ alkenyl, C$_{2-8}$ haloalkenyl, C$_{5-10}$ cycloalkenyl, C$_{5-10}$ halocycloalkenyl, C$_{2-8}$ alkynyl, C$_{2-8}$ haloalkynyl, phenyl, phenyl substituted with $(Z^a)_{p1}$ or D1 to D38, R$^{32}$ is C$_{1-6}$ alkyl, C$_{1-6}$ haloalkyl, (C$_{1-4}$) alkyl optionally substituted with R$^{35}$, C$_{3-6}$ cycloalkyl, E4, E5, C$_{2-8}$ alkenyl, C$_{2-8}$ haloalkenyl, C$_{3-8}$ alkynyl or phenyl, R$^{33}$ is C$_{1-6}$ alkyl, C$_{1-6}$ haloalkyl, (C$_{1-4}$) alkyl optionally substituted with R$^{35}$, C$_{3-6}$ cycloalkyl, E4, E5, E12, C$_{2-8}$ alkenyl, C$_{2-8}$ haloalkenyl, C$_{3-8}$ alkynyl, phenyl, phenyl substituted with $(Z^a)_{p1}$, D1 to D25 or D27 to D38, R$^{34}$ is a hydrogen atom, C$_{1-6}$ alkyl, C$_{1-6}$ haloalkyl, C$_{3-8}$ cycloalkyl, C$_{3-6}$ alkenyl or C$_{3-6}$ alkynyl, or R$^{34}$ together with R$^{33}$ may form a C$_{2-5}$ alkylene chain to form together with a nitrogen atom to which R$^{33}$ and R$^{34}$ are bonded, a 3- to 6-membered ring, and in this case, the alkylene chain may contain one oxygen atom, sulfur atom or nitrogen atom and may be optionally substituted with a halogen atom, a C$_{1-4}$ alkyl group, a C$_{1-4}$ alkoxy group, a —CHO group, a C$_{1-4}$ alkylcarbonyl group, a C$_{1-4}$ alkoxycarbonyl group, a phenyl group or a phenyl group substituted with $(Z^a)_{p1}$, R$^{35}$ is cyano, C$_{3-6}$ cycloalkyl, C$_{3-6}$ halocycloalkyl, E4, E5, E12, E13, C$_{1-4}$ alkoxy, C$_{1-4}$ haloalkoxy, phenoxy, phenoxy substituted with $(Z^a)_{p1}$, C$_{1-4}$ alkylthio, C$_{1-4}$ haloalkylthio, phenylthio, phenylthio substituted with $(Z^a)_{p1}$, C$_{1-4}$ alkylsulfonyl, C$_{1-4}$ haloalkylsulfonyl, phenylsulfonyl, phenylsulfonyl substituted with $(Z^a)_{p1}$, —N(R$^{37}$)R$^{36}$, C$_{1-6}$ alkylcarbonyl, C$_{1-6}$ haloalkylcarbonyl, C$_{1-6}$ alkoxycarbonyl, di(C$_{1-6}$ alkyl) aminocarbonyl, tri(C$_{1-4}$ alkyl) silyl, phenyl, phenyl substituted with $(Z^a)_{p1}$, naphthyl or D1 to D38, R$^{36}$ is a hydrogen atom, C$_{1-6}$ alkyl, C$_{1-6}$ alkylcarbonyl, C$_{1-6}$ haloalkylcarbonyl, C$_{1-6}$ alkoxycarbonyl, phenylcarbonyl or phenylcarbonyl substituted with $(Z^a)_{p1}$, R$^{37}$ is a hydrogen atom or C$_{1-6}$ alkyl, m is an integer of 0 to 5,
n is an integer of 0 to 4,
p1 is an integer of 1 to 5,
p2 is an integer of 0 to 4,
p3 is an integer of 0 to 3,
p4 is an integer of 0 to 2,
p5 is an integer of 0 or 1,
q1 is an integer of 0 to 2,
q2 is an integer of 0 to 3,
q3 is an integer of 0 to 4,
q4 is an integer of 0 to 5,
q5 is an integer of 0 to 6,
q6 is an integer of 0 to 7,
q7 is an integer of 0 to 8,
q8 is an integer of 0 to 9,
r is an integer of 0 to 2, and
t is an integer of 0 or 1].

[2] The substituted dihydroazole compound or the salt of the substituted dihydroazole compound according to [1], in which A$^1$, A$^2$ and A$^4$ are independently C—Y or N,
A$^3$ is C—H or N,
G$^1$ is a benzene ring,
G$^2$ is a structure of G$^2$-1, G$^2$-3, G$^2$-5, G$^2$-6, G$^2$-8 or G$^2$-9,
L is —C(R$^4$)(R$^{4a}$)—, —C(R$^4$)(R$^{4a}$)CH$_2$—, —N(R$^{4b}$)— or —C(R$^4$)(R$^{4a}$)N(R$^{4b}$)—, X is a halogen atom, cyano, nitro, —SF$_5$, C$_{1-6}$ alkyl, C$_{1-6}$ haloalkyl, hydroxy(C$_{1-4}$) haloalkyl, C$_{1-4}$ alkoxy(C$_{1-4}$) haloalkyl, —OR$^6$, —S(O)$_r$R$^6$ or —NH$_2$, and when m is an integer of 2 or more, Xs may be the same as or different from each other, and further, when two Xs are adjacent to each other, the two adjacent Xs may form —CF$_2$OCF$_2$—, —OCF$_2$O—, —CF$_2$OCF$_2$O— or —OCF$_2$CF$_2$O— to form together with carbon atoms to which each of the two Xs is bonded, a 5-membered ring or a 6-membered ring, Y is a hydrogen atom, a halogen atom, cyano, nitro, C$_{1-6}$ alkyl, C$_{1-6}$ haloalkyl, (C$_{1-4}$) alkyl substituted with R$^5$, C$_{2-6}$ alkenyl, C$_{2-6}$ alkynyl, —OR$^6$, —S(O)$_r$R$^6$, —N(R$^8$)R$^7$, —C(S)NH$_2$, D1 to D3, D7, D11 or D22, when two or more Ys exist, the Ys may be the same as or different from each other, and further, when two Ys are adjacent to each other, the two adjacent Ys may form —CH═CHCH═CH— to form together with carbon atoms to which each of the two Ys is bonded, a 6-membered ring, Z is a halogen atom, cyano, nitro, C$_{1-6}$ alkyl, C$_{1-6}$ haloalkyl, —OR$^6$, —S(O)$_r$R$^6$, —NH$_2$, —C(O)N(R$^{12a}$)R$^{11a}$ or —C(S)N(R$^{12a}$)R$^{11a}$, R$^1$ is a hydrogen atom, —C(O)R$^{1a}$, —C(O)OR$^{1b}$, —C(O)SR$^{1b}$, —C(O)N(R$^{1d}$)R$^{1c}$, —C(S)R$^{1a}$ or —C(S)N(R$^{1d}$)R$^{1c}$, R$^{1a}$ is a hydrogen atom, C$_{1-6}$ alkyl, (C$_{1-4}$) alkyl optionally substituted with R$^{15}$, C$_{3-6}$ cycloalkyl, E4, E5, E10, E13, E20, C$_{2-6}$ alkenyl, C$_{2-6}$ haloalkenyl, C$_{2-6}$ alkynyl, —CH═NOR$^{10}$, phenyl substituted with $(Z^a)_{p1}$, D2, D8 or D32, Z$^a$ is a halogen atom, cyano, nitro, C$_{1-4}$ alkyl or C$_{1-4}$ alkylthio, when p1 and p2 are an integer of 2 or more, Zs may be the same as or different from each other, R$^{1b}$ is C$_{1-6}$ alkyl, C$_{1-6}$ haloalkyl, C$_{3-6}$ alkenyl or C$_{3-6}$ alkynyl, R$^{1c}$ is C$_{1-6}$ alkyl, (C$_{1-4}$) alkyl optionally substituted with R$^{15}$, C$_{3-6}$ cycloalkyl, C$_{3-6}$ alkenyl, C$_{3-6}$ alkynyl, C$_{1-6}$ alkoxy, C$_{1-6}$ alkylsulfonyl or —N(R$^{17}$)R$^{16}$, R$^{1d}$ is a hydrogen atom or C$_{1-6}$ alkyl, or R$^{1d}$ together with R$^{1c}$ may form a C$_{4-5}$ alkylene chain to form together with a nitrogen atom to which R$^{1c}$ and R$^{1d}$ are bonded, a 5- to 6-membered ring, and in this case, the alkylene chain may contain one oxygen atom or sulfur atom and may be optionally substituted with a methyl group or an oxo group, R$^2$ is a hydrogen atom, C$_{1-6}$ alkyl, (C$_{1-4}$) alkyl optionally substituted with R$^{15a}$, C$_{3-6}$ alkenyl, C$_{3-6}$ alkynyl or C$_{1-6}$ alkoxy, R$^3$ is C$_{1-6}$ haloalkyl or C$_{3-8}$ halocycloalkyl,
R$^{3a}$ is a hydrogen atom or C$_{1-4}$ alkyl,
R$^4$ is a hydrogen atom, cyano, C$_{1-4}$ alkyl, C$_{1-4}$ haloalkyl, C$_{3-4}$ cycloalkyl, C$_{2-4}$ alkynyl, —C(O)NH$_2$, —C(S)NH$_2$, phenyl, D9 or D10, R$^{4a}$ is a hydrogen atom or C$_{1-4}$ alkyl, or R$^{4a}$ together with R$^4$ may form an ethylene chain to form together with a carbon atom to which R$^4$ and R$^{4a}$ are bonded, a cyclopropyl ring, R$^{4b}$ is a hydrogen atom, C$_{1-4}$ alkyl, C$_{1-4}$ alkylcarbonyl, C$_{3-6}$ cycloalkylcarbonyl or C$_{1-4}$ alkoxycarbonyl, R$^5$ is —OH, C$_{1-4}$ alkoxy, C$_{1-4}$ alkylthio, C$_{1-4}$ alkylsulfonyl or C$_{1-4}$ alkylsulfonyl, R$^6$ is C$_{1-6}$ alkyl, C$_{1-6}$ haloalkyl or C$_{1-4}$ haloalkoxy(C$_{1-4}$) haloalkyl, R$^7$ is a hydrogen atom, C$_{1-6}$ alkyl, —CHO, C$_{1-6}$ alkylcarbonyl or C$_{1-6}$ alkoxycarbonyl, R$^8$ is a hydrogen atom or C$_{1-6}$ alkyl,
R$^{10}$ is C$_{1-4}$ alkyl, $R^{11a}$ is a hydrogen atom, $C_{1-4}$ alkyl, $C_{1-4}$ haloalkyl, $(C_{1-2})$ alkyl substituted with $R^{22}$, $C_{3-4}$ cycloalkyl, E4, —CH=NOR$^{10}$, —C(O)OR$^{10}$, —C(O)NH$_2$, —N(R$^{12b}$)R$^{11b}$, D34 or D35, $R^{12a}$ is a hydrogen atom, $(C_{1-2})$ alkyl substituted with $R^{22a}$, $C_{1-4}$ alkylcarbonyl, cyclopropylcarbonyl or $C_{1-4}$ alkoxycarbonyl, $R^{11b}$ is phenyl or D34, $R^{12b}$ is $C_{1-4}$ alkyl, $R^{14}$ is $C_{1-4}$ alkyl, $R^{15}$ is a halogen atom, cyano, $C_{3-4}$ cycloalkyl, $C_{1-4}$ alkoxy, $C_{1-4}$ haloalkoxy, —N(R$^{24}$)R$^{23}$, —S(O)$_r$R$^{25}$, —S(O)$_t$(R$^{25}$)=NR$^{21}$ or —C(O)N(R$^{29}$)R$^{28}$, $R^{15a}$ is a halogen atom, cyano, $C_{3-4}$ cycloalkyl, $C_{1-4}$ alkoxy, $C_{1-4}$ haloalkoxy, $C_{1-4}$ alkylthio, —N(R$^{24}$)R$^{23}$, $C_{1-4}$ alkoxycarbonyl, —C(O)N(R$^{29}$)R$^{28}$ or —C(S)NH$_2$, $R^{16}$ is a hydrogen atom, $C_{1-6}$ alkyl or $C_{1-6}$ alkoxycarbonyl, $R^{17}$ is a hydrogen atom or $C_{1-6}$ alkyl, $R^{21}$ is a hydrogen atom, cyano or $C_{1-4}$ haloalkylcarbonyl, $R^{22}$ is $C_{1-4}$ alkoxy, $C_{1-4}$ haloalkoxy, $C_{1-4}$ haloalkylaminocarbonyl, D10 or D32, $R^{22a}$ is cyano or —OR$^{23}$, $R^{23}$ is $C_{1-4}$ alkyl, cyano($C_{1-4}$) alkyl, —C(O)R$^{31}$, —C(O)OR$^{32}$, —C(O)SR$^{32}$ or $C_{1-4}$ alkylsulfonyl, $R^{24}$ is a hydrogen atom, $C_{1-4}$ alkyl, $C_{1-4}$ haloalkylcarbonyl, $C_{1-4}$ alkoxycarbonyl or $C_{1-4}$ alkylsulfonyl, $R^{25}$ is $C_{1-4}$ alkyl, $(C_{1-4})$ alkyl optionally substituted with $R^{30}$, $C_{3-4}$ cycloalkyl, $C_{3-4}$ alkenyl, $C_{3-4}$ alkynyl, —C(O)R$^{31}$, —CO(O)R$^{32}$ or —C(O)N(R$^{34}$)R$^{33}$, $R^{28}$ is a hydrogen atom, $C_{1-4}$ alkyl, $C_{1-4}$ haloalkyl or cyclopropylmethyl, $R^{29}$ is a hydrogen atom or $C_{1-4}$ alkyl, $R^{30}$ is a halogen atom, cyano or —C(O)N(R$^{34}$)R$^{33}$, $R^{31}$ is $C_{1-4}$ alkyl, $C_{1-4}$ haloalkyl, $C_{3-4}$ cycloalkyl, D7, D11 or D22, $R^{32}$ is $C_{1-4}$ alkyl, $R^{33}$ is $C_{1-4}$ alkyl or $C_{1-4}$ haloalkyl, $R^{34}$ is a hydrogen atom or $C_{1-4}$ alkyl, m is an integer of 1 to 3, n is an integer of 0 or 1, p1 is an integer of 1 to 3, p2 is an integer of 0 to 2, p3 and p4 are an integer of 0 or 1, and q4, q6 and q8 are 0.

[3] The substituted dihydroazole compound or the salt of the substituted dihydroazole compound according to [2], in which $A^1$ is C—Y or N, $A^2$ and $A^3$ are C—H, $A^4$ is C—H or N, $A^5$ is —CH$_2$— or S, L is —C(R$^4$)(R$^{4a}$)—, X is a halogen atom, cyano, nitro, —SF$_5$, $C_{1-4}$ alkyl, $C_{1-4}$ haloalkyl, $C_{1-4}$ alkoxy, $C_{1-4}$ haloalkoxy, $C_{1-4}$ alkylthio or $C_{1-4}$ haloalkylthio, when m is 2 or 3, Xs may be the same as or different from each other, Y is a hydrogen atom, a halogen atom, cyano, nitro, $C_{1-4}$ alkyl, $C_{1-4}$ haloalkyl, $C_{2-4}$ alkynyl, $C_{1-4}$ alkoxy, $C_{1-4}$ haloalkoxy, $C_{1-4}$ alkylthio, $C_{1-4}$ haloalkylthio or —C(S)NH$_2$, Z is a halogen atom, cyano, nitro, $C_{1-4}$ alkyl, —NH$_2$, —C(O)NHR$^{11a}$ or —C(S)NHR$^{11a}$, $R^3$ is $C_{1-4}$ haloalkyl, $R^4$ is a hydrogen atom, cyano, methyl, trifluoromethyl, ethynyl, —C(S)NH$_2$ or D10, $R^{4a}$ is a hydrogen atom, or $R^{4a}$ together with $R^4$ may form an ethylene chain to form together with a carbon atom to which $R^4$ and $R^{4a}$ are bonded, a cyclopropyl ring, $R^{11a}$ is a hydrogen atom, $C_{1-4}$ alkyl, $C_{1-4}$ haloalkyl, $(C_{1-2})$ alkyl substituted with $R^{22}$, cyclopropyl, E4 or —CH=NOR$^{10}$, $R^{10}$ is $C_{1-2}$ alkyl, and $R^{22}$ is $C_{1-2}$ alkoxy, $C_{1-2}$ haloalkoxy, $C_{1-2}$ haloalkylaminocarbonyl, D10 or D32.

[4] The substituted dihydroazole compound or the salt of the substituted dihydroazole compound according to [3], in which $A^5$ is —CH$_2$—, $G^2$ is a structure of $G^2$-1, $G^2$-6 or $G^2$-9, L is —CH(R$^4$)—, X is a halogen atom, cyano, —SF$_5$, $C_{1-2}$ haloalkyl, $C_{1-2}$ haloalkoxy or $C_{1-2}$ haloalkylthio, when m is 2 or 3, Xs may be the same as or different from each other, Y is a hydrogen atom, a halogen atom, cyano, nitro, $C_{1-2}$ alkyl, $C_{1-2}$ haloalkyl, $C_{2-3}$ alkynyl, $C_{1-2}$ haloalkoxy, $C_{1-2}$ haloalkylthio or —C(S)NH$_2$, Z is a halogen atom, nitro, methyl or —NH$_2$, $R^1$ is —C(O)R$^{1a}$, —C(O)SR$^{1b}$, —C(O)N(R$^{1d}$)R$^{1c}$ or —C(S)R$^{1a}$, $R^{1a}$ is $C_{1-4}$ alkyl, $(C_{1-4})$ alkyl optionally substituted with $R^{15}$, $C_{3-4}$ cycloalkyl, E4, E5, $C_{2-4}$ alkenyl, $C_{2-4}$ haloalkenyl, $C_{2-4}$ alkynyl, phenyl substituted with $(Z^a)_{p1}$ or D32, $Z^a$ is a halogen atom, cyano, nitro or $C_{1-4}$ alkylthio, when p1 and p2 are an integer of 2 or more, $Z^a$s may be the same as or different from each other, $R^{1b}$ is $C_{1-4}$ alkyl or $C_{1-4}$ haloalkyl, $R^{1c}$ is $C_{1-4}$ alkyl, $C_{1-4}$ haloalkyl, $C_{3-4}$ cycloalkyl or $C_{3-4}$ alkynyl, $R^{1d}$ is a hydrogen atom or $C_{1-4}$ alkyl, $R^2$ is a hydrogen atom, $C_{1-4}$ alkyl, $(C_{1-2})$ alkyl substituted with $R^{15a}$, $C_{3-4}$ alkenyl or $C_{3-4}$ alkynyl, $R^3$ is $C_{1-2}$ haloalkyl, $R^4$ is a hydrogen atom, cyano, methyl, ethynyl or —C(S)NH$_2$, $R^{15}$ is a halogen atom, $C_{3-4}$ cycloalkyl, $C_{1-2}$ alkoxy, $C_{1-2}$ haloalkoxy, —N(R$^{24}$)R$^{23}$, —S(O)$_r$R$^{25}$, —S(O)$_t$(R$^{25}$)=NR$^{21}$ or —C(O)N(R$^{29}$)R$^{28}$, $R^{15a}$ is cyano, $C_{3-4}$ cycloalkyl, $C_{1-2}$ alkoxy, $C_{1-2}$ haloalkoxy, —N(R$^{24}$)R$^{23}$, $C_{1-2}$ alkoxycarbonyl, —C(O)N(R$^{29}$)R$^{28}$ or —C(S)NH$_2$, $R^{21}$ is a hydrogen atom or $C_{1-2}$ haloalkylcarbonyl, $R^{23}$ is cyano($C_{1-2}$) alkyl, —C(O)R$^{31}$ or $C_{1-2}$ alkoxycarbonyl, $R^{24}$ is a hydrogen atom or $C_{1-2}$ alkoxycarbonyl, $R^{25}$ is $C_{1-2}$ alkyl, $C_{1-2}$ haloalkyl or cyanomethyl, $R^{28}$ is a hydrogen atom or $C_{1-2}$ alkyl, $R^{29}$ is a hydrogen atom or methyl, and $R^{31}$ is $C_{1-2}$ alkyl, $C_{1-2}$ haloalkyl or cyclopropyl.

[5] The substituted dihydroazole compound or the salt of the substituted dihydroazole compound according to [4], in which $A^1$ is C—Y, $A^4$ is C—H, $G^2$ is a structure of $G^2$-1, X is a halogen atom or trifluoromethyl, when m is 2 or 3, Xs may be the same as or different from each other, Y is a hydrogen atom, a halogen atom, nitro or methyl, $R^1$ is —C(O)R$^{1a}$ or —C(O)NHR$^{1c}$, $R^{1a}$ is $C_{1-4}$ alkyl, $C_{1-4}$ haloalkyl, $(C_{1-2})$ alkyl optionally substituted with $R^{15}$, cyclopropyl, E4 or E5, $R^{1c}$ is $C_{1-3}$ alkyl, $C_{1-3}$ haloalkyl, cyclopropyl or propargyl, $R^2$ is a hydrogen atom, $C_{1-2}$ alkyl, cyclopropylmethyl, $C_{1-2}$ alkoxymethyl, cyanomethyl, allyl or propargyl, $R^3$ is trifluoromethyl or chlorodifluoromethyl, $R^4$ is a hydrogen atom, cyano or methyl, $R^{15}$ is cyclopropyl or —S(O)$_r$R$^{25}$, and
$R^{25}$ is $C_{1-2}$ alkyl or $C_{1-2}$ haloalkyl.

[6] The substituted dihydroazole compound or the salt of the substituted dihydroazole compound according to [4], in which
$A^1$ is C—Y,
$A^4$ is C—H,
$G^2$ is a structure of $G^2$-6 or $G^2$-9,
X is a halogen atom or trifluoromethyl, when m is 2 or 3, Xs may be the same as or different from each other,
Y is a hydrogen atom, cyano or nitro,
$R^3$ is trifluoromethyl or chlorodifluoromethyl, and
n is 0.

[7] A pest control agent containing as active ingredient(s), one type or two or more types selected from the substituted dihydroazole compound and the salt of the substituted dihydroazole compound as described in any one of [1] to [6].

[8] An agricultural chemical containing as active ingredient(s), one type or two or more types selected from the substituted dihydroazole compound and the salt of the substituted dihydroazole compound as described in any one of [1] to [6].

[9] A control agent against internal or external parasites of mammals or birds containing as active ingredient(s), one type or two or more types selected from the substituted dihydroazole compound and the salt of the substituted dihydroazole compound as described in any one of [1] to [6].

[10] An insecticide or a miticide containing as active ingredient(s), one type or two or more types selected from the substituted dihydroazole compound and the salt of the substituted dihydroazole compound as described in any one of [1] to [6].

Effects of the Invention

The compound of the present invention has excellent insecticidal and miticidal activity with respect to a number of agricultural insect pests, spider mites and internal or external parasites of mammals or birds, and also exerts satisfactory control effect on insect pests which have acquired resistance to conventional pesticides. Furthermore, the compound has substantially no adverse effect on mammals, fish and beneficial insects, and has a low residual property to have the least effect on the environment.

Accordingly, the present invention can provide a useful novel pest control agent.

BEST MODES FOR CARRYING OUT THE INVENTION

In the compounds included in the present invention, although geometric isomers of an E-form and a Z-form may exist depending on a substituent type, the present invention includes the E-form, the Z-form or a mixture containing the E-form and the Z-form at any ratio. Furthermore, although the compounds included in the present invention include optically active substances due to the presence of one or more asymmetric carbon atom(s), the present invention includes all of the optically active compounds or racemates.

Among the compounds included in the present invention, compounds capable of being converted into acid addition salts by a conventional method may be converted into, for example, salts of hydrohalic acids such as hydrofluoric acid, hydrochloric acid, hydrobromic acid and hydroiodic acid; salts of inorganic acids such as nitric acid, sulfuric acid, phosphoric acid, chloric acid and perchloric acid; salts of sulfonic acids such as methanesulfonic acid, ethanesulfonic acid, trifluoromethanesulfonic acid, benzenesulfonic acid and p-toluenesulfonic acid; salts of carboxylic acids such as formic acid, acetic acid, propionic acid, trifluoroacetic acid, fumaric acid, tartaric acid, oxalic acid, maleic acid, malic acid, succinic acid, benzoic acid, mandelic acid, ascorbic acid, lactic acid, gluconic acid and citric acid; or salts of amino acids such as glutamic acid and aspartic acid.

In addition, among the compounds included in the present invention, compounds capable of being converted into metal salts by a common method may be converted into, for example, salts of alkali metals such as lithium, sodium and potassium; salts of alkaline earth metals such as calcium, barium and magnesium; or salts of aluminum.

Next, specific examples of each substituent shown in the present specification are shown below. Here, n-, i-, s- and tert-mean normal, iso, secondary and tertiary, respectively, and Ph means phenyl.

Examples of the halogen atom in the compound of the present invention include a fluorine atom, a chlorine atom, a bromine atom and an iodine atom. Here, the expression "halo" in the present specification also is these halogen atoms.

The expression "$C_{a-b}$ alkyl" in the present specification is straight-chain or branched-chain hydrocarbon groups having carbon atom number of a to b. Specific examples of the "$C_{a-b}$ alkyl" include a methyl group, an ethyl group, an n-propyl group, an i-propyl group, an n-butyl group, an i-butyl group, an s-butyl group, a tert-butyl group, an n-pentyl group, a 2,2-dimethylpropyl group and an n-hexyl group, and the like, and each of the alkyl groups is selected within the range of the specified number of carbon atoms.

The expression "$C_{a-b}$ haloalkyl" in the present specification is straight-chain or branched-chain hydrocarbon groups having carbon atom number of a to b in which a hydrogen atom bonded to a carbon atom is optionally substituted with a halogen atom. In this case, when hydrogen atoms are substituted with two or more halogen atoms, these halogen atoms may be the same as or different from each other. Specific examples of the "$C_{a-b}$ haloalkyl" include a fluoromethyl group, a chloromethyl group, a bromomethyl group, an iodomethyl group, a difluoromethyl group, a dichloromethyl group, a trifluoromethyl group, a chlorodifluoromethyl group, a trichloromethyl group, a bromodifluoromethyl group, a 2-fluoroethyl group, a 2-chloroethyl group, a 2-bromoethyl group, a 2,2-difluoroethyl group, a 2,2,2-trifluoroethyl group, a 2-chloro-2,2-difluoroethyl group, a 2,2,2-trichloroethyl group, a 2-bromo-2,2-difluoroethyl group, a 1,1,2,2-tetrafluoroethyl group, a 2-chloro-1,1,2-trifluoroethyl group, a pentafluoroethyl group, a 3,3,3-trifluoropropyl group, a 3-bromo-3,3-difluoropropyl group, a 2,2,3,3,3-pentafluoropropyl group, a 1,1,2,3,3,3-hexafluoropropyl group, a heptafluoropropyl group, a 1,2,2,2-tetrafluoro-1-(trifluoromethyl)ethyl group, a 2,2,3,3,4,4,4-heptafluorobutyl group and a nonafluorobutyl group, and the like, and each of the haloalkyl groups is selected within the range of the specified number of carbon atoms.

The expression "$C_{a-b}$ cycloalkyl" in the present specification is cyclic hydrocarbon groups having carbon atom number of a to b, and the "$C_{a-b}$ cycloalkyl" can form a monocyclic or composite ring structure having a 3-membered ring to a 6-membered ring. Furthermore, each ring may be optionally substituted with an alkyl group within the range of the specified number of carbon atoms. Specific examples of the "$C_{a-b}$ cycloalkyl" include a cyclopropyl group, a 1-methylcyclopropyl group, a 2-methylcyclopropyl group, a 2,2-dimethylcyclopropyl group, a cyclobutyl group, a cyclopentyl group and a cyclohexyl group, and the like, and each of the cycloalkyl groups is selected within the range of the specified number of carbon atoms.

The expression "$C_{a-b}$ halocycloalkyl" in the present specification is cyclic hydrocarbon groups having carbon atom number of a to b in which a hydrogen atom bonded to a carbon atom is optionally substituted with a halogen atom, and the "$C_{a-b}$ halocycloalkyl" can form a monocyclic or composite ring structure having a 3-membered ring to a 6-membered ring. Furthermore, each ring may be optionally substituted with an alkyl group within the range of the specified number of carbon atoms, and the substitution with a halogen atom may be on the ring structure part, the side chain part or both of them. In addition, when hydrogen atoms are substituted with two or more halogen atoms, these halogen atoms may be the same as or different from each other. Specific examples of the "$C_{a-b}$ halocycloalkyl" include a 2,2-difluorocyclopropyl group, a 2,2-dichlorocyclopropyl group, a 2,2-dibromocyclopropyl group, a 2,2-difluoro-1-methylcyclopropyl group, a 2,2-dichloro-1-methylcyclopropyl group, a 2,2-dibromo-1-methylcyclopropyl group and a 2,2,3,3-tetrafluorocyclobutyl group, and the like, and each of the halocycloalkyl groups is selected within the range of the specified number of carbon atoms.

The expression "$C_{a-b}$ alkenyl" in the present specification is straight-chain or branched-chain unsaturated hydrocarbon groups having carbon atom number of a to b, and having one or more double bond(s) in the molecule. Specific examples of the "$C_{a-b}$ alkenyl" include a vinyl group, a 1-propenyl group, a 2-propenyl group, a 1-methylethenyl group, a 1-butenyl group, a 2-butenyl group, a 1-methyl-1-propenyl group, a 2-methyl-1-propenyl group, a 2-methyl-2-propenyl group and a 3-methyl-2-butenyl group, and the like, and each of the alkenyl groups is selected within the range of the specified number of carbon atoms.

The expression "$C_{a-b}$ haloalkenyl" in the present specification is straight-chain or branched-chain unsaturated hydrocarbon groups having carbon atom number of a to b and having one or more double bond(s) in the molecule in which a hydrogen atom bonded to a carbon atom is optionally substituted with a halogen atom. In this case, when hydrogen atoms are substituted with two or more halogen atoms, these halogen atoms may be the same as or different from each other. Specific examples of the "$C_{a-b}$ haloalkenyl" include a 2-fluorovinyl group, a 2-chlorovinyl group, a 1,2-dichlorovinyl group, a 2,2-dichlorovinyl group, a 2-fluoro-2-propenyl group, a 2-chloro-2-propenyl group, a 3-chloro-2-propenyl group, a 3,3-difluoro-2-propenyl group, a 2,3-dichloro-2-propenyl group, a 3,3-dichloro-2-propenyl group, a 2,3,3-trifluoro-2-propenyl group, a 2,3,3-trichloro-2-propenyl group, a 1-(trifluoromethyl)ethenyl group, a 4,4-difluoro-3-butenyl group, a 3,4,4-trifluoro-3-butenyl group and a 3-chloro-4,4,4-trifluoro-2-butenyl group, and the like, and each of the haloalkenyl groups is selected within the range of the specified number of carbon atoms.

The expression "$C_{a-b}$ cycloalkenyl" in the present specification is a cyclic unsaturated hydrocarbon groups having carbon atom number of a to b and having one or more double bond(s), and the "$C_{a-b}$ cycloalkenyl" can form a monocyclic or composite ring structure having a 3-membered ring to a 6-membered ring. Furthermore, each ring may be optionally substituted with an alkyl group within the range of the specified number of carbon atoms, and the double bond may be of either an endo-type or an exo-type. Specific examples of the "$C_{a-b}$ cycloalkenyl" include a 1-cyclopentenyl group, a 2-cyclopentenyl group, a 1-cyclohexenyl group, a 2-cyclohexenyl group and a bicyclo[2.2.1]-5-heptene-2-yl group, and the like, and each of the cycloalkenyl groups is selected within the range of the specified number of carbon atoms.

The expression "$C_{a-b}$ halocycloalkenyl" in the present specification is a cyclic unsaturated hydrocarbon groups having carbon atom number of a to b and having one or more double bond(s) in which a hydrogen atom bonded to a carbon atom is optionally substituted with a halogen atom, and the "$C_{a-b}$ halocycloalkenyl" can form a monocyclic or composite ring structure having a 3-membered ring to a 6-membered ring. Furthermore, each ring may be optionally substituted with an alkyl group within the range of the specified number of carbon atoms, and the double bond may be of either an endo-type or an exo-type. In addition, the substitution with a halogen atom may be on the ring structure part, the side chain part or both of them, and when hydrogen atoms are substituted with two or more halogen atoms, these halogen atoms may be the same as or different from each other. Specific examples of the "$C_{a-b}$ halocycloalkenyl" include a 2-fluoro-1-cyclopentenyl group, a 2-chloro-1-cyclopentenyl group, a 3-chloro-2-cyclopentenyl group and 2-fluoro-1-cyclohexenyl group, and the like, and each of the halocycloalkenyl groups is selected within the range of the specified number of carbon atoms.

The expression "$C_{a-b}$ alkylidene" in the present specification is straight-chain or branched-chain hydrocarbon groups having carbon atom number of a to b and bonded through a double bond, and specific examples of the "$C_{a-b}$ alkylidene" include a methylidene group, an ethylidene group, a propylidene group and a 1-methylethylidene group, and the like, and each of the alkylidene groups is selected within the range of the specified number of carbon atoms.

The expression "$C_{a-b}$ alkynyl" in the present specification is straight-chain or branched-chain unsaturated hydrocarbon groups having carbon atom number of a to b and having one or more triple bond(s) in the molecule. Specific examples of the "$C_{a-b}$ alkynyl" include an ethynyl group, a 1-propynyl group, a 2-propynyl group, a 1-butynyl group, a 2-butynyl group, a 3-butynyl group, a 1-methyl-2-propynyl group, a 2-pentynyl group and a 3-hexynyl group, and the like, and each of the alkynyl groups is selected within the range of the specified number of carbon atoms.

The expression "$C_{a-b}$ haloalkynyl" in the present specification is straight-chain or branched-chain unsaturated hydrocarbon groups having carbon atom number of a to b and having one or more triple bond(s) in the molecule in which a hydrogen atom bonded to a carbon atom is optionally substituted with a halogen atom. In this case, when hydrogen atoms are substituted with two or more halogen atoms, these halogen atoms may be the same as or different from each other. Specific examples of the "$C_{a-b}$ haloalkynyl" include a 2-chloroethynyl group, a 2-bromoethynyl group, a 2-iodoethynyl group, a 3-chloro-2-propynyl group, a 3-bromo-2-propynyl group and a 3-iodo-2-propynyl group, and the like, and each of the haloalkynyl groups is selected within the range of the specified number of carbon atoms.

The expression "$C_{a-b}$ alkoxy" in the present specification represents an alkyl-O— group in which the alkyl is as defined above having carbon atom number of a to b. Specific examples of the "$C_{a-b}$ alkoxy" include a methoxy group, an ethoxy group, an n-propyloxy group, an i-propyloxy group, an n-butyloxy group, an i-butyloxy group, an s-butyloxy group and a tert-butyloxy group, and the like, and each of the alkoxy groups is selected within the range of the specified number of carbon atoms.

The expression "$C_{a-b}$ haloalkoxy" in the present specification represents a haloalkyl-O— group in which the haloalkyl is as defined above having carbon atom number of a to b.

Specific examples of the "$C_{a-b}$ haloalkoxy" include a difluoromethoxy group, a trifluoromethoxy group, a chlorodifluoromethoxy group, a bromodifluoromethoxy group, a 2-fluoroethoxy group, a 2-chloroethoxy group, a 2,2,2-trifluoroethoxy group, a 1,1,2,2-tetrafluoroethoxy group, a 2-chloro-1,1,2-trifluoroethoxy group and a 1,1,2,3,3,3-hexafluoropropyloxy group, and the like, and each of the haloalkoxy groups is selected within the range of the specified number of carbon atoms.

The expression "$C_{a-b}$ alkenyloxy" in the present specification is an alkenyl-O— group in which the alkenyl is as defined above having carbon atom number of a to b. Specific examples of the "$C_{a-b}$ alkenyloxy" include a 2-propenyloxy group, a 2-butenyloxy group, a 2-methyl-2-propenyloxy group and a 3-methyl-2-butenyloxy group, and the like, and each of the alkenyloxy groups is selected within the range of the specified number of carbon atoms.

The expression "$C_a$-$C_b$ alkylthio" in the present specification represents an alkyl-S— group in which the alkyl is as defined above having carbon atom number of a to b. Specific examples of the "$C_a$-$C_b$ alkylthio" include a methylthio group, an ethylthio group, an n-propylthio group, an i-propylthio group, an n-butylthio group, an i-butylthio group, an s-butylthio group and a tert-butylthio group, and the like, and each of the alkylthio groups is selected within the range of the specified number of carbon atoms.

The expression "$C_a$-$C_b$ haloalkylthio" in the present specification represents a haloalkyl-S— group in which the haloalkyl is as defined above having carbon atom number of a to b. Specific examples of the "$C_a$-$C_b$ haloalkylthio" include a difluoromethylthio group, a trifluoromethylthio group, a chlorodifluoromethylthio group, a bromodifluoromethylthio group, a 2,2,2-trifluoroethylthio group, a 1,1,2,2-tetrafluoroethylthio group, a 2-chloro-1,1,2-trifluoroethylthio group, a pentafluoroethylthio group, a 1,1,2,3,3,3-hexafluoropropylthio group, a heptafluoropropylthio group, a 1,2,2,2-tetrafluoro-1-(trifluoromethyl)ethylthio group and a nonafluorobutylthio group, and the like, and each of the haloalkylthio groups is selected within the range of the specified number of carbon atoms.

The expression "$C_a$-$C_b$ alkylsulfinyl" in the present specification represents an alkyl-S(O)— group in which the alkyl is as defined above having carbon atom number of a to b. Specific examples of the "$C_a$-$C_b$ alkylsulfinyl" include a methylsulfinyl group, an ethylsulfinyl group, an n-propylsulfinyl group, an i-propylsulfinyl group, an n-butylsulfinyl group, an i-butylsulfinyl group, an s-butylsulfinyl group and a tert-butylsulfinyl group, and the like, and each of the alkylsulfinyl groups is selected within the range of the specified number of carbon atoms.

The expression "$C_a$-$C_b$ haloalkylsulfinyl" in the present specification represents a haloalkyl-S(O)— group in which the haloalkyl is as defined above having carbon atom number of a to b. Specific examples of the "$C_a$-$C_b$ haloalkylsulfinyl" include a difluoromethylsulfinyl group, a trifluoromethylsulfinyl group, a chlorodifluoromethylsulfinyl group, a bromodifluoromethylsulfinyl group, a 2,2,2-trifluoroethylsulfinyl group, a 1,2,2,2-tetrafluoro-1-(trifluoromethyl)ethylsulfinyl group and a nonafluorobutylsulfinyl group, and the like, and each of the haloalkylsulfinyl groups is selected within the range of the specified number of carbon atoms.

The expression "$C_a$-$C_b$ alkylsulfonyl" in the present specification represents an alkyl-SO$_2$— group in which the alkyl is as defined above having carbon atom number of a to b. Specific examples of the "$C_a$-$C_b$ alkylsulfonyl" include a methylsulfonyl group, an ethylsulfonyl group, an n-propylsulfonyl group, an i-propylsulfonyl group, an n-butylsulfonyl group, an i-butylsulfonyl group, an s-butylsulfonyl group and a tert-butylsulfonyl group, and the like, and each of the alkylsulfonyl groups is selected within the range of the specified number of carbon atoms.

The expression "$C_a$-$C_b$ haloalkylsulfonyl" in the present specification represents a haloalkyl-SO$_2$— group in which the haloalkyl is as defined above having carbon atom number of a to b. Specific examples of the "$C_a$-$C_b$ haloalkylsulfonyl" include a difluoromethylsulfonyl group, a trifluoromethylsulfonyl group, a chlorodifluoromethylsulfonyl group, a bromodifluoromethylsulfonyl group, a 2,2,2-trifluoroethylsulfonyl group, a 1,1,2,2-tetrafluoroethylsulfonyl group and a 2-chloro-1,1,2-trifluoroethylsulfonyl group, and the like, and each of the haloalkylsulfonyl groups is selected within the range of the specified number of carbon atoms.

The expression "$C_{a-b}$ alkylamino" in the present specification is an amino group in which one of the hydrogen atoms is substituted with the alkyl group as defined above having carbon atom number of a to b. Specific examples of the "$C_{a-b}$ alkylamino" include a methylamino group, an ethylamino group, an n-propylamino group, an i-propylamino group, an n-butylamino group, an i-butylamino group and a tert-butylamino group, and the like, and each of the alkylamino groups is selected within the range of the specified number of carbon atoms.

The expression "di($C_{a-b}$ alkyl)amino" in the present specification is an amino group in which both of the hydrogen atoms are substituted with the alkyl groups as defined above having carbon atom number of a to b and the alkyl groups may be the same as or different from each other. Specific examples of the "di($C_{a-b}$ alkyl)amino" include a dimethylamino group, an ethyl(methyl)amino group, a diethylamino group, a di(n-propyl)amino group and a di(n-butyl)amino group, and the like, and each of the dialkylamino groups is selected within the range of the specified number of carbon atoms.

The expression "$C_{a-b}$ alkylimino" in the present specification is a $C_{a-b}$ alkyl-N=group in which the alkyl is as defined above having carbon atom number of a to b. Specific examples of the "$C_{a-b}$ alkylimino" include a methylimino group, an ethylimino group, an n-propylimino group, an i-propylimino group, an n-butylimino group, an i-butylimino group and an s-butylimino group, and the like, and each of the alkylimino groups is selected within the range of the specified number of carbon atoms.

The expression "$C_{a-b}$ alkoxyimino" in the present specification is a $C_{a-b}$ alkoxy-N= group in which the alkoxy is as defined above having carbon atom number of a to b. Specific examples of the "$C_{a-b}$ alkoxyimino" include a methoxyimino group, an ethoxyimino group, an n-propyloxyimino group, an i-propyloxyimino group and an n-butyloxyimino group, and the like, and each of the alkoxyimino groups is selected within the range of the specified number of carbon atoms.

The expression "$C_a$-$C_b$ alkylcarbonyl" in the present specification represents an alkyl-C(O)— group in which the alkyl is as defined above having carbon atom number of a to b. Specific examples of the "$C_a$-$C_b$ alkylcarbonyl" include an acetyl group, a propionyl group, a butyryl group, an isobutyryl group, a valeryl group, an isovaleryl group, a 2-methylbutanoyl group, a pivaloyl group, and the like, and each of the alkylcarbonyl groups is selected within the range of the specified number of carbon atoms.

The expression "$C_a$-$C_b$ haloalkylcarbonyl" in the present specification represents a haloalkyl-C(O)— group in which the haloalkyl is as defined above having carbon atom number of a to b. Specific examples of the "$C_a$-$C_b$ haloalkylcarbonyl" include a fluoroacetyl group, a chloroacetyl group, a difluoroacetyl group, a dichloroacetyl group, a trifluoroacetyl group, a chlorodifluoroacetyl group, a bromodifluoroacetyl group, a trichloroacetyl group, a pentafluoropropionyl group, a heptafluorobutanoyl group and a 3-chloro-2,2-dimethylpropanoyl group, and the like, and each of the haloalkylcarbonyl groups is selected within the range of the specified number of carbon atoms.

The expression "$C_a$-$C_b$ alkoxycarbonyl" in the present specification represents an alkyl-O—C(O)— group in which the alkyl is as defined above having carbon atom number of a to b. Specific examples of the "$C_a$-$C_b$ alkoxycarbonyl" include a methoxycarbonyl group, an ethoxycarbonyl group, an n-propyloxycarbonyl group, an i-propyloxycarbonyl group, an n-butoxycarbonyl group, an i-butoxycarbonyl group and a tert-butoxycarbonyl group, and the like, and each of the alkoxycarbonyl groups is selected within the range of the specified number of carbon atoms.

The expression "$C_a$-$C_b$ haloalkoxycarbonyl" in the present specification represents a haloalkyl-O—C(O)— group in which the haloalkyl is as defined above having carbon atom number of a to b. Specific examples of the "$C_a$-$C_b$ haloalkoxycarbonyl" include a chloromethoxycarbonyl group, a 2-chloroethoxycarbonyl group, a 2,2-difluoroethoxycarbonyl group, a 2,2,2-trifluoroethoxycarbonyl group and a 2,2,2-trichloroethoxycarbonyl group, and the like, and each of the haloalkoxycarbonyl groups is selected within the range of the specified number of carbon atoms.

The expression "$C_{a-b}$ alkylaminocarbonyl" in the present specification is a carbamoyl group in which one of the hydrogen atoms is substituted with the alkyl group as defined above having carbon atom number of a to b. Specific examples of the "$C_{a-b}$ alkylaminocarbonyl" include a methylcarbamoyl group, an ethylcarbamoyl group, an n-propylcarbamoyl group, an i-propylcarbamoyl group, an n-butylcarbamoyl group, an i-butylcarbamoyl group, an s-butylcarbamoyl group and a tert-butylcarbamoyl group, and the like, and each of the alkylamino carbonyl groups is selected within the range of the specified number of carbon atoms.

The expression "$C_{a-b}$ haloalkylaminocarbonyl" in the present specification is a carbamoyl group in which one of the hydrogen atoms is substituted with the haloalkyl group as defined above having carbon atom number of a to b. Specific examples of the "$C_{a-b}$ haloalkylaminocarbonyl" include a 2-fluoroethylcarbamoyl group, a 2-chloroethylcarbamoyl group, a 2,2-difluoroethylcarbamoyl group and a 2,2,2-trifluoroethylcarbamoyl group, and the like, and each of the haloalkylaminocarbonyl groups is selected within the range of the specified number of carbon atoms.

The expression "di($C_{a-b}$ alkyl)aminocarbonyl" in the present specification is an carbamoyl group in which both of the hydrogen atoms are substituted with the alkyl groups as defined above having carbon atom number of a to b and the alkyl groups may be the same as or different from each other. Specific examples of the "di($C_{a-b}$ alkyl)aminocarbonyl" include an N,N-dimethylcarbamoyl group, an N-ethyl-N-methylcarbamoyl group, an N,N-diethylcarbamoyl group, an N,N-di(n-propyl) carbamoyl group and an N,N-di(n-butyl) carbamoyl group, and the like, and each of the dialkylaminocarbonyl groups is selected within the range of the specified number of carbon atoms.

The expression "$C_{a-b}$ alkylaminosulfonyl" in the present specification is a sulfamoyl group in which one of the hydrogen atoms is substituted with the alkyl group as defined above having carbon atom number of a to b. Specific examples of the "$C_{a-b}$ alkylaminosulfonyl" include a methylsulfamoyl group, an ethylsulfamoyl group, an n-propylsulfamoyl group, an i-propylsulfamoyl group, an n-butylsulfamoyl group, an i-butylsulfamoyl group, an s-butyl sulfamoyl group and a tert-butylsulfamoyl group, and the like, and each of the alkylaminosulfamoyl groups is selected within the range of the specified number of carbon atoms.

The expression "di($C_{a-b}$ alkyl)aminosulfonyl" in the present specification is a sulfamoyl group in which both of the hydrogen atoms are substituted with the alkyl groups as defined above having carbon atom number of a to b and the alkyl groups may be the same as or different from each other. Specific examples of the "di($C_{a-b}$ alkyl)aminosulfonyl" include an N,N-dimethylsulfamoyl group, an N-ethyl-N-methylsulfamoyl group, an N,N-diethylsulfamoyl group an N,N-di(n-propyl) sulfamoyl group and an N,N-di(n-butyl) sulfamoyl group, and the like, and each of the dialkylaminosulfamoyl groups is selected within the range of the specified number of carbon atoms.

The expression "tri($C_{a-b}$ alkyl) silyl" in the present specification is a silyl group substituted with the alkyl groups as defined above having carbon atom number of a to b and the alkyl groups may be the same as or different from each other. Specific examples of the "tri($C_{a-b}$ alkyl)silyl" include a trimethylsilyl group, a triethylsilyl group, a tri(n-propyl) silyl group, an ethyldimethylsilyl group, an n-propyldimethylsilyl group, an n-butyldimethylsilyl group, an i-butyldimethylsilyl group and a tert-butyldimethylsilyl group, and the like, and each of the trialkylsilyl groups is selected within the range of the specified number of carbon atoms.

The expression "$C_{a-b}$ alkylsulfonyloxy" in the present specification is an alkylsulfonyl-O— group in which the alkylsulfonyl is as defined above having carbon atom number of a to b. Specific examples of the "$C_{a-b}$ alkylsulfonyloxy" include a methylsulfonyloxy group, an ethylsulfonyloxy group, an n-propylsulfonyloxy group and an i-propylsulfonyloxy group, and the like, and each of the alkylsulfonyloxy groups is selected within the range of the specified number of carbon atoms.

The expression "$C_{a-b}$ haloalkylsulfonyloxy" in the present specification is a haloalkylsulfonyl-O— group in which the haloalkylsulfonyl is as defined above having carbon atom number of a to b. Specific examples of the "$C_{a-b}$ haloalkylsulfonyloxy" include a difluoromethylsulfonyloxy group, a trifluoromethylsulfonyloxy group, a chlorodifluoromethylsulfonyloxy group and a bromodifluoromethylsulfonyloxy group, and the like, and each of the haloalkylsulfonyloxy groups is selected within the range of the specified number of carbon atoms.

Each expression "$C_{a-b}$ cycloalkyl($C_{d-e}$) alkyl", "hydroxy ($C_{d-e}$) alkyl", "$C_{a-b}$ alkoxy($C_{d-e}$) alkyl", "$C_{a-b}$ haloalkoxy ($C_{d-e}$) alkyl", "$C_{a-b}$ alkylthio($C_{d-e}$) alkyl", "$C_{a-b}$ haloalkylthio ($C_{d-e}$) alkyl", "$C_{a-b}$ alkylsulfinyl($C_{d-e}$) alkyl", "$C_{a-b}$ haloalkylsulfinyl($C_{d-e}$) alkyl", "$C_{a-b}$ alkylsulfonyl($C_{d-e}$) alkyl", "$C_{a-b}$ haloalkylsulfonyl($C_{d-e}$) alkyl", "cyano($C_{d-e}$) alkyl", "$C_{a-b}$ alkoxycarbonyl($C_{d-e}$) alkyl", "$C_{a-b}$ haloalkoxycarbonyl($C_{d-e}$) alkyl", "phenyl($C_{d-e}$) alkyl" or "phenyl ($C_{d-e}$) alkyl substituted with $(Z^a)_{p1}$" in the present specification is a $C_{d-e}$ alkyl group as defined above in which a hydrogen atom bonded to a carbon atom is substituted with any of a $C_{a-b}$ cycloalkyl group, a $C_{a-b}$ alkoxy group, a $C_{a-b}$ haloalkoxy group, a $C_{a-b}$ alkylthio group, a $C_{a-b}$ haloalkylthio group, a $C_{a-b}$ alkylsulfinyl group, a $C_{a-b}$ haloalkylsulfinyl group, a $C_{a-b}$ alkylsulfonyl group, a $C_{a-b}$ haloalkylsulfonyl group, a $C_{a-b}$ alkoxycarbonyl group, a $C_{a-b}$ haloalkoxycarbonyl group, a hydroxy group, a cyano group, a phenyl group or a phenyl group substituted with $(Z^a)_{p1}$, each as defined above, and each of the alkyl groups is selected within the range of the specified number of carbon atoms.

Each expression "($C_{a-b}$) alkyl optionally substituted with $R^5$", "($C_{a-b}$) alkyl optionally substituted with $R^{15}$", "($C_{a-b}$)

alkyl optionally substituted with $R^{15a}$", "$(C_{a-b})$ alkyl optionally substituted with $R^{22}$", "$(C_{a-b})$ alkyl optionally substituted with $R^{30}$", "$(C_{a-b})$ alkyl optionally substituted with $R^{35}$" or the like in the present specification is a $C_{a-b}$ alkyl group as defined above in which a hydrogen atom bonded to a carbon atom is optionally substituted with any of $R^5$, $R^{15}$, $R^{15a}$, $R^{22}$, $R^{30}$ or $R^{35}$, and each of the alkyl groups is selected within the range of the specified number of carbon atoms. In this case, when the number of substituents $R^5$, $R^{15}$, $R^{15a}$, $R^{22}$, $R^{30}$ or $R^{35}$ on each $(C_{a-b})$ alkyl group is two or more, $R^5$s, $R^{15}$s, $R^{15a}$s, $R^{22}$s, $R^{30}$s or $R^{35}$s may be the same as or different from each other.

Each expression "hydroxy$(C_{d-e})$ haloalkyl", "$C_{a-b}$ alkoxy$(C_{d-e})$ haloalkyl" or "$C_{a-b}$ haloalkoxy$(C_{d-e})$ haloalkyl" in the present specification is a $C_{d-e}$ haloalkyl group as defined above in which a hydrogen atom or a halogen atom bonded to a carbon atom is substituted with any of a $C_{a-b}$ alkoxy group, a $C_{a-b}$ haloalkoxy group or a hydroxy group as defined above, and each of the haloalkyl groups is selected within the range of the specified number of carbon atoms.

Each expression "hydroxy$(C_{d-e})$ cycloalkyl" or "$C_{a-b}$ alkoxy$(C_{d-e})$ cycloalkyl" in the present specification is a $C_{d-e}$ cycloalkyl group as defined above in which a hydrogen atom bonded to a carbon atom is substituted with any of a $C_{a-b}$ alkoxy group or a hydroxy group as defined above, and each of the cycloalkyl groups is selected within the range of the specified number of carbon atoms.

Each expression "$(C_{a-b})$ cycloalkyl optionally substituted with $R^5$", "$(C_{a-b})$ cycloalkyl optionally substituted with $R^{15}$", "$(C_{a-b})$ cycloalkyl optionally substituted with $R^{22}$", "$(C_{a-b})$ cycloalkyl optionally substituted with $R^{30}$" or the like in the present specification is a $C_{a-b}$ cycloalkyl group as defined above in which a hydrogen atom bonded to a carbon atom is optionally substituted with any of $R^5$, $R^{15}$, $R^{22}$ or $R^{30}$, and each of the cycloalkyl groups is selected within the range of the specified number of carbon atoms. In this case, the substitution with $R^5$, $R^{15}$, $R^{22}$ or $R^{30}$ may be on the ring structure part, the side chain part or both of them and further, when the number of substituents $R^5$, $R^{15}$, $R^{22}$ or $R^{30}$ on each $(C_{a-b})$ cycloalkyl group is two or more, $R^5$s, $R^{15}$s, $R^{22}$s or $R^{30}$s may be the same as or different from each other.

Each expression "$(C_{a-b})$ alkenyl optionally substituted with $R^5$", "$(C_{a-b})$ alkenyl optionally substituted with $R^{15}$", "$(C_{a-b})$ alkenyl optionally substituted with $R^{22}$" or "$(C_{a-b})$ alkenyl optionally substituted with $R^{30}$" in the present specification is a $C_{a-b}$ alkenyl group as defined above in which a hydrogen atom bonded to a carbon atom is optionally substituted with any of $R^5$, $R^{15}$, $R^{22}$ or $R^{30}$, and each of the alkenyl groups is selected within the range of the specified number of carbon atoms. In this case, when the number of substituents $R^5$, $R^{15}$, $R^{22}$ or $R^{30}$ on each $(C_{a-b})$ alkenyl group is two or more, $R^5$s, $R^{15}$s, $R^{22}$s or $R^{30}$s may be the same as or different from each other.

Each expression "$(C_{a-b})$ alkynyl optionally substituted with $R^5$", "$(C_{a-b})$ alkynyl optionally substituted with $R^{15}$", "$(C_{a-b})$ alkynyl optionally substituted with $R^{22}$" or "$(C_{a-b})$ alkynyl optionally substituted with $R^{30}$" in the present specification is a $C_{a-b}$ alkynyl group as defined above in which a hydrogen atom bonded to a carbon atom is optionally substituted with any of $R^5$, $R^{15}$, $R^{22}$ or $R^{30}$, and each of the alkynyl groups is selected within the range of the specified number of carbon atoms. In this case, when the number of substituents $R^5$, $R^{15}$, $R^{22}$ or $R^{30}$ on each $(C_{a-b})$ alkynyl group is two or more, $R^5$s, $R^{15}$s, $R^{22}$s or $R^{30}$s may be the same as or different from each other.

Specific examples of the expressions in the present specification of ($R^{1d}$ together with $R^{1c}$ may form a $C_{2-6}$ alkylene chain to form together with a nitrogen atom to which $R^{1c}$ and $R^{1d}$ are bonded, a 3- to 7-membered ring, and in this case, the alkylene chain may contain one oxygen atom, sulfur atom or nitrogen atom and may be optionally substituted with an oxo group or a thioxo group), ($R^2$ together with $R^1$ may form a $C_{4-6}$ alkylene chain to form together with a nitrogen atom to which $R^1$ and $R^2$ are bonded, a 5- to 7-membered ring, and in this case, the alkylene chain may contain one oxygen atom, sulfur atom or nitrogen atom and may be optionally substituted with an oxo group or a thioxo group), ($R^8$ together with $R^7$ may form a $C_{2-6}$ alkylene chain to form together with a nitrogen atom to which $R^7$ and $R^8$ are bonded, a 3- to 7-membered ring, and in this case, the alkylene chain may contain one oxygen atom, sulfur atom or nitrogen atom and may be optionally substituted with an oxo group or a thioxo group), ($R^{24}$ together with $R^{23}$ may form a $C_{2-5}$ alkylene chain to form together with a nitrogen atom to which $R^{23}$ and $R^{24}$ are bonded, a 3- to 6-membered ring, and in this case, the alkylene chain may contain one oxygen atom, sulfur atom or nitrogen atom and may be optionally substituted with an oxo group or a thioxo group), ($R^{29}$ together with $R^{28}$ may form a $C_{2-5}$ alkylene chain to form together with a nitrogen atom to which $R^{28}$ and $R^{29}$ are bonded, a 3- to 6-membered ring, and in this case, the alkylene chain may contain one oxygen atom, sulfur atom or nitrogen atom and may be optionally substituted with an oxo group), and the like include aziridine, azetidine, azetidine-2-one, pyrrolidine, pyrrolidine-2-one, oxazolidine, oxazolidine-2-one, oxazolidine-2-thione, thiazolidine, thiazolidine-2-one, thiazolidine-2-thione, imidazolidine, imidazolidine-2-one, imidazolidine-2-thione, piperidine, piperidine-2-one, piperidine-2-thione, 2H-3,4,5,6-tetrahydro-1,3-oxazine-2-one, 2H-3,4,5,6-tetrahydro-1,3-oxazine-2-thione, morpholine, 2H-3,4,5,6-tetrahydro-1,3-thiazine-2-one, 2H-3,4,5,6-tetrahydro-1,3-thiazine-2-thione, thiomorpholine, thiomorpholine-1-oxide, thiomorpholine-1,1-dioxide, perhydropyrimidine-2-one, piperazine, homopiperidine, homopiperidine-2-one and heptamethyleneimine. Each of the rings is selected within the range of the specified number of atoms.

Specific examples of the expression in the present specification of ($R^{4a}$ (It together with $R^4$ may form a $C_{2-5}$ alkylene chain to form together with a carbon atom to which $R^4$ and $R^{4a}$ are bonded, a 3- to 6-membered ring, and in this case, the alkylene chain may contain one oxygen atom, sulfur atom or nitrogen atom), include a cyclopropane ring, a cyclobutane ring, a cyclopentane ring, a tetrahydrofuran ring, a tetrahydrothiophene ring, a pyrrolidine ring, a cyclohexane ring, a tetrahydropyran ring, a tetrahydrothiopyran ring, a piperidine ring, a cycloheptane ring, an oxepane ring, a thiepane ring and an azepane ring. Each of the rings is selected within the range of the specified number of atoms.

Specific examples of the expression in the present specification of ($R^{8a}$ together with $R^{7a}$ may form a $C_{4-6}$ alkylene chain to form together with a carbon atom to which $R^{7a}$ and $R^{8a}$ are bonded, a 5- to 7-membered ring, and in this case, the alkylene chain may contain one oxygen atom or sulfur atom), include cyclopentylidene, tetrahydrofuran-3-ylidene, tetrahydrothiophene-3-ylidene, cyclohexylidene, tetrahydropyran-3-ylidene, tetrahydropyran-4-ylidene, tetrahydrothiopyran-3-ylidene and tetrahydrothiopyran-4-ylidene. Each of the rings is selected within the range of the specified number of atoms.

Specific examples of the expressions in the present specification of ($R^{12}$ together with $R^{11}$ may form a $C_{2-6}$ alkylene chain to form together with a nitrogen atom to which $R^{11}$ and $R^{12}$ are bonded, a 3- to 7-membered ring, and in this case, the alkylene chain may contain one oxygen atom, sulfur atom or nitrogen atom), ($R^{17}$ together with $R^{16}$ may form a $C_{2-6}$ alkylene chain to form together with a nitrogen atom to which $R^{16}$ and $R^{17}$ are bonded, a 3- to 7-membered ring, and in this case, the alkylene chain may contain one oxygen atom, sulfur atom or nitrogen atom), ($R^{17a}$ together with $R^{16a}$ may form a $C_{4-7}$ alkylene chain to form together with a nitrogen atom to which $R^{16a}$ and $R^{17a}$ are bonded, a 5- to 8-membered ring, and in this case, the alkylene chain may contain one oxygen atom or sulfur atom), ($R^{34}$ together with $R^{33}$ may form a $C_{2-5}$ alkylene chain to form together with a nitrogen atom to which $R^{33}$ and $R^{34}$ are bonded, a 3- to 6-membered ring, and in this case, the alkylene chain may contain one oxygen atom, sulfur atom or nitrogen atom), and the like include aziridine, azetidine, pyrrolidine, oxazolidine, thiazolidine, imidazolidine, piperidine, morpholine, thiomorpholine, thiomorpholine-1-oxide, thiomorpholine-1,1-dioxide, piperazine, homopiperidine and heptamethyleneimine. Each of the rings is selected within the range of the specified number of atoms.

In the compounds included in the present invention, examples of the combination of atoms of $A^1$, $A^2$, $A^3$ and $A^4$ include the following groups.

That is, A-I: $A^1$ is C—Y, and $A^2$, $A^3$ and $A^4$ are C—H.

A-II: $A^1$ is C—Y, $A^2$ and $A^3$ are C—H, and $A^4$ is N.

A-III: $A^1$ is N, and $A^2$, $A^3$ and $A^4$ are C—H.

A-IV: $A^1$ is C—Y, $A^2$ and $A^4$ are C—H, and $A^3$ is N.

A-V: $A^1$ is C—Y, $A^2$ is N, and $A^3$ and $A^4$ are C—H.

A-VI: $A^1$ is C—Y, $A^2$ and $A^3$ are N, and $A^4$ is C—H.

A-VII: $A^1$ is C—Y, $A^2$ and $A^4$ are N, and $A^3$ is C—H.

A-VIII: $A^1$ is C—Y, $A^2$ is C—H, and $A^3$ and $A^4$ are N.

A-IX: $A^1$ and $A^4$ are N, and $A^2$ and $A^3$ are C—H.

A-X: $A^1$, $A^2$, $A^3$ and $A^4$ are C—Y or N.

Among them, more preferred combinations of atoms of $A^1$, $A^2$, $A^3$ and $A^4$ are A-I, A-II, A-III, A-IV and A-V, and specifically preferred is A-I, A-II and A-III.

In the compounds included in the present invention, examples of the atom of $A^5$ include —CH($R^{3a}$)— (where $R^{1a}$ is a hydrogen atom, $C_{1-6}$ alkyl or $C_{1-6}$ haloalkyl), O and S. Among them, preferred are —CH($R^{3a}$)— (where $R^{3a}$ is a hydrogen atom or $C_{1-4}$ alkyl) and S, and further, specifically preferred is —CH$_2$—.

In the compounds included in the present invention, examples of the substituent of $G^1$ include: 6-membered aromatic rings such as a benzene ring, a pyridine ring, a pyrimidine ring, a pyrazine ring and a pyridazine ring; and a 5-membered aromatic ring such as a furan ring, a thiophene ring, an isoxazole ring, an isothiazole ring, a pyrazole ring, an oxazole ring, a thiazole ring and an imidazole ring. Among them, preferred are a phenyl group, a 3-pyridyl group, a 4-pyridyl group, a 2-thienyl group, a 3-thienyl group, a 3-pyrazolyl group, a 4-pyrazolyl group, a 2-thiazolyl group, a 4-thiazolyl group and a 5-thiazolyl group, and further, specifically preferred is a phenyl group.

In the compounds included in the present invention, examples of the substituent of $G^2$ include the following structures of $G^2$-1 to $G^2$-10. Among them, preferred are $G^2$-1, $G^2$-3, $G^2$-5, $G^2$-6, $G^2$-8 and $G^2$-9, and further, specifically preferred are $G^2$-1, $G^2$-6 and $G^2$-9.

$G^2$-1:

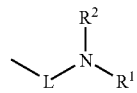

$G^2$-2:

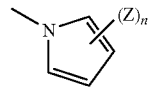

$G^2$-3:

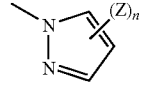

$G^2$-4:

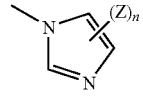

$G^2$-5:

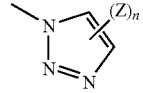

$G^2$-6:

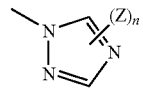

$G^2$-7:

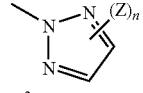

$G^2$-8:

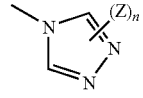

$G^2$-9:

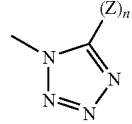

$G^2$-10:

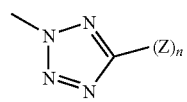

In the compounds included in the present invention, examples of the preferred range of the structure of L include the following groups.

That is, L-I: —CH($R^4$)— (where $R^4$ is a hydrogen atom, cyano or methyl).

L-II: —CH($R^4$)— (where $R^4$ is a hydrogen atom, cyano, methyl, ethynyl or —C(S)NH$_2$).

L-III: —C($R^4$)($R^{4a}$) (where $R^4$ is hydrogen atom, cyano, methyl, trifluoromethyl, ethynyl, —C(S)NH$_2$ or D10, $R^{4a}$ is a hydrogen atom, and p4 is 0).

L-IV: —C($R^4$)($R^{4a}$)— (where $R^4$ and $R^{4a}$ together form an ethylene chain to form together with a carbon atom to which $R^4$ and $R^{4a}$ are bonded, a cyclopropyl ring).

L-V: —C($R^4$)($R^{4a}$)— (where $R^4$ is a hydrogen atom, cyano, $C_{1-4}$ alkyl, $C_{1-4}$ haloalkyl, $C_{3-4}$ cycloalkyl, $C_{2-4}$ alkynyl, —C(O)$NH_2$, —C(S)$NH_2$, phenyl, D9 or D10, $R^{4a}$ is a hydrogen atom, and p4 is 0).

L-VI: —C($R^4$)($R^{4a}$)— where $R^4$ is cyano or $C_{1-4}$ alkyl, and $R^{4a}$ is $C_{1-4}$ alkyl, or $R^4$ and $R^{4a}$ together may form an ethylene chain to form together with a carbon atom to which $R^4$ and $R^{4a}$ are bonded, a cyclopropyl ring).

L-VII: —C($R^4$)($R^{4a}$)$CH_2$— (where $R^4$ is a hydrogen atom, methyl, cyano or —C(S)$NH_2$, and $R^{4a}$ is a hydrogen atom).

L-VIII: —N($R^{4b}$)— and —C($R^4$)($R^{4a}$)N($R^{4b}$)— (where $R^4$ is a hydrogen atom or methyl, $R^{4a}$ is a hydrogen atom, and $R^{4b}$ is a hydrogen atom, $C_{1-4}$ alkyl, $C_{1-4}$ alkylcarbonyl, $C_{3-6}$ cycloalkylcarbonyl or $C_{1-4}$ alkoxycarbonyl).

Among them, as the structure of L, more preferred are L-I, L-II, L-III and L-IV, and further, specifically preferred are L-I and L-II.

In the compounds included in the present invention, examples of the range of the substituent of X include the following groups. In this case, in each of the following groups, when m is an integer of 2 or more, Xs may be the same as or different from each other.

That is, X-I: a halogen atom or trifluoromethyl (where m is an integer of 1 to 3).

X-II: a halogen atom, cyano, —$SF_5$, $C_{1-2}$ haloalkyl, $C_{1-2}$ haloalkoxy and $C_{1-2}$ haloalkylthio (where m is an integer of 1 to 3).

X-III: a halogen atom, cyano, nitro, —$SF_5$, $C_{1-4}$ alkyl, $C_{1-4}$ haloalkyl, $C_{1-4}$ alkoxy, $C_{1-4}$ haloalkoxy, $C_{1-4}$ alkylthio and $C_{1-4}$ haloalkylthio (where m is an integer of 1 to 3).

X-IV: a halogen atom, —$SF_5$, $C_{1-6}$ haloalkyl, hydroxy($C_{1-4}$) haloalkyl, $C_{1-4}$ alkoxy($C_{1-4}$) haloalkyl, —$OR^6$ and —S(O)$_r R^6$ (where $R^6$ is $C_{1-6}$ haloalkyl or $C_{1-4}$ haloalkoxy ($C_{1-4}$) haloalkyl, r is an integer of 0 to 2, and m is 1).

X-V: a halogen atom, cyano, nitro, —$SF_5$, $C_{1-6}$ alkyl, $C_{1-6}$ haloalkyl, hydroxy($C_{1-4}$) haloalkyl, $C_{1-4}$ alkoxy($C_{1-4}$) haloalkyl, —$NH_2$, —$OR^6$ and —S(O)$_r R^6$ (where $R^6$ is $C_{1-6}$ alkyl, $C_{1-6}$ haloalkyl or $C_{1-4}$ haloalkoxy($C_{1-4}$) haloalkyl, r is an integer of 0 to 2, and m is an integer of 2 or 3).

X-VI: m is 2, two Xs adjacent to each other form —$CF_2OCF_2$—, —$OCF_2O$—, —$CF_2OCF_2O$— or —$OCF_2CF_2O$— to form together with a carbon atom to which the two Xs are bonded, a 5-membered ring or a 6-membered ring.

In the compounds included in the present invention, examples of m, which is the number of substituents of X, include integers of 0 to 5, and among them, m is preferably 1, 2 or 3.

In the compounds included in the present invention, examples of the range of the substituent of Y include the following groups. In this case, when the number of substituents of Y is 2 or more, Ys may be the same as or different from each other.

That is, Y-I: a hydrogen atom, a halogen atom, nitro or methyl.

Y-II: a hydrogen atom, a halogen atom, cyano, nitro, $C_{1-2}$ alkyl, $C_{1-2}$ haloalkyl, $C_{2-3}$ alkynyl, $C_{1-2}$ haloalkoxy, $C_{1-2}$ haloalkylthio and —C(S)$NH_2$.

Y-III: a hydrogen atom, a halogen atom, cyano, nitro, $C_{1-4}$ alkyl, $C_{1-4}$ haloalkyl, $C_{2-4}$ alkynyl, $C_{1-4}$ alkoxy, $C_{1-4}$ haloalkoxy, $C_{1-4}$ alkylthio, $C_{1-4}$ haloalkylthio and —C(S)$NH_2$.

Y-IV: a hydrogen atom, a halogen atom, cyano, nitro, $C_{1-6}$ alkyl, $C_{1-6}$ haloalkyl, ($C_{1-4}$) alkyl substituted with $R^5$ (where $R^5$ is —OH, $C_{1-4}$ alkoxy, $C_{1-4}$ alkylthio, $C_{1-4}$ alkylsulfinyl or $C_{1-4}$ alkylsulfonyl), $C_{2-6}$ alkenyl, $C_{2-6}$ alkynyl and —C(S)$NH_2$.

Y-V: —$OR^6$, —S(O)$_r R^6$ (where $R^6$ is $C_{1-6}$ alkyl or $C_{1-6}$ haloalkyl, and r is an integer of 0 to 2) and —N($R^8$)($R^7$) (where $R^7$ is a hydrogen atom, $C_{1-6}$ alkyl, —CHO, $C_{1-6}$ alkylcarbonyl or $C_{1-6}$ alkoxycarbonyl, and $R^8$ is a hydrogen atom or $C_{1-6}$ alkyl).

Y-VI: D1 to D3, D7, D11 and D22 (where p2, p3 and p4 are 0).

Y-VII: two Ys adjacent to each other form —CH=CHCH=CH— to form together with a carbon atom to which the two Ys are bonded, a 6-membered ring.

In the compounds included in the present invention, examples of the range of the substituent of Z include the following groups. In this case, in each of the following groups, when n is an integer of 2 or more, Zs may be the same as or different from each other.

That is, Z-I: a halogen atom, nitro, methyl and —$NH_2$.

Z-II: a halogen atom, cyano, nitro, $C_{1-4}$ alkyl, —$NH_2$, —C(O)$NHR^{11a}$ and —C(S)$NHR^{11a}$ (where $R^{11a}$ is a hydrogen atom, $C_{1-4}$ alkyl, $C_{1-4}$ haloalkyl, ($C_{1-2}$) alkyl substituted with $R^{22}$, cyclopropyl, E4 or —CH=$NOR^{10}$, $R^{10}$ is $C_{1-2}$ alkyl, $R^{22}$ is $C_{1-2}$ alkoxy, $C_{1-2}$ haloalkoxy, $C_{1-2}$ haloalkylaminocarbonyl, D10 or D32, and p2, p4, q6 and t are 0).

Z-III: a halogen atom, cyano, nitro, $C_{1-6}$ alkyl, $C_{1-6}$ haloalkyl, —$OR^6$, —S(O)$_r R^6$ (where $R^6$ is $C_{1-6}$ alkyl or $C_{1-6}$ haloalkyl, and r is an integer of 0 to 2) and —$NH_2$.

Z-IV: —C(O)N($R^{12a}$)$R^{11a}$ and —C(S)N($R^{12a}$)$R^{11a}$ (where $R^{11a}$ is a hydrogen atom, $C_{1-4}$ alkyl, $C_{1-4}$ haloalkyl, ($C_{1-2}$) alkyl substituted with $R^{22}$, $C_{3-4}$ cycloalkyl, E4, —CH=$NOR^{10}$, —C(O)$OR^{10}$, —C(O)$NH_2$, —N($R^{12b}$)$R^{11b}$, D34 or D35, $R^{10}$ is $C_{1-4}$ alkyl, $R^{11b}$ is phenyl or D34, $R^{12b}$ is $C_{1-4}$ alkyl, $R^{12a}$ is a hydrogen atom, ($C_{1-2}$) alkyl substituted with $R^{22a}$, $C_{1-4}$ alkylcarbonyl, cyclopropylcarbonyl or $C_{1-4}$ alkoxycarbonyl, $R^{22}$ is $C_{1-4}$ alkoxy, $C_{1-4}$ haloalkoxy, $C_{1-4}$ haloalkylaminocarbonyl, D10 or D32, $R^{22a}$ is cyano or —$OR^{23}$, $R^{23}$ is $C_{1-4}$ alkyl, —C(O)$R^{31}$ or —C(O)$OR^{32}$, $R^{31}$ is $C_{1-4}$ alkyl, $C_{1-4}$ haloalkyl or $C_{3-4}$ cycloalkyl, $R^{32}$ is $C_{1-4}$ alkyl, p2, p4, q6 and t are 0, and p3 is an integer of 0 or 1).

In the compounds included in the present invention, examples of n, which is the number of substituents of Z, include integers of 0 to 4, and among them, n is preferably 0 and 1.

In the compounds included in the present invention, examples of the range of the substituent of $R^1$ include the following groups.

That is, $R^1$-I: —C(O)$R^{1a}$ (where $R^{1a}$ is $C_{1-4}$ alkyl, $C_{1-4}$ haloalkyl, ($C_{1-2}$)alkyl optionally substituted with $R^{15}$, cyclopropyl, E4 or E5, $R^{15}$ is cyclopropyl or —S(O)$_r R^{25}$, $R^{25}$ is $C_{1-2}$ alkyl or $C_{1-2}$ haloalkyl, q6 is 0, and r is an integer of 0 to 2).

$R^1$-II: —C(O)$NHR^{1c}$ (where $R^{1c}$ is $C_{1-3}$ alkyl, $C_{1-3}$ haloalkyl, cyclopropyl or propargyl).

$R^1$-III: —C(O)$R^{1a}$ and —C(S)$R^{1a}$ (where $R^{1a}$ is $C_{1-4}$ alkyl, ($C_{1-4}$) alkyl optionally substituted with $R^{15}$, $C_{3-4}$ cycloalkyl, E4, E5, $C_{2-4}$ alkenyl, $C_{2-4}$ haloalkenyl, $C_{2-4}$ alkynyl, phenyl substituted with ($Z^a$)$_{p1}$ or D32, $R^{15}$ is a halogen atom, $C_{3-4}$ cycloalkyl, $C_{1-2}$ alkoxy, $C_{1-2}$ haloalkoxy, —N($R^{24}$)$R^{23}$, —S(O)$_r R^{25}$, —S(O)$_t$($R^{25}$)=$NR^{21}$ or —C(O)N($R^{29}$)$R^{28}$, $R^{21}$ is a hydrogen atom or $C_{1-2}$ haloalkylcarbonyl, $R^{23}$ is cyano ($C_{1-2}$) alkyl, $R^{24}$ is a hydrogen atom or $C_{1-2}$ alkoxycarbonyl, $R^{25}$ is $C_{1-2}$ alkyl, $C_{1-2}$ haloalkyl or cyanomethyl, $R^{28}$ is a hydrogen atom or $C_{1-2}$ alkyl, $R^{29}$ is a hydrogen atom or methyl, $Z^a$ is a halogen atom, cyano, nitro or $C_{1-4}$ alkylthio, when p1 and p2 are an integer of 2 or more, $Z^a$s may be the same as or different from each other, p1 is an integer of 1 to 3, p2 is an integer of 0 to 2, q6 is 0, r is an integer of 0 to 2, and t is an integer of 0 or 1).

$R^1$-IV: —C(O)$SR^{1b}$ (where $R^{1b}$ is $C_{1-4}$ alkyl or $C_{1-4}$ haloalkyl).

$R^1$-V: —C(O)N($R^{1d}$)$R^{1c}$ (where $R^{1c}$ is $C_{1-4}$ alkyl, $C_{1-4}$ haloalkyl, $C_{3-4}$ cycloalkyl or $C_{3-4}$ alkynyl, $R^{1d}$ is a hydrogen atom or $C_{1-4}$ alkyl).

$R^1$-VI: a hydrogen atom, —C(O)$R^{1a}$ and —C(S)$R^{1a}$ (where $R^{1a}$ is a hydrogen atom, $C_{1-6}$ alkyl, ($C_{1-4}$) alkyl optionally substituted with $R^{15}$, $C_{3-6}$ cycloalkyl, E4, E5, E10, E13, E20, $C_{2-6}$ alkenyl, $C_{2-6}$ haloalkenyl, $C_{2-6}$ alkynyl, —CH=$NOR^{10}$, phenyl optionally substituted with $(Z^a)_{p1}$, D2, D8 or D32, $R^{10}$ is $C_{1-4}$ alkyl, $R^{14}$ is $C_{1-4}$ alkyl, $R^{15}$ is a halogen atom, cyano, $C_{3-4}$ cycloalkyl, $C_{1-4}$ alkoxy, $C_{1-4}$ haloalkoxy, —N($R^{24}$)$R^{23}$, —S(O)$_r R^{25}$, —S(O)$_t (R^{25})$=$NR^{21}$ or —C(O)N($R^{29}$)$R^{28}$, $R^{21}$ is a hydrogen atom, cyano or $C_{1-4}$ haloalkylcarbonyl, $R^{23}$ is $C_{1-4}$ alkyl, cyano($C_{1-4}$) alkyl or $C_{1-4}$ haloalkylcarbonyl, $R^{24}$ is a hydrogen atom, $C_{1-4}$ alkyl, $C_{1-4}$ haloalkylcarbonyl, $C_{1-4}$ alkoxycarbonyl or $C_{1-4}$ alkylsulfonyl, $R^{25}$ is $C_{1-4}$ alkyl, ($C_{1-4}$) alkyl optionally substituted with $R^{30}$, $C_{3-4}$ cycloalkyl, $C_{3-4}$ alkenyl, $C_{3-4}$ alkynyl, —C(O)$R^{31}$, —C(O)$OR^{32}$ or —C(O)N($R^{34}$)$R^{33}$, $R^{28}$ is a hydrogen atom, $C_{1-4}$ alkyl, $C_{1-4}$ haloalkyl or cyclopropylmethyl, $R^{29}$ is a hydrogen atom or $C_{1-4}$ alkyl, $R^{30}$ is a halogen atom, cyano or —C(O)N($R^{34}$)$R^{33}$, $R^{31}$ is $C_{1-4}$ alkyl, $C_{1-4}$ haloalkyl, $C_{3-4}$ cycloalkyl, D7, D11 or D22, $R^{32}$ is $C_{1-4}$ alkyl, $R^{33}$ is $C_{1-4}$ alkyl or $C_{1-4}$ haloalkyl, $R^{34}$ is a hydrogen atom or $C_{1-4}$ alkyl, $Z^a$ is a halogen atom, cyano, nitro, $C_{1-4}$ alkyl or $C_{1-4}$ alkylthio, when p1 and p2 are an integer of 2 or more, Zs may be the same as or different from each other, p1 is an integer of 1 to 3, p2 is an integer of 0 to 2, p3 and p4 are an integer of 0 or 1, q4, q6 and q8 are 0, r is an integer of 0 to 2, and t is 0 or 1).

$R^1$-VII: a hydrogen atom, —C(O)$OR^{1b}$ and —C(O)$SR^{1b}$ (where $R^{1b}$ is $C_{1-6}$ alkyl, $C_{1-6}$ haloalkyl, $C_{3-6}$ alkenyl or $C_{3-6}$ alkynyl).

$R^1$-VIII: a hydrogen atom, —C(O)N($R^{1d}$)$R^{1c}$ and —C(S)N($R^{1d}$)$R^{1c}$ (where $R^{1C}$ is $C_{1-6}$ alkyl, ($C_{1-4}$) alkyl optionally substituted with $R^{15}$, $C_{3-6}$ cycloalkyl, $C_{3-6}$ alkenyl, $C_{3-6}$ alkynyl, $C_{1-6}$ alkoxy, $C_{1-6}$ alkylsulfonyl or —N($R^{17}$)$^{R16}$, $R^{15}$ is cyano, $C_{1-4}$ alkoxy or —C(O)N($R^{29}$)$R^{28}$, $R^{16}$ is a hydrogen atom, $C_{1-6}$ alkyl or $C_{1-6}$ alkoxycarbonyl, $R^{17}$ is a hydrogen atom or $C_{1-6}$ alkyl, $R^{28}$ is $C_{1-4}$ alkyl or $C_{1-4}$ haloalkyl, $R^{29}$ is a hydrogen atom or $C_{1-4}$ alkyl, $R^{1d}$ is a hydrogen atom or $C_{1-6}$ alkyl, or $R^{1d}$ together with $R^{1c}$ may form a $C_{4-5}$ alkylene chain to form together with a nitrogen atom to which $R^{1c}$ and $R^{1d}$ are bonded, a 5- to 6-membered ring, and in this case, the alkylene chain may contain one oxygen atom or sulfur atom and may be optionally substituted with a methyl group or an oxo group).

In the compounds included in the present invention, examples of the range of the substituent of $R^2$ include the following groups.

That is, $R^2$-I: a hydrogen atom.

$R^2$-II: $C_{1-2}$ alkyl, cyclopropylmethyl, $C_{1-2}$ alkoxymethyl, cyanomethyl, allyl and propargyl.

$R^2$-III: $C_{1-4}$ alkyl, ($C_{1-2}$) alkyl substituted with $R^{15a}$ (where $R^{15a}$ is cyano, $C_{3-4}$ cycloalkyl, $C_{1-2}$ alkoxycarbonyl, —C(O)N($R^{29}$)$R^{28}$ or —C(S)$NH_2$, $R^{28}$ is a hydrogen atom or $C_{1-2}$ alkyl, $R^{29}$ is a hydrogen atom or methyl), $C_{3-4}$ alkenyl and $C_{3-4}$ alkynyl.

$R^2$-IV: ($C_{1-2}$) alkyl substituted with $R^{15a}$ (where $R^{15a}$ is $C_{1-2}$ alkoxy, $C_{1-2}$ haloalkoxy or —N($R^{24}$)$R^{23}$, $R^{23}$ is —C(O)$R^{31}$ or $C_{1-2}$ alkoxycarbonyl, $R^{24}$ is a hydrogen atom, $R^{31}$ is $C_{1-2}$ alkyl, $C_{1-2}$ haloalkyl or cyclopropyl).

$R^2$-V: $C_{1-6}$ alkyl, $C_{1-4}$ haloalkyl, $C_{3-4}$ cycloalkyl($C_{1-2}$) alkyl, $C_{3-6}$ alkenyl, $C_{3-6}$ alkynyl and $C_{1-6}$ alkoxy.

$R^2$-VI: ($C_{1-2}$) alkyl substituted with $R^{15a}$ (where $R^{15a}$ is $C_{1-4}$ alkoxy, $C_{1-4}$ haloalkoxy, $C_{1-4}$ alkylthio or —N($R^{24}$)$R^{23}$, $R^{23}$ is —C(O)$R^{31}$, —C(O)$OR^{32}$, —C(O)$SR^{32}$ or $C_{1-4}$ alkylsulfonyl, $R^{24}$ is a hydrogen atom, $R^{31}$ is $C_{1-4}$ alkyl, $C_{1-4}$ haloalkyl or $C_{3-4}$ cycloalkyl, and $R^{32}$ is $C_{1-4}$ alkyl).

$R^2$-VII: ($C_{1-2}$) alkyl substituted with $R^{15a}$ (where $R^{15a}$ is cyano, $C_{1-4}$ alkoxycarbonyl, —C(O)N($R^{29}$)$R^{28}$ or —C(S)$NH_2$, $R^{28}$ is a hydrogen atom, $C_{1-4}$ alkyl or $C_{1-4}$ haloalkyl, and $R^{29}$ is a hydrogen atom or $C_{1-4}$ alkyl).

In the compounds included in the present invention, examples of the preferred range of the substituent of $R^3$ include the following groups.

That is, $R^3$-I: trifluoromethyl and chlorodifluoromethyl.

$R^3$-II: difluoromethyl, trifluoromethyl, chlorodifluoromethyl, bromodifluoromethyl, 1,1,2,2-tetrafluoroethyl and pentafluoroethyl.

$R^3$-III: $C_{1-2}$ alkyl optionally substituted with two or more of any halogen atoms.

$R^3$-IV: $C_{1-2}$ haloalkyl.

$R^3$-V: $C_{1-4}$ haloalkyl.

$R^3$-VI: $C_{1-6}$ haloalkyl or $C_{3-8}$ halocycloalkyl.

Among them, as a more preferred range of the substituent of $R^3$, $R^3$-I and $R^3$-II are more preferred and $R^3$-I is specifically preferred.

These groups representing the range of each substituent in the compounds included in the present invention may be optionally combined, each of which is the range of the compound of the present invention.

When $G^2$ is a structure of $G^2$-1, examples of the combination of ranges of X, Y, $R^1$ and $R^2$ include combinations shown in Table 1. However, the combinations in Table 1 are only for exemplification, and the present invention is not limited to these combinations.

TABLE 1

| X | Y | $R^1$ | $R^2$ |
|---|---|---|---|
| X-I | Y-I | $R^1$-I | $R^2$-I |
| X-I | Y-I | $R^1$-I | $R^2$-II |
| X-I | Y-I | $R^1$-I | $R^2$-III |
| X-I | Y-I | $R^1$-I | $R^2$-IV |
| X-I | Y-I | $R^1$-I | $R^2$-V |
| X-I | Y-I | $R^1$-I | $R^2$-VI |
| X-I | Y-I | $R^1$-I | $R^2$-VII |
| X-I | Y-I | $R^1$-II | $R^2$-I |
| X-I | Y-I | $R^1$-II | $R^2$-II |
| X-I | Y-I | $R^1$-II | $R^2$-III |
| X-I | Y-I | $R^1$-II | $R^2$-IV |
| X-I | Y-I | $R^1$-II | $R^2$-V |
| X-I | Y-I | $R^1$-II | $R^2$-VI |
| X-I | Y-I | $R^1$-II | $R^2$-VII |
| X-I | Y-I | $R^1$-III | $R^2$-I |
| X-I | Y-I | $R^1$-III | $R^2$-II |
| X-I | Y-I | $R^1$-III | $R^2$-III |
| X-I | Y-I | $R^1$-III | $R^2$-IV |
| X-I | Y-I | $R^1$-IV | $R^2$-I |
| X-I | Y-I | $R^1$-IV | $R^2$-II |
| X-I | Y-I | $R^1$-IV | $R^2$-III |
| X-I | Y-I | $R^1$-IV | $R^2$-IV |
| X-I | Y-I | $R^1$-V | $R^2$-I |
| X-I | Y-I | $R^1$-V | $R^2$-II |
| X-I | Y-I | $R^1$-V | $R^2$-III |
| X-I | Y-I | $R^1$-V | $R^2$-IV |
| X-I | Y-I | $R^1$-VI | $R^2$-I |
| X-I | Y-I | $R^1$-VI | $R^2$-II |
| X-I | Y-I | $R^1$-VII | $R^2$-I |
| X-I | Y-I | $R^1$-VII | $R^2$-II |
| X-I | Y-I | $R^1$-VIII | $R^2$-I |
| X-I | Y-I | $R^1$-VIII | $R^2$-II |
| X-I | Y-II | $R^1$-I | $R^2$-I |
| X-I | Y-II | $R^1$-I | $R^2$-II |
| X-I | Y-II | $R^1$-I | $R^2$-III |

TABLE 1-continued

| X | Y | R¹ | R² |
|---|---|---|---|
| X-I | Y-II | R¹-I | R²-IV |
| X-I | Y-II | R¹-II | R²-I |
| X-I | Y-II | R¹-II | R²-II |
| X-I | Y-II | R¹-II | R²-III |
| X-I | Y-II | R¹-II | R²-IV |
| X-I | Y-II | R¹-III | R²-I |
| X-I | Y-II | R¹-III | R²-II |
| X-I | Y-II | R¹-IV | R²-I |
| X-I | Y-II | R¹-IV | R²-II |
| X-I | Y-II | R¹-V | R²-I |
| X-I | Y-II | R¹-V | R²-II |
| X-I | Y-II | R¹-VI | R²-I |
| X-I | Y-II | R¹-VII | R²-I |
| X-I | Y-II | R¹-VIII | R²-I |
| X-I | Y-III | R¹-I | R²-I |
| X-I | Y-III | R¹-I | R²-II |
| X-I | Y-III | R¹-II | R²-I |
| X-I | Y-III | R¹-II | R²-II |
| X-I | Y-III | R¹-III | R²-I |
| X-I | Y-III | R¹-IV | R²-I |
| X-I | Y-III | R¹-V | R²-I |
| X-I | Y-IV | R¹-I | R²-I |
| X-I | Y-IV | R¹-II | R²-I |
| X-I | Y-V | R¹-I | R²-I |
| X-I | Y-V | R¹-II | R²-I |
| X-I | Y-VI | R¹-I | R²-I |
| X-I | Y-VI | R¹-II | R²-I |
| X-I | Y-VII | R¹-I | R²-I |
| X-I | Y-VII | R¹-II | R²-I |
| X-II | Y-I | R¹-I | R²-I |
| X-II | Y-I | R¹-I | R²-II |
| X-II | Y-I | R¹-I | R²-III |
| X-II | Y-I | R¹-I | R²-IV |
| X-II | Y-I | R¹-II | R²-I |
| X-II | Y-I | R¹-II | R²-II |
| X-II | Y-I | R¹-II | R²-III |
| X-II | Y-I | R¹-II | R²-IV |
| X-II | Y-I | R¹-III | R²-I |
| X-II | Y-I | R¹-III | R²-II |
| X-II | Y-I | R¹-IV | R²-I |
| X-II | Y-I | R¹-IV | R²-II |
| X-II | Y-I | R¹-V | R²-I |
| X-II | Y-I | R¹-V | R²-II |
| X-II | Y-I | R¹-VI | R²-I |
| X-II | Y-I | R¹-VII | R²-I |
| X-II | Y-I | R¹-VIII | R²-I |
| X-II | Y-II | R¹-I | R²-I |
| X-II | Y-II | R¹-I | R²-II |
| X-II | Y-II | R¹-I | R²-III |
| X-II | Y-II | R¹-I | R²-IV |
| X-II | Y-II | R¹-II | R²-I |
| X-II | Y-II | R¹-II | R²-II |
| X-II | Y-II | R¹-II | R²-III |
| X-II | Y-II | R¹-II | R²-IV |
| X-II | Y-II | R¹-III | R²-I |
| X-II | Y-II | R¹-III | R²-II |
| X-II | Y-II | R¹-IV | R²-I |
| X-II | Y-II | R¹-IV | R²-II |
| X-II | Y-II | R¹-V | R²-I |
| X-II | Y-II | R¹-V | R²-II |
| X-II | Y-II | R¹-VI | R²-I |
| X-II | Y-II | R¹-VII | R²-I |
| X-II | Y-II | R¹-VIII | R²-I |
| X-II | Y-III | R¹-I | R²-I |
| X-II | Y-III | R¹-I | R²-II |
| X-II | Y-III | R¹-II | R²-I |
| X-II | Y-IV | R¹-I | R²-I |
| X-II | Y-V | R¹-I | R²-I |
| X-II | Y-VI | R¹-I | R²-I |
| X-II | Y-VII | R¹-I | R²-I |
| X-III | Y-I | R¹-I | R²-I |
| X-III | Y-I | R¹-I | R²-II |
| X-III | Y-I | R¹-II | R²-I |
| X-III | Y-I | R¹-II | R²-II |
| X-III | Y-I | R¹-III | R²-I |
| X-III | Y-I | R¹-IV | R²-I |
| X-III | Y-I | R¹-V | R²-I |
| X-III | Y-II | R¹-I | R²-I |
| X-III | Y-II | R¹-I | R²-II |
| X-III | Y-II | R¹-II | R²-I |
| X-III | Y-III | R¹-I | R²-I |
| X-III | Y-III | R¹-I | R²-II |
| X-IV | Y-I | R¹-I | R²-I |
| X-IV | Y-I | R¹-II | R²-I |
| X-IV | Y-II | R¹-I | R²-I |
| X-V | Y-I | R¹-I | R²-I |
| X-V | Y-I | R¹-II | R²-I |
| X-V | Y-II | R¹-I | R²-I |
| X-VI | Y-I | R¹-I | R²-I |
| X-VI | Y-I | R¹-II | R²-I |
| X-VI | Y-II | R¹-I | R²-I |

The compound of the present invention can be produced, for example, by the following methods.

Production Method A

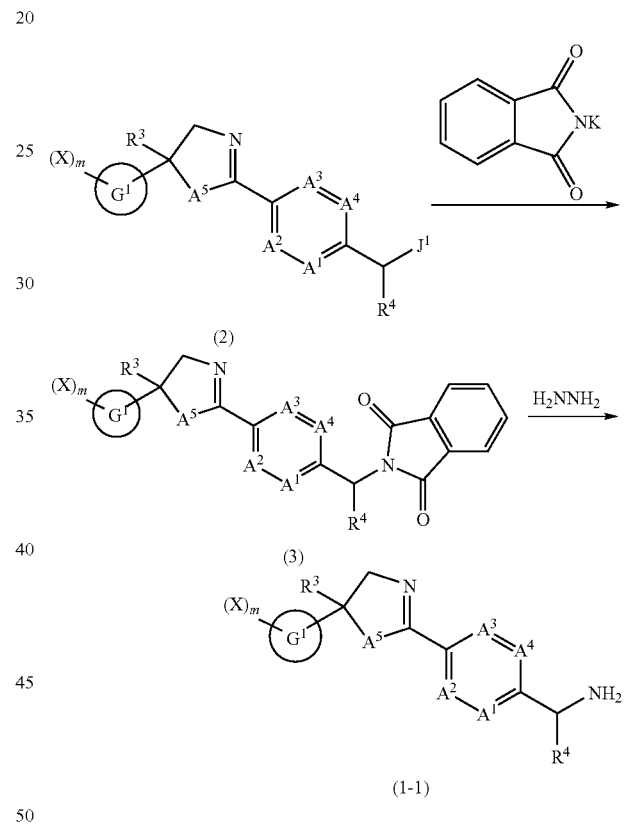

For example, according to a method described in Journal of Heterocyclic Chemistry (J. Heterocyclic Chem.), vol. 40, p. 229 (2003) or the like, a compound of General Formula (3) (where $A^1$, $A^2$, $A^3$, $A^4$, $A^5$, $G^1$, X, $R^3$, $R^4$ and m are the same as the respective definitions in the above) is obtained by reacting 1 equivalent of a compound of General Formula (2) (where $A^1$, $A^2$, $A^3$, $A^4$, $A^5$, $G^1$, X, $R^3$, $R^4$ and m are the same as the respective definitions in the above; and J' is a chlorine atom, a bromine atom, an iodine atom, a $C_{1-4}$ alkylsulfonate group (for example, a methanesulfonyloxy group) or a $C_{1-4}$ haloalkylsulfonate group (for example, a trifluoromethanesulfonyloxy group)) with 1 to 1.5 equivalent(s) of phthalimide potassium, using, for example, toluene, dichloromethane, tetrahydrofuran, 1,4-dioxane, acetone, N,N-dimethylformamide, N,N-dimethylacetamide, dimethylsulfoxide or the like as a solvent, if necessary in the presence of 0.1 to 2 equivalents of a base such as sodium carbonate, potassium carbonate and sodium hydrogen carbonate and if necessary in the presence of 0.1 to 1 equivalent(s) of a catalyst such as tetrabutylammonium iodide, tributylhexadecylphosphonium bromide and crown ether (18-Crown-6), at a temperature ranging from room temperature to a reflux temperature of the reaction mixture for 0.5 to 24 hours. By reacting the compound of General Formula (3) with hydrazine monohydrate or a hydrazine aqueous solution in an amount of 1 to 4 equivalent(s) based on 1 equivalent of the compound of General Formula (3), using, for example, toluene, dichloromethane, chloroform, methanol, ethanol, tetrahydrofuran, 1,4-dioxane, water or a mixture of two or more types thereof in any mixing ratio as a solvent, if necessary in an atmosphere of an inert gas such as nitrogen and argon, at a temperature ranging from room temperature to a reflux temperature of the reaction mixture for 1 to 24 hour(s), a compound of the present invention of General Formula (1-1) (where $A^1$, $A^2$, $A^3$, $A^4$, $A^5$, $G^1$, X, $R^3$, $R^4$ and m are the same as the respective definitions in the above) corresponding to General Formula (1) in which $G^2$ is $G^2$-1, L is —$CH(R^4)$—, and $R^1$ and $R^2$ are a hydrogen atom can be obtained.

Production Method B

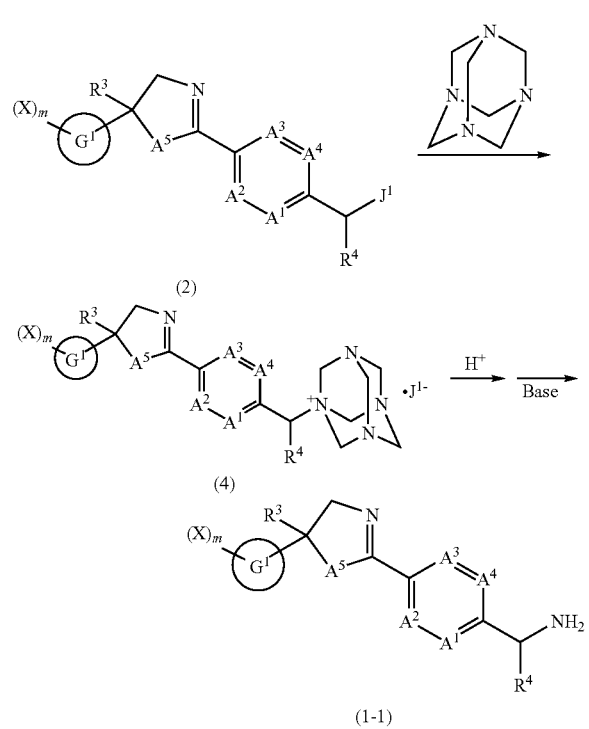

For example, according to a method described in the Journal of Organic Chemistry (J. Org. Chem.), vol. 64, p. 1015 (1999) or the like, a quaternary ammonium salt of General Formula (4) (where $A^1$, $A^2$, $A^3$, $A^4$, $A^5$, $G^1$, X, $R^3$, $R^4$, m and $J^1$ are the same as the respective definitions in the above) is obtained by reacting 1 equivalent of a compound of General Formula (2) (where $A^1$, $A^2$, $A^3$, $A^4$, $A^5$, $G^1$, X, $R^3$, $R^4$, m and $J^1$ are the same as the respective definitions in the above) with 1 to 1.3 equivalent(s) of hexamethylenetetramine, using, for example, benzene, toluene, chlorobenzene, dichloromethane, chloroform, 1,2-dichloroethane, methanol, ethanol or the like as a solvent, at a temperature ranging from room temperature to a reflux temperature of the reaction mixture for 0.5 to 24 hours. By hydrolyzing the quaternary ammonium salt of General Formula (4), using, for example, methanol, ethanol, acetic acid, propionic acid, water or a mixture of two or more types thereof in any mixing ratio as a solvent in the presence of an acid catalyst such as hydrochloric acid, hydrobromic acid, propionic acid and phosphoric acid in an amount of 5 to 100 equivalents relative to 1 equivalent of the compound of General Formula (4) at a temperature ranging from room temperature to a reflux temperature of the reaction mixture for 0.5 to 24 hours, a compound of the present invention of General Formula (1-1) (where $A^1$, $A^2$, $A^3$, $A^4$, $A^5$, $G^1$, X, $R^3$, $R^4$ and m are the same as the respective definitions in the above) corresponding to General Formula (1) in which $G^2$ is $G^2$-1, L is —$CH(R^4)$—, and $R^1$ and $R^2$ are a hydrogen atom can be obtained.

Production Method C

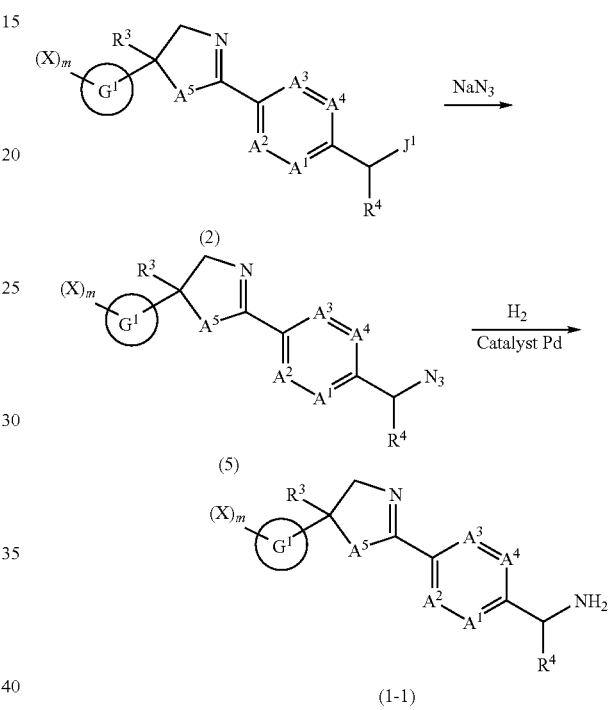

For example, according to a method described in Journal of Medicinal Chemistry (J. Med. Chem.), vol. 36, p. 2558 (1993) or the like, a compound of General Formula (5) (where $A^1$, $A^2$, $A^3$, $A^4$, $A^5$, $G^1$, X, $R^3$, $R^4$ and m are the same as the respective definitions in the above) is obtained by reacting 1 equivalent of a compound of General Formula (2) (where $A^1$, $A^2$, $A^3$, $A^4$, $A^5$, $G^1$, X, $R^3$, $R^4$, m and $J^1$ are the same as the respective definitions in the above) with 1.1 to 3.0 equivalents of sodium azide or lithium azide, if necessary in an atmosphere of an inert gas such as nitrogen and argon, using, for example, chloroform, ethanol, acetone, N,N-dimethylformamide, DMPU (N,N'-dimethylpropyleneurea), acetonitrile, dimethylsulfoxide, water or a mixture of two or more types thereof in any mixing ratio as a solvent, if necessary in the presence of 0.005 to 0.3 equivalents of a catalyst such as tetrabutylammonium hydrogen sulfate, methyltrioctylammonium chloride, lithium iodide and potassium iodide, at a temperature ranging from room temperature to a reflux temperature of the reaction mixture for 0.5 to 48 hours. By reacting the compound of General Formula (5) with triphenyl phosphine in an amount of 1 to 1.5 equivalent(s) and water in an amount of 2 to 5 equivalents each relative to 1 equivalent of the compound of General Formula (5), using, for example, ethanol, tetrahydrofuran, acetonitrile or a mixture of two or more types thereof in any mixing ratio as a solvent, at a temperature ranging from room temperature to a reflux temperature of the reaction mixture for 2 to 24 hours, a compound of the present invention of General Formula (1-1) (where $A^1$, $A^2$, $A^3$, $A^4$, $A^5$, $G^1$, X, $R^4$, $R^4$ and m are the same as the respective definitions in the above) corresponding to General Formula (1) in which $G^2$ is $G^2$-1, L is —CH($R^4$)—, and $R^1$ and $R^2$ are a hydrogen atom can be obtained.

In addition, according to a method described in Journal of Medicinal Chemistry (J. Med. Chem.), vol. 46, p. 3116 (2003) or the like, by hydrogenating a compound of General Formula (5), for example in a solvent such as dichloromethane, methanol, ethanol, ethyl acetate and a mixture of two or more types thereof in any mixing ratio, using a catalyst such as platinum (IV) oxide and palladium-carbon in an atmosphere of a hydrogen gas having 1 to 4 atm(s) at room temperature for 20 minutes to 24 hours, a compound of the present invention of General Formula (1-1) can be also obtained.

Production Method D

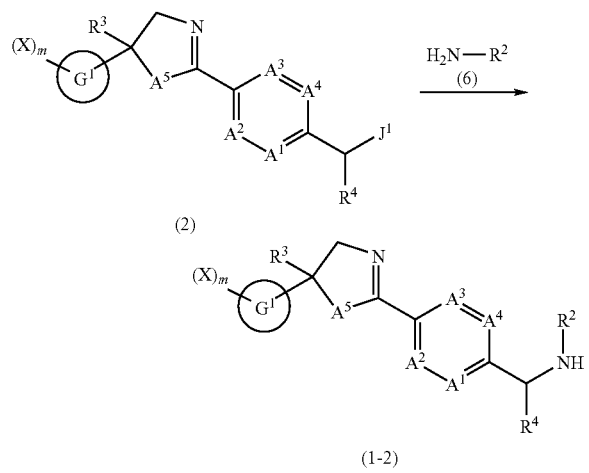

By reacting 1 equivalent of a compound of General Formula (2) (where $A^1, A^2, A^3, A^4, A^5, G^1, X, R^3, R^4$, m and $J^1$ are the same as the respective definitions in the above) with 1 to 40 equivalent(s) of an amine of General Formula (6) (where $R^2$ is a hydrogen atom, an alkyl group, a substituted alkyl group, an alkenyl group, an alkynyl group or the like) or a salt of the amine, if necessary using benzene, toluene, dichloromethane, chloroform, 1,2-dichloroethane, methanol, ethanol, tert-butyl methyl ether, 1,2-dimethoxyethane, tetrahydrofuran, 1,4-dioxane, N,N-dimethylformamide, DMPU (N,N'-dimethylpropyleneurea), acetonitrile, water or a mixture of two or more types thereof in any mixing ratio as a solvent, if necessary in the presence of 1 to 10 equivalent(s) of a base such as lithium hydroxide, sodium hydroxide, potassium hydroxide, sodium carbonate, potassium carbonate, triethylamine and ethyldiisopropylamine and if necessary in the presence of 0.1 to 0.5 equivalents of a catalyst such as sodium iodide and potassium iodide, at a temperature ranging from 0° C. to a reflux temperature of the reaction mixture for 1 to 48 hour(s), a compound of the present invention of General Formula (1-2) (where $A^1, A^2, A^3, A^4, A^5, G^1, X, R^3, R^4$ and m are the same as the respective definitions in the above, and $R^2$ is a hydrogen atom, an alkyl group, a substituted alkyl group, an alkenyl group, an alkynyl group or the like) corresponding to General Formula (1) in which $G^2$ is $G^2$-1, L is —CH($R^4$)—, and $R^1$ is a hydrogen atom can be obtained.

The primary amines of General Formula (6) used here are publicly-known compounds, and some of them are commercially available. The others can be readily synthesized according to general synthetic methods of primary amines described in the literatures.

Production Method E

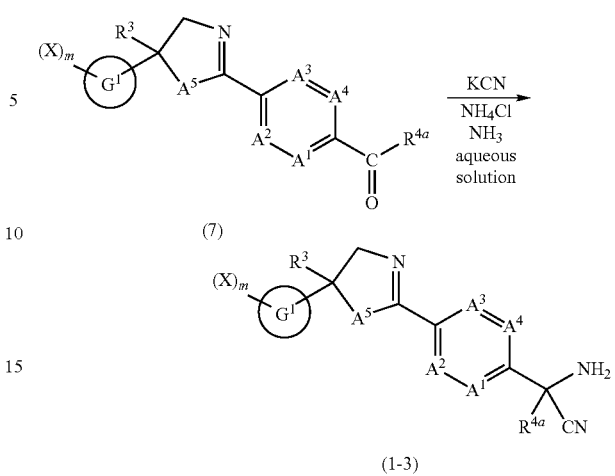

By reacting a compound of General Formula (7) (where $A^1, A^2, A^3, A^4, A^5, G^1, X, R^3$ and m are the same as the respective definitions in the above, $R^{4a}$ is a hydrogen atom, an alkyl group or the like) according to a general Strecker reaction described in literatures, for example, according to reaction conditions described in Chemistry Letters (Chem. Lett.), p. 687 (1987), Journal of Medicinal Chemistry (J. Med. Chem.), vol. 28, p. 1280 (1985) or the like, a compound of the present invention of General Formula (1-3) (where $A^1, A^2, A^3, A^4, A^5, G^1, X, R^3$ and m are the same as the respective definitions in the above, and $R^{4a}$ is a hydrogen atom, an alkyl group or the like) corresponding to General Formula (1) in which $G^2$ is $G^2$-1, L is —C($R^{4a}$)(CN)—, and $R^1$ and $R^2$ are a hydrogen atom can be obtained.

Production Method F

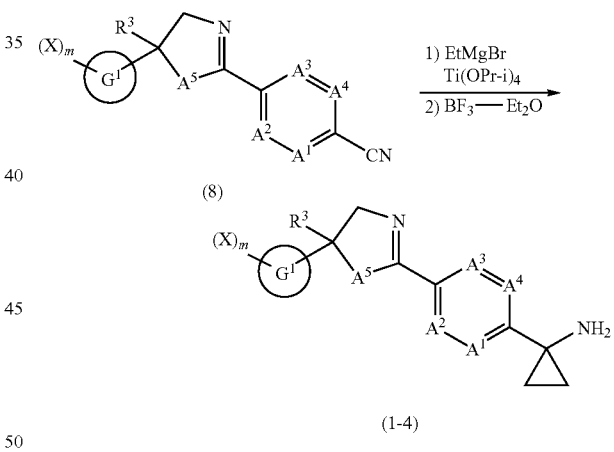

By reacting a compound of General Formula (8) (where $A^1, A^2, A^3, A^4, A^5, G^1, X, R^3$ and m are the same as the respective definitions in the above) with ethyl magnesium bromide and thereafter, with a boron trifluoride-diethyl ether complex, for example according to a method described in The Journal of Organic Chemistry (J. Org. Chem.), vol. 68, p. 7133 (2003) in the presence of titanium tetra-1-propoxide, a compound of the present invention of General Formula (1-4) (where $A^1, A^2, A^3, A^4, A^5, G^1, X, R^3$ and m are the same as the respective definitions in the above) corresponding to General Formula (1) in which $G^2$ is $G^2$-1, L is a cyclopropylidene group, and $R^1$ and $R^2$ are a hydrogen atom can be obtained.

Some of the compounds of General Formula (8) used here are publicly-known compounds described in Japanese Patent Application Publication (No. JP 2007/091708), and the others can be synthesized according to the method described in the literature in substantially the same manner as that for synthesizing the publicly-known compounds.

Production Method G

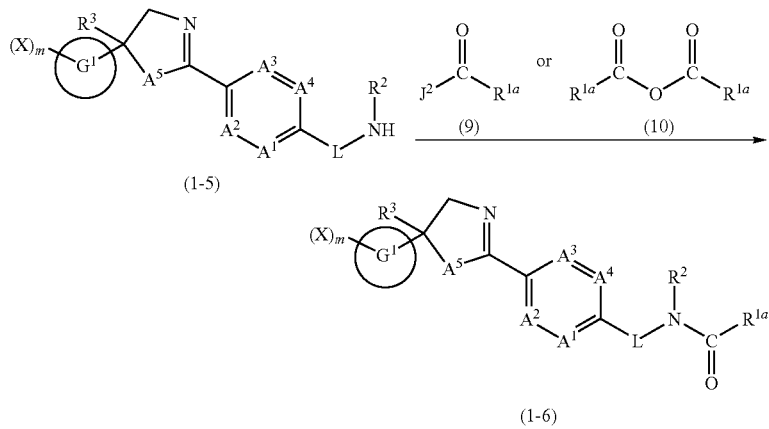

By reacting 1 equivalent of a compound of the present invention of General Formula (1-5) (where $A^1, A^2, A^3, A^4, A^5, G^1, L, X, R^2, R^3$ and m are the same as the respective definitions in the above) corresponding to General Formula (1) in which $G^2$ is $G^2$-1, and $R^1$ is a hydrogen atom with 1 to 1.5 equivalent(s) of a publicly-known carboxylic acid derivative of General Formula (9) (where $R^{1a}$ is the same as defined above, $J^2$ is a chlorine atom, a bromine atom, a $C_{1-4}$ alkylcarbonyloxy group (for example, a pivaloyloxy group), a $C_{1-4}$ alkoxycarbonyloxy group (for example, an isobutyloxycarbonyloxy group) or an azolyl group (for example, an imidazole-1-yl group)) or a publicly-known carboxylic acid anhydride of General Formula (10) (where $R^{1a}$ is the same as defined above) using, for example, dichloromethane, chloroform, diethyl ether, tert-butyl methyl ether, tetrahydrofuran, 1,4-dioxane, ethyl acetate, acetonitrile or the like as a solvent, if necessary in the presence of 1 to 2 equivalent(s) of a base such as sodium carbonate, potassium carbonate, triethylamine, pyridine and 4-(dimethylamino) pyridine at a temperature ranging from 0° C. to a reflux temperature of the reaction mixture for 10 minutes to 24 hours, a compound of the present invention of General Formula (1-6) (where $A^1, A^2, A^3, A^4, A^5, G^1, L, X, R^{1a}, R^2, R^3$ and m are the same as the respective definitions in the above) corresponding to General Formula (1) in which $G^2$ is $G^2$-1, and $R^1$ is $—C(O)R^{1a}$ can be obtained.

Production Method H

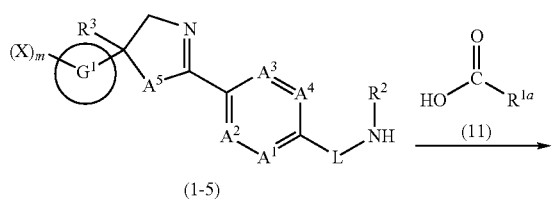

By reacting 1 equivalent of a compound of the present invention of General Formula (1-5) (where $A^1, A^2, A^3, A^4, A^5, G^1, L, X, R^2, R^3$ and m are the same as the respective definitions in the above) corresponding to General Formula (1) in which $G^2$ is $G^2$-1, and $R^1$ is a hydrogen atom with 1 to 1.1 equivalent(s) of a publicly-known carboxylic acid of General Formula (11) (where $R^{III}$ is the same as defined above) using, for example, dichloromethane, chloroform, diethyl ether, tert-butyl methyl ether, tetrahydrofuran, 1,4-dioxane or the like as a solvent, if necessary in the presence of 1 to 4 equivalent(s) of a base such as sodium carbonate, potassium carbonate, triethylamine, pyridine and 4-(dimethylamino) pyridine, using 1 to 4 equivalent(s) of a condensing agent such as WSC (1-ethyl-3-(3-dimethylaminopropyl) carbodiimide hydrochloride) and CDI (carbonyldiimidazole) at a temperature ranging from 0° C. to a reflux temperature of the reaction mixture for 10 minutes to 24 hours, a compound of the present invention of General Formula (1-6) (where $A^1, A^2, A^3, A^4, A^5, G^1, L, X, R^{1a}, R^2, R^3$ and m are the same as the respective definitions in the above) corresponding to General Formula (1) in which $G^2$ is $G^2$-1, and $R^1$ is $—C(O)R^{1a}$ can be obtained.

Production Method I

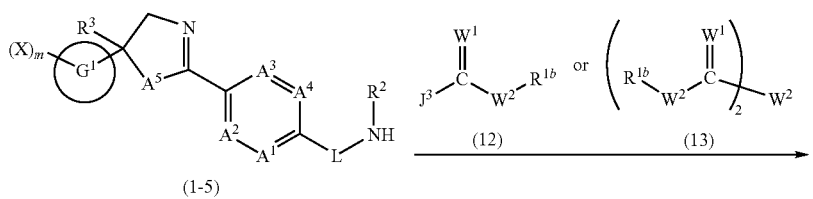

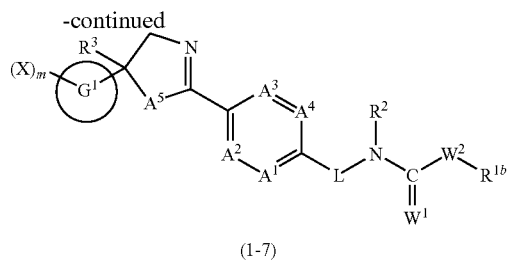

(1-7)

By reacting a compound of the present invention of General Formula (1-5) (where $A^1, A^2, A^3, A^4, A^5, G^1, L, X, R^2, R^3$ and m are the same as the respective definitions in the above) corresponding to General Formula (1) in which $G^2$ is $G^2$-1, and $R^1$ is a hydrogen atom with a publicly-known compound of General Formula (12) (where $R^{1b}$ is the same as defined above, $J^3$ is a halogen atom such as a chlorine atom and a bromine atom, and $W^1$ and $W^2$ are independently O or S) or a publicly-known compound of General Formula (13) (where $R^{1b}$ is the same as defined above, and $W^1$ and $W^2$ are independently O or S) using substantially the same conditions as those in Production Method G, a compound of the present invention of General Formula (1-7) (where $A^1, A^2, A^3, A^4, A^5$, $G^1, L, X, R^{1b}, R^2, R^3$ and m are the same as the respective definitions in the above, and $W^1$ and $W^2$ are independently O or S) corresponding to General Formula (1) in which $G^2$ is $G^2$-1, and $R^1$ is $-C(W^1)-W^2-R^{1b}$ can be obtained.

Production Method J

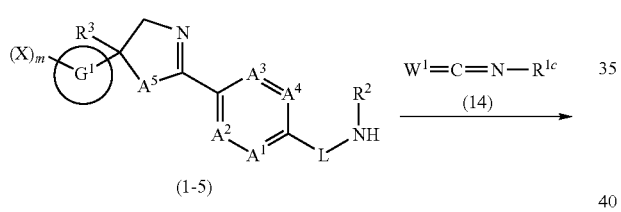

(1-5)

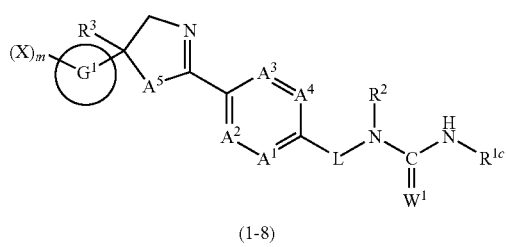

(1-8)

By reacting 1 equivalent of a compound of the present invention of General Formula (1-5) (where $A^1, A^2, A^3, A^4, A^5$, $G^1, L, X, R^2, R^3$ and m are the same as the respective definitions in the above) corresponding to General Formula (1) in which $G^2$ is $G^2$-1, and $R^1$ is a hydrogen atom with 1 to 1.2 equivalent(s) of a publicly-known isocyanate of General Formula (14) (where $R^{1c}$ and $W^1$ are the same as the respective definitions in the above) using, for example, dichloromethane, 1,2-dichloroethane, methanol, ethanol, tetrahydrofuran, 1,4-dioxane, N,N-dimethylformamide, water or the like as a solvent, if necessary in the presence of 1 to 4 equivalent(s) of a base such as sodium carbonate, potassium carbonate, triethylamine, pyridine and 4-(dimethylamino) pyridine at a temperature ranging from 0° C. to a reflux temperature of the reaction mixture for 2 minutes to 24 hours, a compound of the present invention of General Formula (1-8) (where $A^1, A^2$, $A^3, A^4, A^5, G^1, L, W^1, X, R^{1c}, R^2, R^3$ and m are the same as the respective definitions in the above) corresponding to General Formula (1) in which $G^2$ is $G^2$-1, and $R^1$ is $-C(W^1)NHR^{1c}$ can be obtained.

Production Method K

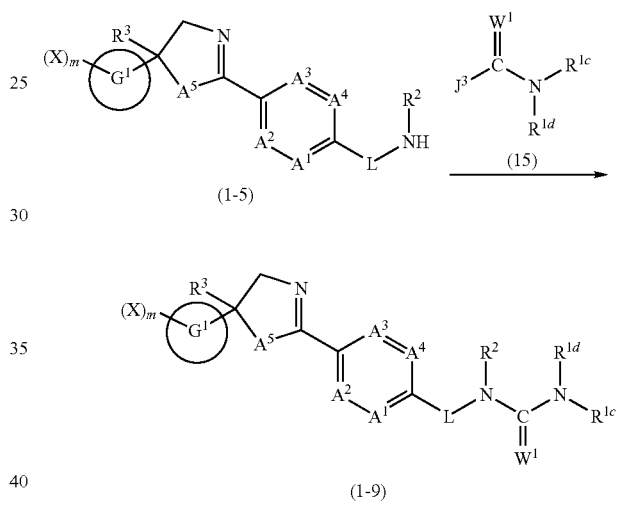

By reacting a compound of the present invention of General Formula (1-5) (where $A^1, A^2, A^3, A^4, A^5, G^1, L, X, R^2, R^3$ and m are the same as the respective definitions in the above) corresponding to General Formula (1) in which $G^2$ is $G^2$-1, and $R^1$ is a hydrogen atom with a publicly-known compound of General Formula (15) (where $R^{1c}, R^{1d}, W^1$ and $J^3$ are the same as defined above) using substantially the same conditions as those in Production Method G, a compound of the present invention of General Formula (1-9) (where $A^1, A^2$, $A^3, A^4, A^5, G^1, L, W^1, X, R^{1c}, R^{1d}, R^2, R^3$ and m are the same as the respective definitions in the above) corresponding to General Formula (1) in which $G^2$ is $G^2$-1, and $R^1$ is $-C(W^1)N(R^{1d})R^{1c}$ can be obtained.

Production Method L

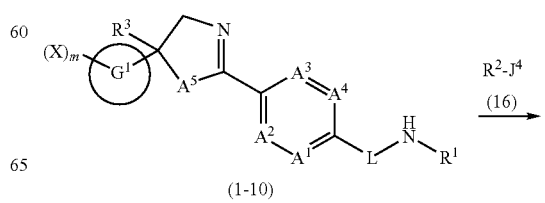

(1-10)

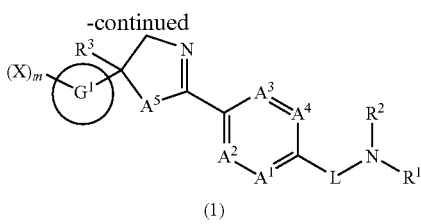

(1)

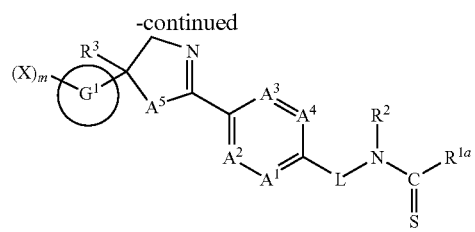

(1-11)

By reacting 1 equivalent of a compound of the present invention of General Formula (1-10) (where $A^1$, $A^2$, $A^3$, $A^4$, $A^5$, $G^1$, L, X, $R^1$, $R^3$ and m are the same as the respective definitions in the above) corresponding to General Formula (1) in which $G^2$ is $G^2$-1, and $R^2$ is a hydrogen atom with 1 to 10 equivalent(s) of a compound of General Formula (16) (where $R^2$ is the same as defined above except a hydrogen atom, $J^4$ is an advantageous leaving group such as a chlorine atom, a bromine atom, an iodine atom, a $C_{1-4}$ alkylcarbonyloxy group (for example, a pivaloyloxy group), a $C_{1-4}$ alkylsulfonate group (for example, a methanesulfonyloxy group), a $C_{1-4}$ haloalkylsulfonate group (for example, a trifluoromethanesulfonyloxy group), an arylsulfonate group (for example, a benzenesulfonyloxy group, a p-toluenesulfonyloxy group) and an azolyl group (for example, an imidazole-1-yl group)) using, for example, tert-butyl methyl ether, tetrahydrofuran, 1,4-dioxane, N,N-dimethylformamide, acetonitrile or the like as a solvent, if necessary in the presence of 1 to 3 equivalent(s) of a base such as sodium hydride, sodium hydroxide, potassium hydroxide, potassium tert-butoxide, sodium carbonate, potassium carbonate, triethylamine and pyridine at a temperature ranging from 0 to 90° C. for 10 minutes to 24 hours, a compound of the present invention of General Formula (1) (where $A^1$, $A^2$, $A^3$, $A^4$, $A^5$, $G^1$, L, X, $R^1$, $R^3$ and m are the same as the respective definitions in the above, and $R^2$ is the same as defined above except a hydrogen atom) can be obtained.

Some of the compounds of General Formula (16) used here are publicly-known compounds, and some of them are commercially available. The others can be readily synthesized according to general synthetic methods described in the literatures such as Chemistry Letters (Chem. Lett.), p. 373 (1976), Journal of the American Chemical Society (J. Am. Chem. Soc.), vol. 86, p. 4383 (1964), the Journal of Organic Chemistry (J. Org. Chem.), vol. 41, p. 4028 (1976) and vol. 43, p. 3244 (1978), Organic Synthesis (Org. Synth.), collective vol. 6, p. 101 (1988), Tetrahedron Letters (Tetrahedron Lett.), p. 4339 (1972), U.K. Patent Application Publication (No. GB 2,161,802) and European Patent Application Publication (No. EP 0,051,273).

Production Method M

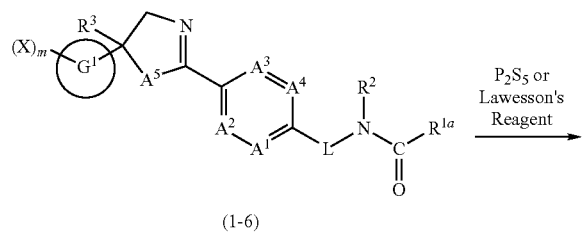

By reacting 1 equivalent of a compound of the present invention of General Formula (1-6) (where $A^1$, $A^2$, $A^3$, $A^4$, $A^5$, $G^1$, L, X, $R^{1a}$, $R^2R^3$ and m are the same as the respective definitions in the above) corresponding to General Formula (1) in which $G^2$ is $G^2$-1, and $R^1$ is —C(O)$R^{1a}$ with 1 to 10 equivalent(s) of a sulfurizing agent such as diphosphorus pentasulfide, diphosphorus pentasulfide-HMDO (hexamethyldisiloxane) and Lawesson's Reagent (2,4-bis(4-methoxyphenyl)-1,3,2,4-dithiadiphosphetane=2,4-disulfide), if necessary: either using benzene, toluene, chlorobenzene, dichloromethane, chloroform, 1,2-dichloroethane, tert-butyl methyl ether, 1,2-dimethoxyethane, tetrahydrofuran, 1,4-dioxane, HMPA (hexamethylphosphoric triamide) or the like as a solvent, if necessary in the presence of 1 to 4 equivalent(s) of a base such as sodium carbonate, potassium carbonate, sodium hydrogen carbonate, triethylamine and pyridine at a temperature ranging from room temperature to a reflux temperature of the reaction mixture for 10 minutes to 50 hours; or using a base such as pyridine as a solvent at a temperature ranging from 80° C. to a reflux temperature of the reaction mixture for 1 to 3 hour(s), a compound of the present invention of General Formula (1-11) (where $A^1$, $A^2$, $A^3$, $A^4$, $A^5$, $G^1$, L, X, $R^{1a}$, $R^2$, $R^3$ and m are the same as the respective definitions in the above) corresponding to General Formula (1) in which $G^2$ is $G^2$-1, and $R^1$ is —C(S)$R^{1a}$ can be obtained.

Production Method N

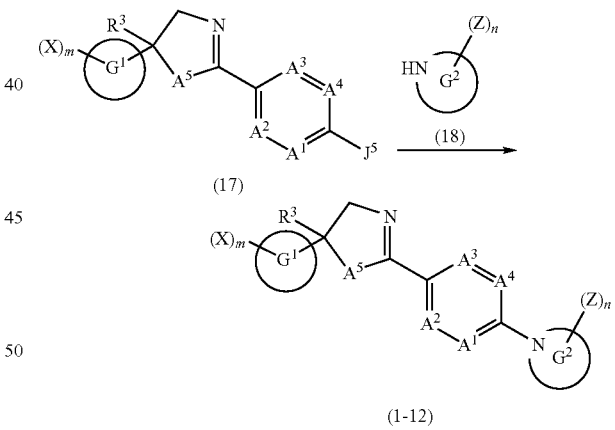

(1-12)

By reacting 1 equivalent of a compound of General Formula (17) (where $A^1$, $A^2$, $A^3$, $A^4$, $A^5$, $G^1$, X, $R^3$ and m are the same as the respective definitions in the above, and $J^5$ is a fluorine atom, a chlorine atom, a bromine atom, an iodine atom or a $C_{1-4}$ haloalkylsulfonate group (for example, a trifluoromethanesulfonyloxy group)) with 1 to 10 equivalent(s) of a compound of General Formula (18) (where $G^2$ is an azolyl group of $G^2$-2 to $G^2$-10, and Z and n are the same as the respective definitions in the above), using, for example, tetrahydrofuran, 1,4-dioxane, acetonitrile, N,N-dimethylformamide or the like as a solvent, if necessary in the presence of 1 to 3 equivalent(s) of a base such as sodium hydride, potassium tert-butoxide, potassium hydroxide, potassium carbonate, triethylamine and pyridine at a temperature ranging from 0° C.

to 90° C. for 10 minutes to 24 hours, a compound of the present invention of General Formula (1-12) (where $A^1$, $A^2$, $A^3$, $A^4$, $A^5$, $G^1$, X, Z, $R^3$, m and n are the same as the respective definitions in the above) corresponding to General Formula (1) in which $G^2$ is an azolyl group of $G^2$-2 to $G^2$-10 can be obtained.

Some of the compounds of General Formula (17) used here are publicly-known compounds described in Japanese Patent Application Publication (No. JP 2007-091708), and the others can be synthesized according to the method described in the literature in the same manner as that for synthesizing the publicly-known compounds.

In addition, some of the compounds of General Formula (18) are publicly-known compounds and some of them are commercially available. The others can be synthesized according to general synthetic methods of substituted azoles described in literatures.

Production Method O

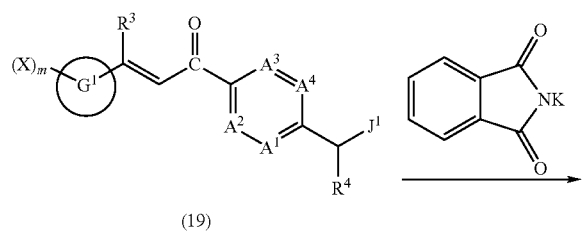

(19)

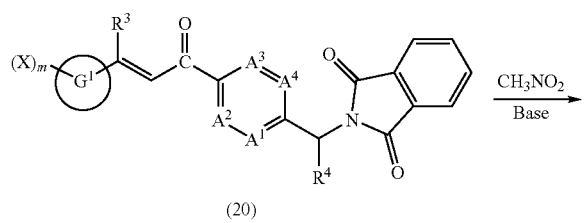

(20)

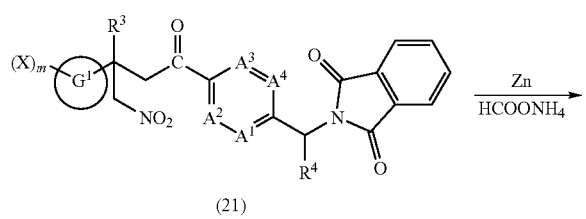

(21)

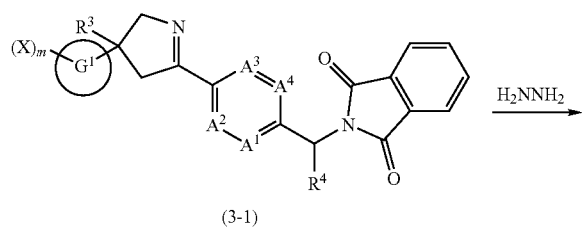

(3-1)

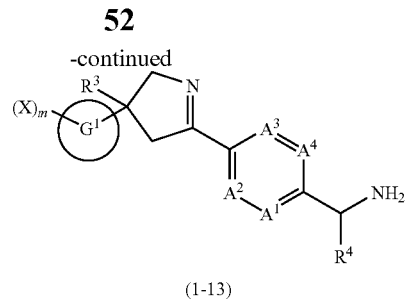

(1-13)

By reacting 1 equivalent of a compound of General Formula (20) (where $A^1$, $A^2$, $A^3$, $A^4$, $G^1$, X, $R^3$, $R^4$ and m are the same as the respective definitions in the above) obtained by reacting a compound of General Formula (19) (where $A^1$, $A^2$, $A^3$, $A^4$, $G^1$, X, $R^3$, $R^4$, m and $J^1$ are the same as the respective definitions in the above) with potassium phthalimide using substantially the same conditions as those in Production Method A, with 1.2 to 5 equivalents of nitromethane using, for example, methanol, ethanol, acetonitrile, N,N-dimethylformamide or the like as a solvent, if necessary in the presence of 0.1 to 5 equivalents of a base such as sodium ethoxide, dimethylamine and 1,8-diazabicyclo[5,4,0]-7-undecene at a temperature ranging from room temperature to a reflux temperature of the reaction mixture for 12 to 36 hours, a compound of General Formula (21) (where $A^1$, $A^2$, $A^3$, $A^4$, $G^1$, X, $R^3$, $R^4$ and m are the same as the respective definitions in the above) can be obtained.

By reducing with a metal such as zinc and iron, the thus obtained compound of General Formula (21), for example according to a method described in Synthesis, p. 3301 (2006) or the like using ethanol, tetrahydrofuran, acetic acid, N,N-dimethylformamide, water or a mixture of two or more types thereof in any mixing ratio as a solvent in the presence of hydrochloric acid, ammonium chloride, ammonium acetate, titanium tetrachloride or the like, a compound of General Formula (3-1) (where $A^1$, $A^2$, $A^3$, $A^4$, $G^1$, X, $R^3$, $R^4$ and m are the same as the respective definitions in the above) corresponding to General Formula (3) in which $A^5$ is —$CH_2$— can be obtained. By reacting the compound of General Formula (3-1) with hydrazine monohydrate or a hydrazine aqueous solution using substantially the same conditions as those in Production Method A, a compound of the present invention of General Formula (1-13) (where $A^1$, $A^2$, $A^3$, $A^4$, $G^1$, X, $R^3$, $R^4$ and m are the same as the respective definitions in the above) corresponding to General Formula (1) in which $A^5$ is —$CH_2$—, $G^2$ is $G^2$-1, L is —$CH(R^4)$—, and $R^1$ and $R^2$ are a hydrogen atom can be obtained.

In Production Method A to Production Method O, the objective compound of the present invention can be obtained by subjecting the reaction mixture after the completion of the reaction to a common after treatment: for example, the reaction mixture is directly concentrated; or dissolved in an organic solvent, washed with water, and then concentrated; or charged into ice water, extracted with an organic solvent, and then concentrated. Furthermore, when purification is required, the objective compound can be separated and purified by any purification method such as recrystallization, column chromatography, thin layer chromatography and preparative liquid chromatography.

The compound of General Formula (2) used in Production Method A to Production Method D can be synthesized, for example, according to Reaction Formula 1 to Reaction Formula 4.

Reaction Formula 1

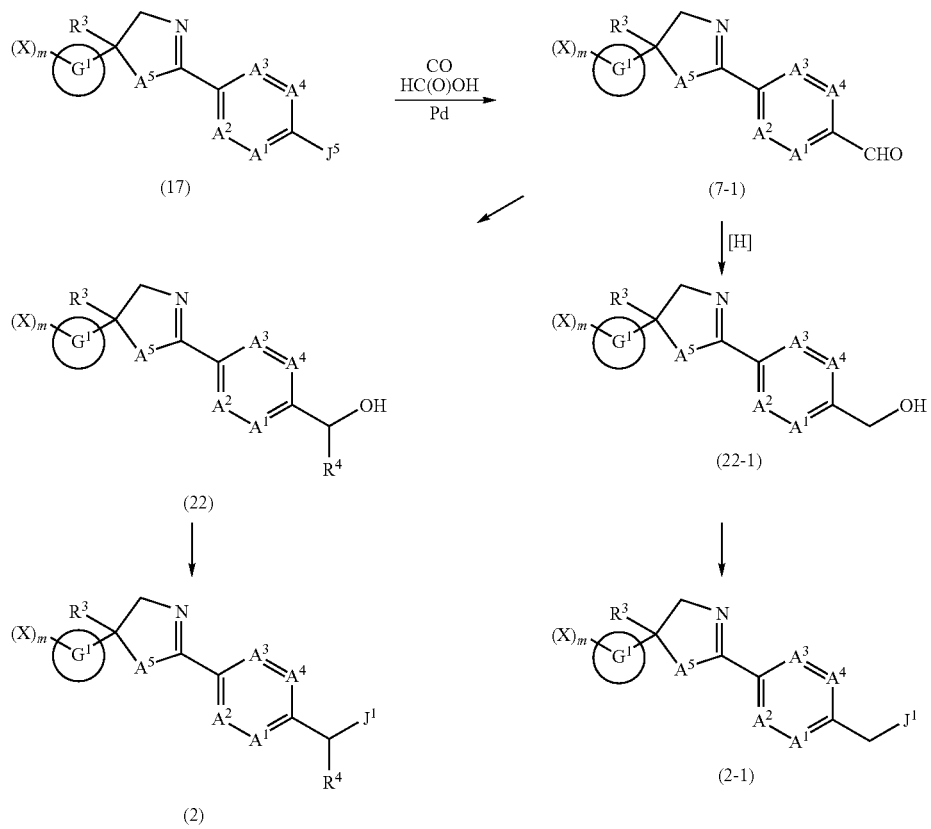

By subjecting a compound of General Formula (17) (where $A^1$, $A^2$, $A^3$, $A^4$, $A^5$, $G^1$, X, $R^3$ and m are the same as the respective definitions in the above, and $J^5$ is a bromine atom, an iodine atom, a $C_{1-4}$ haloalkylsulfonate group (for example, a trifluoromethanesulfonyloxy group) or the like) to a CO insertion reaction using a transition metal catalyst such as palladium in the co-presence of a hydride source such as formic acid according to methods publicly-known in literatures, for example, a method described in Bulletin of the Chemical Society of Japan (Bull. Chem. Soc. Jpn.), vol. 67, p. 2329 (1994) and the like, a compound of General Formula (7-1) (where $A^1$, $A^2$, $A^3$, $A^4$, $A^5$, $G^1$, X, $R^3$ and m are the same as the respective definitions in the above) corresponding to General Formula (7) in which $R^{4a}$ is a hydrogen atom can be synthesized.

By converting the thus obtained compound of General Formula (7-1) into a secondary alcohol of General Formula (22) (where $A^1$, $A^2$, $A^3$, $A^4$, $A^5$, $G^1$, X, $R^3$ and m are the same as the respective definitions in the above, and $R^4$ is the same as defined above except a hydrogen atom) according to methods publicly-known in literatures, for example, a method described in the Journal of Organic Chemistry (J. Org. Chem.), vol. 64, p. 2873 (1999) and vol. 65, p. 4618 (2000) and the like and thereafter, by halogenating the secondary alcohol, for example according to a method described in Journal of the American Chemical Society (J. Am. Chem. Soc.), vol. 108, p. 6819 (1986) or the like or by sulfonyl-esterification of the secondary alcohol, for example according to a method described in the Journal of Organic Chemistry (J. Org. Chem.), vol. 69, p. 1227 (2004) or the like, a compound of General Formula (2) (where $A^1$, $A^2$, $A^3$, $A^4$, $A^5$, $G^1$, X, $R^3$, m and $J^1$ are the same as the respective definitions in the above, and $R^4$ is the same as defined above except a hydrogen atom) can be synthesized.

In addition, by reducing the compound of General Formula (7-1) to a compound of General Formula (22-1) (where $A^1$, $A^2$, $A^3$, $A^4$, $A^5$, $G^1$, X, $R^3$ and m are the same as the respective definitions in the above) corresponding to General Formula (22) in which $R^4$ is a hydrogen atom according to publicly-known methods described in literatures, for example, a method described in Journal of Medicinal Chemistry (J. Med. Chem.), vol. 50, p. 2424 (2007) and thereafter, by halogenating the compound of General Formula (22-1) or by sulfonyl-esterification of the compound of General Formula (22-1), for example, according to a method described in Bioorganic and Medicinal Chemistry (Bioorganic & Med. Chem.), vol. 7, p. 2647 (1999), a compound of General Formula (2-1) (where $A^1$, $A^2$, $A^3$, $A^4$, $A^5$, $G^1$, X, $R^3$, m and $J^1$ are the same as the respective definitions in the above) corresponding to General Formula (2) in which $R^4$ is a hydrogen atom can be synthesized.

Reaction Formula 2

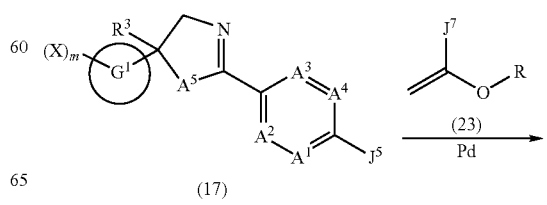

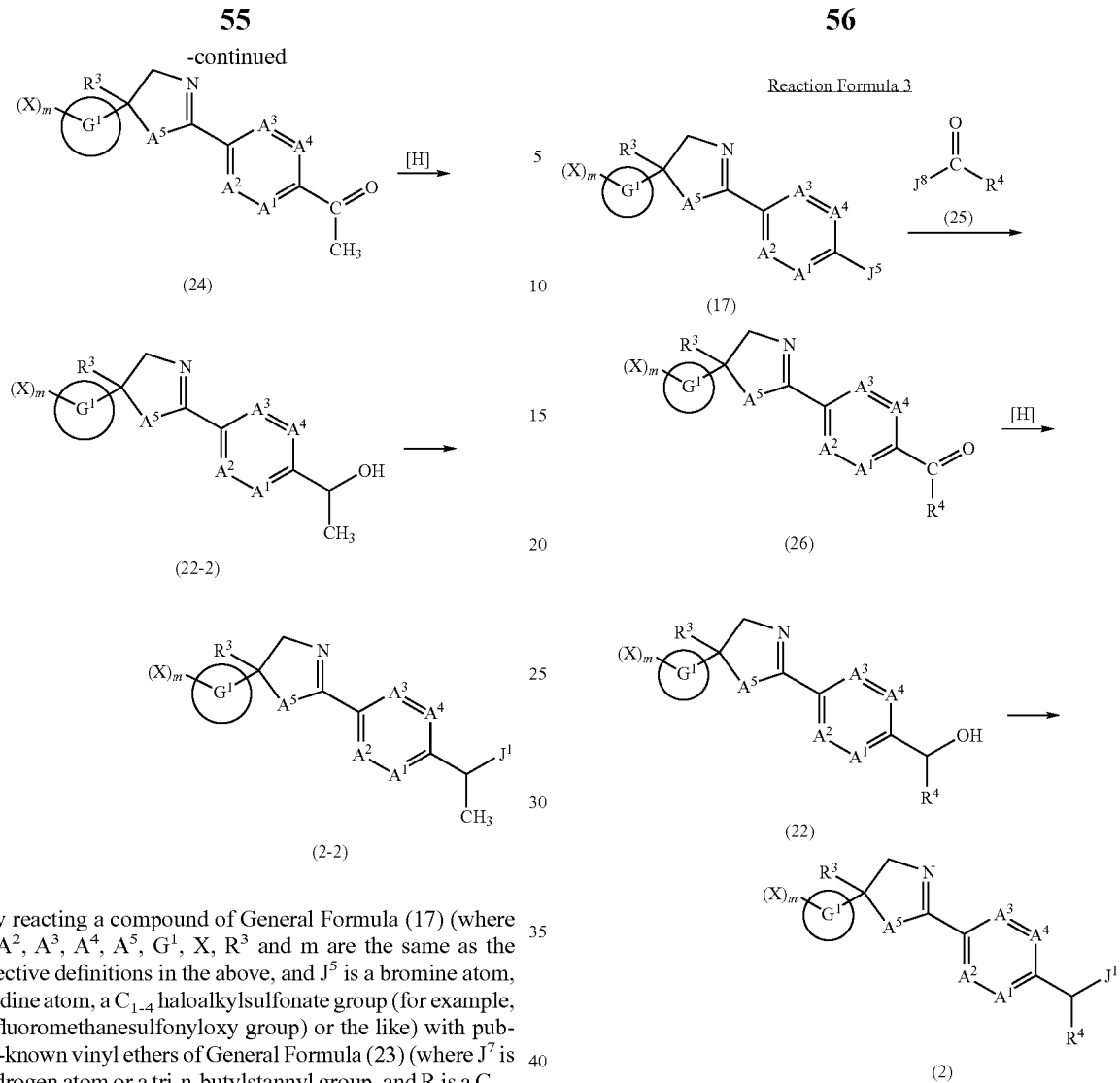

By reacting a compound of General Formula (17) (where $A^1$, $A^2$, $A^3$, $A^4$, $A^5$, $G^1$, X, $R^3$ and m are the same as the respective definitions in the above, and $J^5$ is a bromine atom, an iodine atom, a $C_{1-4}$ haloalkylsulfonate group (for example, a trifluoromethanesulfonyloxy group) or the like) with publicly-known vinyl ethers of General Formula (23) (where $J^7$ is a hydrogen atom or a tri-n-butylstannyl group, and R is a $C_{1-8}$ alkyl group, a 2-hydroxyethyl group, a 2-vinyloxyethyl group or the like) according to publicly-known methods described in literatures, for example, a method described in the Journal of Organic Chemistry (J. Org. Chem.), vol. 66, p. 4340 (2001) using a transition metal catalyst such as palladium, a compound of General Formula (24) (where $A^1$, $A^2$, $A^3$, $A^4$, $A^5$, $G^1$, X, $R^3$ and m are the same as the respective definitions in the above) can be synthesized.

By reducing the thus obtained compound of General Formula (24) to a compound of General Formula (22-2) (where $A^1$, $A^2$, $A^3$, $A^4$, $A^5$, $G^1$, X, $R^3$ and m are the same as the respective definitions in the above) corresponding to General Formula (22) in which $R^4$ is a methyl group according to publicly-known methods described in literatures, for example, a method described in Chemical and Pharmaceutical Bulletin (Chem. Pharm. Bull.), vol. 49, p. 799 (2001) and thereafter, by halogenating the compound of General Formula (22-2) or by sulfonyl-esterification of the compound of General Formula (22-2), for example according to a method described in Journal of Medicinal Chemistry (J. Med. Chem.), vol. 44, p. 3343 (2001), a compound of General Formula (2-2) (where $A^1$, $A^2$, $A^3$, $A^4$, $A^5$, $G^1$, X, $R^3$, m and $J^1$ are the same as the respective definitions in the above) corresponding to General Formula (2) in which $R^4$ is a methyl group can be synthesized.

By reacting a compound of General Formula (17) (where $A^1$, $A^2$, $A^3$, $A^4$, $A^5$, $G^1$, X, $R^3$ and m are the same as the respective definitions in the above, and $J^5$ is a bromine atom or an iodine atom) with a compound of General Formula (25) (where $R^4$ is the same as defined above, and $J^8$ is a $C_{1-4}$ alkoxy group, a di($C_{1-4}$ alkyl)amino group, a piperidino group, a morpholino group, a methoxy(methyl)amino group or the like) according to publicly-known methods described in literatures, for example, a method described in Journal of Medicinal Chemistry (J. Med. Chem.), vol. 47, p. 2405 (2004), a compound of General Formula (26) (where $A^1$, $A^2$, $A^3$, $A^4$, $A^5$, $G^1$, X, $R^3$, $R^4$ and m are the same as the respective definitions in the above) can be synthesized.

Some of the compounds of General Formula (25) used here are publicly-known compounds and some of them are commercially available. The others can be readily synthesized according to general methods for synthesizing publicly-known compounds described in literatures.

By reacting the thus obtained compound of General Formula (26) in substantially the same manner as that of Reaction Formula 2, a compound of General Formula (2)(where $A^1$, $A^2$, $A^3$, $A^4$, $A^5$, $G^1$, X, $R^3$, $R^4$, m and $J^1$ are the same as the respective definitions in the above) can be synthesized.

Reaction Formula 4

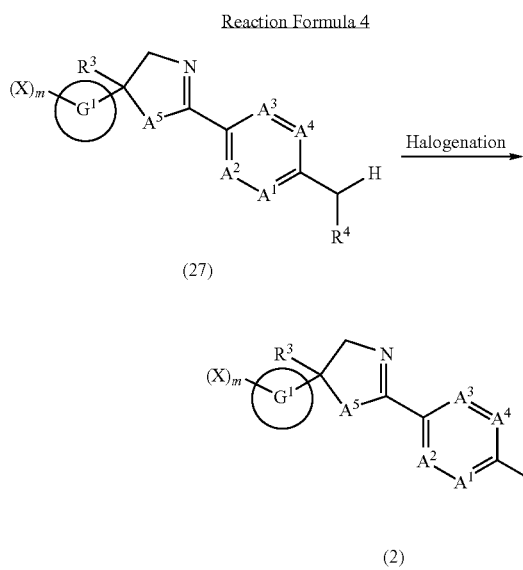

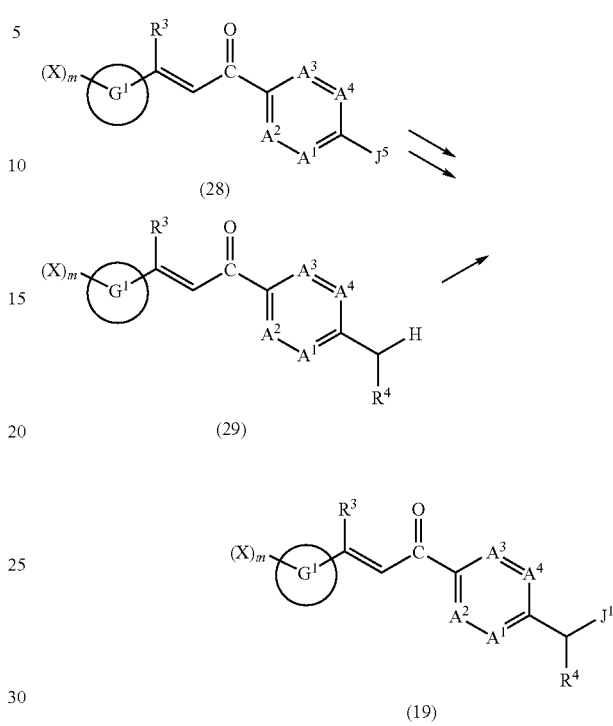

By halogenating a compound of General Formula (27) (where $A^1, A^2, A^3, A^4, A^5, G^1, X, R^3, R^4$ and m are the same as the respective definitions in the above) according to publicly-known methods described in literatures, for example, a method described in Journal of Medicinal Chemistry (J. Med. Chem.), vol. 34, p. 2209 (1991) using N-chlorosuccinimide, N-bromosuccinimide or the like, a compound of General Formula (2) (where $A^1, A^2, A^3, A^4, A^5, G^1, X, R^3, R^4$ and m are the same as the respective definitions in the above, and $J^1$ is a chlorine atom, a bromine atom or the like) can be synthesized.

The compound of General Formula (7) used in Production Method E can be synthesized in substantially the same manner as those for, for example the compound of General Formula (7-1) in Reaction Formula 1, the compound of General Formula (24) in Reaction Formula 2 and the compound of General Formula (26) in Reaction Formula 3.

The compound of General Formula (19) used in Production Method 0 can be synthesized by reacting a compound of General Formula (28) (where $A^1, A^2, A^3, A^4, G^1, X, R^3$ and m are the same as the respective definitions in the above, and $J^5$ is a bromine atom or an iodine atom) in substantially the same manner as those of Reaction Formula 1 to Reaction Formula 3 or by reacting a compound of General Formula (29) (where $A^1, A^2, A^3, A^4, G^1, X, R^3, R^4$ and m are the same as the respective definitions in the above) in substantially the same manner as that of Reaction Formula 4.

Some of the compounds of General Formula (28) and of the compounds of General Formula (29) that are used here are publicly-known compounds described in International Patent Application Publication (No. WO 2007/074789), and the others can be synthesized according to the method described in the literature in substantially the same manner as that for synthesizing the publicly-known compounds.

In each of the reactions, each of the production intermediates to be the starting materials of Production Method A to Production Method O can be obtained by common after treatment after the completion of the reaction.

Furthermore, each of the production intermediates produced by these methods can be also used in a reaction of the next process as they are without isolation and purification.

Specific examples of the active compounds of Structural Formulae [1]-1 to [1]-54 included in the present invention include compounds shown in Table 2 and Table 3. However, the compounds in Table 2 and Table 3 are only for exemplification, and the present invention is not limited to these compounds.

TABLE 2

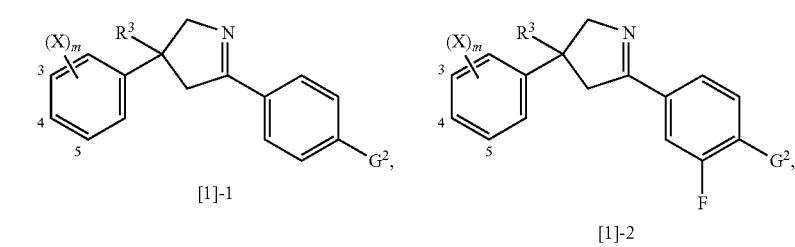

TABLE 2-continued
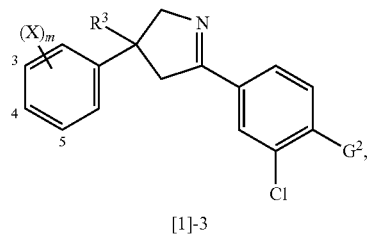
[1]-3
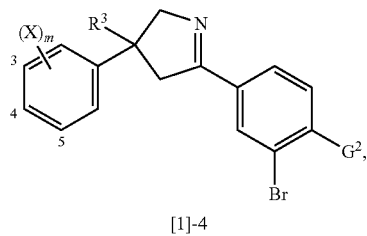
[1]-4
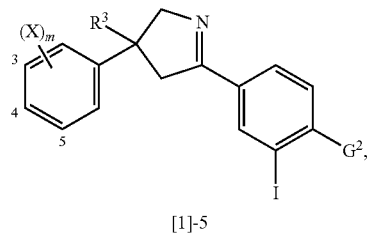
[1]-5
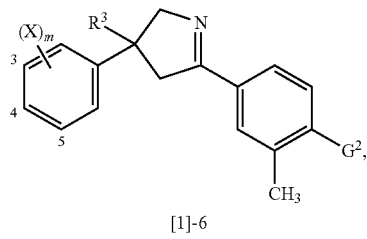
[1]-6
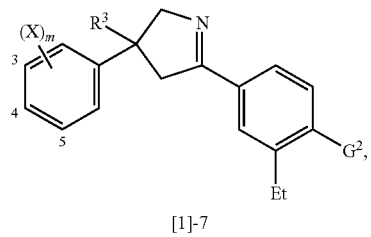
[1]-7
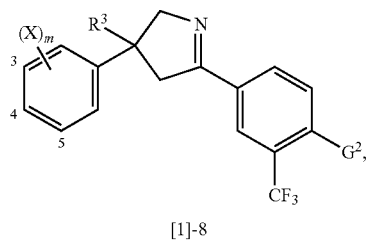
[1]-8
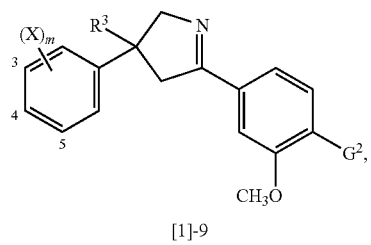
[1]-9
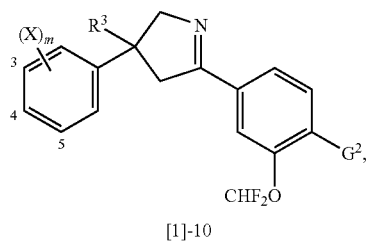
[1]-10
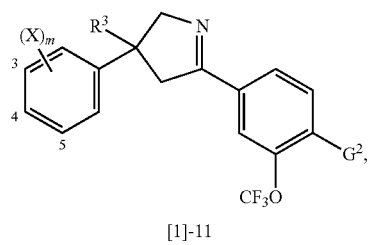
[1]-11
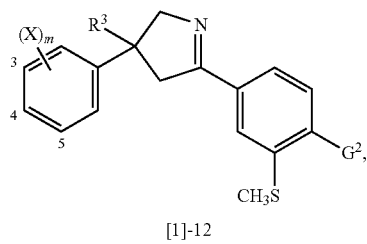
[1]-12
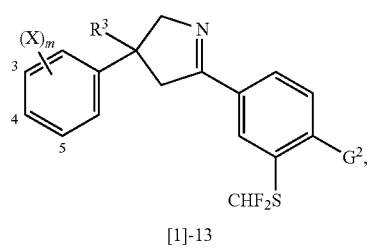
[1]-13
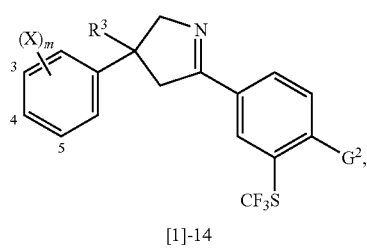
[1]-14

TABLE 2-continued
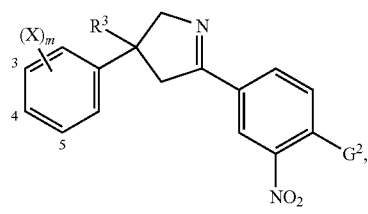
[1]-15
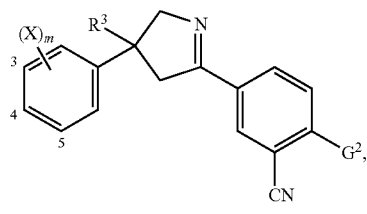
[1]-16
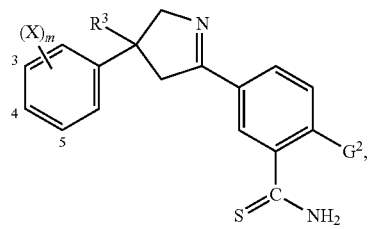
[1]-17
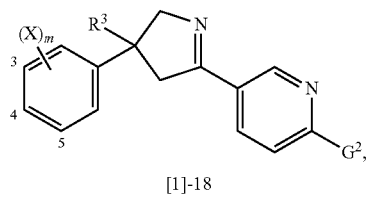
[1]-18
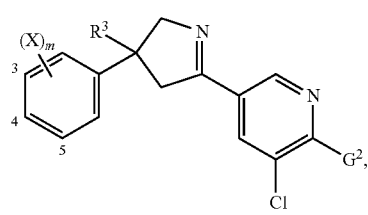
[1]-19
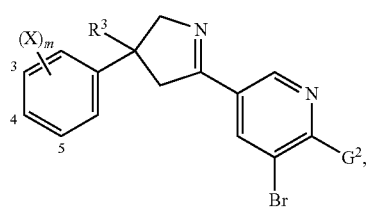
[1]-20
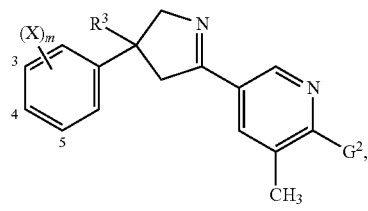
[1]-21
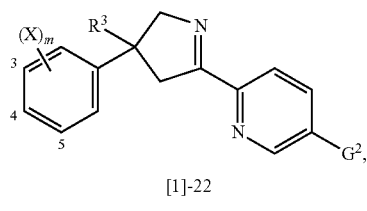
[1]-22
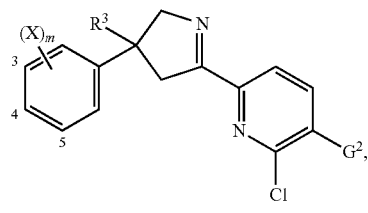
[1]-23
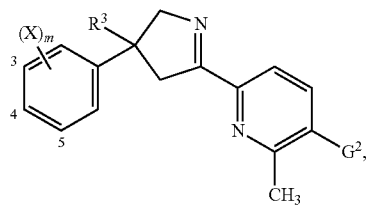
[1]-24
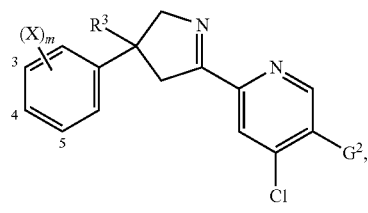
[1]-25
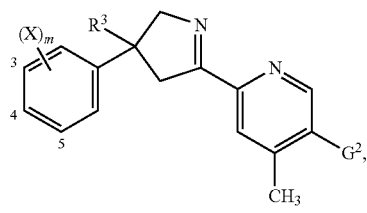
[1]-26

TABLE 2-continued
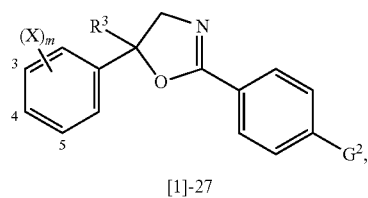
[1]-27
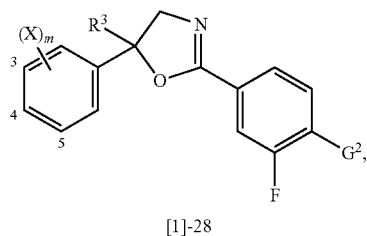
[1]-28
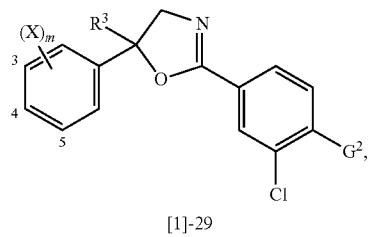
[1]-29
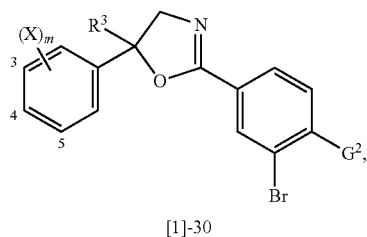
[1]-30
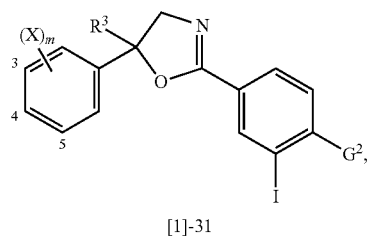
[1]-31
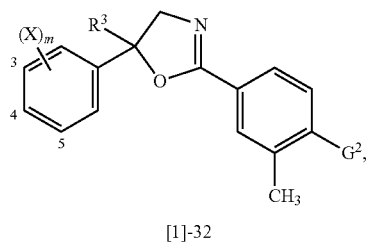
[1]-32
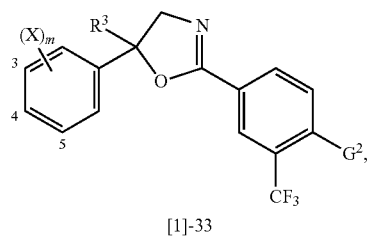
[1]-33
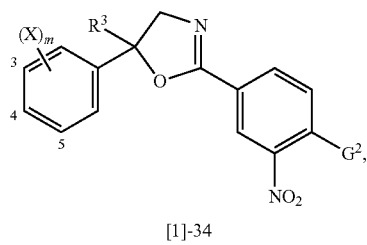
[1]-34
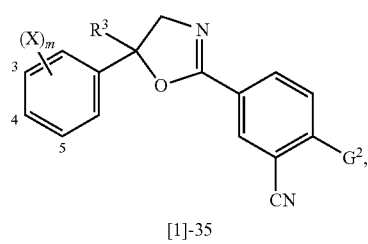
[1]-35
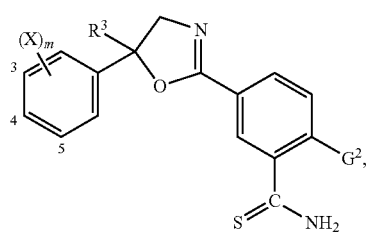
[1]-36
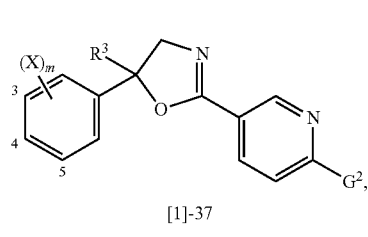
[1]-37
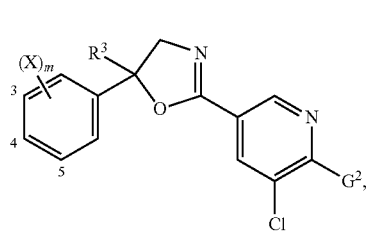
[1]-38

TABLE 2-continued
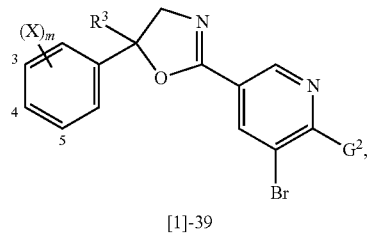
[1]-39
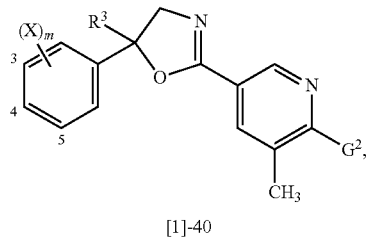
[1]-40
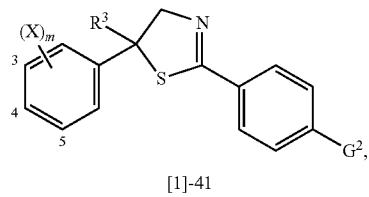
[1]-41
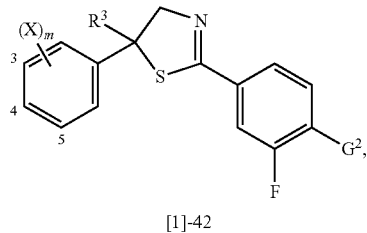
[1]-42
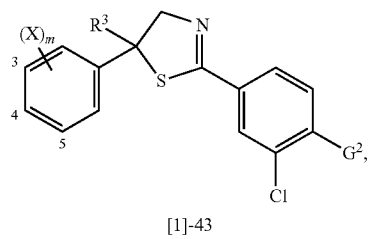
[1]-43
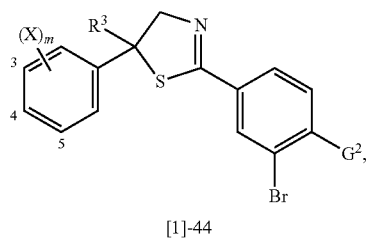
[1]-44
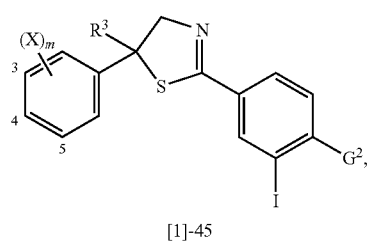
[1]-45
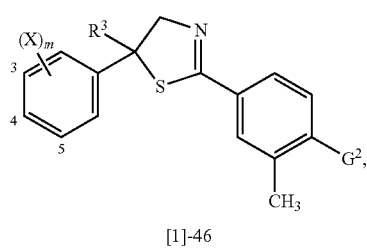
[1]-46
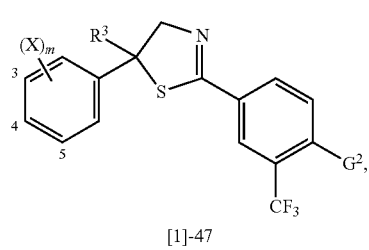
[1]-47
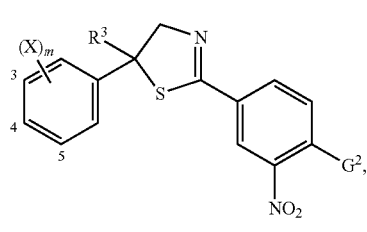
[1]-48
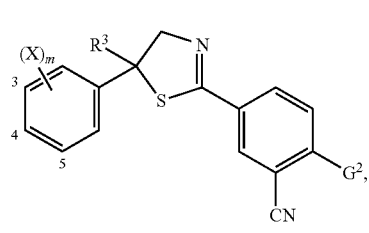
[1]-49
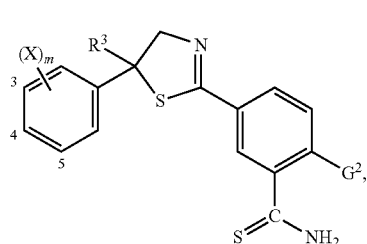
[1]-50

TABLE 2-continued

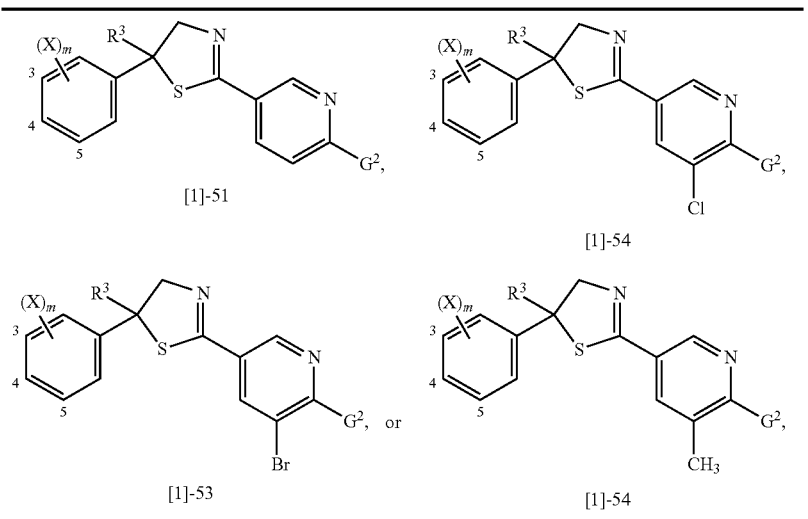

Compounds of Structural Formulae [1]-1 to [1]-54 having a structure in which $G^2$ is $G^2$-1.

$G^2$-1:

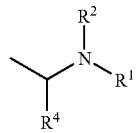

In Table, each of the numbers representing the substituted sites of the substituent $(X)_m$ corresponds to the site indicated by the number in the above Structure Formulae [1]-1 to [1]-54.

In addition, in Table, an aromatic heterocycle of D32-2b is the following structure:

D32-2b:

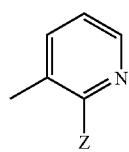

for example, the expression of [C(O)(D32-2b)Cl] is 2-chloronicotinoyl group, and in Table, aliphatic heterocycles of E4-2a, E5-1a, E5-1b and E5-1c respectively are the following structures:

E4-2a:

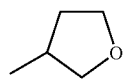

E5-1a:

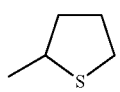

E5-1b:

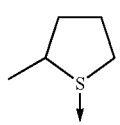

E5-1c:

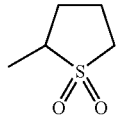

for example, the expression of [C(O)(E4-2a)] is 3-tetrahydrofurylcarbonyl group.

Further, in Table, T-1 to T-3 respectively are the following structures:

T-1:

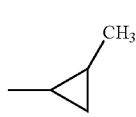

T-2:

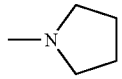

T-3:

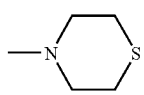

and in Table, an expression as Et is an ethyl group, an expression as Pr-n is a normal propyl group, an expression as Pr-i is an isopropyl group, an expression as Pr-c is a cyclopropyl group, an expression as Bu-i is an isobutyl group, and an expression as Bu-c is a cyclobutyl group.

TABLE 3

| (X)$_m$ | R$^3$ | R$^4$ | R$^2$ | R$^1$ |
|---|---|---|---|---|
| 3-F | CF$_3$ | H | H | C(O)CH$_3$ |
| 3-Cl | CF$_3$ | H | H | C(O)CH$_3$ |
| 3-Cl | CF$_3$ | H | H | C(O)Et |
| 3-Cl | CF$_3$ | H | H | C(O)Pr-n |
| 3-Cl | CF$_3$ | H | H | C(O)Pr-c |
| 3-Cl | CF$_3$ | H | H | C(O)CH$_2$Pr-c |
| 3-Cl | CF$_3$ | H | H | C(O)CH$_2$CF$_3$ |
| 3-Cl | CF$_3$ | H | H | C(O)CH$_2$SCH$_3$ |
| 3-Cl | CF$_3$ | H | H | C(O)CH$_2$S(O)CH$_3$ |
| 3-Cl | CF$_3$ | H | H | C(O)CH$_2$SO$_2$CH$_3$ |
| 3-Cl | CF$_3$ | H | H | C(O)CH$_2$SEt |
| 3-Cl | CF$_3$ | H | H | C(O)CH$_2$S(O)Et |
| 3-Cl | CF$_3$ | H | H | C(O)CH$_2$SO$_2$Et |
| 3-Br | CF$_3$ | H | H | C(O)CH$_3$ |
| 3-Br | CF$_3$ | H | H | C(O)Et |
| 3-Br | CF$_3$ | H | H | C(O)Pr-n |
| 3-Br | CF$_3$ | H | H | C(O)Pr-c |
| 3-Br | CF$_3$ | H | H | C(O)CH$_2$Pr-c |
| 3-Br | CF$_3$ | CH$_3$ | H | C(O)CH$_2$Pr-c |
| 3-Br | CF$_3$ | H | H | C(O)CH$_2$CF$_3$ |
| 3-Br | CF$_3$ | CH$_3$ | H | C(O)CH$_2$CF$_3$ |
| 3-Br | CF$_3$ | CH$_3$ | H | C(O)(E4-2a) |
| 3-Br | CF$_3$ | H | H | C(O)CH$_2$SCH$_3$ |
| 3-Br | CF$_3$ | H | H | C(O)CH$_2$S(O)CH$_3$ |
| 3-Br | CF$_3$ | H | H | C(O)CH$_2$SO$_2$CH$_3$ |
| 3-Br | CF$_3$ | H | H | C(O)CH$_2$SEt |
| 3-Br | CF$_3$ | H | H | C(O)CH$_2$S(O)Et |
| 3-Br | CF$_3$ | H | H | C(O)CH$_2$SO$_2$Et |
| 3-Br | CF$_3$ | H | H | C(O)CH(SCH$_3$)$_2$ |
| 3-Br | CF$_3$ | H | H | C(O)CH[S(O)CH$_3$]$_2$ |
| 3-I | CF$_3$ | H | H | C(O)CH$_3$ |
| 3-I | CF$_3$ | H | Et | C(O)CH$_3$ |
| 3-I | CF$_3$ | H | H | C(O)Et |
| 3-I | CF$_3$ | H | H | C(O)Pr-n |
| 3-I | CF$_3$ | H | H | C(O)Pr-i |
| 3-I | CF$_3$ | H | H | C(O)Pr-c |
| 3-I | CF$_3$ | CH$_3$ | H | C(O)Pr-c |
| 3-I | CF$_3$ | H | H | C(O)Bu-i |
| 3-I | CF$_3$ | H | H | C(O)CH$_2$Pr-c |
| 3-I | CF$_3$ | CH$_3$ | H | C(O)CH$_2$Pr-c |
| 3-I | CF$_3$ | H | H | C(O)CH$_2$CF$_3$ |
| 3-I | CF$_3$ | CH$_3$ | H | C(O)CH$_2$CF$_3$ |
| 3-I | CF$_3$ | CH$_3$ | H | C(O)(E4-2a) |
| 3-I | CF$_3$ | H | H | C(O)CH$_2$SCH$_3$ |
| 3-I | CF$_3$ | H | CH$_2$C≡CH | C(O)CH$_2$SCH$_3$ |
| 3-I | CF$_3$ | CH$_3$ | H | C(O)CH$_2$SCH$_3$ |
| 3-I | CF$_3$ | H | H | C(O)CH$_2$S(O)CH$_3$ |
| 3-I | CF$_3$ | H | H | C(O)CH$_2$SO$_2$CH$_3$ |
| 3-I | CF$_3$ | H | CH$_3$ | C(O)CH$_2$SO$_2$CH$_3$ |
| 3-I | CF$_3$ | H | H | C(O)CH$_2$SEt |
| 3-I | CF$_3$ | H | H | C(O)CH$_2$S(O)Et |
| 3-I | CF$_3$ | H | H | C(O)CH$_2$SO$_2$Et |
| 3-I | CF$_3$ | H | H | C(O)CH(SCH$_3$)$_2$ |
| 3-I | CF$_3$ | H | H | C(O)CH[S(O)CH$_3$]$_2$ |
| 3-I | CF$_3$ | H | H | C(O)NHPr-c |
| 3-I | CF$_2$Cl | H | H | C(O)CH$_3$ |
| 3-I | CF$_2$Cl | H | H | C(O)Et |
| 3-I | CF$_2$Cl | H | H | C(O)Pr-n |
| 3-I | CF$_2$Cl | H | H | C(O)Pr-c |
| 3-I | CF$_2$Cl | H | H | C(O)CH$_2$Pr-c |
| 3-I | CF$_2$Cl | H | H | C(O)CH$_2$CF$_3$ |
| 3-I | CF$_2$Cl | H | H | C(O)CH$_2$SCH$_3$ |
| 3-I | CF$_2$Cl | H | H | C(O)CH$_2$S(O)CH$_3$ |
| 3-I | CF$_2$Cl | H | H | C(O)CH$_2$SO$_2$CH$_3$ |
| 3-I | CF$_2$Cl | H | H | C(O)CH$_2$SEt |
| 3-I | CF$_2$Cl | H | H | C(O)CH$_2$S(O)Et |
| 3-I | CF$_2$Cl | H | H | C(O)CH$_2$SO$_2$Et |
| 3-CF$_3$ | CF$_3$ | H | H | C(O)CH$_3$ |
| 3-CF$_3$ | CF$_3$ | H | Et | C(O)CH$_3$ |
| 3-CF$_3$ | CF$_3$ | H | H | C(O)Et |
| 3-CF$_3$ | CF$_3$ | H | H | C(O)Pr-n |
| 3-CF$_3$ | CF$_3$ | H | H | C(O)Pr-i |
| 3-CF$_3$ | CF$_3$ | H | H | C(O)Pr-c |
| 3-CF$_3$ | CF$_3$ | CH$_3$ | H | C(O)Pr-c |
| 3-CF$_3$ | CF$_3$ | H | H | C(O)Bu-i |
| 3-CF$_3$ | CF$_3$ | H | H | C(O)CH$_2$Pr-c |
| 3-CF$_3$ | CF$_3$ | CH$_3$ | H | C(O)CH$_2$Pr-c |
| 3-CF$_3$ | CF$_3$ | H | H | C(O)CH$_2$CF$_3$ |

TABLE 3-continued

| $(X)_m$ | $R^3$ | $R^4$ | $R^2$ | $R^1$ |
|---|---|---|---|---|
| 3-CF$_3$ | CF$_3$ | CH$_3$ | H | C(O)CH$_2$CF$_3$ |
| 3-CF$_3$ | CF$_3$ | CH$_3$ | H | C(O)(E4-2a) |
| 3-CF$_3$ | CF$_3$ | H | H | C(O)CH$_2$SCH$_3$ |
| 3-CF$_3$ | CF$_3$ | H | CH$_2$C≡CH | C(O)CH$_2$SCH$_3$ |
| 3-CF$_3$ | CF$_3$ | CH$_3$ | H | C(O)CH$_2$SCH$_3$ |
| 3-CF$_3$ | CF$_3$ | H | H | C(O)CH$_2$S(O)CH$_3$ |
| 3-CF$_3$ | CF$_3$ | H | H | C(O)CH$_2$SO$_2$CH$_3$ |
| 3-CF$_3$ | CF$_3$ | H | CH$_3$ | C(O)CH$_2$SO$_2$CH$_3$ |
| 3-CF$_3$ | CF$_3$ | H | H | C(O)CH$_2$SEt |
| 3-CF$_3$ | CF$_3$ | H | H | C(O)CH$_2$S(O)Et |
| 3-CF$_3$ | CF$_3$ | H | H | C(O)CH$_2$SO$_2$Et |
| 3-CF$_3$ | CF$_3$ | H | H | C(O)CH(SCH$_3$)$_2$ |
| 3-CF$_3$ | CF$_3$ | H | H | C(O)CH[S(O)CH$_3$]$_2$ |
| 3-CF$_3$ | CF$_3$ | H | H | C(O)NHPr-c |
| 3-CF$_3$ | CF$_2$Cl | H | H | C(O)CH$_3$ |
| 3-CF$_3$ | CF$_2$Cl | H | H | C(O)Et |
| 3-CF$_3$ | CF$_2$Cl | H | H | C(O)Pr-n |
| 3-CF$_3$ | CF$_2$Cl | H | H | C(O)Pr-c |
| 3-CF$_3$ | CF$_2$Cl | H | H | C(O)CH$_2$Pr-c |
| 3-CF$_3$ | CF$_2$Cl | H | H | C(O)CH$_2$CF$_3$ |
| 3-CF$_3$ | CF$_2$Cl | H | H | C(O)CH$_2$SCH$_3$ |
| 3-CF$_3$ | CF$_2$Cl | H | H | C(O)CH$_2$S(O)CH$_3$ |
| 3-CF$_3$ | CF$_2$Cl | H | H | C(O)CH$_2$SO$_2$CH$_3$ |
| 3-CF$_3$ | CF$_2$Cl | H | H | C(O)CH$_2$SEt |
| 3-CF$_3$ | CF$_2$Cl | H | H | C(O)CH$_2$S(O)Et |
| 3-CF$_3$ | CF$_2$Cl | H | H | C(O)CH$_2$SO$_2$Et |
| 3-CF$_2$CF$_3$ | CF$_3$ | H | H | C(O)CH$_3$ |
| 3-CF$_2$CF$_3$ | CF$_3$ | H | H | C(O)Et |
| 3-CF$_2$CF$_3$ | CF$_3$ | H | H | C(O)Pr-n |
| 3-CF$_2$CF$_3$ | CF$_3$ | H | H | C(O)Pr-c |
| 3-CF$_2$CF$_3$ | CF$_3$ | H | H | C(O)CH$_2$Pr-c |
| 3-CF$_2$CF$_3$ | CF$_3$ | CH$_3$ | H | C(O)CH$_2$Pr-c |
| 3-CF$_2$CF$_3$ | CF$_3$ | H | H | C(O)CH$_2$CF$_3$ |
| 3-CF$_2$CF$_3$ | CF$_3$ | CH$_3$ | H | C(O)CH$_2$CF$_3$ |
| 3-CF$_2$CF$_3$ | CF$_3$ | CH$_3$ | H | C(O)(E4-2a) |
| 3-CF$_2$CF$_3$ | CF$_3$ | H | H | C(O)CH$_2$SCH$_3$ |
| 3-CF$_2$CF$_3$ | CF$_3$ | H | H | C(O)CH$_2$S(O)CH$_3$ |
| 3-CF$_2$CF$_3$ | CF$_3$ | H | H | C(O)CH$_2$SO$_2$CH$_3$ |
| 3-CF$_2$CF$_3$ | CF$_3$ | H | H | C(O)CH$_2$SEt |
| 3-CF$_2$CF$_3$ | CF$_3$ | H | H | C(O)CH$_2$S(O)Et |
| 3-CF$_2$CF$_3$ | CF$_3$ | H | H | C(O)CH$_2$SO$_2$Et |
| 3-CF$_2$CF$_3$ | CF$_3$ | H | H | C(O)CH(SCH$_3$)$_2$ |
| 3-CF$_2$CF$_3$ | CF$_3$ | H | H | C(O)CH[S(O)CH$_3$]$_2$ |
| 3-CF$_2$CF$_2$CF$_3$ | CF$_3$ | H | H | C(O)CH$_3$ |
| 3-CF$_2$CF$_2$CF$_3$ | CF$_3$ | H | H | C(O)Et |
| 3-CF$_2$CF$_2$CF$_3$ | CF$_3$ | H | H | C(O)Pr-n |
| 3-CF$_2$CF$_2$CF$_3$ | CF$_3$ | H | H | C(O)Pr-c |
| 3-CF$_2$CF$_2$CF$_3$ | CF$_3$ | H | H | C(O)CH$_2$Pr-c |
| 3-CF$_2$CF$_2$CF$_3$ | CF$_3$ | H | H | C(O)CH$_2$CF$_3$ |
| 3-CF$_2$CF$_2$CF$_3$ | CF$_3$ | H | H | C(O)CH$_2$SCH$_3$ |
| 3-CF$_2$CF$_2$CF$_3$ | CF$_3$ | H | H | C(O)CH$_2$S(O)CH$_3$ |
| 3-CF$_2$CF$_2$CF$_3$ | CF$_3$ | H | H | C(O)CH$_2$SO$_2$CH$_3$ |
| 3-CF$_2$CF$_2$CF$_3$ | CF$_3$ | H | H | C(O)CH$_2$SEt |
| 3-CF$_2$CF$_2$CF$_3$ | CF$_3$ | H | H | C(O)CH$_2$S(O)Et |
| 3-CF$_2$CF$_2$CF$_3$ | CF$_3$ | H | H | C(O)CH$_2$SO$_2$Et |
| 3-CF(CF$_3$)$_2$ | CF$_3$ | H | H | C(O)CH$_3$ |
| 3-CF(CF$_3$)$_2$ | CF$_3$ | H | H | C(O)Et |
| 3-CF(CF$_3$)$_2$ | CF$_3$ | H | H | C(O)Pr-n |
| 3-CF(CF$_3$)$_2$ | CF$_3$ | H | H | C(O)Pr-c |
| 3-CF(CF$_3$)$_2$ | CF$_3$ | H | H | C(O)CH$_2$Pr-c |
| 3-CF(CF$_3$)$_2$ | CF$_3$ | H | H | C(O)CH$_2$CF$_3$ |
| 3-CF(CF$_3$)$_2$ | CF$_3$ | H | H | C(O)CH$_2$SCH$_3$ |
| 3-CF(CF$_3$)$_2$ | CF$_3$ | H | H | C(O)CH$_2$S(O)CH$_3$ |
| 3-CF(CF$_3$)$_2$ | CF$_3$ | H | H | C(O)CH$_2$SO$_2$CH$_3$ |
| 3-CF(CF$_3$)$_2$ | CF$_3$ | H | H | C(O)CH$_2$SEt |
| 3-CF(CF$_3$)$_2$ | CF$_3$ | H | H | C(O)CH$_2$S(O)Et |
| 3-CF(CF$_3$)$_2$ | CF$_3$ | H | H | C(O)CH$_2$SO$_2$Et |
| 3-CF$_2$CF$_2$CF$_2$CF$_3$ | CF$_3$ | H | H | C(O)Et |
| 3-C(CF$_3$)$_2$OH | CF$_3$ | H | H | C(O)Pr-n |
| 3-C(CF$_3$)$_2$OCH$_3$ | CF$_3$ | H | H | C(O)Pr-c |
| 3-OCF$_3$ | CF$_3$ | H | H | C(O)CH$_3$ |
| 3-OCF$_3$ | CF$_3$ | H | H | C(O)Et |
| 3-OCF$_3$ | CF$_3$ | H | H | C(O)Pr-n |
| 3-OCF$_3$ | CF$_3$ | H | H | C(O)Pr-c |
| 3-OCF$_3$ | CF$_3$ | H | H | C(O)CH$_2$Pr-c |
| 3-OCF$_3$ | CF$_3$ | CH$_3$ | H | C(O)CH$_2$Pr-c |
| 3-OCF$_3$ | CF$_3$ | H | H | C(O)CH$_2$CF$_3$ |
| 3-OCF$_3$ | CF$_3$ | CH$_3$ | H | C(O)CH$_2$CF$_3$ |

TABLE 3-continued

| (X)$_m$ | R$^3$ | R$^4$ | R$^2$ | R$^1$ |
|---|---|---|---|---|
| 3-OCF$_3$ | CF$_3$ | CH$_3$ | H | C(O)(E4-2a) |
| 3-OCF$_3$ | CF$_3$ | H | H | C(O)CH$_2$SCH$_3$ |
| 3-OCF$_3$ | CF$_3$ | H | H | C(O)CH$_2$S(O)CH$_3$ |
| 3-OCF$_3$ | CF$_3$ | H | H | C(O)CH$_2$SO$_2$CH$_3$ |
| 3-OCF$_3$ | CF$_3$ | H | H | C(O)CH$_2$SEt |
| 3-OCF$_3$ | CF$_3$ | H | H | C(O)CH$_2$S(O)Et |
| 3-OCF$_3$ | CF$_3$ | H | H | C(O)CH$_2$SO$_2$Et |
| 3-OCF$_3$ | CF$_3$ | H | H | C(O)CH(SCH$_3$)$_2$ |
| 3-OCF$_3$ | CF$_3$ | H | H | C(O)CH[S(O)CH$_3$]$_2$ |
| 3-OCF$_2$Br | CF$_3$ | H | H | C(O)CH$_3$ |
| 3-OCF$_2$Br | CF$_3$ | H | H | C(O)Et |
| 3-OCF$_2$Br | CF$_3$ | H | H | C(O)Pr-n |
| 3-OCF$_2$Br | CF$_3$ | H | H | C(O)Pr-c |
| 3-OCF$_2$Br | CF$_3$ | H | H | C(O)CH$_2$Pr-c |
| 3-OCF$_2$Br | CF$_3$ | H | H | C(O)CH$_2$CF$_3$ |
| 3-OCF$_2$Br | CF$_3$ | H | H | C(O)CH$_2$SCH$_3$ |
| 3-OCF$_2$Br | CF$_3$ | H | H | C(O)CH$_2$S(O)CH$_3$ |
| 3-OCF$_2$Br | CF$_3$ | H | H | C(O)CH$_2$SO$_2$CH$_3$ |
| 3-OCF$_2$Br | CF$_3$ | H | H | C(O)CH$_2$SEt |
| 3-OCF$_2$Br | CF$_3$ | H | H | C(O)CH$_2$S(O)Et |
| 3-OCF$_2$Br | CF$_3$ | H | H | C(O)CH$_2$SO$_2$Et |
| 3-OCF$_2$CHF$_2$ | CF$_3$ | H | H | C(O)CH$_2$Pr-c |
| 3-OCF$_2$CHFCl | CF$_3$ | H | H | C(O)CH$_2$CF$_3$ |
| 3-OCF$_2$CHFCF$_3$ | CF$_3$ | H | H | C(O)CH$_2$SCH$_3$ |
| 3-OCF$_2$CHFOCF$_3$ | CF$_3$ | H | H | C(O)CH$_2$S(O)CH$_3$ |
| 3-SCF$_3$ | CF$_3$ | H | H | C(O)CH$_3$ |
| 3-SCF$_3$ | CF$_3$ | H | H | C(O)Et |
| 3-SCF$_3$ | CF$_3$ | H | H | C(O)Pr-n |
| 3-SCF$_3$ | CF$_3$ | H | H | C(O)Pr-c |
| 3-SCF$_3$ | CF$_3$ | H | H | C(O)CH$_2$Pr-c |
| 3-SCF$_3$ | CF$_3$ | CH$_3$ | H | C(O)CH$_2$Pr-c |
| 3-SCF$_3$ | CF$_3$ | H | H | C(O)CH$_2$CF$_3$ |
| 3-SCF$_3$ | CF$_3$ | CH$_3$ | H | C(O)CH$_2$CF$_3$ |
| 3-SCF$_3$ | CF$_3$ | CH$_3$ | H | C(O)(E4-2a) |
| 3-SCF$_3$ | CF$_3$ | H | H | C(O)CH$_2$SCH$_3$ |
| 3-SCF$_3$ | CF$_3$ | H | H | C(O)CH$_2$S(O)CH$_3$ |
| 3-SCF$_3$ | CF$_3$ | H | H | C(O)CH$_2$SO$_2$CH$_3$ |
| 3-SCF$_3$ | CF$_3$ | H | H | C(O)CH$_2$SEt |
| 3-SCF$_3$ | CF$_3$ | H | H | C(O)CH$_2$S(O)Et |
| 3-SCF$_3$ | CF$_3$ | H | H | C(O)CH$_2$SO$_2$Et |
| 3-SCF$_3$ | CF$_3$ | H | H | C(O)CH(SCH$_3$)$_2$ |
| 3-SCF$_3$ | CF$_3$ | H | H | C(O)CH[S(O)CH$_3$]$_2$ |
| 3-SCF$_2$Cl | CF$_3$ | H | H | C(O)CH$_3$ |
| 3-SCF$_2$Cl | CF$_3$ | H | H | C(O)Et |
| 3-SCF$_2$Cl | CF$_3$ | H | H | C(O)Pr-n |
| 3-SCF$_2$Cl | CF$_3$ | H | H | C(O)Pr-c |
| 3-SCF$_2$Cl | CF$_3$ | H | H | C(O)CH$_2$Pr-c |
| 3-SCF$_2$Cl | CF$_3$ | H | H | C(O)CH$_2$CF$_3$ |
| 3-SCF$_2$Cl | CF$_3$ | H | H | C(O)CH$_2$SCH$_3$ |
| 3-SCF$_2$Cl | CF$_3$ | H | H | C(O)CH$_2$S(O)CH$_3$ |
| 3-SCF$_2$Cl | CF$_3$ | H | H | C(O)CH$_2$SO$_2$CH$_3$ |
| 3-SCF$_2$Cl | CF$_3$ | H | H | C(O)CH$_2$SEt |
| 3-SCF$_2$Cl | CF$_3$ | H | H | C(O)CH$_2$S(O)Et |
| 3-SCF$_2$Cl | CF$_3$ | H | H | C(O)CH$_2$SO$_2$Et |
| 3-SCF$_2$Br | CF$_3$ | H | H | C(O)CH$_3$ |
| 3-SCF$_2$Br | CF$_3$ | H | H | C(O)Et |
| 3-SCF$_2$Br | CF$_3$ | H | H | C(O)Pr-n |
| 3-SCF$_2$Br | CF$_3$ | H | H | C(O)Pr-c |
| 3-SCF$_2$Br | CF$_3$ | H | H | C(O)CH$_2$Pr-c |
| 3-SCF$_2$Br | CF$_3$ | H | H | C(O)CH$_2$CF$_3$ |
| 3-SCF$_2$Br | CF$_3$ | H | H | C(O)CH$_2$SCH$_3$ |
| 3-SCF$_2$Br | CF$_3$ | H | H | C(O)CH$_2$S(O)CH$_3$ |
| 3-SCF$_2$Br | CF$_3$ | H | H | C(O)CH$_2$SO$_2$CH$_3$ |
| 3-SCF$_2$Br | CF$_3$ | H | H | C(O)CH$_2$SEt |
| 3-SCF$_2$Br | CF$_3$ | H | H | C(O)CH$_2$S(O)Et |
| 3-SCF$_2$Br | CF$_3$ | H | H | C(O)CH$_2$SO$_2$Et |
| 3-SF$_5$ | CF$_3$ | H | H | C(O)CH$_3$ |
| 3-SF$_5$ | CF$_3$ | H | H | C(O)Et |
| 3-SF$_5$ | CF$_3$ | H | H | C(O)Pr-n |
| 3-SF$_5$ | CF$_3$ | H | H | C(O)Pr-c |
| 3-SF$_5$ | CF$_3$ | H | H | C(O)CH$_2$Pr-c |
| 3-SF$_5$ | CF$_3$ | CH$_3$ | H | C(O)CH$_2$Pr-c |
| 3-SF$_5$ | CF$_3$ | H | H | C(O)CH$_2$CF$_3$ |
| 3-SF$_5$ | CF$_3$ | CH$_3$ | H | C(O)CH$_2$CF$_3$ |
| 3-SF$_5$ | CF$_3$ | CH$_3$ | H | C(O)(E4-2a) |
| 3-SF$_5$ | CF$_3$ | H | H | C(O)CH$_2$SCH$_3$ |
| 3-SF$_5$ | CF$_3$ | H | H | C(O)CH$_2$S(O)CH$_3$ |
| 3-SF$_5$ | CF$_3$ | H | H | C(O)CH$_2$SO$_2$CH$_3$ |

TABLE 3-continued

| (X)$_m$ | R$^3$ | R$^4$ | R$^2$ | R$^1$ |
|---|---|---|---|---|
| 3-SF$_5$ | CF$_3$ | H | H | C(O)CH$_2$SEt |
| 3-SF$_5$ | CF$_3$ | H | H | C(O)CH$_2$S(O)Et |
| 3-SF$_5$ | CF$_3$ | H | H | C(O)CH$_2$SO$_2$Et |
| 3-SF$_5$ | CF$_3$ | H | H | C(O)CH(SCH$_3$)$_2$ |
| 3-SF$_5$ | CF$_3$ | H | H | C(O)CH[S(O)CH$_3$]$_2$ |
| 3,4-F$_2$ | CF$_3$ | H | H | C(O)CH$_2$SO$_2$CH$_3$ |
| 3,5-F$_2$ | CF$_3$ | H | H | C(O)CH$_2$SEt |
| 3-Cl-4-F | CF$_3$ | H | H | C(O)CH$_3$ |
| 3-Cl-4-F | CF$_3$ | H | Et | C(O)CH$_3$ |
| 3-Cl-4-F | CF$_3$ | H | H | C(O)Et |
| 3-Cl-4-F | CF$_3$ | H | H | C(O)Pr-n |
| 3-Cl-4-F | CF$_3$ | H | H | C(O)Pr-i |
| 3-Cl-4-F | CF$_3$ | H | H | C(O)Pr-c |
| 3-Cl-4-F | CF$_3$ | CH$_3$ | H | C(O)Pr-c |
| 3-Cl-4-F | CF$_3$ | H | H | C(O)Bu-i |
| 3-Cl-4-F | CF$_3$ | H | H | C(O)CH$_2$Pr-c |
| 3-Cl-4-F | CF$_3$ | CH$_3$ | H | C(O)CH$_2$Pr-c |
| 3-Cl-4-F | CF$_3$ | H | H | C(O)CH$_2$CF$_3$ |
| 3-Cl-4-F | CF$_3$ | CH$_3$ | H | C(O)CH$_2$CF$_3$ |
| 3-Cl-4-F | CF$_3$ | CH$_3$ | H | C(O)(E4-2a) |
| 3-Cl-4-F | CF$_3$ | H | H | C(O)CH$_2$SCH$_3$ |
| 3-Cl-4-F | CF$_3$ | H | CH$_2$C≡CH | C(O)CH$_2$SCH$_3$ |
| 3-Cl-4-F | CF$_3$ | CH$_3$ | H | C(O)CH$_2$SCH$_3$ |
| 3-Cl-4-F | CF$_3$ | H | H | C(O)CH$_2$S(O)CH$_3$ |
| 3-Cl-4-F | CF$_3$ | H | H | C(O)CH$_2$SO$_2$CH$_3$ |
| 3-Cl-4-F | CF$_3$ | H | CH$_3$ | C(O)CH$_2$SO$_2$CH$_3$ |
| 3-Cl-4-F | CF$_3$ | H | H | C(O)CH$_2$SEt |
| 3-Cl-4-F | CF$_3$ | H | H | C(O)CH$_2$S(O)Et |
| 3-Cl-4-F | CF$_3$ | H | H | C(O)CH$_2$SO$_2$Et |
| 3-Cl-4-F | CF$_3$ | H | H | C(O)CH(SCH$_3$)$_2$ |
| 3-Cl-4-F | CF$_3$ | H | H | C(O)CH[S(O)CH$_3$]$_2$ |
| 3-Cl-4-F | CF$_3$ | H | H | C(O)NHPr-c |
| 3-Cl-4-F | CF$_2$Cl | H | H | C(O)CH$_3$ |
| 3-Cl-4-F | CF$_2$Cl | H | H | C(O)Et |
| 3-Cl-4-F | CF$_2$Cl | H | H | C(O)Pr-n |
| 3-Cl-4-F | CF$_2$Cl | H | H | C(O)Pr-c |
| 3-Cl-4-F | CF$_2$Cl | H | H | C(O)CH$_2$Pr-c |
| 3-Cl-4-F | CF$_2$Cl | H | H | C(O)CH$_2$CF$_3$ |
| 3-Cl-4-F | CF$_2$Cl | H | H | C(O)CH$_2$SCH$_3$ |
| 3-Cl-4-F | CF$_2$Cl | H | H | C(O)CH$_2$S(O)CH$_3$ |
| 3-Cl-4-F | CF$_2$Cl | H | H | C(O)CH$_2$SO$_2$CH$_3$ |
| 3-Cl-4-F | CF$_2$Cl | H | H | C(O)CH$_2$SEt |
| 3-Cl-4-F | CF$_2$Cl | H | H | C(O)CH$_2$S(O)Et |
| 3-Cl-4-F | CF$_2$Cl | H | H | C(O)CH$_2$SO$_2$Et |
| 3-F-5-Cl | CF$_3$ | H | H | C(O)CH$_3$ |
| 3-F-5-Cl | CF$_3$ | H | Et | C(O)CH$_3$ |
| 3-F-5-Cl | CF$_3$ | H | H | C(O)Et |
| 3-F-5-Cl | CF$_3$ | H | H | C(O)Pr-n |
| 3-F-5-Cl | CF$_3$ | H | H | C(O)Pr-i |
| 3-F-5-Cl | CF$_3$ | H | H | C(O)Pr-c |
| 3-F-5-Cl | CF$_3$ | CH$_3$ | H | C(O)Pr-c |
| 3-F-5-Cl | CF$_3$ | H | H | C(O)Bu-i |
| 3-F-5-Cl | CF$_3$ | H | H | C(O)CH$_2$Pr-c |
| 3-F-5-Cl | CF$_3$ | CH$_3$ | H | C(O)CH$_2$Pr-c |
| 3-F-5-Cl | CF$_3$ | H | H | C(O)CH$_2$CF$_3$ |
| 3-F-5-Cl | CF$_3$ | CH$_3$ | H | C(O)CH$_2$CF$_3$ |
| 3-F-5-Cl | CF$_3$ | CH$_3$ | H | C(O)(E4-2a) |
| 3-F-5-Cl | CF$_3$ | H | H | C(O)CH$_2$SCH$_3$ |
| 3-F-5-Cl | CF$_3$ | H | CH$_2$C≡CH | C(O)CH$_2$SCH$_3$ |
| 3-F-5-Cl | CF$_3$ | CH$_3$ | H | C(O)CH$_2$SCH$_3$ |
| 3-F-5-Cl | CF$_3$ | H | H | C(O)CH$_2$S(O)CH$_3$ |
| 3-F-5-Cl | CF$_3$ | H | H | C(O)CH$_2$SO$_2$CH$_3$ |
| 3-F-5-Cl | CF$_3$ | H | CH$_3$ | C(O)CH$_2$SO$_2$CH$_3$ |
| 3-F-5-Cl | CF$_3$ | H | H | C(O)CH$_2$SEt |
| 3-F-5-Cl | CF$_3$ | H | H | C(O)CH$_2$S(O)Et |
| 3-F-5-Cl | CF$_3$ | H | H | C(O)CH$_2$SO$_2$Et |
| 3-F-5-Cl | CF$_3$ | H | H | C(O)CH(SCH$_3$)$_2$ |
| 3-F-5-Cl | CF$_3$ | H | H | C(O)CH[S(O)CH$_3$]$_2$ |
| 3-F-5-Cl | CF$_3$ | H | H | C(O)NHPr-c |
| 3-F-5-Cl | CF$_2$Cl | H | H | C(O)CH$_3$ |
| 3-F-5-Cl | CF$_2$Cl | H | H | C(O)Et |
| 3-F-5-Cl | CF$_2$Cl | H | H | C(O)Pr-n |
| 3-F-5-Cl | CF$_2$Cl | H | H | C(O)Pr-c |
| 3-F-5-Cl | CF$_2$Cl | H | H | C(O)CH$_2$Pr-c |
| 3-F-5-Cl | CF$_2$Cl | H | H | C(O)CH$_2$CF$_3$ |
| 3-F-5-Cl | CF$_2$Cl | H | H | C(O)CH$_2$SCH$_3$ |
| 3-F-5-Cl | CF$_2$Cl | H | H | C(O)CH$_2$S(O)CH$_3$ |
| 3-F-5-Cl | CF$_2$Cl | H | H | C(O)CH$_2$SO$_2$CH$_3$ |

TABLE 3-continued

| (X)$_m$ | R$^3$ | R$^4$ | R$^2$ | R$^1$ |
|---|---|---|---|---|
| 3-F-5-Cl | CF$_2$Cl | H | H | C(O)CH$_2$SEt |
| 3-F-5-Cl | CF$_2$Cl | H | H | C(O)CH$_2$S(O)Et |
| 3-F-5-Cl | CF$_2$Cl | H | H | C(O)CH$_2$SO$_2$Et |
| 3,4-Cl$_2$ | CF$_3$ | H | H | C(O)CH$_3$ |
| 3,4-Cl$_2$ | CF$_3$ | H | Et | C(O)CH$_3$ |
| 3,4-Cl$_2$ | CF$_3$ | H | H | C(O)Et |
| 3,4-Cl$_2$ | CF$_3$ | H | H | C(O)Pr-n |
| 3,4-Cl$_2$ | CF$_3$ | H | H | C(O)Pr-i |
| 3,4-Cl$_2$ | CF$_3$ | H | H | C(O)Pr-c |
| 3,4-Cl$_2$ | CF$_3$ | CH$_3$ | H | C(O)Pr-c |
| 3,4-Cl$_2$ | CF$_3$ | H | H | C(O)Bu-i |
| 3,4-Cl$_2$ | CF$_3$ | H | H | C(O)CH$_2$Pr-c |
| 3,4-Cl$_2$ | CF$_3$ | CH$_3$ | H | C(O)CH$_2$Pr-c |
| 3,4-Cl$_2$ | CF$_3$ | H | H | C(O)CH$_2$CF$_3$ |
| 3,4-Cl$_2$ | CF$_3$ | CH$_3$ | H | C(O)CH$_2$CF$_3$ |
| 3,4-Cl$_2$ | CF$_3$ | CH$_3$ | H | C(O)(E4-2a) |
| 3,4-Cl$_2$ | CF$_3$ | H | H | C(O)CH$_2$SCH$_3$ |
| 3,4-Cl$_2$ | CF$_3$ | H | CH$_2$C≡CH | C(O)CH$_2$SCH$_3$ |
| 3,4-Cl$_2$ | CF$_3$ | CH$_3$ | H | C(O)CH$_2$SCH$_3$ |
| 3,4-Cl$_2$ | CF$_3$ | H | H | C(O)CH$_2$S(O)CH$_3$ |
| 3,4-Cl$_2$ | CF$_3$ | H | H | C(O)CH$_2$SO$_2$CH$_3$ |
| 3,4-Cl$_2$ | CF$_3$ | H | CH$_3$ | C(O)CH$_2$SO$_2$CH$_3$ |
| 3,4-Cl$_2$ | CF$_3$ | H | H | C(O)CH$_2$SEt |
| 3,4-Cl$_2$ | CF$_3$ | H | H | C(O)CH$_2$S(O)Et |
| 3,4-Cl$_2$ | CF$_3$ | H | H | C(O)CH$_2$SO$_2$Et |
| 3,4-Cl$_2$ | CF$_3$ | H | H | C(O)CH(SCH$_3$)$_2$ |
| 3,4-Cl$_2$ | CF$_3$ | H | H | C(O)CH[S(O)CH$_3$]$_2$ |
| 3,4-Cl$_2$ | CF$_3$ | H | H | C(O)NHPr-c |
| 3,4-Cl$_2$ | CF$_2$Cl | H | H | C(O)CH$_3$ |
| 3,4-Cl$_2$ | CF$_2$Cl | H | H | C(O)Et |
| 3,4-Cl$_2$ | CF$_2$Cl | H | H | C(O)Pr-n |
| 3,4-Cl$_2$ | CF$_2$Cl | H | H | C(O)Pr-c |
| 3,4-Cl$_2$ | CF$_2$Cl | H | H | C(O)CH$_2$Pr-c |
| 3,4-Cl$_2$ | CF$_2$Cl | H | H | C(O)CH$_2$CF$_3$ |
| 3,4-Cl$_2$ | CF$_2$Cl | H | H | C(O)CH$_2$SCH$_3$ |
| 3,4-Cl$_2$ | CF$_2$Cl | H | H | C(O)CH$_2$S(O)CH$_3$ |
| 3,4-Cl$_2$ | CF$_2$Cl | H | H | C(O)CH$_2$SO$_2$CH$_3$ |
| 3,4-Cl$_2$ | CF$_2$Cl | H | H | C(O)CH$_2$SEt |
| 3,4-Cl$_2$ | CF$_2$Cl | H | H | C(O)CH$_2$S(O)Et |
| 3,4-Cl$_2$ | CF$_2$Cl | H | H | C(O)CH$_2$SO$_2$Et |
| 3,5-Cl$_2$ | CHF$_2$ | H | H | C(O)CH$_2$S(O)Et |
| 3,5-Cl$_2$ | CF$_3$ | H | H | C(O)CH$_3$ |
| 3,5-Cl$_2$ | CF$_3$ | H | Et | C(O)CH$_3$ |
| 3,5-Cl$_2$ | CF$_3$ | H | CH$_2$OCH$_3$ | C(O)CH$_3$ |
| 3,5-Cl$_2$ | CF$_3$ | H | CH$_2$CN | C(O)CH$_3$ |
| 3,5-Cl$_2$ | CF$_3$ | H | CH$_2$C≡CH | C(O)CH$_3$ |
| 3,5-Cl$_2$ | CF$_3$ | H | H | C(O)Et |
| 3,5-Cl$_2$ | CF$_3$ | CH$_3$ | H | C(O)Et |
| 3,5-Cl$_2$ | CF$_3$ | H | H | C(O)Pr-n |
| 3,5-Cl$_2$ | CF$_3$ | CH$_3$ | H | C(O)Pr-n |
| 3,5-Cl$_2$ | CF$_3$ | H | H | C(O)Pr-i |
| 3,5-Cl$_2$ | CF$_3$ | CH$_3$ | H | C(O)Pr-i |
| 3,5-Cl$_2$ | CF$_3$ | H | H | C(O)Pr-c |
| 3,5-Cl$_2$ | CF$_3$ | CH$_3$ | H | C(O)Pr-c |
| 3,5-Cl$_2$ | CF$_3$ | CH$_3$(S) | H | C(O)Pr-c |
| 3,5-Cl$_2$ | CF$_3$ | H | H | C(O)Bu-i |
| 3,5-Cl$_2$ | CF$_3$ | H | H | C(O)CH$_2$Pr-c |
| 3,5-Cl$_2$ | CF$_3$ | CH$_3$ | H | C(O)CH$_2$Pr-c |
| 3,5-Cl$_2$ | CF$_3$ | CH$_3$(S) | H | C(O)CH$_2$Pr-c |
| 3,5-Cl$_2$ | CF$_3$ | H | H | C(O)CH$_2$CF$_3$ |
| 3,5-Cl$_2$ | CF$_3$ | CH$_3$ | H | C(O)CH$_2$CF$_3$ |
| 3,5-Cl$_2$ | CF$_3$ | CH$_3$(S) | H | C(O)CH$_2$CF$_3$ |
| 3,5-Cl$_2$ | CF$_3$ | H | H | C(O)(E4-2a) |
| 3,5-Cl$_2$ | CF$_3$ | CH$_3$ | H | C(O)(E4-2a) |
| 3,5-Cl$_2$ | CF$_3$ | CH$_3$(S) | H | C(O)(E4-2a) |
| 3,5-Cl$_2$ | CF$_3$ | H | H | C(O)CH$_2$SCH$_3$ |
| 3,5-Cl$_2$ | CF$_3$ | H | CH$_2$C≡CH | C(O)CH$_2$SCH$_3$ |
| 3,5-Cl$_2$ | CF$_3$ | CH$_3$ | H | C(O)CH$_2$SCH$_3$ |
| 3,5-Cl$_2$ | CF$_3$ | H | H | C(O)CH$_2$S(O)CH$_3$ |
| 3,5-Cl$_2$ | CF$_3$ | H | H | C(O)CH$_2$SO$_2$CH$_3$ |
| 3,5-Cl$_2$ | CF$_3$ | H | CH$_3$ | C(O)CH$_2$SO$_2$CH$_3$ |
| 3,5-Cl$_2$ | CF$_3$ | H | H | C(O)CH$_2$SEt |
| 3,5-Cl$_2$ | CF$_3$ | CH$_3$ | H | C(O)CH$_2$SEt |
| 3,5-Cl$_2$ | CF$_3$ | H | H | C(O)CH$_2$S(O)Et |
| 3,5-Cl$_2$ | CF$_3$ | H | CH$_3$ | C(O)CH$_2$S(O)Et |
| 3,5-Cl$_2$ | CF$_3$ | H | H | C(O)CH$_2$SO$_2$Et |
| 3,5-Cl$_2$ | CF$_3$ | H | CH$_3$ | C(O)CH$_2$SO$_2$Et |
| 3,5-Cl$_2$ | CF$_3$ | H | H | C(O)CH(CH$_3$)SCH$_3$ |

TABLE 3-continued

| $(X)_m$ | $R^3$ | $R^4$ | $R^2$ | $R^1$ |
|---|---|---|---|---|
| 3,5-Cl$_2$ | CF$_3$ | H | H | C(O)(E5-1a) |
| 3,5-Cl$_2$ | CF$_3$ | H | H | C(O)CH(SCH$_3$)$_2$ |
| 3,5-Cl$_2$ | CF$_3$ | H | H | C(O)CH[S(O)CH$_3$]$_2$ |
| 3,5-Cl$_2$ | CF$_3$ | H | H | C(O)CH(SEt)$_2$ |
| 3,5-Cl$_2$ | CF$_3$ | H | H | C(O)CH(SEt)S(O)Et |
| 3,5-Cl$_2$ | CF$_3$ | H | H | C(O)CH(SEt)SO$_2$Et |
| 3,5-Cl$_2$ | CF$_3$ | H | H | C(O)(D32-2b)Cl |
| 3,5-Cl$_2$ | CF$_3$ | H | H | C(O)NHEt |
| 3,5-Cl$_2$ | CF$_3$ | H | H | C(O)NHPr-c |
| 3,5-Cl$_2$ | CF$_3$ | CH$_3$ | H | C(O)NHPr-c |
| 3,5-Cl$_2$ | CF$_3$ | CH$_3$ | H | C(O)NHCH$_2$C≡CH |
| 3,5-Cl$_2$ | CF$_2$Cl | H | H | C(O)CH$_3$ |
| 3,5-Cl$_2$ | CF$_2$Cl | H | H | C(O)Et |
| 3,5-Cl$_2$ | CF$_2$Cl | H | H | C(O)Pr-n |
| 3,5-Cl$_2$ | CF$_2$Cl | H | H | C(O)Pr-c |
| 3,5-Cl$_2$ | CF$_2$Cl | H | H | C(O)CH$_2$Pr-c |
| 3,5-Cl$_2$ | CF$_2$Cl | CH$_3$ | H | C(O)CH$_2$Pr-c |
| 3,5-Cl$_2$ | CF$_2$Cl | H | H | C(O)CH$_2$CF$_3$ |
| 3,5-Cl$_2$ | CF$_2$Cl | CH$_3$ | H | C(O)CH$_2$CF$_3$ |
| 3,5-Cl$_2$ | CF$_2$Cl | CH$_3$ | H | C(O)(E4-2a) |
| 3,5-Cl$_2$ | CF$_2$Cl | H | H | C(O)CH$_2$SCH$_3$ |
| 3,5-Cl$_2$ | CF$_2$Cl | H | H | C(O)CH$_2$S(O)CH$_3$ |
| 3,5-Cl$_2$ | CF$_2$Cl | H | H | C(O)CH$_2$SO$_2$CH$_3$ |
| 3,5-Cl$_2$ | CF$_2$Cl | H | H | C(O)CH$_2$SEt |
| 3,5-Cl$_2$ | CF$_2$Cl | H | H | C(O)CH$_2$S(O)Et |
| 3,5-Cl$_2$ | CF$_2$Cl | H | H | C(O)CH$_2$SO$_2$Et |
| 3,5-Cl$_2$ | CF$_2$Cl | H | H | C(O)CH(SCH$_3$)$_2$ |
| 3,5-Cl$_2$ | CF$_2$Cl | H | H | C(O)CH[S(O)CH$_3$]$_2$ |
| 3-Br-4-F | CF$_3$ | H | H | C(O)CH$_3$ |
| 3-Br-4-F | CF$_3$ | H | Et | C(O)CH$_3$ |
| 3-Br-4-F | CF$_3$ | H | H | C(O)Et |
| 3-Br-4-F | CF$_3$ | H | H | C(O)Pr-n |
| 3-Br-4-F | CF$_3$ | H | H | C(O)Pr-i |
| 3-Br-4-F | CF$_3$ | H | H | C(O)Pr-c |
| 3-Br-4-F | CF$_3$ | CH$_3$ | H | C(O)Pr-c |
| 3-Br-4-F | CF$_3$ | H | H | C(O)Bu-i |
| 3-Br-4-F | CF$_3$ | H | H | C(O)CH$_2$Pr-c |
| 3-Br-4-F | CF$_3$ | CH$_3$ | H | C(O)CH$_2$Pr-c |
| 3-Br-4-F | CF$_3$ | H | H | C(O)CH$_2$CF$_3$ |
| 3-Br-4-F | CF$_3$ | CH$_3$ | H | C(O)CH$_2$CF$_3$ |
| 3-Br-4-F | CF$_3$ | CH$_3$ | H | C(O)(E4-2a) |
| 3-Br-4-F | CF$_3$ | H | H | C(O)CH$_2$SCH$_3$ |
| 3-Br-4-F | CF$_3$ | H | CH$_2$C≡CH | C(O)CH$_2$SCH$_3$ |
| 3-Br-4-F | CF$_3$ | CH$_3$ | H | C(O)CH$_2$SCH$_3$ |
| 3-Br-4-F | CF$_3$ | H | H | C(O)CH$_2$S(O)CH$_3$ |
| 3-Br-4-F | CF$_3$ | H | H | C(O)CH$_2$SO$_2$CH$_3$ |
| 3-Br-4-F | CF$_3$ | H | CH$_3$ | C(O)CH$_2$SO$_2$CH$_3$ |
| 3-Br-4-F | CF$_3$ | H | H | C(O)CH$_2$SEt |
| 3-Br-4-F | CF$_3$ | H | H | C(O)CH$_2$S(O)Et |
| 3-Br-4-F | CF$_3$ | H | H | C(O)CH$_2$SO$_2$Et |
| 3-Br-4-F | CF$_3$ | H | H | C(O)CH(SCH$_3$)$_2$ |
| 3-Br-4-F | CF$_3$ | H | H | C(O)CH[S(O)CH$_3$]$_2$ |
| 3-Br-4-F | CF$_3$ | H | H | C(O)NHPr-c |
| 3-Br-4-F | CF$_2$Cl | H | H | C(O)CH$_3$ |
| 3-Br-4-F | CF$_2$Cl | H | H | C(O)Et |
| 3-Br-4-F | CF$_2$Cl | H | H | C(O)Pr-n |
| 3-Br-4-F | CF$_2$Cl | H | H | C(O)Pr-c |
| 3-Br-4-F | CF$_2$Cl | H | H | C(O)CH$_2$Pr-c |
| 3-Br-4-F | CF$_2$Cl | H | H | C(O)CH$_2$CF$_3$ |
| 3-Br-4-F | CF$_2$Cl | H | H | C(O)CH$_2$SCH$_3$ |
| 3-Br-4-F | CF$_2$Cl | H | H | C(O)CH$_2$S(O)CH$_3$ |
| 3-Br-4-F | CF$_2$Cl | H | H | C(O)CH$_2$SO$_2$CH$_3$ |
| 3-Br-4-F | CF$_2$Cl | H | H | C(O)CH$_2$SEt |
| 3-Br-4-F | CF$_2$Cl | H | H | C(O)CH$_2$S(O)Et |
| 3-Br-4-F | CF$_2$Cl | H | H | C(O)CH$_2$SO$_2$Et |
| 3-F-5-Br | CF$_3$ | H | H | C(O)CH$_3$ |
| 3-F-5-Br | CF$_3$ | H | Et | C(O)CH$_3$ |
| 3-F-5-Br | CF$_3$ | H | H | C(O)Et |
| 3-F-5-Br | CF$_3$ | H | H | C(O)Pr-n |
| 3-F-5-Br | CF$_3$ | H | H | C(O)Pr-i |
| 3-F-5-Br | CF$_3$ | H | H | C(O)Pr-c |
| 3-F-5-Br | CF$_3$ | CH$_3$ | H | C(O)Pr-c |
| 3-F-5-Br | CF$_3$ | H | H | C(O)Bu-i |
| 3-F-5-Br | CF$_3$ | H | H | C(O)CH$_2$Pr-c |
| 3-F-5-Br | CF$_3$ | CH$_3$ | H | C(O)CH$_2$Pr-c |
| 3-F-5-Br | CF$_3$ | H | H | C(O)CH$_2$CF$_3$ |
| 3-F-5-Br | CF$_3$ | CH$_3$ | H | C(O)CH$_2$CF$_3$ |
| 3-F-5-Br | CF$_3$ | CH$_3$ | H | C(O)(E4-2a) |

TABLE 3-continued

| (X)$_m$ | R$^3$ | R$^4$ | R$^2$ | R$^1$ |
|---|---|---|---|---|
| 3-F-5-Br | CF$_3$ | H | H | C(O)CH$_2$SCH$_3$ |
| 3-F-5-Br | CF$_3$ | H | CH$_2$C≡CH | C(O)CH$_2$SCH$_3$ |
| 3-F-5-Br | CF$_3$ | CH$_3$ | H | C(O)CH$_2$SCH$_3$ |
| 3-F-5-Br | CF$_3$ | H | H | C(O)CH$_2$S(O)CH$_3$ |
| 3-F-5-Br | CF$_3$ | H | H | C(O)CH$_2$SO$_2$CH$_3$ |
| 3-F-5-Br | CF$_3$ | H | CH$_3$ | C(O)CH$_2$SO$_2$CH$_3$ |
| 3-F-5-Br | CF$_3$ | H | H | C(O)CH$_2$SEt |
| 3-F-5-Br | CF$_3$ | H | H | C(O)CH$_2$S(O)Et |
| 3-F-5-Br | CF$_3$ | H | H | C(O)CH$_2$SO$_2$Et |
| 3-F-5-Br | CF$_3$ | H | H | C(O)CH(SCH$_3$)$_2$ |
| 3-F-5-Br | CF$_3$ | H | H | C(O)CH[S(O)CH$_3$]$_2$ |
| 3-F-5-Br | CF$_3$ | H | H | C(O)NHPr-c |
| 3-F-5-Br | CF$_2$Cl | H | H | C(O)CH$_3$ |
| 3-F-5-Br | CF$_2$Cl | H | H | C(O)Et |
| 3-F-5-Br | CF$_2$Cl | H | H | C(O)Pr-n |
| 3-F-5-Br | CF$_2$Cl | H | H | C(O)Pr-c |
| 3-F-5-Br | CF$_2$Cl | H | H | C(O)CH$_2$Pr-c |
| 3-F-5-Br | CF$_2$Cl | H | H | C(O)CH$_2$CF$_3$ |
| 3-F-5-Br | CF$_2$Cl | H | H | C(O)CH$_2$SCH$_3$ |
| 3-F-5-Br | CF$_2$Cl | H | H | C(O)CH$_2$S(O)CH$_3$ |
| 3-F-5-Br | CF$_2$Cl | H | H | C(O)CH$_2$SO$_2$CH$_3$ |
| 3-F-5-Br | CF$_2$Cl | H | H | C(O)CH$_2$SEt |
| 3-F-5-Br | CF$_2$Cl | H | H | C(O)CH$_2$S(O)Et |
| 3-F-5-Br | CF$_2$Cl | H | H | C(O)CH$_2$SO$_2$Et |
| 3-Br-4-Cl | CF$_3$ | H | H | C(O)CH$_3$ |
| 3-Br-4-Cl | CF$_3$ | H | H | C(O)Et |
| 3-Br-4-Cl | CF$_3$ | H | H | C(O)Pr-n |
| 3-Br-4-Cl | CF$_3$ | H | H | C(O)Pr-c |
| 3-Br-4-Cl | CF$_3$ | H | H | C(O)CH$_2$Pr-c |
| 3-Br-4-Cl | CF$_3$ | CH$_3$ | H | C(O)CH$_2$Pr-c |
| 3-Br-4-Cl | CF$_3$ | H | H | C(O)CH$_2$CF$_3$ |
| 3-Br-4-Cl | CF$_3$ | CH$_3$ | H | C(O)CH$_2$CF$_3$ |
| 3-Br-4-Cl | CF$_3$ | CH$_3$ | H | C(O)(E4-2a) |
| 3-Br-4-Cl | CF$_3$ | H | H | C(O)CH$_2$SCH$_3$ |
| 3-Br-4-Cl | CF$_3$ | H | H | C(O)CH$_2$S(O)CH$_3$ |
| 3-Br-4-Cl | CF$_3$ | H | H | C(O)CH$_2$SO$_2$CH$_3$ |
| 3-Br-4-Cl | CF$_3$ | H | H | C(O)CH$_2$SEt |
| 3-Br-4-Cl | CF$_3$ | H | H | C(O)CH$_2$S(O)Et |
| 3-Br-4-Cl | CF$_3$ | H | H | C(O)CH$_2$SO$_2$Et |
| 3-Br-4-Cl | CF$_3$ | H | H | C(O)CH(SCH$_3$)$_2$ |
| 3-Br-4-Cl | CF$_3$ | H | H | C(O)CH[S(O)CH$_3$]$_2$ |
| 3-Cl-4-Br | CF$_3$ | H | H | C(O)CH$_3$ |
| 3-Cl-4-Br | CF$_3$ | H | H | C(O)Et |
| 3-Cl-4-Br | CF$_3$ | H | H | C(O)Pr-n |
| 3-Cl-4-Br | CF$_3$ | H | H | C(O)Pr-c |
| 3-Cl-4-Br | CF$_3$ | H | H | C(O)CH$_2$Pr-c |
| 3-Cl-4-Br | CF$_3$ | CH$_3$ | H | C(O)CH$_2$Pr-c |
| 3-Cl-4-Br | CF$_3$ | H | H | C(O)CH$_2$CF$_3$ |
| 3-Cl-4-Br | CF$_3$ | CH$_3$ | H | C(O)CH$_2$CF$_3$ |
| 3-Cl-4-Br | CF$_3$ | CH$_3$ | H | C(O)(E4-2a) |
| 3-Cl-4-Br | CF$_3$ | H | H | C(O)CH$_2$SCH$_3$ |
| 3-Cl-4-Br | CF$_3$ | H | H | C(O)CH$_2$S(O)CH$_3$ |
| 3-Cl-4-Br | CF$_3$ | H | H | C(O)CH$_2$SO$_2$CH$_3$ |
| 3-Cl-4-Br | CF$_3$ | H | H | C(O)CH$_2$SEt |
| 3-Cl-4-Br | CF$_3$ | H | H | C(O)CH$_2$S(O)Et |
| 3-Cl-4-Br | CF$_3$ | H | H | C(O)CH$_2$SO$_2$Et |
| 3-Cl-4-Br | CF$_3$ | H | H | C(O)CH(SCH$_3$)$_2$ |
| 3-Cl-4-Br | CF$_3$ | H | H | C(O)CH[S(O)CH$_3$]$_2$ |
| 3-Cl-5-Br | CHF$_2$ | H | H | C(O)CH$_2$SO$_2$Et |
| 3-Cl-5-Br | CF$_3$ | H | H | C(O)CH$_3$ |
| 3-Cl-5-Br | CF$_3$ | H | Et | C(O)CH$_3$ |
| 3-Cl-5-Br | CF$_3$ | H | CH$_2$OCH$_3$ | C(O)CH$_3$ |
| 3-Cl-5-Br | CF$_3$ | H | CH$_2$CN | C(O)CH$_3$ |
| 3-Cl-5-Br | CF$_3$ | H | CH$_2$C≡CH | C(O)CH$_3$ |
| 3-Cl-5-Br | CF$_3$ | H | H | C(O)Et |
| 3-Cl-5-Br | CF$_3$ | CH$_3$ | H | C(O)Et |
| 3-Cl-5-Br | CF$_3$ | H | H | C(O)Pr-n |
| 3-Cl-5-Br | CF$_3$ | CH$_3$ | H | C(O)Pr-n |
| 3-Cl-5-Br | CF$_3$ | H | H | C(O)Pr-i |
| 3-Cl-5-Br | CF$_3$ | CH$_3$ | H | C(O)Pr-i |
| 3-Cl-5-Br | CF$_3$ | H | H | C(O)Pr-c |
| 3-Cl-5-Br | CF$_3$ | CH$_3$ | H | C(O)Pr-c |
| 3-Cl-5-Br | CF$_3$ | CH$_3$(S) | H | C(O)Pr-c |
| 3-Cl-5-Br | CF$_3$ | H | H | C(O)Bu-i |
| 3-Cl-5-Br | CF$_3$ | H | H | C(O)CH$_2$Pr-c |
| 3-Cl-5-Br | CF$_3$ | CH$_3$ | H | C(O)CH$_2$Pr-c |
| 3-Cl-5-Br | CF$_3$ | CH$_3$(S) | H | C(O)CH$_2$Pr-c |
| 3-Cl-5-Br | CF$_3$ | H | H | C(O)CH$_2$CF$_3$ |

TABLE 3-continued

| (X)$_m$ | R$^3$ | R$^4$ | R$^2$ | R$^1$ |
|---|---|---|---|---|
| 3-Cl-5-Br | CF$_3$ | CH$_3$ | H | C(O)CH$_2$CF$_3$ |
| 3-Cl-5-Br | CF$_3$ | CH$_3$(S) | H | C(O)CH$_2$CF$_3$ |
| 3-Cl-5-Br | CF$_3$ | H | H | C(O)(E4-2a) |
| 3-Cl-5-Br | CF$_3$ | CH$_3$ | H | C(O)(E4-2a) |
| 3-Cl-5-Br | CF$_3$ | CH$_3$(S) | H | C(O)(E4-2a) |
| 3-Cl-5-Br | CF$_3$ | H | H | C(O)CH$_2$SCH$_3$ |
| 3-Cl-5-Br | CF$_3$ | H | CH$_2$C≡CH | C(O)CH$_2$SCH$_3$ |
| 3-Cl-5-Br | CF$_3$ | CH$_3$ | H | C(O)CH$_2$SCH$_3$ |
| 3-Cl-5-Br | CF$_3$ | H | H | C(O)CH$_2$S(O)CH$_3$ |
| 3-Cl-5-Br | CF$_3$ | H | H | C(O)CH$_2$SO$_2$CH$_3$ |
| 3-Cl-5-Br | CF$_3$ | H | CH$_3$ | C(O)CH$_2$SO$_2$CH$_3$ |
| 3-Cl-5-Br | CF$_3$ | H | H | C(O)CH$_2$SEt |
| 3-Cl-5-Br | CF$_3$ | CH$_3$ | H | C(O)CH$_2$SEt |
| 3-Cl-5-Br | CF$_3$ | H | H | C(O)CH$_2$S(O)Et |
| 3-Cl-5-Br | CF$_3$ | H | CH$_3$ | C(O)CH$_2$S(O)Et |
| 3-Cl-5-Br | CF$_3$ | H | H | C(O)CH$_2$SO$_2$Et |
| 3-Cl-5-Br | CF$_3$ | H | CH$_3$ | C(O)CH$_2$SO$_2$Et |
| 3-Cl-5-Br | CF$_3$ | H | H | C(O)CH(CH$_3$)SCH$_3$ |
| 3-Cl-5-Br | CF$_3$ | H | H | C(O)(E5-1a) |
| 3-Cl-5-Br | CF$_3$ | H | H | C(O)CH(SCH$_3$)$_2$ |
| 3-Cl-5-Br | CF$_3$ | H | H | C(O)CH[S(O)CH$_3$]$_2$ |
| 3-Cl-5-Br | CF$_3$ | H | H | C(O)CH(SEt)$_2$ |
| 3-Cl-5-Br | CF$_3$ | H | H | C(O)CH(SEt)S(O)Et |
| 3-Cl-5-Br | CF$_3$ | H | H | C(O)CH(SEt)SO$_2$Et |
| 3-Cl-5-Br | CF$_3$ | H | H | C(O)(D32-2b)Cl |
| 3-Cl-5-Br | CF$_3$ | H | H | C(O)NHEt |
| 3-Cl-5-Br | CF$_3$ | H | H | C(O)NHPr-c |
| 3-Cl-5-Br | CF$_3$ | CH$_3$ | H | C(O)NHPr-c |
| 3-Cl-5-Br | CF$_3$ | CH$_3$ | H | C(O)NHCH$_2$C≡CH |
| 3-Cl-5-Br | CF$_2$Cl | H | H | C(O)CH$_3$ |
| 3-Cl-5-Br | CF$_2$Cl | H | H | C(O)Et |
| 3-Cl-5-Br | CF$_2$Cl | H | H | C(O)Pr-n |
| 3-Cl-5-Br | CF$_2$Cl | H | H | C(O)Pr-c |
| 3-Cl-5-Br | CF$_2$Cl | H | H | C(O)CH$_2$Pr-c |
| 3-Cl-5-Br | CF$_2$Cl | CH$_3$ | H | C(O)CH$_2$Pr-c |
| 3-Cl-5-Br | CF$_2$Cl | H | H | C(O)CH$_2$CF$_3$ |
| 3-Cl-5-Br | CF$_2$Cl | CH$_3$ | H | C(O)CH$_2$CF$_3$ |
| 3-Cl-5-Br | CF$_2$Cl | CH$_3$ | H | C(O)(E4-2a) |
| 3-Cl-5-Br | CF$_2$Cl | H | H | C(O)CH$_2$SCH$_3$ |
| 3-Cl-5-Br | CF$_2$Cl | H | H | C(O)CH$_2$S(O)CH$_3$ |
| 3-Cl-5-Br | CF$_2$Cl | H | H | C(O)CH$_2$SO$_2$CH$_3$ |
| 3-Cl-5-Br | CF$_2$Cl | H | H | C(O)CH$_2$SEt |
| 3-Cl-5-Br | CF$_2$Cl | H | H | C(O)CH$_2$S(O)Et |
| 3-Cl-5-Br | CF$_2$Cl | H | H | C(O)CH$_2$SO$_2$Et |
| 3-Cl-5-Br | CF$_2$Cl | H | H | C(O)CH(SCH$_3$)$_2$ |
| 3-Cl-5-Br | CF$_2$Cl | H | H | C(O)CH[S(O)CH$_3$]$_2$ |
| 3,4-Br$_2$ | CF$_3$ | H | H | C(O)CH$_3$ |
| 3,4-Br$_2$ | CF$_3$ | H | H | C(O)Et |
| 3,4-Br$_2$ | CF$_3$ | H | H | C(O)Pr-n |
| 3,4-Br$_2$ | CF$_3$ | H | H | C(O)Pr-c |
| 3,4-Br$_2$ | CF$_3$ | H | H | C(O)CH$_2$Pr-c |
| 3,4-Br$_2$ | CF$_3$ | CH$_3$ | H | C(O)CH$_2$Pr-c |
| 3,4-Br$_2$ | CF$_3$ | H | H | C(O)CH$_2$CF$_3$ |
| 3,4-Br$_2$ | CF$_3$ | CH$_3$ | H | C(O)CH$_2$CF$_3$ |
| 3,4-Br$_2$ | CF$_3$ | CH$_3$ | H | C(O)(E4-2a) |
| 3,4-Br$_2$ | CF$_3$ | H | H | C(O)CH$_2$SCH$_3$ |
| 3,4-Br$_2$ | CF$_3$ | H | H | C(O)CH$_2$S(O)CH$_3$ |
| 3,4-Br$_2$ | CF$_3$ | H | H | C(O)CH$_2$SO$_2$CH$_3$ |
| 3,4-Br$_2$ | CF$_3$ | H | H | C(O)CH$_2$SEt |
| 3,4-Br$_2$ | CF$_3$ | H | H | C(O)CH$_2$S(O)Et |
| 3,4-Br$_2$ | CF$_3$ | H | H | C(O)CH$_2$SO$_2$Et |
| 3,4-Br$_2$ | CF$_3$ | H | H | C(O)CH(SCH$_3$)$_2$ |
| 3,4-Br$_2$ | CF$_3$ | H | H | C(O)CH[S(O)CH$_3$]$_2$ |
| 3,5-Br$_2$ | CHF$_2$ | H | H | C(O)CH$_3$ |
| 3,5-Br$_2$ | CF$_3$ | H | H | C(O)CH$_3$ |
| 3,5-Br$_2$ | CF$_3$ | H | Et | C(O)CH$_3$ |
| 3,5-Br$_2$ | CF$_3$ | H | CH$_2$OCH$_3$ | C(O)CH$_3$ |
| 3,5-Br$_2$ | CF$_3$ | H | CH$_2$CN | C(O)CH$_3$ |
| 3,5-Br$_2$ | CF$_3$ | H | CH$_2$C≡CH | C(O)CH$_3$ |
| 3,5-Br$_2$ | CF$_3$ | H | H | C(O)Et |
| 3,5-Br$_2$ | CF$_3$ | CH$_3$ | H | C(O)Et |
| 3,5-Br$_2$ | CF$_3$ | H | H | C(O)Pr-n |
| 3,5-Br$_2$ | CF$_3$ | CH$_3$ | H | C(O)Pr-n |
| 3,5-Br$_2$ | CF$_3$ | H | H | C(O)Pr-i |
| 3,5-Br$_2$ | CF$_3$ | CH$_3$ | H | C(O)Pr-i |
| 3,5-Br$_2$ | CF$_3$ | H | H | C(O)Pr-c |
| 3,5-Br$_2$ | CF$_3$ | CH$_3$ | H | C(O)Pr-c |
| 3,5-Br$_2$ | CF$_3$ | CH$_3$(S) | H | C(O)Pr-c |

TABLE 3-continued

| (X)$_m$ | R$^3$ | R$^4$ | R$^2$ | R$^1$ |
|---|---|---|---|---|
| 3,5-Br$_2$ | CF$_3$ | H | H | C(O)Bu-i |
| 3,5-Br$_2$ | CF$_3$ | H | H | C(O)CH$_2$Pr-c |
| 3,5-Br$_2$ | CF$_3$ | CH$_3$ | H | C(O)CH$_2$Pr-c |
| 3,5-Br$_2$ | CF$_3$ | CH$_3$(S) | H | C(O)CH$_2$Pr-c |
| 3,5-Br$_2$ | CF$_3$ | H | H | C(O)CH$_2$CF$_3$ |
| 3,5-Br$_2$ | CF$_3$ | CH$_3$ | H | C(O)CH$_2$CF$_3$ |
| 3,5-Br$_2$ | CF$_3$ | CH$_3$(S) | H | C(O)CH$_2$CF$_3$ |
| 3,5-Br$_2$ | CF$_3$ | H | H | C(O)(E4-2a) |
| 3,5-Br$_2$ | CF$_3$ | CH$_3$ | H | C(O)(E4-2a) |
| 3,5-Br$_2$ | CF$_3$ | CH$_3$(S) | H | C(O)(E4-2a) |
| 3,5-Br$_2$ | CF$_3$ | H | H | C(O)CH$_2$SCH$_3$ |
| 3,5-Br$_2$ | CF$_3$ | H | CH$_2$C≡CH | C(O)CH$_2$SCH$_3$ |
| 3,5-Br$_2$ | CF$_3$ | CH$_3$ | H | C(O)CH$_2$SCH$_3$ |
| 3,5-Br$_2$ | CF$_3$ | H | H | C(O)CH$_2$S(O)CH$_3$ |
| 3,5-Br$_2$ | CF$_3$ | H | H | C(O)CH$_2$SO$_2$CH$_3$ |
| 3,5-Br$_2$ | CF$_3$ | H | CH$_3$ | C(O)CH$_2$SO$_2$CH$_3$ |
| 3,5-Br$_2$ | CF$_3$ | H | H | C(O)CH$_2$SEt |
| 3,5-Br$_2$ | CF$_3$ | CH$_3$ | H | C(O)CH$_2$SEt |
| 3,5-Br$_2$ | CF$_3$ | H | H | C(O)CH$_2$S(O)Et |
| 3,5-Br$_2$ | CF$_3$ | H | CH$_3$ | C(O)CH$_2$S(O)Et |
| 3,5-Br$_2$ | CF$_3$ | H | H | C(O)CH$_2$SO$_2$Et |
| 3,5-Br$_2$ | CF$_3$ | H | CH$_3$ | C(O)CH$_2$SO$_2$Et |
| 3,5-Br$_2$ | CF$_3$ | H | H | C(O)CH(CH$_3$)SCH$_3$ |
| 3,5-Br$_2$ | CF$_3$ | H | H | C(O)(E5-1a) |
| 3,5-Br$_2$ | CF$_3$ | H | H | C(O)CH(SCH$_3$)$_2$ |
| 3,5-Br$_2$ | CF$_3$ | H | H | C(O)CH[S(O)CH$_3$]$_2$ |
| 3,5-Br$_2$ | CF$_3$ | H | H | C(O)CH(SEt)$_2$ |
| 3,5-Br$_2$ | CF$_3$ | H | H | C(O)CH(SEt)S(O)Et |
| 3,5-Br$_2$ | CF$_3$ | H | H | C(O)CH(SEt)SO$_2$Et |
| 3,5-Br$_2$ | CF$_3$ | H | H | C(O)(D32-2b)Cl |
| 3,5-Br$_2$ | CF$_3$ | H | H | C(O)NHEt |
| 3,5-Br$_2$ | CF$_3$ | H | H | C(O)NHPr-c |
| 3,5-Br$_2$ | CF$_3$ | CH$_3$ | H | C(O)NHPr-c |
| 3,5-Br$_2$ | CF$_3$ | CH$_3$ | H | C(O)NHCH$_2$C≡CH |
| 3,5-Br$_2$ | CF$_2$Cl | H | H | C(O)CH$_3$ |
| 3,5-Br$_2$ | CF$_2$Cl | H | H | C(O)Et |
| 3,5-Br$_2$ | CF$_2$Cl | H | H | C(O)Pr-n |
| 3,5-Br$_2$ | CF$_2$Cl | H | H | C(O)Pr-c |
| 3,5-Br$_2$ | CF$_2$Cl | H | H | C(O)CH$_2$Pr-c |
| 3,5-Br$_2$ | CF$_2$Cl | CH$_3$ | H | C(O)CH$_2$Pr-c |
| 3,5-Br$_2$ | CF$_2$Cl | H | H | C(O)CH$_2$CF$_3$ |
| 3,5-Br$_2$ | CF$_2$Cl | CH$_3$ | H | C(O)CH$_2$CF$_3$ |
| 3,5-Br$_2$ | CF$_2$Cl | CH$_3$ | H | C(O)(E4-2a) |
| 3,5-Br$_2$ | CF$_2$Cl | H | H | C(O)CH$_2$SCH$_3$ |
| 3,5-Br$_2$ | CF$_2$Cl | H | H | C(O)CH$_2$S(O)CH$_3$ |
| 3,5-Br$_2$ | CF$_2$Cl | H | H | C(O)CH$_2$SO$_2$CH$_3$ |
| 3,5-Br$_2$ | CF$_2$Cl | H | H | C(O)CH$_2$SEt |
| 3,5-Br$_2$ | CF$_2$Cl | H | H | C(O)CH$_2$S(O)Et |
| 3,5-Br$_2$ | CF$_2$Cl | H | H | C(O)CH$_2$SO$_2$Et |
| 3,5-Br$_2$ | CF$_2$Cl | H | H | C(O)CH(SCH$_3$)$_2$ |
| 3,5-Br$_2$ | CF$_2$Cl | H | H | C(O)CH[S(O)CH$_3$]$_2$ |
| 3-I-4-F | CF$_3$ | H | H | C(O)CH$_3$ |
| 3-I-4-F | CF$_3$ | H | H | C(O)Et |
| 3-I-4-F | CF$_3$ | H | H | C(O)Pr-n |
| 3-I-4-F | CF$_3$ | H | H | C(O)Pr-c |
| 3-I-4-F | CF$_3$ | H | H | C(O)CH$_2$Pr-c |
| 3-I-4-F | CF$_3$ | CH$_3$ | H | C(O)CH$_2$Pr-c |
| 3-I-4-F | CF$_3$ | H | H | C(O)CH$_2$CF$_3$ |
| 3-I-4-F | CF$_3$ | CH$_3$ | H | C(O)CH$_2$CF$_3$ |
| 3-I-4-F | CF$_3$ | CH$_3$ | H | C(O)(E4-2a) |
| 3-I-4-F | CF$_3$ | H | H | C(O)CH$_2$SCH$_3$ |
| 3-I-4-F | CF$_3$ | H | H | C(O)CH$_2$S(O)CH$_3$ |
| 3-I-4-F | CF$_3$ | H | H | C(O)CH$_2$SO$_2$CH$_3$ |
| 3-I-4-F | CF$_3$ | H | H | C(O)CH$_2$SEt |
| 3-I-4-F | CF$_3$ | H | H | C(O)CH$_2$S(O)Et |
| 3-I-4-F | CF$_3$ | H | H | C(O)CH$_2$SO$_2$Et |
| 3-I-4-F | CF$_3$ | H | H | C(O)CH(SCH$_3$)$_2$ |
| 3-I-4-F | CF$_3$ | H | H | C(O)CH[S(O)CH$_3$]$_2$ |
| 3-F-5-I | CF$_3$ | H | H | C(O)CH$_3$ |
| 3-F-5-I | CF$_3$ | H | H | C(O)Et |
| 3-F-5-I | CF$_3$ | H | H | C(O)Pr-n |
| 3-F-5-I | CF$_3$ | H | H | C(O)Pr-c |
| 3-F-5-I | CF$_3$ | H | H | C(O)CH$_2$Pr-c |
| 3-F-5-I | CF$_3$ | CH$_3$ | H | C(O)CH$_2$Pr-c |
| 3-F-5-I | CF$_3$ | H | H | C(O)CH$_2$CF$_3$ |
| 3-F-5-I | CF$_3$ | CH$_3$ | H | C(O)CH$_2$CF$_3$ |
| 3-F-5-I | CF$_3$ | CH$_3$ | H | C(O)(E4-2a) |
| 3-F-5-I | CF$_3$ | H | H | C(O)CH$_2$SCH$_3$ |

TABLE 3-continued

| (X)$_m$ | R$^3$ | R$^4$ | R$^2$ | R$^1$ |
|---|---|---|---|---|
| 3-F-5-I | CF$_3$ | H | H | C(O)CH$_2$S(O)CH$_3$ |
| 3-F-5-I | CF$_3$ | H | H | C(O)CH$_2$SO$_2$CH$_3$ |
| 3-F-5-I | CF$_3$ | H | H | C(O)CH$_2$SEt |
| 3-F-5-I | CF$_3$ | H | H | C(O)CH$_2$S(O)Et |
| 3-F-5-I | CF$_3$ | H | H | C(O)CH$_2$SO$_2$Et |
| 3-F-5-I | CF$_3$ | H | H | C(O)CH(SCH$_3$)$_2$ |
| 3-F-5-I | CF$_3$ | H | H | C(O)CH[S(O)CH$_3$]$_2$ |
| 3-Cl-5-I | CF$_3$ | H | H | C(O)CH$_3$ |
| 3-Cl-5-I | CF$_3$ | H | Et | C(O)CH$_3$ |
| 3-Cl-5-I | CF$_3$ | H | H | C(O)Et |
| 3-Cl-5-I | CF$_3$ | H | H | C(O)Pr-n |
| 3-Cl-5-I | CF$_3$ | H | H | C(O)Pr-i |
| 3-Cl-5-I | CF$_3$ | H | H | C(O)Pr-c |
| 3-Cl-5-I | CF$_3$ | CH$_3$ | H | C(O)Pr-c |
| 3-Cl-5-I | CF$_3$ | H | H | C(O)Bu-i |
| 3-Cl-5-I | CF$_3$ | H | H | C(O)CH$_2$Pr-c |
| 3-Cl-5-I | CF$_3$ | CH$_3$ | H | C(O)CH$_2$Pr-c |
| 3-Cl-5-I | CF$_3$ | H | H | C(O)CH$_2$CF$_3$ |
| 3-Cl-5-I | CF$_3$ | CH$_3$ | H | C(O)CH$_2$CF$_3$ |
| 3-Cl-5-I | CF$_3$ | CH$_3$ | H | C(O)(E4-2a) |
| 3-Cl-5-I | CF$_3$ | H | H | C(O)CH$_2$SCH$_3$ |
| 3-Cl-5-I | CF$_3$ | H | CH$_2$C≡CH | C(O)CH$_2$SCH$_3$ |
| 3-Cl-5-I | CF$_3$ | CH$_3$ | H | C(O)CH$_2$SCH$_3$ |
| 3-Cl-5-I | CF$_3$ | H | H | C(O)CH$_2$S(O)CH$_3$ |
| 3-Cl-5-I | CF$_3$ | H | H | C(O)CH$_2$SO$_2$CH$_3$ |
| 3-Cl-5-I | CF$_3$ | H | CH$_3$ | C(O)CH$_2$SO$_2$CH$_3$ |
| 3-Cl-5-I | CF$_3$ | H | H | C(O)CH$_2$SEt |
| 3-Cl-5-I | CF$_3$ | H | H | C(O)CH$_2$S(O)Et |
| 3-Cl-5-I | CF$_3$ | H | H | C(O)CH$_2$SO$_2$Et |
| 3-Cl-5-I | CF$_3$ | H | H | C(O)CH(SCH$_3$)$_2$ |
| 3-Cl-5-I | CF$_3$ | H | H | C(O)CH[S(O)CH$_3$]$_2$ |
| 3-Cl-5-I | CF$_3$ | H | H | C(O)NHPr-c |
| 3-Cl-5-I | CF$_2$Cl | H | H | C(O)CH$_3$ |
| 3-Cl-5-I | CF$_2$Cl | H | H | C(O)Et |
| 3-Cl-5-I | CF$_2$Cl | H | H | C(O)Pr-n |
| 3-Cl-5-I | CF$_2$Cl | H | H | C(O)Pr-c |
| 3-Cl-5-I | CF$_2$Cl | H | H | C(O)CH$_2$Pr-c |
| 3-Cl-5-I | CF$_2$Cl | H | H | C(O)CH$_2$CF$_3$ |
| 3-Cl-5-I | CF$_2$Cl | H | H | C(O)CH$_2$SCH$_3$ |
| 3-Cl-5-I | CF$_2$Cl | H | H | C(O)CH$_2$S(O)CH$_3$ |
| 3-Cl-5-I | CF$_2$Cl | H | H | C(O)CH$_2$SO$_2$CH$_3$ |
| 3-Cl-5-I | CF$_2$Cl | H | H | C(O)CH$_2$SEt |
| 3-Cl-5-I | CF$_2$Cl | H | H | C(O)CH$_2$S(O)Et |
| 3-Cl-5-I | CF$_2$Cl | H | H | C(O)CH$_2$SO$_2$Et |
| 3,5-I$_2$ | CF$_3$ | H | H | C(O)Et |
| 3-CH$_3$-4-F | CF$_3$ | H | H | C(O)Pr-n |
| 3-Cl-4-CH$_3$ | CF$_3$ | H | H | C(O)Pr-c |
| 3-Cl-5-CH$_3$ | CF$_3$ | H | H | C(O)CH$_3$ |
| 3-Cl-5-CH$_3$ | CF$_3$ | H | H | C(O)Et |
| 3-Cl-5-CH$_3$ | CF$_3$ | H | H | C(O)Pr-n |
| 3-Cl-5-CH$_3$ | CF$_3$ | H | H | C(O)Pr-c |
| 3-Cl-5-CH$_3$ | CF$_3$ | H | H | C(O)CH$_2$Pr-c |
| 3-Cl-5-CH$_3$ | CF$_3$ | H | H | C(O)CH$_2$CF$_3$ |
| 3-Cl-5-CH$_3$ | CF$_3$ | H | H | C(O)CH$_2$SCH$_3$ |
| 3-Cl-5-CH$_3$ | CF$_3$ | H | H | C(O)CH$_2$S(O)CH$_3$ |
| 3-Cl-5-CH$_3$ | CF$_3$ | H | H | C(O)CH$_2$SO$_2$CH$_3$ |
| 3-Cl-5-CH$_3$ | CF$_3$ | H | H | C(O)CH$_2$SEt |
| 3-Cl-5-CH$_3$ | CF$_3$ | H | H | C(O)CH$_2$S(O)Et |
| 3-Cl-5-CH$_3$ | CF$_3$ | H | H | C(O)CH$_2$SO$_2$Et |
| 3-Br-4-CH$_3$ | CF$_3$ | H | H | C(O)CH$_2$Pr-c |
| 3-Br-5-CH$_3$ | CF$_3$ | H | H | C(O)CH$_3$ |
| 3-Br-5-CH$_3$ | CF$_3$ | H | H | C(O)Et |
| 3-Br-5-CH$_3$ | CF$_3$ | H | H | C(O)Pr-n |
| 3-Br-5-CH$_3$ | CF$_3$ | H | H | C(O)Pr-c |
| 3-Br-5-CH$_3$ | CF$_3$ | H | H | C(O)CH$_2$Pr-c |
| 3-Br-5-CH$_3$ | CF$_3$ | H | H | C(O)CH$_2$CF$_3$ |
| 3-Br-5-CH$_3$ | CF$_3$ | H | H | C(O)CH$_2$SCH$_3$ |
| 3-Br-5-CH$_3$ | CF$_3$ | H | H | C(O)CH$_2$S(O)CH$_3$ |
| 3-Br-5-CH$_3$ | CF$_3$ | H | H | C(O)CH$_2$SO$_2$CH$_3$ |
| 3-Br-5-CH$_3$ | CF$_3$ | H | H | C(O)CH$_2$SEt |
| 3-Br-5-CH$_3$ | CF$_3$ | H | H | C(O)CH$_2$S(O)Et |
| 3-Br-5-CH$_3$ | CF$_3$ | H | H | C(O)CH$_2$SO$_2$Et |
| 3,5-(CH$_3$)$_2$ | CF$_3$ | H | H | C(O)CH$_2$CF$_3$ |
| 3-CF$_3$-4-F | CF$_3$ | H | H | C(O)CH$_3$ |
| 3-CF$_3$-4-F | CF$_3$ | H | Et | C(O)CH$_3$ |
| 3-CF$_3$-4-F | CF$_3$ | H | H | C(O)Et |
| 3-CF$_3$-4-F | CF$_3$ | H | H | C(O)Pr-n |
| 3-CF$_3$-4-F | CF$_3$ | H | H | C(O)Pr-i |

TABLE 3-continued

| (X)$_m$ | R$^3$ | R$^4$ | R$^2$ | R$^1$ |
|---|---|---|---|---|
| 3-CF$_3$-4-F | CF$_3$ | H | H | C(O)Pr-c |
| 3-CF$_3$-4-F | CF$_3$ | CH$_3$ | H | C(O)Pr-c |
| 3-CF$_3$-4-F | CF$_3$ | H | H | C(O)Bu-i |
| 3-CF$_3$-4-F | CF$_3$ | H | H | C(O)CH$_2$Pr-c |
| 3-CF$_3$-4-F | CF$_3$ | CH$_3$ | H | C(O)CH$_2$Pr-c |
| 3-CF$_3$-4-F | CF$_3$ | H | H | C(O)CH$_2$CF$_3$ |
| 3-CF$_3$-4-F | CF$_3$ | CH$_3$ | H | C(O)CH$_2$CF$_3$ |
| 3-CF$_3$-4-F | CF$_3$ | CH$_3$ | H | C(O)(E4-2a) |
| 3-CF$_3$-4-F | CF$_3$ | H | H | C(O)CH$_2$SCH$_3$ |
| 3-CF$_3$-4-F | CF$_3$ | H | CH$_2$C≡CH | C(O)CH$_2$SCH$_3$ |
| 3-CF$_3$-4-F | CF$_3$ | CH$_3$ | H | C(O)CH$_2$SCH$_3$ |
| 3-CF$_3$-4-F | CF$_3$ | H | H | C(O)CH$_2$S(O)CH$_3$ |
| 3-CF$_3$-4-F | CF$_3$ | H | H | C(O)CH$_2$SO$_2$CH$_3$ |
| 3-CF$_3$-4-F | CF$_3$ | H | CH$_3$ | C(O)CH$_2$SO$_2$CH$_3$ |
| 3-CF$_3$-4-F | CF$_3$ | H | H | C(O)CH$_2$SEt |
| 3-CF$_3$-4-F | CF$_3$ | H | H | C(O)CH$_2$S(O)Et |
| 3-CF$_3$-4-F | CF$_3$ | H | H | C(O)CH$_2$SO$_2$Et |
| 3-CF$_3$-4-F | CF$_3$ | H | H | C(O)CH(SCH$_3$)$_2$ |
| 3-CF$_3$-4-F | CF$_3$ | H | H | C(O)CH[S(O)CH$_3$]$_2$ |
| 3-CF$_3$-4-F | CF$_3$ | H | H | C(O)NHPr-c |
| 3-CF$_3$-4-F | CF$_2$Cl | H | H | C(O)CH$_3$ |
| 3-CF$_3$-4-F | CF$_2$Cl | H | H | C(O)Et |
| 3-CF$_3$-4-F | CF$_2$Cl | H | H | C(O)Pr-n |
| 3-CF$_3$-4-F | CF$_2$Cl | H | H | C(O)Pr-c |
| 3-CF$_3$-4-F | CF$_2$Cl | H | H | C(O)CH$_2$Pr-c |
| 3-CF$_3$-4-F | CF$_2$Cl | H | H | C(O)CH$_2$CF$_3$ |
| 3-CF$_3$-4-F | CF$_2$Cl | H | H | C(O)CH$_2$SCH$_3$ |
| 3-CF$_3$-4-F | CF$_2$Cl | H | H | C(O)CH$_2$S(O)CH$_3$ |
| 3-CF$_3$-4-F | CF$_2$Cl | H | H | C(O)CH$_2$SO$_2$CH$_3$ |
| 3-CF$_3$-4-F | CF$_2$Cl | H | H | C(O)CH$_2$SEt |
| 3-CF$_3$-4-F | CF$_2$Cl | H | H | C(O)CH$_2$S(O)Et |
| 3-CF$_3$-4-F | CF$_2$Cl | H | H | C(O)CH$_2$SO$_2$Et |
| 3-F-5-CF$_3$ | CF$_3$ | H | H | C(O)CH$_3$ |
| 3-F-5-CF$_3$ | CF$_3$ | H | Et | C(O)CH$_3$ |
| 3-F-5-CF$_3$ | CF$_3$ | H | H | C(O)Et |
| 3-F-5-CF$_3$ | CF$_3$ | H | H | C(O)Pr-n |
| 3-F-5-CF$_3$ | CF$_3$ | H | H | C(O)Pr-i |
| 3-F-5-CF$_3$ | CF$_3$ | H | H | C(O)Pr-c |
| 3-F-5-CF$_3$ | CF$_3$ | CH$_3$ | H | C(O)Pr-c |
| 3-F-5-CF$_3$ | CF$_3$ | H | H | C(O)Bu-i |
| 3-F-5-CF$_3$ | CF$_3$ | H | H | C(O)CH$_2$Pr-c |
| 3-F-5-CF$_3$ | CF$_3$ | CH$_3$ | H | C(O)CH$_2$Pr-c |
| 3-F-5-CF$_3$ | CF$_3$ | H | H | C(O)CH$_2$CF$_3$ |
| 3-F-5-CF$_3$ | CF$_3$ | CH$_3$ | H | C(O)CH$_2$CF$_3$ |
| 3-F-5-CF$_3$ | CF$_3$ | CH$_3$ | H | C(O)(E4-2a) |
| 3-F-5-CF$_3$ | CF$_3$ | H | H | C(O)CH$_2$SCH$_3$ |
| 3-F-5-CF$_3$ | CF$_3$ | H | CH$_2$C≡CH | C(O)CH$_2$SCH$_3$ |
| 3-F-5-CF$_3$ | CF$_3$ | CH$_3$ | H | C(O)CH$_2$SCH$_3$ |
| 3-F-5-CF$_3$ | CF$_3$ | H | H | C(O)CH$_2$S(O)CH$_3$ |
| 3-F-5-CF$_3$ | CF$_3$ | H | H | C(O)CH$_2$SO$_2$CH$_3$ |
| 3-F-5-CF$_3$ | CF$_3$ | H | CH$_3$ | C(O)CH$_2$SO$_2$CH$_3$ |
| 3-F-5-CF$_3$ | CF$_3$ | H | H | C(O)CH$_2$SEt |
| 3-F-5-CF$_3$ | CF$_3$ | H | H | C(O)CH$_2$S(O)Et |
| 3-F-5-CF$_3$ | CF$_3$ | H | H | C(O)CH$_2$SO$_2$Et |
| 3-F-5-CF$_3$ | CF$_3$ | H | H | C(O)CH(SCH$_3$)$_2$ |
| 3-F-5-CF$_3$ | CF$_3$ | H | H | C(O)CH[S(O)CH$_3$]$_2$ |
| 3-F-5-CF$_3$ | CF$_3$ | H | H | C(O)NHPr-c |
| 3-F-5-CF$_3$ | CF$_2$Cl | H | H | C(O)CH$_3$ |
| 3-F-5-CF$_3$ | CF$_2$Cl | H | H | C(O)Et |
| 3-F-5-CF$_3$ | CF$_2$Cl | H | H | C(O)Pr-n |
| 3-F-5-CF$_3$ | CF$_2$Cl | H | H | C(O)Pr-c |
| 3-F-5-CF$_3$ | CF$_2$Cl | H | H | C(O)CH$_2$Pr-c |
| 3-F-5-CF$_3$ | CF$_2$Cl | H | H | C(O)CH$_2$CF$_3$ |
| 3-F-5-CF$_3$ | CF$_2$Cl | H | H | C(O)CH$_2$SCH$_3$ |
| 3-F-5-CF$_3$ | CF$_2$Cl | H | H | C(O)CH$_2$S(O)CH$_3$ |
| 3-F-5-CF$_3$ | CF$_2$Cl | H | H | C(O)CH$_2$SO$_2$CH$_3$ |
| 3-F-5-CF$_3$ | CF$_2$Cl | H | H | C(O)CH$_2$SEt |
| 3-F-5-CF$_3$ | CF$_2$Cl | H | H | C(O)CH$_2$S(O)Et |
| 3-F-5-CF$_3$ | CF$_2$Cl | H | H | C(O)CH$_2$SO$_2$Et |
| 3-CF$_3$-4-Cl | CF$_3$ | H | H | C(O)CH$_3$ |
| 3-CF$_3$-4-Cl | CF$_3$ | H | Et | C(O)CH$_3$ |
| 3-CF$_3$-4-Cl | CF$_3$ | H | H | C(O)Et |
| 3-CF$_3$-4-Cl | CF$_3$ | H | H | C(O)Pr-n |
| 3-CF$_3$-4-Cl | CF$_3$ | H | H | C(O)Pr-i |
| 3-CF$_3$-4-Cl | CF$_3$ | H | H | C(O)Pr-c |
| 3-CF$_3$-4-Cl | CF$_3$ | CH$_3$ | H | C(O)Pr-c |
| 3-CF$_3$-4-Cl | CF$_3$ | H | H | C(O)Bu-i |
| 3-CF$_3$-4-Cl | CF$_3$ | H | H | C(O)CH$_2$Pr-c |

TABLE 3-continued

| (X)$_m$ | R$^3$ | R$^4$ | R$^2$ | R$^1$ |
|---|---|---|---|---|
| 3-CF$_3$-4-Cl | CF$_3$ | CH$_3$ | H | C(O)CH$_2$Pr-c |
| 3-CF$_3$-4-Cl | CF$_3$ | H | H | C(O)CH$_2$CF$_3$ |
| 3-CF$_3$-4-Cl | CF$_3$ | CH$_3$ | H | C(O)CH$_2$CF$_3$ |
| 3-CF$_3$-4-Cl | CF$_3$ | CH$_3$ | H | C(O)(E4-2a) |
| 3-CF$_3$-4-Cl | CF$_3$ | H | H | C(O)CH$_2$SCH$_3$ |
| 3-CF$_3$-4-Cl | CF$_3$ | H | CH$_2$C≡CH | C(O)CH$_2$SCH$_3$ |
| 3-CF$_3$-4-Cl | CF$_3$ | CH$_3$ | H | C(O)CH$_2$SCH$_3$ |
| 3-CF$_3$-4-Cl | CF$_3$ | H | H | C(O)CH$_2$S(O)CH$_3$ |
| 3-CF$_3$-4-Cl | CF$_3$ | H | H | C(O)CH$_2$SO$_2$CH$_3$ |
| 3-CF$_3$-4-Cl | CF$_3$ | H | CH$_3$ | C(O)CH$_2$SO$_2$CH$_3$ |
| 3-CF$_3$-4-Cl | CF$_3$ | H | H | C(O)CH$_2$SEt |
| 3-CF$_3$-4-Cl | CF$_3$ | H | H | C(O)CH$_2$S(O)Et |
| 3-CF$_3$-4-Cl | CF$_3$ | H | H | C(O)CH$_2$SO$_2$Et |
| 3-CF$_3$-4-Cl | CF$_3$ | H | H | C(O)CH(SCH$_3$)$_2$ |
| 3-CF$_3$-4-Cl | CF$_3$ | H | H | C(O)CH[S(O)CH$_3$]$_2$ |
| 3-CF$_3$-4-Cl | CF$_3$ | H | H | C(O)NHPr-c |
| 3-CF$_3$-4-Cl | CF$_2$Cl | H | H | C(O)CH$_3$ |
| 3-CF$_3$-4-Cl | CF$_2$Cl | H | H | C(O)Et |
| 3-CF$_3$-4-Cl | CF$_2$Cl | H | H | C(O)Pr-n |
| 3-CF$_3$-4-Cl | CF$_2$Cl | H | H | C(O)Pr-c |
| 3-CF$_3$-4-Cl | CF$_2$Cl | H | H | C(O)CH$_2$Pr-c |
| 3-CF$_3$-4-Cl | CF$_2$Cl | H | H | C(O)CH$_2$CF$_3$ |
| 3-CF$_3$-4-Cl | CF$_2$Cl | H | H | C(O)CH$_2$SCH$_3$ |
| 3-CF$_3$-4-Cl | CF$_2$Cl | H | H | C(O)CH$_2$S(O)CH$_3$ |
| 3-CF$_3$-4-Cl | CF$_2$Cl | H | H | C(O)CH$_2$SO$_2$CH$_3$ |
| 3-CF$_3$-4-Cl | CF$_2$Cl | H | H | C(O)CH$_2$SEt |
| 3-CF$_3$-4-Cl | CF$_2$Cl | H | H | C(O)CH$_2$S(O)Et |
| 3-CF$_3$-4-Cl | CF$_2$Cl | H | H | C(O)CH$_2$SO$_2$Et |
| 3-Cl-5-CF$_3$ | CHF$_2$ | H | H | C(O)CH$_3$ |
| 3-Cl-5-CF$_3$ | CHF$_2$ | H | H | C(O)Et |
| 3-Cl-5-CF$_3$ | CHF$_2$ | H | H | C(O)Pr-n |
| 3-Cl-5-CF$_3$ | CHF$_2$ | H | H | C(O)Pr-c |
| 3-Cl-5-CF$_3$ | CHF$_2$ | H | H | C(O)CH$_2$Pr-c |
| 3-Cl-5-CF$_3$ | CHF$_2$ | CH$_3$ | H | C(O)CH$_2$Pr-c |
| 3-Cl-5-CF$_3$ | CHF$_2$ | H | H | C(O)CH$_2$CF$_3$ |
| 3-Cl-5-CF$_3$ | CHF$_2$ | CH$_3$ | H | C(O)CH$_2$CF$_3$ |
| 3-Cl-5-CF$_3$ | CHF$_2$ | CH$_3$ | H | C(O)(E4-2a) |
| 3-Cl-5-CF$_3$ | CHF$_2$ | H | H | C(O)CH$_2$SCH$_3$ |
| 3-Cl-5-CF$_3$ | CHF$_2$ | H | H | C(O)CH$_2$S(O)CH$_3$ |
| 3-Cl-5-CF$_3$ | CHF$_2$ | H | H | C(O)CH$_2$SO$_2$CH$_3$ |
| 3-Cl-5-CF$_3$ | CHF$_2$ | H | H | C(O)CH$_2$SEt |
| 3-Cl-5-CF$_3$ | CHF$_2$ | H | H | C(O)CH$_2$S(O)Et |
| 3-Cl-5-CF$_3$ | CHF$_2$ | H | H | C(O)CH$_2$SO$_2$Et |
| 3-Cl-5-CF$_3$ | CHF$_2$ | H | H | C(O)CH(SCH$_3$)$_2$ |
| 3-Cl-5-CF$_3$ | CHF$_2$ | H | H | C(O)CH[S(O)CH$_3$]$_2$ |
| 3-Cl-5-CF$_3$ | CF$_3$ | H | H | C(O)CH$_3$ |
| 3-Cl-5-CF$_3$ | CF$_3$ | H | Et | C(O)CH$_3$ |
| 3-Cl-5-CF$_3$ | CF$_3$ | H | CH$_2$Pr-c | C(O)CH$_3$ |
| 3-Cl-5-CF$_3$ | CF$_3$ | H | CH$_2$OCH$_3$ | C(O)CH$_3$ |
| 3-Cl-5-CF$_3$ | CF$_3$ | H | CH$_2$CN | C(O)CH$_3$ |
| 3-Cl-5-CF$_3$ | CF$_3$ | H | CH$_2$C(S)NH$_2$ | C(O)CH$_3$ |
| 3-Cl-5-CF$_3$ | CF$_3$ | H | CH$_2$C≡CH | C(O)CH$_3$ |
| 3-Cl-5-CF$_3$ | CF$_3$ | CH$_3$ | H | C(O)CH$_3$ |
| 3-Cl-5-CF$_3$ | CF$_3$ | H | H | C(O)Et |
| 3-Cl-5-CF$_3$ | CF$_3$ | H | Et | C(O)Et |
| 3-Cl-5-CF$_3$ | CF$_3$ | H | CH$_2$OCH$_3$ | C(O)Et |
| 3-Cl-5-CF$_3$ | CF$_3$ | H | CH$_2$CN | C(O)Et |
| 3-Cl-5-CF$_3$ | CF$_3$ | H | CH$_2$C(S)NH$_2$ | C(O)Et |
| 3-Cl-5-CF$_3$ | CF$_3$ | H | CH$_2$CH═CH$_2$ | C(O)Et |
| 3-Cl-5-CF$_3$ | CF$_3$ | H | CH$_2$C≡CH | C(O)Et |
| 3-Cl-5-CF$_3$ | CF$_3$ | CH$_3$ | H | C(O)Et |
| 3-Cl-5-CF$_3$ | CF$_3$ | CH$_3$(S) | H | C(O)Et |
| 3-Cl-5-CF$_3$ | CF$_3$ | CN | H | C(O)Et |
| 3-Cl-5-CF$_3$ | CF$_3$ | C(S)NH$_2$ | H | C(O)Et |
| 3-Cl-5-CF$_3$ | CF$_3$ | H | H | C(O)Pr-n |
| 3-Cl-5-CF$_3$ | CF$_3$ | H | Et | C(O)Pr-n |
| 3-Cl-5-CF$_3$ | CF$_3$ | H | CH$_2$OCH$_3$ | C(O)Pr-n |
| 3-Cl-5-CF$_3$ | CF$_3$ | H | CH$_2$CN | C(O)Pr-n |
| 3-Cl-5-CF$_3$ | CF$_3$ | H | CH$_2$C(S)NH$_2$ | C(O)Pr-n |
| 3-Cl-5-CF$_3$ | CF$_3$ | H | CH$_2$C≡CH | C(O)Pr-n |
| 3-Cl-5-CF$_3$ | CF$_3$ | CH$_3$ | H | C(O)Pr-n |
| 3-Cl-5-CF$_3$ | CF$_3$ | CN | H | C(O)Pr-n |
| 3-Cl-5-CF$_3$ | CF$_3$ | C(S)NH$_2$ | H | C(O)Pr-n |
| 3-Cl-5-CF$_3$ | CF$_3$ | H | H | C(O)Pr-i |
| 3-Cl-5-CF$_3$ | CF$_3$ | H | Et | C(O)Pr-i |
| 3-Cl-5-CF$_3$ | CF$_3$ | H | CH$_2$CN | C(O)Pr-i |
| 3-Cl-5-CF$_3$ | CF$_3$ | H | CH$_2$C≡CH | C(O)Pr-i |
| 3-Cl-5-CF$_3$ | CF$_3$ | CH$_3$ | H | C(O)Pr-i |

TABLE 3-continued

| (X)$_m$ | R$^3$ | R$^4$ | R$^2$ | R$^1$ |
|---|---|---|---|---|
| 3-Cl-5-CF$_3$ | CF$_3$ | CN | H | C(O)Pr-i |
| 3-Cl-5-CF$_3$ | CF$_3$ | C(S)NH$_2$ | H | C(O)Pr-i |
| 3-Cl-5-CF$_3$ | CF$_3$ | H | H | C(O)Pr-c |
| 3-Cl-5-CF$_3$ | CF$_3$ | H | CH$_3$ | C(O)Pr-c |
| 3-Cl-5-CF$_3$ | CF$_3$ | H | Et | C(O)Pr-c |
| 3-Cl-5-CF$_3$ | CF$_3$ | H | CH$_2$Pr-c | C(O)Pr-c |
| 3-Cl-5-CF$_3$ | CF$_3$ | H | CH$_2$OCH$_3$ | C(O)Pr-c |
| 3-Cl-5-CF$_3$ | CF$_3$ | H | CH$_2$CN | C(O)Pr-c |
| 3-Cl-5-CF$_3$ | CF$_3$ | H | CH$_2$C(S)NH$_2$ | C(O)Pr-c |
| 3-Cl-5-CF$_3$ | CF$_3$ | H | CH$_2$CH=CH$_2$ | C(O)Pr-c |
| 3-Cl-5-CF$_3$ | CF$_3$ | H | CH$_2$C≡CH | C(O)Pr-c |
| 3-Cl-5-CF$_3$ | CF$_3$ | CH$_3$ | H | C(O)Pr-c |
| 3-Cl-5-CF$_3$ | CF$_3$ | CH$_3$(S) | H | C(O)Pr-c |
| 3-Cl-5-CF$_3$ | CF$_3$ | CH$_3$ | Et | C(O)Pr-c |
| 3-Cl-5-CF$_3$ | CF$_3$ | CH$_3$ | CH$_2$Pr-c | C(O)Pr-c |
| 3-Cl-5-CF$_3$ | CF$_3$ | CH$_3$ | CH$_2$CN | C(O)Pr-c |
| 3-Cl-5-CF$_3$ | CF$_3$ | CH$_3$ | CH$_2$C≡CH | C(O)Pr-c |
| 3-Cl-5-CF$_3$ | CF$_3$ | CN | H | C(O)Pr-c |
| 3-Cl-5-CF$_3$ | CF$_3$ | C(S)NH$_2$ | H | C(O)Pr-c |
| 3-Cl-5-CF$_3$ | CF$_3$ | C≡CH | H | C(O)Pr-c |
| 3-Cl-5-CF$_3$ | CF$_3$ | H | H | C(O)Bu-i |
| 3-Cl-5-CF$_3$ | CF$_3$ | H | H | C(O)CH$_2$Pr-c |
| 3-Cl-5-CF$_3$ | CF$_3$ | H | CH$_3$ | C(O)CH$_2$Pr-c |
| 3-Cl-5-CF$_3$ | CF$_3$ | H | Et | C(O)CH$_2$Pr-c |
| 3-Cl-5-CF$_3$ | CF$_3$ | H | CH$_2$Pr-c | C(O)CH$_2$Pr-c |
| 3-Cl-5-CF$_3$ | CF$_3$ | H | CH$_2$OCH$_3$ | C(O)CH$_2$Pr-c |
| 3-Cl-5-CF$_3$ | CF$_3$ | H | CH$_2$CN | C(O)CH$_2$Pr-c |
| 3-Cl-5-CF$_3$ | CF$_3$ | H | CH$_2$C(S)NH$_2$ | C(O)CH$_2$Pr-c |
| 3-Cl-5-CF$_3$ | CF$_3$ | H | CH$_2$CH=CH$_2$ | C(O)CH$_2$Pr-c |
| 3-Cl-5-CF$_3$ | CF$_3$ | H | CH$_2$C≡CH | C(O)CH$_2$Pr-c |
| 3-Cl-5-CF$_3$ | CF$_3$ | CH$_3$ | H | C(O)CH$_2$Pr-c |
| 3-Cl-5-CF$_3$ | CF$_3$ | CH$_3$(S) | H | C(O)CH$_2$Pr-c |
| 3-Cl-5-CF$_3$ | CF$_3$ | CH$_3$ | Et | C(O)CH$_2$Pr-c |
| 3-Cl-5-CF$_3$ | CF$_3$ | CH$_3$ | CH$_2$CN | C(O)CH$_2$Pr-c |
| 3-Cl-5-CF$_3$ | CF$_3$ | CH$_3$ | CH$_2$C≡CH | C(O)CH$_2$Pr-c |
| 3-Cl-5-CF$_3$ | CF$_3$ | CN | H | C(O)CH$_2$Pr-c |
| 3-Cl-5-CF$_3$ | CF$_3$ | C(S)NH$_2$ | H | C(O)CH$_2$Pr-c |
| 3-Cl-5-CF$_3$ | CF$_3$ | H | H | C(O)(T-1) |
| 3-Cl-5-CF$_3$ | CF$_3$ | H | H | C(O)Bu-c |
| 3-Cl-5-CF$_3$ | CF$_3$ | H | H | C(O)CF$_3$ |
| 3-Cl-5-CF$_3$ | CF$_3$ | H | H | C(O)CH$_2$CH$_2$Cl |
| 3-Cl-5-CF$_3$ | CF$_3$ | H | H | C(O)CH$_2$CF$_3$ |
| 3-Cl-5-CF$_3$ | CF$_3$ | H | Et | C(O)CH$_2$CF$_3$ |
| 3-Cl-5-CF$_3$ | CF$_3$ | H | CH$_2$OCH$_3$ | C(O)CH$_2$CF$_3$ |
| 3-Cl-5-CF$_3$ | CF$_3$ | H | CH$_2$CN | C(O)CH$_2$CF$_3$ |
| 3-Cl-5-CF$_3$ | CF$_3$ | H | CH$_2$C(S)NH$_2$ | C(O)CH$_2$CF$_3$ |
| 3-Cl-5-CF$_3$ | CF$_3$ | H | CH$_2$C≡CH | C(O)CH$_2$CF$_3$ |
| 3-Cl-5-CF$_3$ | CF$_3$ | CH$_3$ | H | C(O)CH$_2$CF$_3$ |
| 3-Cl-5-CF$_3$ | CF$_3$ | CH$_3$(S) | H | C(O)CH$_2$CF$_3$ |
| 3-Cl-5-CF$_3$ | CF$_3$ | CH$_3$ | Et | C(O)CH$_2$CF$_3$ |
| 3-Cl-5-CF$_3$ | CF$_3$ | CH$_3$ | CH$_2$CN | C(O)CH$_2$CF$_3$ |
| 3-Cl-5-CF$_3$ | CF$_3$ | CH$_3$ | CH$_2$C≡CH | C(O)CH$_2$CF$_3$ |
| 3-Cl-5-CF$_3$ | CF$_3$ | CN | H | C(O)CH$_2$CF$_3$ |
| 3-Cl-5-CF$_3$ | CF$_3$ | C(S)NH$_2$ | H | C(O)CH$_2$CF$_3$ |
| 3-Cl-5-CF$_3$ | CF$_3$ | H | H | C(O)CH$_2$CH$_2$CF$_3$ |
| 3-Cl-5-CF$_3$ | CF$_3$ | H | H | C(O)CH$_2$OCH$_3$ |
| 3-Cl-5-CF$_3$ | CF$_3$ | H | H | C(O)(E4-2a) |
| 3-Cl-5-CF$_3$ | CF$_3$ | CH$_3$ | H | C(O)(E4-2a) |
| 3-Cl-5-CF$_3$ | CF$_3$ | CH$_3$(S) | H | C(O)(E4-2a) |
| 3-Cl-5-CF$_3$ | CF$_3$ | H | H | C(O)CH$_2$SCH$_3$ |
| 3-Cl-5-CF$_3$ | CF$_3$ | H | CH$_3$ | C(O)CH$_2$SCH$_3$ |
| 3-Cl-5-CF$_3$ | CF$_3$ | H | Et | C(O)CH$_2$SCH$_3$ |
| 3-Cl-5-CF$_3$ | CF$_3$ | H | CH$_2$CN | C(O)CH$_2$SCH$_3$ |
| 3-Cl-5-CF$_3$ | CF$_3$ | H | CH$_2$C≡CH | C(O)CH$_2$SCH$_3$ |
| 3-Cl-5-CF$_3$ | CF$_3$ | CH$_3$ | H | C(O)CH$_2$SCH$_3$ |
| 3-Cl-5-CF$_3$ | CF$_3$ | H | H | C(O)CH$_2$S(O)CH$_3$ |
| 3-Cl-5-CF$_3$ | CF$_3$ | H | CH$_3$ | C(O)CH$_2$S(O)CH$_3$ |
| 3-Cl-5-CF$_3$ | CF$_3$ | H | Et | C(O)CH$_2$S(O)CH$_3$ |
| 3-Cl-5-CF$_3$ | CF$_3$ | H | CH$_2$CN | C(O)CH$_2$S(O)CH$_3$ |
| 3-Cl-5-CF$_3$ | CF$_3$ | H | CH$_2$C≡CH | C(O)CH$_2$S(O)CH$_3$ |
| 3-Cl-5-CF$_3$ | CF$_3$ | CH$_3$ | H | C(O)CH$_2$S(O)CH$_3$ |
| 3-Cl-5-CF$_3$ | CF$_3$ | H | H | C(O)CH$_2$SO$_2$CH$_3$ |
| 3-Cl-5-CF$_3$ | CF$_3$ | H | CH$_3$ | C(O)CH$_2$SO$_2$CH$_3$ |
| 3-Cl-5-CF$_3$ | CF$_3$ | H | Et | C(O)CH$_2$SO$_2$CH$_3$ |
| 3-Cl-5-CF$_3$ | CF$_3$ | H | CH$_2$CN | C(O)CH$_2$SO$_2$CH$_3$ |
| 3-Cl-5-CF$_3$ | CF$_3$ | H | CH$_2$C≡CH | C(O)CH$_2$SO$_2$CH$_3$ |
| 3-Cl-5-CF$_3$ | CF$_3$ | CH$_3$ | H | C(O)CH$_2$SO$_2$CH$_3$ |
| 3-Cl-5-CF$_3$ | CF$_3$ | H | H | C(O)CH$_2$SEt |

TABLE 3-continued

| (X)$_m$ | R$^3$ | R$^4$ | R$^2$ | R$^1$ |
|---|---|---|---|---|
| 3-Cl-5-CF$_3$ | CF$_3$ | H | CH$_3$ | C(O)CH$_2$SEt |
| 3-Cl-5-CF$_3$ | CF$_3$ | H | Et | C(O)CH$_2$SEt |
| 3-Cl-5-CF$_3$ | CF$_3$ | H | CH$_2$CN | C(O)CH$_2$SEt |
| 3-Cl-5-CF$_3$ | CF$_3$ | H | CH$_2$CH=CH$_2$ | C(O)CH$_2$SEt |
| 3-Cl-5-CF$_3$ | CF$_3$ | H | CH$_2$C≡CH | C(O)CH$_2$SEt |
| 3-Cl-5-CF$_3$ | CF$_3$ | CH$_3$ | H | C(O)CH$_2$SEt |
| 3-Cl-5-CF$_3$ | CF$_3$ | H | H | C(O)CH$_2$S(O)Et |
| 3-Cl-5-CF$_3$ | CF$_3$ | H | CH$_3$ | C(O)CH$_2$S(O)Et |
| 3-Cl-5-CF$_3$ | CF$_3$ | H | Et | C(O)CH$_2$S(O)Et |
| 3-Cl-5-CF$_3$ | CF$_3$ | H | CH$_2$CN | C(O)CH$_2$S(O)Et |
| 3-Cl-5-CF$_3$ | CF$_3$ | H | CH$_2$C≡CH | C(O)CH$_2$S(O)Et |
| 3-Cl-5-CF$_3$ | CF$_3$ | CH$_3$ | H | C(O)CH$_2$S(O)Et |
| 3-Cl-5-CF$_3$ | CF$_3$ | H | H | C(O)CH$_2$SO$_2$Et |
| 3-Cl-5-CF$_3$ | CF$_3$ | H | CH$_3$ | C(O)CH$_2$SO$_2$Et |
| 3-Cl-5-CF$_3$ | CF$_3$ | H | Et | C(O)CH$_2$SO$_2$Et |
| 3-Cl-5-CF$_3$ | CF$_3$ | H | CH$_2$CN | C(O)CH$_2$SO$_2$Et |
| 3-Cl-5-CF$_3$ | CF$_3$ | H | CH$_2$C≡CH | C(O)CH$_2$SO$_2$Et |
| 3-Cl-5-CF$_3$ | CF$_3$ | CH$_3$ | H | C(O)CH$_2$SO$_2$Et |
| 3-Cl-5-CF$_3$ | CF$_3$ | H | H | C(O)CH(CH$_3$)SCH$_3$ |
| 3-Cl-5-CF$_3$ | CF$_3$ | H | H | C(O)CH(CH$_3$)S(O)CH$_3$ |
| 3-Cl-5-CF$_3$ | CF$_3$ | H | H | C(O)CH(CH$_3$)SO$_2$CH$_3$ |
| 3-Cl-5-CF$_3$ | CF$_3$ | H | H | C(O)(E5-1a) |
| 3-Cl-5-CF$_3$ | CF$_3$ | H | H | C(O)(E5-1b) |
| 3-Cl-5-CF$_3$ | CF$_3$ | H | H | C(O)(E5-1c) |
| 3-Cl-5-CF$_3$ | CF$_3$ | H | H | C(O)CF$_2$S(O)CH$_3$ |
| 3-Cl-5-CF$_3$ | CF$_3$ | H | H | C(O)CF$_2$SO$_2$CH$_3$ |
| 3-Cl-5-CF$_3$ | CF$_3$ | H | H | C(O)CH(SCH$_3$)$_2$ |
| 3-Cl-5-CF$_3$ | CF$_3$ | H | H | C(O)CH(SCH$_3$)S(O)CH$_3$ |
| 3-Cl-5-CF$_3$ | CF$_3$ | H | H | C(O)CH[S(O)CH$_3$]$_2$ |
| 3-Cl-5-CF$_3$ | CF$_3$ | H | H | C(O)CH(SCH$_3$)SO$_2$CH$_3$ |
| 3-Cl-5-CF$_3$ | CF$_3$ | H | H | C(O)CH[S(O)CH$_3$]SO$_2$CH$_3$ |
| 3-Cl-5-CF$_3$ | CF$_3$ | H | H | C(O)CH(SEt)$_2$ |
| 3-Cl-5-CF$_3$ | CF$_3$ | H | H | C(O)CH(SEt)S(O)Et |
| 3-Cl-5-CF$_3$ | CF$_3$ | H | H | C(O)CH[S(O)Et]$_2$ |
| 3-Cl-5-CF$_3$ | CF$_3$ | H | H | C(O)CH(SEt)SO$_2$Et |
| 3-Cl-5-CF$_3$ | CF$_3$ | H | H | C(O)CH[S(O)Et]SO$_2$Et |
| 3-Cl-5-CF$_3$ | CF$_3$ | H | H | C(O)CH$_2$C(O)NH$_2$ |
| 3-Cl-5-CF$_3$ | CF$_3$ | H | H | C(O)CH=CH$_2$ |
| 3-Cl-5-CF$_3$ | CF$_3$ | H | H | C(O)CH=CHCH$_3$ |
| 3-Cl-5-CF$_3$ | CF$_3$ | H | H | C(O)C(CH$_3$)=CHCH$_3$ |
| 3-Cl-5-CF$_3$ | CF$_3$ | H | H | C(O)C≡CCH$_3$ |
| 3-Cl-5-CF$_3$ | CF$_3$ | H | H | C(O)CH$_2$CH$_2$C≡CH |
| 3-Cl-5-CF$_3$ | CF$_3$ | H | H | C(O)(Ph-2,4,6-F$_3$) |
| 3-Cl-5-CF$_3$ | CF$_3$ | CH$_3$ | H | C(O)(Ph-2,4,6-F$_3$) |
| 3-Cl-5-CF$_3$ | CF$_3$ | H | H | C(O)(D32-2b)Cl |
| 3-Cl-5-CF$_3$ | CF$_3$ | H | H | C(O)NHEt |
| 3-Cl-5-CF$_3$ | CF$_3$ | H | CH$_2$CH=CH$_2$ | C(O)NHEt |
| 3-Cl-5-CF$_3$ | CF$_3$ | H | CH$_2$C≡CH | C(O)NHEt |
| 3-Cl-5-CF$_3$ | CF$_3$ | CH$_3$ | H | C(O)NHEt |
| 3-Cl-5-CF$_3$ | CF$_3$ | H | H | C(O)NHPr-c |
| 3-Cl-5-CF$_3$ | CF$_3$ | CH$_3$ | H | C(O)NHPr-c |
| 3-Cl-5-CF$_3$ | CF$_3$ | CH$_3$(S) | H | C(O)NHPr-c |
| 3-Cl-5-CF$_3$ | CF$_3$ | H | H | C(O)NHCH$_2$CF$_3$ |
| 3-Cl-5-CF$_3$ | CF$_3$ | CH$_3$ | H | C(O)NHCH$_2$CF$_3$ |
| 3-Cl-5-CF$_3$ | CF$_3$ | H | H | C(O)NHCH$_2$C≡CH |
| 3-Cl-5-CF$_3$ | CF$_3$ | CH$_3$ | H | C(O)NHCH$_2$C≡CH |
| 3-Cl-5-CF$_3$ | CF$_3$ | H | H | C(O)(T-2) |
| 3-Cl-5-CF$_3$ | CF$_3$ | H | H | C(O)(T-3) |
| 3-Cl-5-CF$_3$ | CF$_3$ | H | H | C(S)CH$_2$SCH$_3$ |
| 3-Cl-5-CF$_3$ | CF$_3$ | H | H | C(S)CH$_2$SEt |
| 3-Cl-5-CF$_3$ | CF$_2$Cl | H | H | C(O)CH$_3$ |
| 3-Cl-5-CF$_3$ | CF$_2$Cl | H | Et | C(O)CH$_3$ |
| 3-Cl-5-CF$_3$ | CF$_2$Cl | H | H | C(O)Et |
| 3-Cl-5-CF$_3$ | CF$_2$Cl | H | H | C(O)Pr-n |
| 3-Cl-5-CF$_3$ | CF$_2$Cl | H | H | C(O)Pr-i |
| 3-Cl-5-CF$_3$ | CF$_2$Cl | H | H | C(O)Pr-c |
| 3-Cl-5-CF$_3$ | CF$_2$Cl | CH$_3$ | H | C(O)Pr-c |
| 3-Cl-5-CF$_3$ | CF$_2$Cl | H | H | C(O)Bu-i |
| 3-Cl-5-CF$_3$ | CF$_2$Cl | H | H | C(O)CH$_2$Pr-c |
| 3-Cl-5-CF$_3$ | CF$_2$Cl | CH$_3$ | H | C(O)CH$_2$Pr-c |
| 3-Cl-5-CF$_3$ | CF$_2$Cl | H | H | C(O)CH$_2$CF$_3$ |
| 3-Cl-5-CF$_3$ | CF$_2$Cl | CH$_3$ | H | C(O)CH$_2$CF$_3$ |
| 3-Cl-5-CF$_3$ | CF$_2$Cl | CH$_3$ | H | C(O)(E4-2a) |
| 3-Cl-5-CF$_3$ | CF$_2$Cl | H | H | C(O)CH$_2$SCH$_3$ |
| 3-Cl-5-CF$_3$ | CF$_2$Cl | H | CH$_2$C≡CH | C(O)CH$_2$SCH$_3$ |
| 3-Cl-5-CF$_3$ | CF$_2$Cl | CH$_3$ | H | C(O)CH$_2$SCH$_3$ |
| 3-Cl-5-CF$_3$ | CF$_2$Cl | H | H | C(O)CH$_2$S(O)CH$_3$ |
| 3-Cl-5-CF$_3$ | CF$_2$Cl | H | H | C(O)CH$_2$SO$_2$CH$_3$ |

TABLE 3-continued

| (X)$_m$ | R$^3$ | R$^4$ | R$^2$ | R$^1$ |
|---|---|---|---|---|
| 3-Cl-5-CF$_3$ | CF$_2$Cl | H | CH$_3$ | C(O)CH$_2$SO$_2$CH$_3$ |
| 3-Cl-5-CF$_3$ | CF$_2$Cl | H | H | C(O)CH$_2$SEt |
| 3-Cl-5-CF$_3$ | CF$_2$Cl | H | H | C(O)CH$_2$S(O)Et |
| 3-Cl-5-CF$_3$ | CF$_2$Cl | H | H | C(O)CH$_2$SO$_2$Et |
| 3-Cl-5-CF$_3$ | CF$_2$Cl | H | H | C(O)CH(SCH$_3$)$_2$ |
| 3-Cl-5-CF$_3$ | CF$_2$Cl | H | H | C(O)CH[S(O)CH$_3$]$_2$ |
| 3-Cl-5-CF$_3$ | CF$_2$Cl | H | H | C(O)NHPr-c |
| 3-Cl-5-CF$_3$ | CF$_2$Br | H | H | C(O)CH$_2$SCH$_3$ |
| 3-Cl-5-CF$_3$ | CF$_2$CHF$_2$ | H | H | C(O)CH$_2$S(O)CH$_3$ |
| 3-Cl-5-CF$_3$ | CF$_2$CF$_3$ | H | H | C(O)CH$_2$SO$_2$CH$_3$ |
| 3-Br-5-CF$_3$ | CHF$_2$ | H | H | C(O)CH$_3$ |
| 3-Br-5-CF$_3$ | CHF$_2$ | H | H | C(O)Et |
| 3-Br-5-CF$_3$ | CHF$_2$ | H | H | C(O)Pr-n |
| 3-Br-5-CF$_3$ | CHF$_2$ | H | H | C(O)Pr-c |
| 3-Br-5-CF$_3$ | CHF$_2$ | H | H | C(O)CH$_2$Pr-c |
| 3-Br-5-CF$_3$ | CHF$_2$ | CH$_3$ | H | C(O)CH$_2$Pr-c |
| 3-Br-5-CF$_3$ | CHF$_2$ | H | H | C(O)CH$_2$CF$_3$ |
| 3-Br-5-CF$_3$ | CHF$_2$ | CH$_3$ | H | C(O)CH$_2$CF$_3$ |
| 3-Br-5-CF$_3$ | CHF$_2$ | CH$_3$ | H | C(O)(E4-2a) |
| 3-Br-5-CF$_3$ | CHF$_2$ | H | H | C(O)CH$_2$SCH$_3$ |
| 3-Br-5-CF$_3$ | CHF$_2$ | H | H | C(O)CH$_2$S(O)CH$_3$ |
| 3-Br-5-CF$_3$ | CHF$_2$ | H | H | C(O)CH$_2$SO$_2$CH$_3$ |
| 3-Br-5-CF$_3$ | CHF$_2$ | H | H | C(O)CH$_2$SEt |
| 3-Br-5-CF$_3$ | CHF$_2$ | H | H | C(O)CH$_2$S(O)Et |
| 3-Br-5-CF$_3$ | CHF$_2$ | H | H | C(O)CH$_2$SO$_2$Et |
| 3-Br-5-CF$_3$ | CHF$_2$ | H | H | C(O)CH(SCH$_3$)$_2$ |
| 3-Br-5-CF$_3$ | CHF$_2$ | H | H | C(O)CH[S(O)CH$_3$]$_2$ |
| 3-Br-5-CF$_3$ | CF$_3$ | H | H | C(O)CH$_3$ |
| 3-Br-5-CF$_3$ | CF$_3$ | H | Et | C(O)CH$_3$ |
| 3-Br-5-CF$_3$ | CF$_3$ | H | CH$_2$Pr-c | C(O)CH$_3$ |
| 3-Br-5-CF$_3$ | CF$_3$ | H | CH$_2$OCH$_3$ | C(O)CH$_3$ |
| 3-Br-5-CF$_3$ | CF$_3$ | H | CH$_2$CN | C(O)CH$_3$ |
| 3-Br-5-CF$_3$ | CF$_3$ | H | CH$_2$C(S)NH$_2$ | C(O)CH$_3$ |
| 3-Br-5-CF$_3$ | CF$_3$ | H | CH$_2$C≡CH | C(O)CH$_3$ |
| 3-Br-5-CF$_3$ | CF$_3$ | CH$_3$ | H | C(O)CH$_3$ |
| 3-Br-5-CF$_3$ | CF$_3$ | H | H | C(O)Et |
| 3-Br-5-CF$_3$ | CF$_3$ | H | Et | C(O)Et |
| 3-Br-5-CF$_3$ | CF$_3$ | H | CH$_2$CN | C(O)Et |
| 3-Br-5-CF$_3$ | CF$_3$ | H | CH$_2$C≡CH | C(O)Et |
| 3-Br-5-CF$_3$ | CF$_3$ | CH$_3$ | H | C(O)Et |
| 3-Br-5-CF$_3$ | CF$_3$ | CH$_3$(S) | H | C(O)Et |
| 3-Br-5-CF$_3$ | CF$_3$ | H | H | C(O)Pr-n |
| 3-Br-5-CF$_3$ | CF$_3$ | CH$_3$ | H | C(O)Pr-n |
| 3-Br-5-CF$_3$ | CF$_3$ | H | H | C(O)Pr-i |
| 3-Br-5-CF$_3$ | CF$_3$ | CH$_3$ | H | C(O)Pr-i |
| 3-Br-5-CF$_3$ | CF$_3$ | H | H | C(O)Pr-c |
| 3-Br-5-CF$_3$ | CF$_3$ | H | Et | C(O)Pr-c |
| 3-Br-5-CF$_3$ | CF$_3$ | H | CH$_2$Pr-c | C(O)Pr-c |
| 3-Br-5-CF$_3$ | CF$_3$ | H | CH$_2$OCH$_3$ | C(O)Pr-c |
| 3-Br-5-CF$_3$ | CF$_3$ | H | CH$_2$CN | C(O)Pr-c |
| 3-Br-5-CF$_3$ | CF$_3$ | H | CH$_2$C(S)NH$_2$ | C(O)Pr-c |
| 3-Br-5-CF$_3$ | CF$_3$ | H | CH$_2$C≡CH | C(O)Pr-c |
| 3-Br-5-CF$_3$ | CF$_3$ | CH$_3$ | H | C(O)Pr-c |
| 3-Br-5-CF$_3$ | CF$_3$ | CH$_3$(S) | H | C(O)Pr-c |
| 3-Br-5-CF$_3$ | CF$_3$ | CH$_3$ | Et | C(O)Pr-c |
| 3-Br-5-CF$_3$ | CF$_3$ | CH$_3$ | CH$_2$CN | C(O)Pr-c |
| 3-Br-5-CF$_3$ | CF$_3$ | CH$_3$ | CH$_2$C≡CH | C(O)Pr-c |
| 3-Br-5-CF$_3$ | CF$_3$ | H | H | C(O)Bu-i |
| 3-Br-5-CF$_3$ | CF$_3$ | H | H | C(O)CH$_2$Pr-c |
| 3-Br-5-CF$_3$ | CF$_3$ | H | Et | C(O)CH$_2$Pr-c |
| 3-Br-5-CF$_3$ | CF$_3$ | H | CH$_2$CN | C(O)CH$_2$Pr-c |
| 3-Br-5-CF$_3$ | CF$_3$ | H | CH$_2$C≡CH | C(O)CH$_2$Pr-c |
| 3-Br-5-CF$_3$ | CF$_3$ | CH$_3$ | H | C(O)CH$_2$Pr-c |
| 3-Br-5-CF$_3$ | CF$_3$ | CH$_3$(S) | H | C(O)CH$_2$Pr-c |
| 3-Br-5-CF$_3$ | CF$_3$ | CN | H | C(O)CH$_2$Pr-c |
| 3-Br-5-CF$_3$ | CF$_3$ | C(S)NH$_2$ | H | C(O)CH$_2$Pr-c |
| 3-Br-5-CF$_3$ | CF$_3$ | H | H | C(O)CH$_2$CF$_3$ |
| 3-Br-5-CF$_3$ | CF$_3$ | CH$_3$ | H | C(O)CH$_2$CF$_3$ |
| 3-Br-5-CF$_3$ | CF$_3$ | CH$_3$(S) | H | C(O)CH$_2$CF$_3$ |
| 3-Br-5-CF$_3$ | CF$_3$ | CN | H | C(O)CH$_2$CF$_3$ |
| 3-Br-5-CF$_3$ | CF$_3$ | C(S)NH$_2$ | H | C(O)CH$_2$CF$_3$ |
| 3-Br-5-CF$_3$ | CF$_3$ | H | H | C(O)CH$_2$CH$_2$CF$_3$ |
| 3-Br-5-CF$_3$ | CF$_3$ | H | H | C(O)(E4-2a) |
| 3-Br-5-CF$_3$ | CF$_3$ | CH$_3$ | H | C(O)(E4-2a) |
| 3-Br-5-CF$_3$ | CF$_3$ | CH$_3$(S) | H | C(O)(E4-2a) |
| 3-Br-5-CF$_3$ | CF$_3$ | H | H | C(O)CH$_2$SCH$_3$ |
| 3-Br-5-CF$_3$ | CF$_3$ | H | CH$_2$C≡CH | C(O)CH$_2$SCH$_3$ |
| 3-Br-5-CF$_3$ | CF$_3$ | CH$_3$ | H | C(O)CH$_2$SCH$_3$ |

TABLE 3-continued

| (X)$_m$ | R$^3$ | R$^4$ | R$^2$ | R$^1$ |
|---|---|---|---|---|
| 3-Br-5-CF$_3$ | CF$_3$ | H | H | C(O)CH$_2$S(O)CH$_3$ |
| 3-Br-5-CF$_3$ | CF$_3$ | H | CH$_2$C≡CH | C(O)CH$_2$S(O)CH$_3$ |
| 3-Br-5-CF$_3$ | CF$_3$ | H | H | C(O)CH$_2$SO$_2$CH$_3$ |
| 3-Br-5-CF$_3$ | CF$_3$ | H | CH$_3$ | C(O)CH$_2$SO$_2$CH$_3$ |
| 3-Br-5-CF$_3$ | CF$_3$ | CH$_3$ | H | C(O)CH$_2$SO$_2$CH$_3$ |
| 3-Br-5-CF$_3$ | CF$_3$ | H | H | C(O)CH$_2$SEt |
| 3-Br-5-CF$_3$ | CF$_3$ | H | CH$_3$ | C(O)CH$_2$SEt |
| 3-Br-5-CF$_3$ | CF$_3$ | H | Et | C(O)CH$_2$SEt |
| 3-Br-5-CF$_3$ | CF$_3$ | H | CH$_2$CH=CH$_2$ | C(O)CH$_2$SEt |
| 3-Br-5-CF$_3$ | CF$_3$ | H | CH$_2$C≡CH | C(O)CH$_2$SEt |
| 3-Br-5-CF$_3$ | CF$_3$ | CH$_3$ | H | C(O)CH$_2$SEt |
| 3-Br-5-CF$_3$ | CF$_3$ | H | H | C(O)CH$_2$S(O)Et |
| 3-Br-5-CF$_3$ | CF$_3$ | H | CH$_3$ | C(O)CH$_2$S(O)Et |
| 3-Br-5-CF$_3$ | CF$_3$ | CH$_3$ | H | C(O)CH$_2$S(O)Et |
| 3-Br-5-CF$_3$ | CF$_3$ | H | H | C(O)CH$_2$SO$_2$Et |
| 3-Br-5-CF$_3$ | CF$_3$ | H | CH$_3$ | C(O)CH$_2$SO$_2$Et |
| 3-Br-5-CF$_3$ | CF$_3$ | H | CH$_2$C≡CH | C(O)CH$_2$SO$_2$Et |
| 3-Br-5-CF$_3$ | CF$_3$ | CH$_3$ | H | C(O)CH$_2$SO$_2$Et |
| 3-Br-5-CF$_3$ | CF$_3$ | H | H | C(O)CH(CH$_3$)SCH$_3$ |
| 3-Br-5-CF$_3$ | CF$_3$ | H | H | C(O)(E5-1a) |
| 3-Br-5-CF$_3$ | CF$_3$ | H | H | C(O)CH(SCH$_3$)$_2$ |
| 3-Br-5-CF$_3$ | CF$_3$ | H | H | C(O)CH(SCH$_3$)S(O)CH$_3$ |
| 3-Br-5-CF$_3$ | CF$_3$ | H | H | C(O)CH[S(O)CH$_3$]$_2$ |
| 3-Br-5-CF$_3$ | CF$_3$ | H | H | C(O)CH(SEt)$_2$ |
| 3-Br-5-CF$_3$ | CF$_3$ | H | H | C(O)CH(SEt)S(O)Et |
| 3-Br-5-CF$_3$ | CF$_3$ | H | H | C(O)CH(SEt)SO$_2$Et |
| 3-Br-5-CF$_3$ | CF$_3$ | H | H | C(O)(D32-2b)Cl |
| 3-Br-5-CF$_3$ | CF$_3$ | H | H | C(O)NHEt |
| 3-Br-5-CF$_3$ | CF$_3$ | H | CH$_2$C≡CH | C(O)NHEt |
| 3-Br-5-CF$_3$ | CF$_3$ | CH$_3$ | H | C(O)NHEt |
| 3-Br-5-CF$_3$ | CF$_3$ | H | H | C(O)NHPr-c |
| 3-Br-5-CF$_3$ | CF$_3$ | CH$_3$ | H | C(O)NHPr-c |
| 3-Br-5-CF$_3$ | CF$_3$ | CH$_3$(S) | H | C(O)NHPr-c |
| 3-Br-5-CF$_3$ | CF$_3$ | H | H | C(O)NHCH$_2$CF$_3$ |
| 3-Br-5-CF$_3$ | CF$_3$ | CH$_3$ | H | C(O)NHCH$_2$C≡CH |
| 3-Br-5-CF$_3$ | CF$_3$ | H | H | C(S)CH$_2$SCH$_3$ |
| 3-Br-5-CF$_3$ | CF$_3$ | H | H | C(S)CH$_2$SEt |
| 3-Br-5-CF$_3$ | CF$_2$Cl | H | H | C(O)CH$_3$ |
| 3-Br-5-CF$_3$ | CF$_2$Cl | H | Et | C(O)CH$_3$ |
| 3-Br-5-CF$_3$ | CF$_2$Cl | H | H | C(O)Et |
| 3-Br-5-CF$_3$ | CF$_2$Cl | H | H | C(O)Pr-n |
| 3-Br-5-CF$_3$ | CF$_2$Cl | H | H | C(O)Pr-i |
| 3-Br-5-CF$_3$ | CF$_2$Cl | H | H | C(O)Pr-c |
| 3-Br-5-CF$_3$ | CF$_2$Cl | CH$_3$ | H | C(O)Pr-c |
| 3-Br-5-CF$_3$ | CF$_2$Cl | H | H | C(O)Bu-i |
| 3-Br-5-CF$_3$ | CF$_2$Cl | H | H | C(O)CH$_2$Pr-c |
| 3-Br-5-CF$_3$ | CF$_2$Cl | CH$_3$ | H | C(O)CH$_2$Pr-c |
| 3-Br-5-CF$_3$ | CF$_2$Cl | H | H | C(O)CH$_2$CF$_3$ |
| 3-Br-5-CF$_3$ | CF$_2$Cl | CH$_3$ | H | C(O)CH$_2$CF$_3$ |
| 3-Br-5-CF$_3$ | CF$_2$Cl | CH$_3$ | H | C(O)(E4-2a) |
| 3-Br-5-CF$_3$ | CF$_2$Cl | H | H | C(O)CH$_2$SCH$_3$ |
| 3-Br-5-CF$_3$ | CF$_2$Cl | H | CH$_2$C≡CH | C(O)CH$_2$SCH$_3$ |
| 3-Br-5-CF$_3$ | CF$_2$Cl | CH$_3$ | H | C(O)CH$_2$SCH$_3$ |
| 3-Br-5-CF$_3$ | CF$_2$Cl | H | H | C(O)CH$_2$S(O)CH$_3$ |
| 3-Br-5-CF$_3$ | CF$_2$Cl | H | H | C(O)CH$_2$SO$_2$CH$_3$ |
| 3-Br-5-CF$_3$ | CF$_2$Cl | H | CH$_3$ | C(O)CH$_2$SO$_2$CH$_3$ |
| 3-Br-5-CF$_3$ | CF$_2$Cl | H | H | C(O)CH$_2$SEt |
| 3-Br-5-CF$_3$ | CF$_2$Cl | H | H | C(O)CH$_2$S(O)Et |
| 3-Br-5-CF$_3$ | CF$_2$Cl | H | H | C(O)CH$_2$SO$_2$Et |
| 3-Br-5-CF$_3$ | CF$_2$Cl | H | H | C(O)CH(SCH$_3$)$_2$ |
| 3-Br-5-CF$_3$ | CF$_2$Cl | H | H | C(O)CH[S(O)CH$_3$]$_2$ |
| 3-Br-5-CF$_3$ | CF$_2$Cl | H | H | C(O)NHPr-c |
| 3-Br-5-CF$_3$ | CF$_2$Br | H | H | C(O)CH$_2$SEt |
| 3-Br-5-CF$_3$ | CF$_2$CHF$_2$ | H | H | C(O)CH$_2$S(O)Et |
| 3-Br-5-CF$_3$ | CF$_2$CF$_3$ | H | H | C(O)CH$_2$SO$_2$Et |
| 3-I-5-CF$_3$ | CHF$_2$ | H | H | C(O)CH$_3$ |
| 3-I-5-CF$_3$ | CHF$_2$ | H | H | C(O)Et |
| 3-I-5-CF$_3$ | CHF$_2$ | H | H | C(O)Pr-n |
| 3-I-5-CF$_3$ | CHF$_2$ | H | H | C(O)Pr-c |
| 3-I-5-CF$_3$ | CHF$_2$ | H | H | C(O)CH$_2$Pr-c |
| 3-I-5-CF$_3$ | CHF$_2$ | CH$_3$ | H | C(O)CH$_2$Pr-c |
| 3-I-5-CF$_3$ | CHF$_2$ | H | H | C(O)CH$_2$CF$_3$ |
| 3-I-5-CF$_3$ | CHF$_2$ | CH$_3$ | H | C(O)CH$_2$CF$_3$ |
| 3-I-5-CF$_3$ | CHF$_2$ | CH$_3$ | H | C(O)(E4-2a) |
| 3-I-5-CF$_3$ | CHF$_2$ | H | H | C(O)CH$_2$SCH$_3$ |
| 3-I-5-CF$_3$ | CHF$_2$ | H | H | C(O)CH$_2$S(O)CH$_3$ |
| 3-I-5-CF$_3$ | CHF$_2$ | H | H | C(O)CH$_2$SO$_2$CH$_3$ |
| 3-I-5-CF$_3$ | CHF$_2$ | H | H | C(O)CH$_2$SEt |

TABLE 3-continued

| (X)$_m$ | R$^3$ | R$^4$ | R$^2$ | R$^1$ |
|---|---|---|---|---|
| 3-I-5-CF$_3$ | CHF$_2$ | H | H | C(O)CH$_2$S(O)Et |
| 3-I-5-CF$_3$ | CHF$_2$ | H | H | C(O)CH$_2$SO$_2$Et |
| 3-I-5-CF$_3$ | CHF$_2$ | H | H | C(O)CH(SCH$_3$)$_2$ |
| 3-I-5-CF$_3$ | CHF$_2$ | H | H | C(O)CH[S(O)CH$_3$]$_2$ |
| 3-I-5-CF$_3$ | CF$_3$ | H | H | C(O)CH$_3$ |
| 3-I-5-CF$_3$ | CF$_3$ | H | Et | C(O)CH$_3$ |
| 3-I-5-CF$_3$ | CF$_3$ | H | CH$_2$Pr-c | C(O)CH$_3$ |
| 3-I-5-CF$_3$ | CF$_3$ | H | CH$_2$OCH$_3$ | C(O)CH$_3$ |
| 3-I-5-CF$_3$ | CF$_3$ | H | CH$_2$CN | C(O)CH$_3$ |
| 3-I-5-CF$_3$ | CF$_3$ | H | CH$_2$C(S)NH$_2$ | C(O)CH$_3$ |
| 3-I-5-CF$_3$ | CF$_3$ | H | CH$_2$C≡CH | C(O)CH$_3$ |
| 3-I-5-CF$_3$ | CF$_3$ | CH$_3$ | H | C(O)CH$_3$ |
| 3-I-5-CF$_3$ | CF$_3$ | H | H | C(O)Et |
| 3-I-5-CF$_3$ | CF$_3$ | H | Et | C(O)Et |
| 3-I-5-CF$_3$ | CF$_3$ | H | CH$_2$CN | C(O)Et |
| 3-I-5-CF$_3$ | CF$_3$ | H | CH$_2$C≡CH | C(O)Et |
| 3-I-5-CF$_3$ | CF$_3$ | CH$_3$ | H | C(O)Et |
| 3-I-5-CF$_3$ | CF$_3$ | CH$_3$(S) | H | C(O)Et |
| 3-I-5-CF$_3$ | CF$_3$ | H | H | C(O)Pr-n |
| 3-I-5-CF$_3$ | CF$_3$ | CH$_3$ | H | C(O)Pr-n |
| 3-I-5-CF$_3$ | CF$_3$ | H | H | C(O)Pr-i |
| 3-I-5-CF$_3$ | CF$_3$ | CH$_3$ | H | C(O)Pr-i |
| 3-I-5-CF$_3$ | CF$_3$ | H | H | C(O)Pr-c |
| 3-I-5-CF$_3$ | CF$_3$ | H | Et | C(O)Pr-c |
| 3-I-5-CF$_3$ | CF$_3$ | H | CH$_2$Pr-c | C(O)Pr-c |
| 3-I-5-CF$_3$ | CF$_3$ | H | CH$_2$OCH$_3$ | C(O)Pr-c |
| 3-I-5-CF$_3$ | CF$_3$ | H | CH$_2$CN | C(O)Pr-c |
| 3-I-5-CF$_3$ | CF$_3$ | H | CH$_2$C(S)NH$_2$ | C(O)Pr-c |
| 3-I-5-CF$_3$ | CF$_3$ | H | CH$_2$C≡CH | C(O)Pr-c |
| 3-I-5-CF$_3$ | CF$_3$ | CH$_3$ | H | C(O)Pr-c |
| 3-I-5-CF$_3$ | CF$_3$ | CH$_3$(S) | H | C(O)Pr-c |
| 3-I-5-CF$_3$ | CF$_3$ | CH$_3$ | Et | C(O)Pr-c |
| 3-I-5-CF$_3$ | CF$_3$ | CH$_3$ | CH$_2$CN | C(O)Pr-c |
| 3-I-5-CF$_3$ | CF$_3$ | CH$_3$ | CH$_2$C≡CH | C(O)Pr-c |
| 3-I-5-CF$_3$ | CF$_3$ | H | H | C(O)Bu-i |
| 3-I-5-CF$_3$ | CF$_3$ | H | H | C(O)CH$_2$Pr-c |
| 3-I-5-CF$_3$ | CF$_3$ | H | Et | C(O)CH$_2$Pr-c |
| 3-I-5-CF$_3$ | CF$_3$ | H | CH$_2$CN | C(O)CH$_2$Pr-c |
| 3-I-5-CF$_3$ | CF$_3$ | H | CH$_2$C≡CH | C(O)CH$_2$Pr-c |
| 3-I-5-CF$_3$ | CF$_3$ | CH$_3$ | H | C(O)CH$_2$Pr-c |
| 3-I-5-CF$_3$ | CF$_3$ | CH$_3$(S) | H | C(O)CH$_2$Pr-c |
| 3-I-5-CF$_3$ | CF$_3$ | CN | H | C(O)CH$_2$Pr-c |
| 3-I-5-CF$_3$ | CF$_3$ | C(S)NH$_2$ | H | C(O)CH$_2$Pr-c |
| 3-I-5-CF$_3$ | CF$_3$ | H | H | C(O)CH$_2$CF$_3$ |
| 3-I-5-CF$_3$ | CF$_3$ | CH$_3$ | H | C(O)CH$_2$CF$_3$ |
| 3-I-5-CF$_3$ | CF$_3$ | CH$_3$(S) | H | C(O)CH$_2$CF$_3$ |
| 3-I-5-CF$_3$ | CF$_3$ | CN | H | C(O)CH$_2$CF$_3$ |
| 3-I-5-CF$_3$ | CF$_3$ | C(S)NH$_2$ | H | C(O)CH$_2$CF$_3$ |
| 3-I-5-CF$_3$ | CF$_3$ | H | H | C(O)CH$_2$CH$_2$CF$_3$ |
| 3-I-5-CF$_3$ | CF$_3$ | H | H | C(O)(E4-2a) |
| 3-I-5-CF$_3$ | CF$_3$ | CH$_3$ | H | C(O)(E4-2a) |
| 3-I-5-CF$_3$ | CF$_3$ | CH$_3$(S) | H | C(O)(E4-2a) |
| 3-I-5-CF$_3$ | CF$_3$ | H | H | C(O)CH$_2$SCH$_3$ |
| 3-I-5-CF$_3$ | CF$_3$ | H | CH$_2$C≡CH | C(O)CH$_2$SCH$_3$ |
| 3-I-5-CF$_3$ | CF$_3$ | CH$_3$ | H | C(O)CH$_2$SCH$_3$ |
| 3-I-5-CF$_3$ | CF$_3$ | H | H | C(O)CH$_2$S(O)CH$_3$ |
| 3-I-5-CF$_3$ | CF$_3$ | H | CH$_2$C≡CH | C(O)CH$_2$S(O)CH$_3$ |
| 3-I-5-CF$_3$ | CF$_3$ | H | H | C(O)CH$_2$SO$_2$CH$_3$ |
| 3-I-5-CF$_3$ | CF$_3$ | H | CH$_3$ | C(O)CH$_2$SO$_2$CH$_3$ |
| 3-I-5-CF$_3$ | CF$_3$ | CH$_3$ | H | C(O)CH$_2$SO$_2$CH$_3$ |
| 3-I-5-CF$_3$ | CF$_3$ | H | H | C(O)CH$_2$SEt |
| 3-I-5-CF$_3$ | CF$_3$ | H | CH$_3$ | C(O)CH$_2$SEt |
| 3-I-5-CF$_3$ | CF$_3$ | H | Et | C(O)CH$_2$SEt |
| 3-I-5-CF$_3$ | CF$_3$ | H | CH$_2$CH=CH$_2$ | C(O)CH$_2$SEt |
| 3-I-5-CF$_3$ | CF$_3$ | H | CH$_2$C≡CH | C(O)CH$_2$SEt |
| 3-I-5-CF$_3$ | CF$_3$ | CH$_3$ | H | C(O)CH$_2$SEt |
| 3-I-5-CF$_3$ | CF$_3$ | H | H | C(O)CH$_2$S(O)Et |
| 3-I-5-CF$_3$ | CF$_3$ | H | CH$_3$ | C(O)CH$_2$S(O)Et |
| 3-I-5-CF$_3$ | CF$_3$ | CH$_3$ | H | C(O)CH$_2$S(O)Et |
| 3-I-5-CF$_3$ | CF$_3$ | H | H | C(O)CH$_2$SO$_2$Et |
| 3-I-5-CF$_3$ | CF$_3$ | H | CH$_3$ | C(O)CH$_2$SO$_2$Et |
| 3-I-5-CF$_3$ | CF$_3$ | H | CH$_2$C≡CH | C(O)CH$_2$SO$_2$Et |
| 3-I-5-CF$_3$ | CF$_3$ | CH$_3$ | H | C(O)CH$_2$SO$_2$Et |
| 3-I-5-CF$_3$ | CF$_3$ | H | H | C(O)CH(CH$_3$)SCH$_3$ |
| 3-I-5-CF$_3$ | CF$_3$ | H | H | C(O)(E5-1a) |
| 3-I-5-CF$_3$ | CF$_3$ | H | H | C(O)CH(SCH$_3$)$_2$ |
| 3-I-5-CF$_3$ | CF$_3$ | H | H | C(O)CH(SCH$_3$)S(O)CH$_3$ |
| 3-I-5-CF$_3$ | CF$_3$ | H | H | C(O)CH[S(O)CH$_3$]$_2$ |

TABLE 3-continued

| (X)$_m$ | R$^3$ | R$^4$ | R$^2$ | R$^1$ |
|---|---|---|---|---|
| 3-I-5-CF$_3$ | CF$_3$ | H | H | C(O)CH(SEt)$_2$ |
| 3-I-5-CF$_3$ | CF$_3$ | H | H | C(O)CH(SEt)S(O)Et |
| 3-I-5-CF$_3$ | CF$_3$ | H | H | C(O)CH(SEt)SO$_2$Et |
| 3-I-5-CF$_3$ | CF$_3$ | H | H | C(O)(D32-2b)Cl |
| 3-I-5-CF$_3$ | CF$_3$ | H | H | C(O)NHEt |
| 3-I-5-CF$_3$ | CF$_3$ | H | CH$_2$C≡CH | C(O)NHEt |
| 3-I-5-CF$_3$ | CF$_3$ | CH$_3$ | H | C(O)NHEt |
| 3-I-5-CF$_3$ | CF$_3$ | H | H | C(O)NHPr-c |
| 3-I-5-CF$_3$ | CF$_3$ | CH$_3$ | H | C(O)NHPr-c |
| 3-I-5-CF$_3$ | CF$_3$ | CH$_3$(S) | H | C(O)NHPr-c |
| 3-I-5-CF$_3$ | CF$_3$ | H | H | C(O)NHCH$_2$CF$_3$ |
| 3-I-5-CF$_3$ | CF$_3$ | CH$_3$ | H | C(O)NHCH$_2$C≡CH |
| 3-I-5-CF$_3$ | CF$_3$ | H | H | C(S)CH$_2$SCH$_3$ |
| 3-I-5-CF$_3$ | CF$_3$ | H | H | C(S)CH$_2$SEt |
| 3-I-5-CF$_3$ | CF$_2$Cl | H | H | C(O)CH$_3$ |
| 3-I-5-CF$_3$ | CF$_2$Cl | H | Et | C(O)CH$_3$ |
| 3-I-5-CF$_3$ | CF$_2$Cl | H | H | C(O)Et |
| 3-I-5-CF$_3$ | CF$_2$Cl | H | H | C(O)Pr-n |
| 3-I-5-CF$_3$ | CF$_2$Cl | H | H | C(O)Pr-i |
| 3-I-5-CF$_3$ | CF$_2$Cl | H | H | C(O)Pr-c |
| 3-I-5-CF$_3$ | CF$_2$Cl | CH$_3$ | H | C(O)Pr-c |
| 3-I-5-CF$_3$ | CF$_2$Cl | H | H | C(O)Bu-i |
| 3-I-5-CF$_3$ | CF$_2$Cl | H | H | C(O)CH$_2$Pr-c |
| 3-I-5-CF$_3$ | CF$_2$Cl | CH$_3$ | H | C(O)CH$_2$Pr-c |
| 3-I-5-CF$_3$ | CF$_2$Cl | H | H | C(O)CH$_2$CF$_3$ |
| 3-I-5-CF$_3$ | CF$_2$Cl | CH$_3$ | H | C(O)CH$_2$CF$_3$ |
| 3-I-5-CF$_3$ | CF$_2$Cl | CH$_3$ | H | C(O)(E4-2a) |
| 3-I-5-CF$_3$ | CF$_2$Cl | H | H | C(O)CH$_2$SCH$_3$ |
| 3-I-5-CF$_3$ | CF$_2$Cl | H | CH$_2$C≡CH | C(O)CH$_2$SCH$_3$ |
| 3-I-5-CF$_3$ | CF$_2$Cl | CH$_3$ | H | C(O)CH$_2$SCH$_3$ |
| 3-I-5-CF$_3$ | CF$_2$Cl | H | H | C(O)CH$_2$S(O)CH$_3$ |
| 3-I-5-CF$_3$ | CF$_2$Cl | H | H | C(O)CH$_2$SO$_2$CH$_3$ |
| 3-I-5-CF$_3$ | CF$_2$Cl | H | CH$_3$ | C(O)CH$_2$SO$_2$CH$_3$ |
| 3-I-5-CF$_3$ | CF$_2$Cl | H | H | C(O)CH$_2$SEt |
| 3-I-5-CF$_3$ | CF$_2$Cl | H | H | C(O)CH$_2$S(O)Et |
| 3-I-5-CF$_3$ | CF$_2$Cl | H | H | C(O)CH$_2$SO$_2$Et |
| 3-I-5-CF$_3$ | CF$_2$Cl | H | H | C(O)CH(SCH$_3$)$_2$ |
| 3-I-5-CF$_3$ | CF$_2$Cl | H | H | C(O)CH[S(O)CH$_3$]$_2$ |
| 3-I-5-CF$_3$ | CF$_2$Cl | H | H | C(O)NHPr-c |
| 3-I-5-CF$_3$ | CF$_2$Br | H | H | C(O)CH$_3$ |
| 3-I-5-CF$_3$ | CF$_2$CHF$_2$ | H | H | C(O)Et |
| 3-I-5-CF$_3$ | CF$_2$CF$_3$ | H | H | C(O)Pr-n |
| 3-CH$_3$-5-CF$_3$ | CF$_3$ | H | H | C(O)CH$_3$ |
| 3-CH$_3$-5-CF$_3$ | CF$_3$ | H | H | C(O)Et |
| 3-CH$_3$-5-CF$_3$ | CF$_3$ | H | H | C(O)Pr-n |
| 3-CH$_3$-5-CF$_3$ | CF$_3$ | H | H | C(O)Pr-c |
| 3-CH$_3$-5-CF$_3$ | CF$_3$ | H | H | C(O)CH$_2$Pr-c |
| 3-CH$_3$-5-CF$_3$ | CF$_3$ | H | H | C(O)CH$_2$CF$_3$ |
| 3-CH$_3$-5-CF$_3$ | CF$_3$ | H | H | C(O)CH$_2$SCH$_3$ |
| 3-CH$_3$-5-CF$_3$ | CF$_3$ | H | H | C(O)CH$_2$S(O)CH$_3$ |
| 3-CH$_3$-5-CF$_3$ | CF$_3$ | H | H | C(O)CH$_2$SO$_2$CH$_3$ |
| 3-CH$_3$-5-CF$_3$ | CF$_3$ | H | H | C(O)CH$_2$SEt |
| 3-CH$_3$-5-CF$_3$ | CF$_3$ | H | H | C(O)CH$_2$S(O)Et |
| 3-CH$_3$-5-CF$_3$ | CF$_3$ | H | H | C(O)CH$_2$SO$_2$Et |
| 3,5-(CF$_3$)$_2$ | CHF$_2$ | H | H | C(O)CH$_3$ |
| 3,5-(CF$_3$)$_2$ | CHF$_2$ | H | H | C(O)Et |
| 3,5-(CF$_3$)$_2$ | CHF$_2$ | H | H | C(O)Pr-n |
| 3,5-(CF$_3$)$_2$ | CHF$_2$ | H | H | C(O)Pr-c |
| 3,5-(CF$_3$)$_2$ | CHF$_2$ | H | H | C(O)CH$_2$Pr-c |
| 3,5-(CF$_3$)$_2$ | CHF$_2$ | CH$_3$ | H | C(O)CH$_2$Pr-c |
| 3,5-(CF$_3$)$_2$ | CHF$_2$ | H | H | C(O)CH$_2$CF$_3$ |
| 3,5-(CF$_3$)$_2$ | CHF$_2$ | CH$_3$ | H | C(O)CH$_2$CF$_3$ |
| 3,5-(CF$_3$)$_2$ | CHF$_2$ | CH$_3$ | H | C(O)(E4-2a) |
| 3,5-(CF$_3$)$_2$ | CHF$_2$ | H | H | C(O)CH$_2$SCH$_3$ |
| 3,5-(CF$_3$)$_2$ | CHF$_2$ | H | H | C(O)CH$_2$S(O)CH$_3$ |
| 3,5-(CF$_3$)$_2$ | CHF$_2$ | H | H | C(O)CH$_2$SO$_2$CH$_3$ |
| 3,5-(CF$_3$)$_2$ | CHF$_2$ | H | H | C(O)CH$_2$SEt |
| 3,5-(CF$_3$)$_2$ | CHF$_2$ | H | H | C(O)CH$_2$S(O)Et |
| 3,5-(CF$_3$)$_2$ | CHF$_2$ | H | H | C(O)CH$_2$SO$_2$Et |
| 3,5-(CF$_3$)$_2$ | CHF$_2$ | H | H | C(O)CH(SCH$_3$)$_2$ |
| 3,5-(CF$_3$)$_2$ | CHF$_2$ | H | H | C(O)CH[S(O)CH$_3$]$_2$ |
| 3,5-(CF$_3$)$_2$ | CF$_3$ | H | H | C(O)CH$_3$ |
| 3,5-(CF$_3$)$_2$ | CF$_3$ | H | Et | C(O)CH$_3$ |
| 3,5-(CF$_3$)$_2$ | CF$_3$ | H | CH$_2$Pr-c | C(O)CH$_3$ |
| 3,5-(CF$_3$)$_2$ | CF$_3$ | H | CH$_2$OCH$_3$ | C(O)CH$_3$ |
| 3,5-(CF$_3$)$_2$ | CF$_3$ | H | CH$_2$CN | C(O)CH$_3$ |
| 3,5-(CF$_3$)$_2$ | CF$_3$ | H | CH$_2$C(S)NH$_2$ | C(O)CH$_3$ |
| 3,5-(CF$_3$)$_2$ | CF$_3$ | H | CH$_2$C≡CH | C(O)CH$_3$ |

TABLE 3-continued

| (X)$_m$ | R$^3$ | R$^4$ | R$^2$ | R$^1$ |
|---|---|---|---|---|
| 3,5-(CF$_3$)$_2$ | CF$_3$ | CH$_3$ | H | C(O)CH$_3$ |
| 3,5-(CF$_3$)$_2$ | CF$_3$ | H | H | C(O)Et |
| 3,5-(CF$_3$)$_2$ | CF$_3$ | H | Et | C(O)Et |
| 3,5-(CF$_3$)$_2$ | CF$_3$ | H | CH$_2$CN | C(O)Et |
| 3,5-(CF$_3$)$_2$ | CF$_3$ | H | CH$_2$C≡CH | C(O)Et |
| 3,5-(CF$_3$)$_2$ | CF$_3$ | CH$_3$ | H | C(O)Et |
| 3,5-(CF$_3$)$_2$ | CF$_3$ | CH$_3$(S) | H | C(O)Et |
| 3,5-(CF$_3$)$_2$ | CF$_3$ | H | H | C(O)Pr-n |
| 3,5-(CF$_3$)$_2$ | CF$_3$ | CH$_3$ | H | C(O)Pr-n |
| 3,5-(CF$_3$)$_2$ | CF$_3$ | H | H | C(O)Pr-i |
| 3,5-(CF$_3$)$_2$ | CF$_3$ | CH$_3$ | H | C(O)Pr-i |
| 3,5-(CF$_3$)$_2$ | CF$_3$ | H | H | C(O)Pr-c |
| 3,5-(CF$_3$)$_2$ | CF$_3$ | H | Et | C(O)Pr-c |
| 3,5-(CF$_3$)$_2$ | CF$_3$ | H | CH$_2$Pr-c | C(O)Pr-c |
| 3,5-(CF$_3$)$_2$ | CF$_3$ | H | CH$_2$OCH$_3$ | C(O)Pr-c |
| 3,5-(CF$_3$)$_2$ | CF$_3$ | H | CH$_2$CN | C(O)Pr-c |
| 3,5-(CF$_3$)$_2$ | CF$_3$ | H | CH$_2$C(S)NH$_2$ | C(O)Pr-c |
| 3,5-(CF$_3$)$_2$ | CF$_3$ | H | CH$_2$C≡CH | C(O)Pr-c |
| 3,5-(CF$_3$)$_2$ | CF$_3$ | CH$_3$ | H | C(O)Pr-c |
| 3,5-(CF$_3$)$_2$ | CF$_3$ | CH$_3$(S) | H | C(O)Pr-c |
| 3,5-(CF$_3$)$_2$ | CF$_3$ | CH$_3$ | Et | C(O)Pr-c |
| 3,5-(CF$_3$)$_2$ | CF$_3$ | CH$_3$ | CH$_2$CN | C(O)Pr-c |
| 3,5-(CF$_3$)$_2$ | CF$_3$ | CH$_3$ | CH$_2$C≡CH | C(O)Pr-c |
| 3,5-(CF$_3$)$_2$ | CF$_3$ | H | H | C(O)Bu-i |
| 3,5-(CF$_3$)$_2$ | CF$_3$ | H | H | C(O)CH$_2$Pr-c |
| 3,5-(CF$_3$)$_2$ | CF$_3$ | H | Et | C(O)CH$_2$Pr-c |
| 3,5-(CF$_3$)$_2$ | CF$_3$ | H | CH$_2$CN | C(O)CH$_2$Pr-c |
| 3,5-(CF$_3$)$_2$ | CF$_3$ | H | CH$_2$C≡CH | C(O)CH$_2$Pr-c |
| 3,5-(CF$_3$)$_2$ | CF$_3$ | CH$_3$ | H | C(O)CH$_2$Pr-c |
| 3,5-(CF$_3$)$_2$ | CF$_3$ | CH$_3$(S) | H | C(O)CH$_2$Pr-c |
| 3,5-(CF$_3$)$_2$ | CF$_3$ | CN | H | C(O)CH$_2$Pr-c |
| 3,5-(CF$_3$)$_2$ | CF$_3$ | C(S)NH$_2$ | H | C(O)CH$_2$Pr-c |
| 3,5-(CF$_3$)$_2$ | CF$_3$ | H | H | C(O)CH$_2$CF$_3$ |
| 3,5-(CF$_3$)$_2$ | CF$_3$ | CH$_3$ | H | C(O)CH$_2$CF$_3$ |
| 3,5-(CF$_3$)$_2$ | CF$_3$ | CH$_3$(S) | H | C(O)CH$_2$CF$_3$ |
| 3,5-(CF$_3$)$_2$ | CF$_3$ | CN | H | C(O)CH$_2$CF$_3$ |
| 3,5-(CF$_3$)$_2$ | CF$_3$ | C(S)NH$_2$ | H | C(O)CH$_2$CF$_3$ |
| 3,5-(CF$_3$)$_2$ | CF$_3$ | H | H | C(O)CH$_2$CH$_2$CF$_3$ |
| 3,5-(CF$_3$)$_2$ | CF$_3$ | H | H | C(O)(E4-2a) |
| 3,5-(CF$_3$)$_2$ | CF$_3$ | CH$_3$ | H | C(O)(E4-2a) |
| 3,5-(CF$_3$)$_2$ | CF$_3$ | CH$_3$(S) | H | C(O)(E4-2a) |
| 3,5-(CF$_3$)$_2$ | CF$_3$ | H | H | C(O)CH$_2$SCH$_3$ |
| 3,5-(CF$_3$)$_2$ | CF$_3$ | H | CH$_2$C≡CH | C(O)CH$_2$SCH$_3$ |
| 3,5-(CF$_3$)$_2$ | CF$_3$ | CH$_3$ | H | C(O)CH$_2$SCH$_3$ |
| 3,5-(CF$_3$)$_2$ | CF$_3$ | H | H | C(O)CH$_2$S(O)CH$_3$ |
| 3,5-(CF$_3$)$_2$ | CF$_3$ | H | CH$_2$C≡CH | C(O)CH$_2$S(O)CH$_3$ |
| 3,5-(CF$_3$)$_2$ | CF$_3$ | H | H | C(O)CH$_2$SO$_2$CH$_3$ |
| 3,5-(CF$_3$)$_2$ | CF$_3$ | H | CH$_3$ | C(O)CH$_2$SO$_2$CH$_3$ |
| 3,5-(CF$_3$)$_2$ | CF$_3$ | CH$_3$ | H | C(O)CH$_2$SO$_2$CH$_3$ |
| 3,5-(CF$_3$)$_2$ | CF$_3$ | H | H | C(O)CH$_2$SEt |
| 3,5-(CF$_3$)$_2$ | CF$_3$ | H | CH$_3$ | C(O)CH$_2$SEt |
| 3,5-(CF$_3$)$_2$ | CF$_3$ | H | Et | C(O)CH$_2$SEt |
| 3,5-(CF$_3$)$_2$ | CF$_3$ | H | CH$_2$CH═CH$_2$ | C(O)CH$_2$SEt |
| 3,5-(CF$_3$)$_2$ | CF$_3$ | H | CH$_2$C≡CH | C(O)CH$_2$SEt |
| 3,5-(CF$_3$)$_2$ | CF$_3$ | CH$_3$ | H | C(O)CH$_2$SEt |
| 3,5-(CF$_3$)$_2$ | CF$_3$ | H | H | C(O)CH$_2$S(O)Et |
| 3,5-(CF$_3$)$_2$ | CF$_3$ | H | CH$_3$ | C(O)CH$_2$S(O)Et |
| 3,5-(CF$_3$)$_2$ | CF$_3$ | CH$_3$ | H | C(O)CH$_2$S(O)Et |
| 3,5-(CF$_3$)$_2$ | CF$_3$ | H | H | C(O)CH$_2$SO$_2$Et |
| 3,5-(CF$_3$)$_2$ | CF$_3$ | H | CH$_3$ | C(O)CH$_2$SO$_2$Et |
| 3,5-(CF$_3$)$_2$ | CF$_3$ | H | CH$_2$C≡CH | C(O)CH$_2$SO$_2$Et |
| 3,5-(CF$_3$)$_2$ | CF$_3$ | CH$_3$ | H | C(O)CH$_2$SO$_2$Et |
| 3,5-(CF$_3$)$_2$ | CF$_3$ | H | H | C(O)CH(CH$_3$)SCH$_3$ |
| 3,5-(CF$_3$)$_2$ | CF$_3$ | H | H | C(O)(E5-1a) |
| 3,5-(CF$_3$)$_2$ | CF$_3$ | H | H | C(O)CH(SCH$_3$)$_2$ |
| 3,5-(CF$_3$)$_2$ | CF$_3$ | H | H | C(O)CH(SCH$_3$)S(O)CH$_3$ |
| 3,5-(CF$_3$)$_2$ | CF$_3$ | H | H | C(O)CH[S(O)CH$_3$]$_2$ |
| 3,5-(CF$_3$)$_2$ | CF$_3$ | H | H | C(O)CH(SEt)$_2$ |
| 3,5-(CF$_3$)$_2$ | CF$_3$ | H | H | C(O)CH(SEt)S(O)Et |
| 3,5-(CF$_3$)$_2$ | CF$_3$ | H | H | C(O)CH(SEt)SO$_2$Et |
| 3,5-(CF$_3$)$_2$ | CF$_3$ | H | H | C(O)(D32-2b)Cl |
| 3,5-(CF$_3$)$_2$ | CF$_3$ | H | H | C(O)NHEt |
| 3,5-(CF$_3$)$_2$ | CF$_3$ | H | CH$_2$C≡CH | C(O)NHEt |
| 3,5-(CF$_3$)$_2$ | CF$_3$ | CH$_3$ | H | C(O)NHEt |
| 3,5-(CF$_3$)$_2$ | CF$_3$ | H | H | C(O)NHPr-c |
| 3,5-(CF$_3$)$_2$ | CF$_3$ | CH$_3$ | H | C(O)NHPr-c |
| 3,5-(CF$_3$)$_2$ | CF$_3$ | CH$_3$(S) | H | C(O)NHPr-c |
| 3,5-(CF$_3$)$_2$ | CF$_3$ | H | H | C(O)NHCH$_2$CF$_3$ |

TABLE 3-continued

| (X)$_m$ | R$^3$ | R$^4$ | R$^2$ | R$^1$ |
|---|---|---|---|---|
| 3,5-(CF$_3$)$_2$ | CF$_3$ | CH$_3$ | H | C(O)NHCH$_2$C≡CH |
| 3,5-(CF$_3$)$_2$ | CF$_3$ | H | H | C(S)CH$_2$SCH$_3$ |
| 3,5-(CF$_3$)$_2$ | CF$_3$ | H | H | C(S)CH$_2$SEt |
| 3,5-(CF$_3$)$_2$ | CF$_2$Cl | H | H | C(O)CH$_3$ |
| 3,5-(CF$_3$)$_2$ | CF$_2$Cl | H | Et | C(O)CH$_3$ |
| 3,5-(CF$_3$)$_2$ | CF$_2$Cl | H | H | C(O)Et |
| 3,5-(CF$_3$)$_2$ | CF$_2$Cl | H | H | C(O)Pr-n |
| 3,5-(CF$_3$)$_2$ | CF$_2$Cl | H | H | C(O)Pr-i |
| 3,5-(CF$_3$)$_2$ | CF$_2$Cl | H | H | C(O)Pr-c |
| 3,5-(CF$_3$)$_2$ | CF$_2$Cl | CH$_3$ | H | C(O)Pr-c |
| 3,5-(CF$_3$)$_2$ | CF$_2$Cl | H | H | C(O)Bu-i |
| 3,5-(CF$_3$)$_2$ | CF$_2$Cl | H | H | C(O)CH$_2$Pr-c |
| 3,5-(CF$_3$)$_2$ | CF$_2$Cl | CH$_3$ | H | C(O)CH$_2$Pr-c |
| 3,5-(CF$_3$)$_2$ | CF$_2$Cl | H | H | C(O)CH$_2$CF$_3$ |
| 3,5-(CF$_3$)$_2$ | CF$_2$Cl | CH$_3$ | H | C(O)CH$_2$CF$_3$ |
| 3,5-(CF$_3$)$_2$ | CF$_2$Cl | CH$_3$ | H | C(O)(E4-2a) |
| 3,5-(CF$_3$)$_2$ | CF$_2$Cl | H | H | C(O)CH$_2$SCH$_3$ |
| 3,5-(CF$_3$)$_2$ | CF$_2$Cl | H | CH$_2$C≡CH | C(O)CH$_2$SCH$_3$ |
| 3,5-(CF$_3$)$_2$ | CF$_2$Cl | CH$_3$ | H | C(O)CH$_2$SCH$_3$ |
| 3,5-(CF$_3$)$_2$ | CF$_2$Cl | H | H | C(O)CH$_2$S(O)CH$_3$ |
| 3,5-(CF$_3$)$_2$ | CF$_2$Cl | H | H | C(O)CH$_2$SO$_2$CH$_3$ |
| 3,5-(CF$_3$)$_2$ | CF$_2$Cl | H | CH$_3$ | C(O)CH$_2$SO$_2$CH$_3$ |
| 3,5-(CF$_3$)$_2$ | CF$_2$Cl | H | H | C(O)CH$_2$SEt |
| 3,5-(CF$_3$)$_2$ | CF$_2$Cl | H | H | C(O)CH$_2$S(O)Et |
| 3,5-(CF$_3$)$_2$ | CF$_2$Cl | H | H | C(O)CH$_2$SO$_2$Et |
| 3,5-(CF$_3$)$_2$ | CF$_2$Cl | H | H | C(O)CH(SCH$_3$)$_2$ |
| 3,5-(CF$_3$)$_2$ | CF$_2$Cl | H | H | C(O)CH[S(O)CH$_3$]$_2$ |
| 3,5-(CF$_3$)$_2$ | CF$_2$Cl | H | H | C(O)NHPr-c |
| 3,5-(CF$_3$)$_2$ | CF$_2$Br | H | H | C(O)Pr-c |
| 3,5-(CF$_3$)$_2$ | CF$_2$CHF$_2$ | H | H | C(O)CH$_2$Pr-c |
| 3,5-(CF$_3$)$_2$ | CF$_2$CF$_3$ | H | H | C(O)CH$_2$CF$_3$ |
| 3-Cl-5-CF$_2$CF$_3$ | CF$_3$ | H | H | C(O)CH$_2$SCH$_3$ |
| 3-Br-5-CF$_2$CF$_3$ | CF$_3$ | H | H | C(O)CH$_2$S(O)CH$_3$ |
| 3-CF$_3$-5-OCH$_3$ | CF$_3$ | H | H | C(O)CH$_3$ |
| 3-CF$_3$-5-OCH$_3$ | CF$_3$ | H | H | C(O)Et |
| 3-CF$_3$-5-OCH$_3$ | CF$_3$ | H | H | C(O)Pr-n |
| 3-CF$_3$-5-OCH$_3$ | CF$_3$ | H | H | C(O)Pr-c |
| 3-CF$_3$-5-OCH$_3$ | CF$_3$ | H | H | C(O)CH$_2$Pr-c |
| 3-CF$_3$-5-OCH$_3$ | CF$_3$ | H | H | C(O)CH$_2$CF$_3$ |
| 3-CF$_3$-5-OCH$_3$ | CF$_3$ | H | H | C(O)CH$_2$SCH$_3$ |
| 3-CF$_3$-5-OCH$_3$ | CF$_3$ | H | H | C(O)CH$_2$S(O)CH$_3$ |
| 3-CF$_3$-5-OCH$_3$ | CF$_3$ | H | H | C(O)CH$_2$SO$_2$CH$_3$ |
| 3-CF$_3$-5-OCH$_3$ | CF$_3$ | H | H | C(O)CH$_2$SEt |
| 3-CF$_3$-5-OCH$_3$ | CF$_3$ | H | H | C(O)CH$_2$S(O)Et |
| 3-CF$_3$-5-OCH$_3$ | CF$_3$ | H | H | C(O)CH$_2$SO$_2$Et |
| 3-Cl-5-OCHF$_2$ | CF$_3$ | H | H | C(O)CH$_3$ |
| 3-Cl-5-OCHF$_2$ | CF$_3$ | H | Et | C(O)CH$_3$ |
| 3-Cl-5-OCHF$_2$ | CF$_3$ | H | H | C(O)Et |
| 3-Cl-5-OCHF$_2$ | CF$_3$ | H | H | C(O)Pr-n |
| 3-Cl-5-OCHF$_2$ | CF$_3$ | H | H | C(O)Pr-i |
| 3-Cl-5-OCHF$_2$ | CF$_3$ | H | H | C(O)Pr-c |
| 3-Cl-5-OCHF$_2$ | CF$_3$ | CH$_3$ | H | C(O)Pr-c |
| 3-Cl-5-OCHF$_2$ | CF$_3$ | H | H | C(O)Bu-i |
| 3-Cl-5-OCHF$_2$ | CF$_3$ | H | H | C(O)CH$_2$Pr-c |
| 3-Cl-5-OCHF$_2$ | CF$_3$ | CH$_3$ | H | C(O)CH$_2$Pr-c |
| 3-Cl-5-OCHF$_2$ | CF$_3$ | H | H | C(O)CH$_2$CF$_3$ |
| 3-Cl-5-OCHF$_2$ | CF$_3$ | CH$_3$ | H | C(O)CH$_2$CF$_3$ |
| 3-Cl-5-OCHF$_2$ | CF$_3$ | CH$_3$ | H | C(O)(E4-2a) |
| 3-Cl-5-OCHF$_2$ | CF$_3$ | H | H | C(O)CH$_2$SCH$_3$ |
| 3-Cl-5-OCHF$_2$ | CF$_3$ | H | CH$_2$C≡CH | C(O)CH$_2$SCH$_3$ |
| 3-Cl-5-OCHF$_2$ | CF$_3$ | CH$_3$ | H | C(O)CH$_2$SCH$_3$ |
| 3-Cl-5-OCHF$_2$ | CF$_3$ | H | H | C(O)CH$_2$S(O)CH$_3$ |
| 3-Cl-5-OCHF$_2$ | CF$_3$ | H | H | C(O)CH$_2$SO$_2$CH$_3$ |
| 3-Cl-5-OCHF$_2$ | CF$_3$ | H | CH$_3$ | C(O)CH$_2$SO$_2$CH$_3$ |
| 3-Cl-5-OCHF$_2$ | CF$_3$ | H | H | C(O)CH$_2$SEt |
| 3-Cl-5-OCHF$_2$ | CF$_3$ | H | H | C(O)CH$_2$S(O)Et |
| 3-Cl-5-OCHF$_2$ | CF$_3$ | H | H | C(O)CH$_2$SO$_2$Et |
| 3-Cl-5-OCHF$_2$ | CF$_3$ | H | H | C(O)CH(SCH$_3$)$_2$ |
| 3-Cl-5-OCHF$_2$ | CF$_3$ | H | H | C(O)CH[S(O)CH$_3$]$_2$ |
| 3-Cl-5-OCHF$_2$ | CF$_3$ | H | H | C(O)NHPr-c |
| 3-Cl-5-OCHF$_2$ | CF$_2$Cl | H | H | C(O)CH$_3$ |
| 3-Cl-5-OCHF$_2$ | CF$_2$Cl | H | H | C(O)Et |
| 3-Cl-5-OCHF$_2$ | CF$_2$Cl | H | H | C(O)Pr-n |
| 3-Cl-5-OCHF$_2$ | CF$_2$Cl | H | H | C(O)Pr-c |
| 3-Cl-5-OCHF$_2$ | CF$_2$Cl | H | H | C(O)CH$_2$Pr-c |
| 3-Cl-5-OCHF$_2$ | CF$_2$Cl | H | H | C(O)CH$_2$CF$_3$ |
| 3-Cl-5-OCHF$_2$ | CF$_2$Cl | H | H | C(O)CH$_2$SCH$_3$ |
| 3-Cl-5-OCHF$_2$ | CF$_2$Cl | H | H | C(O)CH$_2$S(O)CH$_3$ |

TABLE 3-continued

| (X)$_m$ | R$^3$ | R$^4$ | R$^2$ | R$^1$ |
|---|---|---|---|---|
| 3-Cl-5-OCHF$_2$ | CF$_2$Cl | H | H | C(O)CH$_2$SO$_2$CH$_3$ |
| 3-Cl-5-OCHF$_2$ | CF$_2$Cl | H | H | C(O)CH$_2$SEt |
| 3-Cl-5-OCHF$_2$ | CF$_2$Cl | H | H | C(O)CH$_2$S(O)Et |
| 3-Cl-5-OCHF$_2$ | CF$_2$Cl | H | H | C(O)CH$_2$SO$_2$Et |
| 3-Br-5-OCHF$_2$ | CF$_3$ | H | H | C(O)CH$_3$ |
| 3-Br-5-OCHF$_2$ | CF$_3$ | H | H | C(O)Et |
| 3-Br-5-OCHF$_2$ | CF$_3$ | H | H | C(O)Pr-n |
| 3-Br-5-OCHF$_2$ | CF$_3$ | H | H | C(O)Pr-c |
| 3-Br-5-OCHF$_2$ | CF$_3$ | H | H | C(O)CH$_2$Pr-c |
| 3-Br-5-OCHF$_2$ | CF$_3$ | CH$_3$ | H | C(O)CH$_2$Pr-c |
| 3-Br-5-OCHF$_2$ | CF$_3$ | H | H | C(O)CH$_2$CF$_3$ |
| 3-Br-5-OCHF$_2$ | CF$_3$ | CH$_3$ | H | C(O)CH$_2$CF$_3$ |
| 3-Br-5-OCHF$_2$ | CF$_3$ | CH$_3$ | H | C(O)(E4-2a) |
| 3-Br-5-OCHF$_2$ | CF$_3$ | H | H | C(O)CH$_2$SCH$_3$ |
| 3-Br-5-OCHF$_2$ | CF$_3$ | H | H | C(O)CH$_2$S(O)CH$_3$ |
| 3-Br-5-OCHF$_2$ | CF$_3$ | H | H | C(O)CH$_2$SO$_2$CH$_3$ |
| 3-Br-5-OCHF$_2$ | CF$_3$ | H | H | C(O)CH$_2$SEt |
| 3-Br-5-OCHF$_2$ | CF$_3$ | H | H | C(O)CH$_2$S(O)Et |
| 3-Br-5-OCHF$_2$ | CF$_3$ | H | H | C(O)CH$_2$SO$_2$Et |
| 3-Br-5-OCHF$_2$ | CF$_3$ | H | H | C(O)CH(SCH$_3$)$_2$ |
| 3-Br-5-OCHF$_2$ | CF$_3$ | H | H | C(O)CH[S(O)CH$_3$]$_2$ |
| 3-CF$_3$-5-OCHF$_2$ | CF$_3$ | H | H | C(O)CH$_3$ |
| 3-CF$_3$-5-OCHF$_2$ | CF$_3$ | H | H | C(O)Et |
| 3-CF$_3$-5-OCHF$_2$ | CF$_3$ | H | H | C(O)Pr-n |
| 3-CF$_3$-5-OCHF$_2$ | CF$_3$ | H | H | C(O)Pr-c |
| 3-CF$_3$-5-OCHF$_2$ | CF$_3$ | H | H | C(O)CH$_2$Pr-c |
| 3-CF$_3$-5-OCHF$_2$ | CF$_3$ | CH$_3$ | H | C(O)CH$_2$Pr-c |
| 3-CF$_3$-5-OCHF$_2$ | CF$_3$ | H | H | C(O)CH$_2$CF$_3$ |
| 3-CF$_3$-5-OCHF$_2$ | CF$_3$ | CH$_3$ | H | C(O)CH$_2$CF$_3$ |
| 3-CF$_3$-5-OCHF$_2$ | CF$_3$ | CH$_3$ | H | C(O)(E4-2a) |
| 3-CF$_3$-5-OCHF$_2$ | CF$_3$ | H | H | C(O)CH$_2$SCH$_3$ |
| 3-CF$_3$-5-OCHF$_2$ | CF$_3$ | H | H | C(O)CH$_2$S(O)CH$_3$ |
| 3-CF$_3$-5-OCHF$_2$ | CF$_3$ | H | H | C(O)CH$_2$SO$_2$CH$_3$ |
| 3-CF$_3$-5-OCHF$_2$ | CF$_3$ | H | H | C(O)CH$_2$SEt |
| 3-CF$_3$-5-OCHF$_2$ | CF$_3$ | H | H | C(O)CH$_2$S(O)Et |
| 3-CF$_3$-5-OCHF$_2$ | CF$_3$ | H | H | C(O)CH$_2$SO$_2$Et |
| 3-CF$_3$-5-OCHF$_2$ | CF$_3$ | H | H | C(O)CH(SCH$_3$)$_2$ |
| 3-CF$_3$-5-OCHF$_2$ | CF$_3$ | H | H | C(O)CH[S(O)CH$_3$]$_2$ |
| 3-Cl-5-OCF$_3$ | CF$_3$ | H | H | C(O)CH$_3$ |
| 3-Cl-5-OCF$_3$ | CF$_3$ | H | Et | C(O)CH$_3$ |
| 3-Cl-5-OCF$_3$ | CF$_3$ | H | H | C(O)Et |
| 3-Cl-5-OCF$_3$ | CF$_3$ | H | H | C(O)Pr-n |
| 3-Cl-5-OCF$_3$ | CF$_3$ | H | H | C(O)Pr-i |
| 3-Cl-5-OCF$_3$ | CF$_3$ | H | H | C(O)Pr-c |
| 3-Cl-5-OCF$_3$ | CF$_3$ | CH$_3$ | H | C(O)Pr-c |
| 3-Cl-5-OCF$_3$ | CF$_3$ | H | H | C(O)Bu-i |
| 3-Cl-5-OCF$_3$ | CF$_3$ | H | H | C(O)CH$_2$Pr-c |
| 3-Cl-5-OCF$_3$ | CF$_3$ | CH$_3$ | H | C(O)CH$_2$Pr-c |
| 3-Cl-5-OCF$_3$ | CF$_3$ | H | H | C(O)CH$_2$CF$_3$ |
| 3-Cl-5-OCF$_3$ | CF$_3$ | CH$_3$ | H | C(O)CH$_2$CF$_3$ |
| 3-Cl-5-OCF$_3$ | CF$_3$ | CH$_3$ | H | C(O)(E4-2a) |
| 3-Cl-5-OCF$_3$ | CF$_3$ | H | H | C(O)CH$_2$SCH$_3$ |
| 3-Cl-5-OCF$_3$ | CF$_3$ | H | CH$_2$C≡CH | C(O)CH$_2$SCH$_3$ |
| 3-Cl-5-OCF$_3$ | CF$_3$ | CH$_3$ | H | C(O)CH$_2$SCH$_3$ |
| 3-Cl-5-OCF$_3$ | CF$_3$ | H | H | C(O)CH$_2$S(O)CH$_3$ |
| 3-Cl-5-OCF$_3$ | CF$_3$ | H | H | C(O)CH$_2$SO$_2$CH$_3$ |
| 3-Cl-5-OCF$_3$ | CF$_3$ | H | CH$_3$ | C(O)CH$_2$SO$_2$CH$_3$ |
| 3-Cl-5-OCF$_3$ | CF$_3$ | H | H | C(O)CH$_2$SEt |
| 3-Cl-5-OCF$_3$ | CF$_3$ | H | H | C(O)CH$_2$S(O)Et |
| 3-Cl-5-OCF$_3$ | CF$_3$ | H | H | C(O)CH$_2$SO$_2$Et |
| 3-Cl-5-OCF$_3$ | CF$_3$ | H | H | C(O)CH(SCH$_3$)$_2$ |
| 3-Cl-5-OCF$_3$ | CF$_3$ | H | H | C(O)CH[S(O)CH$_3$]$_2$ |
| 3-Cl-5-OCF$_3$ | CF$_3$ | H | H | C(O)NHPr-c |
| 3-Cl-5-OCF$_3$ | CF$_2$Cl | H | H | C(O)CH$_3$ |
| 3-Cl-5-OCF$_3$ | CF$_2$Cl | H | H | C(O)Et |
| 3-Cl-5-OCF$_3$ | CF$_2$Cl | H | H | C(O)Pr-n |
| 3-Cl-5-OCF$_3$ | CF$_2$Cl | H | H | C(O)Pr-c |
| 3-Cl-5-OCF$_3$ | CF$_2$Cl | H | H | C(O)CH$_2$Pr-c |
| 3-Cl-5-OCF$_3$ | CF$_2$Cl | H | H | C(O)CH$_2$CF$_3$ |
| 3-Cl-5-OCF$_3$ | CF$_2$Cl | H | H | C(O)CH$_2$SCH$_3$ |
| 3-Cl-5-OCF$_3$ | CF$_2$Cl | H | H | C(O)CH$_2$S(O)CH$_3$ |
| 3-Cl-5-OCF$_3$ | CF$_2$Cl | H | H | C(O)CH$_2$SO$_2$CH$_3$ |
| 3-Cl-5-OCF$_3$ | CF$_2$Cl | H | H | C(O)CH$_2$SEt |
| 3-Cl-5-OCF$_3$ | CF$_2$Cl | H | H | C(O)CH$_2$S(O)Et |
| 3-Cl-5-OCF$_3$ | CF$_2$Cl | H | H | C(O)CH$_2$SO$_2$Et |
| 3-Br-5-OCF$_3$ | CF$_3$ | H | H | C(O)CH$_3$ |
| 3-Br-5-OCF$_3$ | CF$_3$ | H | H | C(O)Et |
| 3-Br-5-OCF$_3$ | CF$_3$ | H | H | C(O)Pr-n |

TABLE 3-continued

| (X)$_m$ | R$^3$ | R$^4$ | R$^2$ | R$^1$ |
|---|---|---|---|---|
| 3-Br-5-OCF$_3$ | CF$_3$ | H | H | C(O)Pr-c |
| 3-Br-5-OCF$_3$ | CF$_3$ | H | H | C(O)CH$_2$Pr-c |
| 3-Br-5-OCF$_3$ | CF$_3$ | CH$_3$ | H | C(O)CH$_2$Pr-c |
| 3-Br-5-OCF$_3$ | CF$_3$ | H | H | C(O)CH$_2$CF$_3$ |
| 3-Br-5-OCF$_3$ | CF$_3$ | CH$_3$ | H | C(O)CH$_2$CF$_3$ |
| 3-Br-5-OCF$_3$ | CF$_3$ | CH$_3$ | H | C(O)(E4-2a) |
| 3-Br-5-OCF$_3$ | CF$_3$ | H | H | C(O)CH$_2$SCH$_3$ |
| 3-Br-5-OCF$_3$ | CF$_3$ | H | H | C(O)CH$_2$S(O)CH$_3$ |
| 3-Br-5-OCF$_3$ | CF$_3$ | H | H | C(O)CH$_2$SO$_2$CH$_3$ |
| 3-Br-5-OCF$_3$ | CF$_3$ | H | H | C(O)CH$_2$SEt |
| 3-Br-5-OCF$_3$ | CF$_3$ | H | H | C(O)CH$_2$S(O)Et |
| 3-Br-5-OCF$_3$ | CF$_3$ | H | H | C(O)CH$_2$SO$_2$Et |
| 3-Br-5-OCF$_3$ | CF$_3$ | H | H | C(O)CH(SCH$_3$)$_2$ |
| 3-Br-5-OCF$_3$ | CF$_3$ | H | H | C(O)CH[S(O)CH$_3$]$_2$ |
| 3-CF$_3$-5-OCF$_3$ | CF$_3$ | H | H | C(O)CH$_3$ |
| 3-CF$_3$-5-OCF$_3$ | CF$_3$ | H | H | C(O)Et |
| 3-CF$_3$-5-OCF$_3$ | CF$_3$ | H | H | C(O)Pr-n |
| 3-CF$_3$-5-OCF$_3$ | CF$_3$ | H | H | C(O)Pr-c |
| 3-CF$_3$-5-OCF$_3$ | CF$_3$ | H | H | C(O)CH$_2$Pr-c |
| 3-CF$_3$-5-OCF$_3$ | CF$_3$ | CH$_3$ | H | C(O)CH$_2$Pr-c |
| 3-CF$_3$-5-OCF$_3$ | CF$_3$ | H | H | C(O)CH$_2$CF$_3$ |
| 3-CF$_3$-5-OCF$_3$ | CF$_3$ | CH$_3$ | H | C(O)CH$_2$CF$_3$ |
| 3-CF$_3$-5-OCF$_3$ | CF$_3$ | CH$_3$ | H | C(O)(E4-2a) |
| 3-CF$_3$-5-OCF$_3$ | CF$_3$ | H | H | C(O)CH$_2$SCH$_3$ |
| 3-CF$_3$-5-OCF$_3$ | CF$_3$ | H | H | C(O)CH$_2$S(O)CH$_3$ |
| 3-CF$_3$-5-OCF$_3$ | CF$_3$ | H | H | C(O)CH$_2$SO$_2$CH$_3$ |
| 3-CF$_3$-5-OCF$_3$ | CF$_3$ | H | H | C(O)CH$_2$SEt |
| 3-CF$_3$-5-OCF$_3$ | CF$_3$ | H | H | C(O)CH$_2$S(O)Et |
| 3-CF$_3$-5-OCF$_3$ | CF$_3$ | H | H | C(O)CH$_2$SO$_2$Et |
| 3-CF$_3$-5-OCF$_3$ | CF$_3$ | H | H | C(O)CH(SCH$_3$)$_2$ |
| 3-CF$_3$-5-OCF$_3$ | CF$_3$ | H | H | C(O)CH[S(O)CH$_3$]$_2$ |
| 3-Cl-5-SCF$_3$ | CF$_3$ | H | H | C(O)CH$_3$ |
| 3-Cl-5-SCF$_3$ | CF$_3$ | H | Et | C(O)CH$_3$ |
| 3-Cl-5-SCF$_3$ | CF$_3$ | H | H | C(O)Et |
| 3-Cl-5-SCF$_3$ | CF$_3$ | H | H | C(O)Pr-n |
| 3-Cl-5-SCF$_3$ | CF$_3$ | H | H | C(O)Pr-i |
| 3-Cl-5-SCF$_3$ | CF$_3$ | H | H | C(O)Pr-c |
| 3-Cl-5-SCF$_3$ | CF$_3$ | CH$_3$ | H | C(O)Pr-c |
| 3-Cl-5-SCF$_3$ | CF$_3$ | H | H | C(O)Bu-i |
| 3-Cl-5-SCF$_3$ | CF$_3$ | H | H | C(O)CH$_2$Pr-c |
| 3-Cl-5-SCF$_3$ | CF$_3$ | CH$_3$ | H | C(O)CH$_2$Pr-c |
| 3-Cl-5-SCF$_3$ | CF$_3$ | H | H | C(O)CH$_2$CF$_3$ |
| 3-Cl-5-SCF$_3$ | CF$_3$ | CH$_3$ | H | C(O)CH$_2$CF$_3$ |
| 3-Cl-5-SCF$_3$ | CF$_3$ | CH$_3$ | H | C(O)(E4-2a) |
| 3-Cl-5-SCF$_3$ | CF$_3$ | H | H | C(O)CH$_2$SCH$_3$ |
| 3-Cl-5-SCF$_3$ | CF$_3$ | H | CH$_2$C≡CH | C(O)CH$_2$SCH$_3$ |
| 3-Cl-5-SCF$_3$ | CF$_3$ | CH$_3$ | H | C(O)CH$_2$SCH$_3$ |
| 3-Cl-5-SCF$_3$ | CF$_3$ | H | H | C(O)CH$_2$S(O)CH$_3$ |
| 3-Cl-5-SCF$_3$ | CF$_3$ | H | H | C(O)CH$_2$SO$_2$CH$_3$ |
| 3-Cl-5-SCF$_3$ | CF$_3$ | H | CH$_3$ | C(O)CH$_2$SO$_2$CH$_3$ |
| 3-Cl-5-SCF$_3$ | CF$_3$ | H | H | C(O)CH$_2$SEt |
| 3-Cl-5-SCF$_3$ | CF$_3$ | H | H | C(O)CH$_2$S(O)Et |
| 3-Cl-5-SCF$_3$ | CF$_3$ | H | H | C(O)CH$_2$SO$_2$Et |
| 3-Cl-5-SCF$_3$ | CF$_3$ | H | H | C(O)CH(SCH$_3$)$_2$ |
| 3-Cl-5-SCF$_3$ | CF$_3$ | H | H | C(O)CH[S(O)CH$_3$]$_2$ |
| 3-Cl-5-SCF$_3$ | CF$_3$ | H | H | C(O)NHPr-c |
| 3-Cl-5-SCF$_3$ | CF$_2$Cl | H | H | C(O)CH$_3$ |
| 3-Cl-5-SCF$_3$ | CF$_2$Cl | H | H | C(O)Et |
| 3-Cl-5-SCF$_3$ | CF$_2$Cl | H | H | C(O)Pr-n |
| 3-Cl-5-SCF$_3$ | CF$_2$Cl | H | H | C(O)Pr-c |
| 3-Cl-5-SCF$_3$ | CF$_2$Cl | H | H | C(O)CH$_2$Pr-c |
| 3-Cl-5-SCF$_3$ | CF$_2$Cl | H | H | C(O)CH$_2$CF$_3$ |
| 3-Cl-5-SCF$_3$ | CF$_2$Cl | H | H | C(O)CH$_2$SCH$_3$ |
| 3-Cl-5-SCF$_3$ | CF$_2$Cl | H | H | C(O)CH$_2$S(O)CH$_3$ |
| 3-Cl-5-SCF$_3$ | CF$_2$Cl | H | H | C(O)CH$_2$SO$_2$CH$_3$ |
| 3-Cl-5-SCF$_3$ | CF$_2$Cl | H | H | C(O)CH$_2$SEt |
| 3-Cl-5-SCF$_3$ | CF$_2$Cl | H | H | C(O)CH$_2$S(O)Et |
| 3-Cl-5-SCF$_3$ | CF$_2$Cl | H | H | C(O)CH$_2$SO$_2$Et |
| 3-Cl-5-S(O)CF$_3$ | CF$_3$ | H | H | C(O)CH$_2$SO$_2$CH$_3$ |
| 3-Cl-5-SO$_2$CF$_3$ | CF$_3$ | H | H | C(O)CH$_3$ |
| 3-Cl-5-SO$_2$CF$_3$ | CF$_3$ | H | H | C(O)Et |
| 3-Cl-5-SO$_2$CF$_3$ | CF$_3$ | H | H | C(O)Pr-n |
| 3-Cl-5-SO$_2$CF$_3$ | CF$_3$ | H | H | C(O)Pr-c |
| 3-Cl-5-SO$_2$CF$_3$ | CF$_3$ | H | H | C(O)CH$_2$Pr-c |
| 3-Cl-5-SO$_2$CF$_3$ | CF$_3$ | H | H | C(O)CH$_2$CF$_3$ |
| 3-Cl-5-SO$_2$CF$_3$ | CF$_3$ | H | H | C(O)CH$_2$SCH$_3$ |
| 3-Cl-5-SO$_2$CF$_3$ | CF$_3$ | H | H | C(O)CH$_2$S(O)CH$_3$ |
| 3-Cl-5-SO$_2$CF$_3$ | CF$_3$ | H | H | C(O)CH$_2$SO$_2$CH$_3$ |

TABLE 3-continued

| $(X)_m$ | $R^3$ | $R^4$ | $R^2$ | $R^1$ |
|---|---|---|---|---|
| 3-Cl-5-SO$_2$CF$_3$ | CF$_3$ | H | H | C(O)CH$_2$SEt |
| 3-Cl-5-SO$_2$CF$_3$ | CF$_3$ | H | H | C(O)CH$_2$S(O)Et |
| 3-Cl-5-SO$_2$CF$_3$ | CF$_3$ | H | H | C(O)CH$_2$SO$_2$Et |
| 3-Br-5-SCF$_3$ | CF$_3$ | H | H | C(O)CH$_3$ |
| 3-Br-5-SCF$_3$ | CF$_3$ | H | H | C(O)Et |
| 3-Br-5-SCF$_3$ | CF$_3$ | H | H | C(O)Pr-n |
| 3-Br-5-SCF$_3$ | CF$_3$ | H | H | C(O)Pr-c |
| 3-Br-5-SCF$_3$ | CF$_3$ | H | H | C(O)CH$_2$Pr-c |
| 3-Br-5-SCF$_3$ | CF$_3$ | CH$_3$ | H | C(O)CH$_2$Pr-c |
| 3-Br-5-SCF$_3$ | CF$_3$ | H | H | C(O)CH$_2$CF$_3$ |
| 3-Br-5-SCF$_3$ | CF$_3$ | CH$_3$ | H | C(O)CH$_2$CF$_3$ |
| 3-Br-5-SCF$_3$ | CF$_3$ | CH$_3$ | H | C(O)(E4-2a) |
| 3-Br-5-SCF$_3$ | CF$_3$ | H | H | C(O)CH$_2$SCH$_3$ |
| 3-Br-5-SCF$_3$ | CF$_3$ | H | H | C(O)CH$_2$S(O)CH$_3$ |
| 3-Br-5-SCF$_3$ | CF$_3$ | H | H | C(O)CH$_2$SO$_2$CH$_3$ |
| 3-Br-5-SCF$_3$ | CF$_3$ | H | H | C(O)CH$_2$SEt |
| 3-Br-5-SCF$_3$ | CF$_3$ | H | H | C(O)CH$_2$S(O)Et |
| 3-Br-5-SCF$_3$ | CF$_3$ | H | H | C(O)CH$_2$SO$_2$Et |
| 3-Br-5-SCF$_3$ | CF$_3$ | H | H | C(O)CH(SCH$_3$)$_2$ |
| 3-Br-5-SCF$_3$ | CF$_3$ | H | H | C(O)CH[S(O)CH$_3$]$_2$ |
| 3-Br-5-S(O)CF$_3$ | CF$_3$ | H | H | C(O)CH$_2$SEt |
| 3-Br-5-SO$_2$CF$_3$ | CF$_3$ | H | H | C(O)CH$_3$ |
| 3-Br-5-SO$_2$CF$_3$ | CF$_3$ | H | H | C(O)Et |
| 3-Br-5-SO$_2$CF$_3$ | CF$_3$ | H | H | C(O)Pr-n |
| 3-Br-5-SO$_2$CF$_3$ | CF$_3$ | H | H | C(O)Pr-c |
| 3-Br-5-SO$_2$CF$_3$ | CF$_3$ | H | H | C(O)CH$_2$Pr-c |
| 3-Br-5-SO$_2$CF$_3$ | CF$_3$ | H | H | C(O)CH$_2$CF$_3$ |
| 3-Br-5-SO$_2$CF$_3$ | CF$_3$ | H | H | C(O)CH$_2$SCH$_3$ |
| 3-Br-5-SO$_2$CF$_3$ | CF$_3$ | H | H | C(O)CH$_2$S(O)CH$_3$ |
| 3-Br-5-SO$_2$CF$_3$ | CF$_3$ | H | H | C(O)CH$_2$SO$_2$CH$_3$ |
| 3-Br-5-SO$_2$CF$_3$ | CF$_3$ | H | H | C(O)CH$_2$SEt |
| 3-Br-5-SO$_2$CF$_3$ | CF$_3$ | H | H | C(O)CH$_2$S(O)Et |
| 3-Br-5-SO$_2$CF$_3$ | CF$_3$ | H | H | C(O)CH$_2$SO$_2$Et |
| 3-Cl-5-SCF$_2$CHFCl | CF$_3$ | H | H | C(O)CH$_2$S(O)Et |
| 3-Br-5-SCF$_2$CHFCl | CF$_3$ | H | H | C(O)CH$_2$SO$_2$Et |
| 3-Cl-5-NO$_2$ | CF$_3$ | H | H | C(O)CH$_3$ |
| 3-Br-5-NO$_2$ | CF$_3$ | H | H | C(O)Et |
| 3-CF$_3$-5-NO$_2$ | CF$_3$ | H | H | C(O)CH$_3$ |
| 3-CF$_3$-5-NO$_2$ | CF$_3$ | H | H | C(O)Et |
| 3-CF$_3$-5-NO$_2$ | CF$_3$ | H | H | C(O)Pr-n |
| 3-CF$_3$-5-NO$_2$ | CF$_3$ | H | H | C(O)Pr-c |
| 3-CF$_3$-5-NO$_2$ | CF$_3$ | H | H | C(O)CH$_2$Pr-c |
| 3-CF$_3$-5-NO$_2$ | CF$_3$ | H | H | C(O)CH$_2$CF$_3$ |
| 3-CF$_3$-5-NO$_2$ | CF$_3$ | H | H | C(O)CH$_2$SCH$_3$ |
| 3-CF$_3$-5-NO$_2$ | CF$_3$ | H | H | C(O)CH$_2$S(O)CH$_3$ |
| 3-CF$_3$-5-NO$_2$ | CF$_3$ | H | H | C(O)CH$_2$SO$_2$CH$_3$ |
| 3-CF$_3$-5-NO$_2$ | CF$_3$ | H | H | C(O)CH$_2$SEt |
| 3-CF$_3$-5-NO$_2$ | CF$_3$ | H | H | C(O)CH$_2$S(O)Et |
| 3-CF$_3$-5-NO$_2$ | CF$_3$ | H | H | C(O)CH$_2$SO$_2$Et |
| 3-Cl-5-CN | CF$_3$ | H | H | C(O)CH$_3$ |
| 3-Cl-5-CN | CF$_3$ | H | H | C(O)Et |
| 3-Cl-5-CN | CF$_3$ | H | H | C(O)Pr-n |
| 3-Cl-5-CN | CF$_3$ | H | H | C(O)Pr-c |
| 3-Cl-5-CN | CF$_3$ | H | H | C(O)CH$_2$Pr-c |
| 3-Cl-5-CN | CF$_3$ | H | H | C(O)CH$_2$CF$_3$ |
| 3-Cl-5-CN | CF$_3$ | H | H | C(O)CH$_2$SCH$_3$ |
| 3-Cl-5-CN | CF$_3$ | H | H | C(O)CH$_2$S(O)CH$_3$ |
| 3-Cl-5-CN | CF$_3$ | H | H | C(O)CH$_2$SO$_2$CH$_3$ |
| 3-Cl-5-CN | CF$_3$ | H | H | C(O)CH$_2$SEt |
| 3-Cl-5-CN | CF$_3$ | H | H | C(O)CH$_2$S(O)Et |
| 3-Cl-5-CN | CF$_3$ | H | H | C(O)CH$_2$SO$_2$Et |
| 3-Br-5-CN | CF$_3$ | H | H | C(O)CH$_3$ |
| 3-Br-5-CN | CF$_3$ | H | H | C(O)Et |
| 3-Br-5-CN | CF$_3$ | H | H | C(O)Pr-n |
| 3-Br-5-CN | CF$_3$ | H | H | C(O)Pr-c |
| 3-Br-5-CN | CF$_3$ | H | H | C(O)CH$_2$Pr-c |
| 3-Br-5-CN | CF$_3$ | H | H | C(O)CH$_2$CF$_3$ |
| 3-Br-5-CN | CF$_3$ | H | H | C(O)CH$_2$SCH$_3$ |
| 3-Br-5-CN | CF$_3$ | H | H | C(O)CH$_2$S(O)CH$_3$ |
| 3-Br-5-CN | CF$_3$ | H | H | C(O)CH$_2$SO$_2$CH$_3$ |
| 3-Br-5-CN | CF$_3$ | H | H | C(O)CH$_2$SEt |
| 3-Br-5-CN | CF$_3$ | H | H | C(O)CH$_2$S(O)Et |
| 3-Br-5-CN | CF$_3$ | H | H | C(O)CH$_2$SO$_2$Et |
| 3-CF$_3$-5-CN | CF$_3$ | H | H | C(O)CH$_3$ |
| 3-CF$_3$-5-CN | CF$_3$ | H | H | C(O)Et |
| 3-CF$_3$-5-CN | CF$_3$ | H | H | C(O)Pr-n |
| 3-CF$_3$-5-CN | CF$_3$ | H | H | C(O)Pr-c |
| 3-CF$_3$-5-CN | CF$_3$ | H | H | C(O)CH$_2$Pr-c |

TABLE 3-continued

| (X)ₘ | R³ | R⁴ | R² | R¹ |
|---|---|---|---|---|
| 3-CF₃-5-CN | CF₃ | CH₃ | H | C(O)CH₂Pr-c |
| 3-CF₃-5-CN | CF₃ | H | H | C(O)CH₂CF₃ |
| 3-CF₃-5-CN | CF₃ | CH₃ | H | C(O)CH₂CF₃ |
| 3-CF₃-5-CN | CF₃ | CH₃ | H | C(O)(E4-2a) |
| 3-CF₃-5-CN | CF₃ | H | H | C(O)CH₂SCH₃ |
| 3-CF₃-5-CN | CF₃ | H | H | C(O)CH₂S(O)CH₃ |
| 3-CF₃-5-CN | CF₃ | H | H | C(O)CH₂SO₂CH₃ |
| 3-CF₃-5-CN | CF₃ | H | H | C(O)CH₂SEt |
| 3-CF₃-5-CN | CF₃ | H | H | C(O)CH₂S(O)Et |
| 3-CF₃-5-CN | CF₃ | H | H | C(O)CH₂SO₂Et |
| 3-CF₃-5-CN | CF₃ | H | H | C(O)CH(SCH₃)₂ |
| 3-CF₃-5-CN | CF₃ | H | H | C(O)CH[S(O)CH₃]₂ |
| 3,4,5-F₃ | CF₃ | H | H | C(O)CH₃ |
| 3,4,5-F₃ | CF₃ | H | H | C(O)Et |
| 3,4,5-F₃ | CF₃ | H | H | C(O)Pr-n |
| 3,4,5-F₃ | CF₃ | H | H | C(O)Pr-c |
| 3,4,5-F₃ | CF₃ | H | H | C(O)CH₂Pr-c |
| 3,4,5-F₃ | CF₃ | CH₃ | H | C(O)CH₂Pr-c |
| 3,4,5-F₃ | CF₃ | H | H | C(O)CH₂CF₃ |
| 3,4,5-F₃ | CF₃ | CH₃ | H | C(O)CH₂CF₃ |
| 3,4,5-F₃ | CF₃ | CH₃ | H | C(O)(E4-2a) |
| 3,4,5-F₃ | CF₃ | H | H | C(O)CH₂SCH₃ |
| 3,4,5-F₃ | CF₃ | H | H | C(O)CH₂S(O)CH₃ |
| 3,4,5-F₃ | CF₃ | H | H | C(O)CH₂SO₂CH₃ |
| 3,4,5-F₃ | CF₃ | H | H | C(O)CH₂SEt |
| 3,4,5-F₃ | CF₃ | H | H | C(O)CH₂S(O)Et |
| 3,4,5-F₃ | CF₃ | H | H | C(O)CH₂SO₂Et |
| 3,4,5-F₃ | CF₃ | H | H | C(O)CH(SCH₃)₂ |
| 3,4,5-F₃ | CF₃ | H | H | C(O)CH[S(O)CH₃]₂ |
| 3,5-Cl₂-4-F | CHF₂ | H | H | C(O)Pr-n |
| 3,5-Cl₂-4-F | CF₃ | H | H | C(O)CH₃ |
| 3,5-Cl₂-4-F | CF₃ | H | Et | C(O)CH₃ |
| 3,5-Cl₂-4-F | CF₃ | H | CH₂OCH₃ | C(O)CH₃ |
| 3,5-Cl₂-4-F | CF₃ | H | CH₂CN | C(O)CH₃ |
| 3,5-Cl₂-4-F | CF₃ | H | CH₂C≡CH | C(O)CH₃ |
| 3,5-Cl₂-4-F | CF₃ | H | H | C(O)Et |
| 3,5-Cl₂-4-F | CF₃ | CH₃ | H | C(O)Et |
| 3,5-Cl₂-4-F | CF₃ | H | H | C(O)Pr-n |
| 3,5-Cl₂-4-F | CF₃ | CH₃ | H | C(O)Pr-n |
| 3,5-Cl₂-4-F | CF₃ | H | H | C(O)Pr-i |
| 3,5-Cl₂-4-F | CF₃ | CH₃ | H | C(O)Pr-i |
| 3,5-Cl₂-4-F | CF₃ | H | H | C(O)Pr-c |
| 3,5-Cl₂-4-F | CF₃ | CH₃ | H | C(O)Pr-c |
| 3,5-Cl₂-4-F | CF₃ | CH₃(S) | H | C(O)Pr-c |
| 3,5-Cl₂-4-F | CF₃ | H | H | C(O)Bu-i |
| 3,5-Cl₂-4-F | CF₃ | H | H | C(O)CH₂Pr-c |
| 3,5-Cl₂-4-F | CF₃ | CH₃ | H | C(O)CH₂Pr-c |
| 3,5-Cl₂-4-F | CF₃ | CH₃(S) | H | C(O)CH₂Pr-c |
| 3,5-Cl₂-4-F | CF₃ | H | H | C(O)CH₂CF₃ |
| 3,5-Cl₂-4-F | CF₃ | CH₃ | H | C(O)CH₂CF₃ |
| 3,5-Cl₂-4-F | CF₃ | CH₃(S) | H | C(O)CH₂CF₃ |
| 3,5-Cl₂-4-F | CF₃ | H | H | C(O)(E4-2a) |
| 3,5-Cl₂-4-F | CF₃ | CH₃ | H | C(O)(E4-2a) |
| 3,5-Cl₂-4-F | CF₃ | CH₃(S) | H | C(O)(E4-2a) |
| 3,5-Cl₂-4-F | CF₃ | H | H | C(O)CH₂SCH₃ |
| 3,5-Cl₂-4-F | CF₃ | H | CH₂C≡CH | C(O)CH₂SCH₃ |
| 3,5-Cl₂-4-F | CF₃ | CH₃ | H | C(O)CH₂SCH₃ |
| 3,5-Cl₂-4-F | CF₃ | H | H | C(O)CH₂S(O)CH₃ |
| 3,5-Cl₂-4-F | CF₃ | H | H | C(O)CH₂SO₂CH₃ |
| 3,5-Cl₂-4-F | CF₃ | H | CH₃ | C(O)CH₂SO₂CH₃ |
| 3,5-Cl₂-4-F | CF₃ | H | H | C(O)CH₂SEt |
| 3,5-Cl₂-4-F | CF₃ | CH₃ | H | C(O)CH₂SEt |
| 3,5-Cl₂-4-F | CF₃ | H | H | C(O)CH₂S(O)Et |
| 3,5-Cl₂-4-F | CF₃ | H | CH₃ | C(O)CH₂S(O)Et |
| 3,5-Cl₂-4-F | CF₃ | H | H | C(O)CH₂SO₂Et |
| 3,5-Cl₂-4-F | CF₃ | H | CH₃ | C(O)CH₂SO₂Et |
| 3,5-Cl₂-4-F | CF₃ | H | H | C(O)CH(CH₃)SCH₃ |
| 3,5-Cl₂-4-F | CF₃ | H | H | C(O)(E5-1a) |
| 3,5-Cl₂-4-F | CF₃ | H | H | C(O)CH(SCH₃)₂ |
| 3,5-Cl₂-4-F | CF₃ | H | H | C(O)CH[S(O)CH₃]₂ |
| 3,5-Cl₂-4-F | CF₃ | H | H | C(O)CH(SEt)₂ |
| 3,5-Cl₂-4-F | CF₃ | H | H | C(O)CH(SEt)S(O)Et |
| 3,5-Cl₂-4-F | CF₃ | H | H | C(O)CH(SEt)SO₂Et |
| 3,5-Cl₂-4-F | CF₃ | H | H | C(O)(D32-2b)Cl |
| 3,5-Cl₂-4-F | CF₃ | H | H | C(O)NHEt |
| 3,5-Cl₂-4-F | CF₃ | H | H | C(O)NHPr-c |
| 3,5-Cl₂-4-F | CF₃ | CH₃ | H | C(O)NHPr-c |
| 3,5-Cl₂-4-F | CF₃ | CH₃ | H | C(O)NHCH₂C≡CH |

TABLE 3-continued

| (X)$_m$ | R$^3$ | R$^4$ | R$^2$ | R$^1$ |
|---|---|---|---|---|
| 3,5-Cl$_2$-4-F | CF$_2$Cl | H | H | C(O)CH$_3$ |
| 3,5-Cl$_2$-4-F | CF$_2$Cl | H | H | C(O)Et |
| 3,5-Cl$_2$-4-F | CF$_2$Cl | H | H | C(O)Pr-n |
| 3,5-Cl$_2$-4-F | CF$_2$Cl | H | H | C(O)Pr-c |
| 3,5-Cl$_2$-4-F | CF$_2$Cl | H | H | C(O)CH$_2$Pr-c |
| 3,5-Cl$_2$-4-F | CF$_2$Cl | CH$_3$ | H | C(O)CH$_2$Pr-c |
| 3,5-Cl$_2$-4-F | CF$_2$Cl | H | H | C(O)CH$_2$CF$_3$ |
| 3,5-Cl$_2$-4-F | CF$_2$Cl | CH$_3$ | H | C(O)CH$_2$CF$_3$ |
| 3,5-Cl$_2$-4-F | CF$_2$Cl | CH$_3$ | H | C(O)(E4-2a) |
| 3,5-Cl$_2$-4-F | CF$_2$Cl | H | H | C(O)CH$_2$SCH$_3$ |
| 3,5-Cl$_2$-4-F | CF$_2$Cl | H | H | C(O)CH$_2$S(O)CH$_3$ |
| 3,5-Cl$_2$-4-F | CF$_2$Cl | H | H | C(O)CH$_2$SO$_2$CH$_3$ |
| 3,5-Cl$_2$-4-F | CF$_2$Cl | H | H | C(O)CH$_2$SEt |
| 3,5-Cl$_2$-4-F | CF$_2$Cl | H | H | C(O)CH$_2$S(O)Et |
| 3,5-Cl$_2$-4-F | CF$_2$Cl | H | H | C(O)CH$_2$SO$_2$Et |
| 3,5-Cl$_2$-4-F | CF$_2$Cl | H | H | C(O)CH(SCH$_3$)$_2$ |
| 3,5-Cl$_2$-4-F | CF$_2$Cl | H | H | C(O)CH[S(O)CH$_3$]$_2$ |
| 3,4,5-Cl$_3$ | CHF$_2$ | H | H | C(O)Pr-c |
| 3,4,5-Cl$_3$ | CF$_3$ | H | H | C(O)CH$_3$ |
| 3,4,5-Cl$_3$ | CF$_3$ | H | Et | C(O)CH$_3$ |
| 3,4,5-Cl$_3$ | CF$_3$ | H | CH$_2$OCH$_3$ | C(O)CH$_3$ |
| 3,4,5-Cl$_3$ | CF$_3$ | H | CH$_2$CN | C(O)CH$_3$ |
| 3,4,5-Cl$_3$ | CF$_3$ | H | CH$_2$C≡CH | C(O)CH$_3$ |
| 3,4,5-Cl$_3$ | CF$_3$ | H | H | C(O)Et |
| 3,4,5-Cl$_3$ | CF$_3$ | CH$_3$ | H | C(O)Et |
| 3,4,5-Cl$_3$ | CF$_3$ | H | H | C(O)Pr-n |
| 3,4,5-Cl$_3$ | CF$_3$ | CH$_3$ | H | C(O)Pr-n |
| 3,4,5-Cl$_3$ | CF$_3$ | H | H | C(O)Pr-i |
| 3,4,5-Cl$_3$ | CF$_3$ | CH$_3$ | H | C(O)Pr-i |
| 3,4,5-Cl$_3$ | CF$_3$ | H | H | C(O)Pr-c |
| 3,4,5-Cl$_3$ | CF$_3$ | CH$_3$ | H | C(O)Pr-c |
| 3,4,5-Cl$_3$ | CF$_3$ | CH$_3$(S) | H | C(O)Pr-c |
| 3,4,5-Cl$_3$ | CF$_3$ | H | H | C(O)Bu-i |
| 3,4,5-Cl$_3$ | CF$_3$ | H | H | C(O)CH$_2$Pr-c |
| 3,4,5-Cl$_3$ | CF$_3$ | CH$_3$ | H | C(O)CH$_2$Pr-c |
| 3,4,5-Cl$_3$ | CF$_3$ | CH$_3$(S) | H | C(O)CH$_2$Pr-c |
| 3,4,5-Cl$_3$ | CF$_3$ | H | H | C(O)CH$_2$CF$_3$ |
| 3,4,5-Cl$_3$ | CF$_3$ | CH$_3$ | H | C(O)CH$_2$CF$_3$ |
| 3,4,5-Cl$_3$ | CF$_3$ | CH$_3$(S) | H | C(O)CH$_2$CF$_3$ |
| 3,4,5-Cl$_3$ | CF$_3$ | H | H | C(O)(E4-2a) |
| 3,4,5-Cl$_3$ | CF$_3$ | CH$_3$ | H | C(O)(E4-2a) |
| 3,4,5-Cl$_3$ | CF$_3$ | CH$_3$(S) | H | C(O)(E4-2a) |
| 3,4,5-Cl$_3$ | CF$_3$ | H | H | C(O)CH$_2$SCH$_3$ |
| 3,4,5-Cl$_3$ | CF$_3$ | H | CH$_2$C≡CH | C(O)CH$_2$SCH$_3$ |
| 3,4,5-Cl$_3$ | CF$_3$ | CH$_3$ | H | C(O)CH$_2$SCH$_3$ |
| 3,4,5-Cl$_3$ | CF$_3$ | H | H | C(O)CH$_2$S(O)CH$_3$ |
| 3,4,5-Cl$_3$ | CF$_3$ | H | H | C(O)CH$_2$SO$_2$CH$_3$ |
| 3,4,5-Cl$_3$ | CF$_3$ | H | CH$_3$ | C(O)CH$_2$SO$_2$CH$_3$ |
| 3,4,5-Cl$_3$ | CF$_3$ | H | H | C(O)CH$_2$SEt |
| 3,4,5-Cl$_3$ | CF$_3$ | CH$_3$ | H | C(O)CH$_2$SEt |
| 3,4,5-Cl$_3$ | CF$_3$ | H | H | C(O)CH$_2$S(O)Et |
| 3,4,5-Cl$_3$ | CF$_3$ | H | CH$_3$ | C(O)CH$_2$S(O)Et |
| 3,4,5-Cl$_3$ | CF$_3$ | H | H | C(O)CH$_2$SO$_2$Et |
| 3,4,5-Cl$_3$ | CF$_3$ | H | CH$_3$ | C(O)CH$_2$SO$_2$Et |
| 3,4,5-Cl$_3$ | CF$_3$ | H | H | C(O)CH(CH$_3$)SCH$_3$ |
| 3,4,5-Cl$_3$ | CF$_3$ | H | H | C(O)(E5-1a) |
| 3,4,5-Cl$_3$ | CF$_3$ | H | H | C(O)CH(SCH$_3$)$_2$ |
| 3,4,5-Cl$_3$ | CF$_3$ | H | H | C(O)CH[S(O)CH$_3$]$_2$ |
| 3,4,5-Cl$_3$ | CF$_3$ | H | H | C(O)CH(SEt)$_2$ |
| 3,4,5-Cl$_3$ | CF$_3$ | H | H | C(O)CH(SEt)S(O)Et |
| 3,4,5-Cl$_3$ | CF$_3$ | H | H | C(O)CH(SEt)SO$_2$Et |
| 3,4,5-Cl$_3$ | CF$_3$ | H | H | C(O)(D32-2b)Cl |
| 3,4,5-Cl$_3$ | CF$_3$ | H | H | C(O)NHEt |
| 3,4,5-Cl$_3$ | CF$_3$ | H | H | C(O)NHPr-c |
| 3,4,5-Cl$_3$ | CF$_3$ | CH$_3$ | H | C(O)NHPr-c |
| 3,4,5-Cl$_3$ | CF$_3$ | CH$_3$ | H | C(O)NHCH$_2$C≡CH |
| 3,4,5-Cl$_3$ | CF$_2$Cl | H | H | C(O)CH$_3$ |
| 3,4,5-Cl$_3$ | CF$_2$Cl | H | H | C(O)Et |
| 3,4,5-Cl$_3$ | CF$_2$Cl | H | H | C(O)Pr-n |
| 3,4,5-Cl$_3$ | CF$_2$Cl | H | H | C(O)Pr-c |
| 3,4,5-Cl$_3$ | CF$_2$Cl | H | H | C(O)CH$_2$Pr-c |
| 3,4,5-Cl$_3$ | CF$_2$Cl | CH$_3$ | H | C(O)CH$_2$Pr-c |
| 3,4,5-Cl$_3$ | CF$_2$Cl | H | H | C(O)CH$_2$CF$_3$ |
| 3,4,5-Cl$_3$ | CF$_2$Cl | CH$_3$ | H | C(O)CH$_2$CF$_3$ |
| 3,4,5-Cl$_3$ | CF$_2$Cl | CH$_3$ | H | C(O)(E4-2a) |
| 3,4,5-Cl$_3$ | CF$_2$Cl | H | H | C(O)CH$_2$SCH$_3$ |
| 3,4,5-Cl$_3$ | CF$_2$Cl | H | H | C(O)CH$_2$S(O)CH$_3$ |
| 3,4,5-Cl$_3$ | CF$_2$Cl | H | H | C(O)CH$_2$SO$_2$CH$_3$ |

TABLE 3-continued

| (X)$_m$ | R$^3$ | R$^4$ | R$^2$ | R$^1$ |
|---|---|---|---|---|
| 3,4,5-Cl$_3$ | CF$_2$Cl | H | H | C(O)CH$_2$SEt |
| 3,4,5-Cl$_3$ | CF$_2$Cl | H | H | C(O)CH$_2$S(O)Et |
| 3,4,5-Cl$_3$ | CF$_2$Cl | H | H | C(O)CH$_2$SO$_2$Et |
| 3,4,5-Cl$_3$ | CF$_2$Cl | H | H | C(O)CH(SCH$_3$)$_2$ |
| 3,4,5-Cl$_3$ | CF$_2$Cl | H | H | C(O)CH[S(O)CH$_3$]$_2$ |
| 3,5-Br$_2$-4-F | CHF$_2$ | H | H | C(O)CH$_3$ |
| 3,5-Br$_2$-4-F | CHF$_2$ | H | H | C(O)Et |
| 3,5-Br$_2$-4-F | CHF$_2$ | H | H | C(O)Pr-n |
| 3,5-Br$_2$-4-F | CHF$_2$ | H | H | C(O)Pr-c |
| 3,5-Br$_2$-4-F | CHF$_2$ | H | H | C(O)CH$_2$Pr-c |
| 3,5-Br$_2$-4-F | CHF$_2$ | CH$_3$ | H | C(O)CH$_2$Pr-c |
| 3,5-Br$_2$-4-F | CHF$_2$ | H | H | C(O)CH$_2$CF$_3$ |
| 3,5-Br$_2$-4-F | CHF$_2$ | CH$_3$ | H | C(O)CH$_2$CF$_3$ |
| 3,5-Br$_2$-4-F | CHF$_2$ | CH$_3$ | H | C(O)(E4-2a) |
| 3,5-Br$_2$-4-F | CHF$_2$ | H | H | C(O)CH$_2$SCH$_3$ |
| 3,5-Br$_2$-4-F | CHF$_2$ | H | H | C(O)CH$_2$S(O)CH$_3$ |
| 3,5-Br$_2$-4-F | CHF$_2$ | H | H | C(O)CH$_2$SO$_2$CH$_3$ |
| 3,5-Br$_2$-4-F | CHF$_2$ | H | H | C(O)CH$_2$SEt |
| 3,5-Br$_2$-4-F | CHF$_2$ | H | H | C(O)CH$_2$S(O)Et |
| 3,5-Br$_2$-4-F | CHF$_2$ | H | H | C(O)CH$_2$SO$_2$Et |
| 3,5-Br$_2$-4-F | CHF$_2$ | H | H | C(O)CH(SCH$_3$)$_2$ |
| 3,5-Br$_2$-4-F | CHF$_2$ | H | H | C(O)CH[S(O)CH$_3$]$_2$ |
| 3,5-Br$_2$-4-F | CF$_3$ | H | H | C(O)CH$_3$ |
| 3,5-Br$_2$-4-F | CF$_3$ | H | Et | C(O)CH$_3$ |
| 3,5-Br$_2$-4-F | CF$_3$ | H | CH$_2$Pr-c | C(O)CH$_3$ |
| 3,5-Br$_2$-4-F | CF$_3$ | H | CH$_2$OCH$_3$ | C(O)CH$_3$ |
| 3,5-Br$_2$-4-F | CF$_3$ | H | CH$_2$CN | C(O)CH$_3$ |
| 3,5-Br$_2$-4-F | CF$_3$ | H | CH$_2$C(S)NH$_2$ | C(O)CH$_3$ |
| 3,5-Br$_2$-4-F | CF$_3$ | H | CH$_2$C≡CH | C(O)CH$_3$ |
| 3,5-Br$_2$-4-F | CF$_3$ | CH$_3$ | H | C(O)CH$_3$ |
| 3,5-Br$_2$-4-F | CF$_3$ | H | H | C(O)Et |
| 3,5-Br$_2$-4-F | CF$_3$ | H | Et | C(O)Et |
| 3,5-Br$_2$-4-F | CF$_3$ | H | CH$_2$CN | C(O)Et |
| 3,5-Br$_2$-4-F | CF$_3$ | H | CH$_2$C≡CH | C(O)Et |
| 3,5-Br$_2$-4-F | CF$_3$ | CH$_3$ | H | C(O)Et |
| 3,5-Br$_2$-4-F | CF$_3$ | CH$_3$(S) | H | C(O)Et |
| 3,5-Br$_2$-4-F | CF$_3$ | H | H | C(O)Pr-n |
| 3,5-Br$_2$-4-F | CF$_3$ | CH$_3$ | H | C(O)Pr-n |
| 3,5-Br$_2$-4-F | CF$_3$ | H | H | C(O)Pr-i |
| 3,5-Br$_2$-4-F | CF$_3$ | CH$_3$ | H | C(O)Pr-i |
| 3,5-Br$_2$-4-F | CF$_3$ | H | H | C(O)Pr-c |
| 3,5-Br$_2$-4-F | CF$_3$ | H | Et | C(O)Pr-c |
| 3,5-Br$_2$-4-F | CF$_3$ | H | CH$_2$Pr-c | C(O)Pr-c |
| 3,5-Br$_2$-4-F | CF$_3$ | H | CH$_2$OCH$_3$ | C(O)Pr-c |
| 3,5-Br$_2$-4-F | CF$_3$ | H | CH$_2$CN | C(O)Pr-c |
| 3,5-Br$_2$-4-F | CF$_3$ | H | CH$_2$C(S)NH$_2$ | C(O)Pr-c |
| 3,5-Br$_2$-4-F | CF$_3$ | H | CH$_2$C≡CH | C(O)Pr-c |
| 3,5-Br$_2$-4-F | CF$_3$ | CH$_3$ | H | C(O)Pr-c |
| 3,5-Br$_2$-4-F | CF$_3$ | CH$_3$(S) | H | C(O)Pr-c |
| 3,5-Br$_2$-4-F | CF$_3$ | CH$_3$ | Et | C(O)Pr-c |
| 3,5-Br$_2$-4-F | CF$_3$ | CH$_3$ | CH$_2$CN | C(O)Pr-c |
| 3,5-Br$_2$-4-F | CF$_3$ | CH$_3$ | CH$_2$C≡CH | C(O)Pr-c |
| 3,5-Br$_2$-4-F | CF$_3$ | H | H | C(O)Bu-i |
| 3,5-Br$_2$-4-F | CF$_3$ | H | H | C(O)CH$_2$Pr-c |
| 3,5-Br$_2$-4-F | CF$_3$ | H | Et | C(O)CH$_2$Pr-c |
| 3,5-Br$_2$-4-F | CF$_3$ | H | CH$_2$CN | C(O)CH$_2$Pr-c |
| 3,5-Br$_2$-4-F | CF$_3$ | H | CH$_2$C≡CH | C(O)CH$_2$Pr-c |
| 3,5-Br$_2$-4-F | CF$_3$ | CH$_3$ | H | C(O)CH$_2$Pr-c |
| 3,5-Br$_2$-4-F | CF$_3$ | CH$_3$(S) | H | C(O)CH$_2$Pr-c |
| 3,5-Br$_2$-4-F | CF$_3$ | CN | H | C(O)CH$_2$Pr-c |
| 3,5-Br$_2$-4-F | CF$_3$ | C(S)NH$_2$ | H | C(O)CH$_2$Pr-c |
| 3,5-Br$_2$-4-F | CF$_3$ | H | H | C(O)CH$_2$CF$_3$ |
| 3,5-Br$_2$-4-F | CF$_3$ | CH$_3$ | H | C(O)CH$_2$CF$_3$ |
| 3,5-Br$_2$-4-F | CF$_3$ | CH$_3$(S) | H | C(O)CH$_2$CF$_3$ |
| 3,5-Br$_2$-4-F | CF$_3$ | CN | H | C(O)CH$_2$CF$_3$ |
| 3,5-Br$_2$-4-F | CF$_3$ | C(S)NH$_2$ | H | C(O)CH$_2$CF$_3$ |
| 3,5-Br$_2$-4-F | CF$_3$ | H | H | C(O)CH$_2$CH$_2$CF$_3$ |
| 3,5-Br$_2$-4-F | CF$_3$ | H | H | C(O)(E4-2a) |
| 3,5-Br$_2$-4-F | CF$_3$ | CH$_3$ | H | C(O)(E4-2a) |
| 3,5-Br$_2$-4-F | CF$_3$ | CH$_3$(S) | H | C(O)(E4-2a) |
| 3,5-Br$_2$-4-F | CF$_3$ | H | H | C(O)CH$_2$SCH$_3$ |
| 3,5-Br$_2$-4-F | CF$_3$ | H | CH$_2$C≡CH | C(O)CH$_2$SCH$_3$ |
| 3,5-Br$_2$-4-F | CF$_3$ | CH$_3$ | H | C(O)CH$_2$SCH$_3$ |
| 3,5-Br$_2$-4-F | CF$_3$ | H | H | C(O)CH$_2$S(O)CH$_3$ |
| 3,5-Br$_2$-4-F | CF$_3$ | H | CH$_2$C≡CH | C(O)CH$_2$S(O)CH$_3$ |
| 3,5-Br$_2$-4-F | CF$_3$ | H | H | C(O)CH$_2$SO$_2$CH$_3$ |
| 3,5-Br$_2$-4-F | CF$_3$ | H | CH$_3$ | C(O)CH$_2$SO$_2$CH$_3$ |
| 3,5-Br$_2$-4-F | CF$_3$ | CH$_3$ | H | C(O)CH$_2$SO$_2$CH$_3$ |

TABLE 3-continued

| $(X)_m$ | $R^3$ | $R^4$ | $R^2$ | $R^1$ |
|---|---|---|---|---|
| 3,5-Br$_2$-4-F | CF$_3$ | H | H | C(O)CH$_2$SEt |
| 3,5-Br$_2$-4-F | CF$_3$ | H | CH$_3$ | C(O)CH$_2$SEt |
| 3,5-Br$_2$-4-F | CF$_3$ | H | Et | C(O)CH$_2$SEt |
| 3,5-Br$_2$-4-F | CF$_3$ | H | CH$_2$CH=CH$_2$ | C(O)CH$_2$SEt |
| 3,5-Br$_2$-4-F | CF$_3$ | H | CH$_2$C≡CH | C(O)CH$_2$SEt |
| 3,5-Br$_2$-4-F | CF$_3$ | CH$_3$ | H | C(O)CH$_2$SEt |
| 3,5-Br$_2$-4-F | CF$_3$ | H | H | C(O)CH$_2$S(O)Et |
| 3,5-Br$_2$-4-F | CF$_3$ | H | CH$_3$ | C(O)CH$_2$S(O)Et |
| 3,5-Br$_2$-4-F | CF$_3$ | CH$_3$ | H | C(O)CH$_2$S(O)Et |
| 3,5-Br$_2$-4-F | CF$_3$ | H | H | C(O)CH$_2$SO$_2$Et |
| 3,5-Br$_2$-4-F | CF$_3$ | H | CH$_3$ | C(O)CH$_2$SO$_2$Et |
| 3,5-Br$_2$-4-F | CF$_3$ | H | CH$_2$C≡CH | C(O)CH$_2$SO$_2$Et |
| 3,5-Br$_2$-4-F | CF$_3$ | CH$_3$ | H | C(O)CH$_2$SO$_2$Et |
| 3,5-Br$_2$-4-F | CF$_3$ | H | H | C(O)CH(CH$_3$)SCH$_3$ |
| 3,5-Br$_2$-4-F | CF$_3$ | H | H | C(O)(E5-1a) |
| 3,5-Br$_2$-4-F | CF$_3$ | H | H | C(O)CH(SCH$_3$)$_2$ |
| 3,5-Br$_2$-4-F | CF$_3$ | H | H | C(O)CH(SCH$_3$)S(O)CH$_3$ |
| 3,5-Br$_2$-4-F | CF$_3$ | H | H | C(O)CH[S(O)CH$_3$]$_2$ |
| 3,5-Br$_2$-4-F | CF$_3$ | H | H | C(O)CH(SEt)$_2$ |
| 3,5-Br$_2$-4-F | CF$_3$ | H | H | C(O)CH(SEt)S(O)Et |
| 3,5-Br$_2$-4-F | CF$_3$ | H | H | C(O)CH(SEt)SO$_2$Et |
| 3,5-Br$_2$-4-F | CF$_3$ | H | H | C(O)(D32-2b)Cl |
| 3,5-Br$_2$-4-F | CF$_3$ | H | H | C(O)NHEt |
| 3,5-Br$_2$-4-F | CF$_3$ | H | CH$_2$C≡CH | C(O)NHEt |
| 3,5-Br$_2$-4-F | CF$_3$ | CH$_3$ | H | C(O)NHEt |
| 3,5-Br$_2$-4-F | CF$_3$ | H | H | C(O)NHPr-c |
| 3,5-Br$_2$-4-F | CF$_3$ | CH$_3$ | H | C(O)NHPr-c |
| 3,5-Br$_2$-4-F | CF$_3$ | CH$_3$(S) | H | C(O)NHPr-c |
| 3,5-Br$_2$-4-F | CF$_3$ | H | H | C(O)NHCH$_2$CF$_3$ |
| 3,5-Br$_2$-4-F | CF$_3$ | CH$_3$ | H | C(O)NHCH$_2$C≡CH |
| 3,5-Br$_2$-4-F | CF$_3$ | H | H | C(S)CH$_2$SCH$_3$ |
| 3,5-Br$_2$-4-F | CF$_3$ | H | H | C(S)CH$_2$SEt |
| 3,5-Br$_2$-4-F | CF$_2$Cl | H | H | C(O)CH$_3$ |
| 3,5-Br$_2$-4-F | CF$_2$Cl | H | Et | C(O)CH$_3$ |
| 3,5-Br$_2$-4-F | CF$_2$Cl | H | H | C(O)Et |
| 3,5-Br$_2$-4-F | CF$_2$Cl | H | H | C(O)Pr-n |
| 3,5-Br$_2$-4-F | CF$_2$Cl | H | H | C(O)Pr-i |
| 3,5-Br$_2$-4-F | CF$_2$Cl | H | H | C(O)Pr-c |
| 3,5-Br$_2$-4-F | CF$_2$Cl | CH$_3$ | H | C(O)Pr-c |
| 3,5-Br$_2$-4-F | CF$_2$Cl | H | H | C(O)Bu-i |
| 3,5-Br$_2$-4-F | CF$_2$Cl | H | H | C(O)CH$_2$Pr-c |
| 3,5-Br$_2$-4-F | CF$_2$Cl | CH$_3$ | H | C(O)CH$_2$Pr-c |
| 3,5-Br$_2$-4-F | CF$_2$Cl | H | H | C(O)CH$_2$CF$_3$ |
| 3,5-Br$_2$-4-F | CF$_2$Cl | H | H | C(O)CH$_2$CF$_3$ |
| 3,5-Br$_2$-4-F | CF$_2$Cl | CH$_3$ | H | C(O)(E4-2a) |
| 3,5-Br$_2$-4-F | CF$_2$Cl | H | H | C(O)CH$_2$SCH$_3$ |
| 3,5-Br$_2$-4-F | CF$_2$Cl | H | CH$_2$C≡CH | C(O)CH$_2$SCH$_3$ |
| 3,5-Br$_2$-4-F | CF$_2$Cl | CH$_3$ | H | C(O)CH$_2$SCH$_3$ |
| 3,5-Br$_2$-4-F | CF$_2$Cl | H | H | C(O)CH$_2$S(O)CH$_3$ |
| 3,5-Br$_2$-4-F | CF$_2$Cl | H | H | C(O)CH$_2$SO$_2$CH$_3$ |
| 3,5-Br$_2$-4-F | CF$_2$Cl | H | CH$_3$ | C(O)CH$_2$SO$_2$CH$_3$ |
| 3,5-Br$_2$-4-F | CF$_2$Cl | H | H | C(O)CH$_2$SEt |
| 3,5-Br$_2$-4-F | CF$_2$Cl | H | H | C(O)CH$_2$S(O)Et |
| 3,5-Br$_2$-4-F | CF$_2$Cl | H | H | C(O)CH$_2$SO$_2$Et |
| 3,5-Br$_2$-4-F | CF$_2$Cl | H | H | C(O)CH(SCH$_3$)$_2$ |
| 3,5-Br$_2$-4-F | CF$_2$Cl | H | H | C(O)CH[S(O)CH$_3$]$_2$ |
| 3,5-Br$_2$-4-F | CF$_2$Cl | H | H | C(O)NHPr-c |
| 3,5-Br$_2$-4-F | CF$_2$Br | H | H | C(O)CH$_2$Pr-c |
| 3,5-Br$_2$-4-F | CF$_2$CHF$_2$ | H | H | C(O)CH$_2$CF$_3$ |
| 3,5-Br$_2$-4-F | CF$_2$CF$_3$ | H | H | C(O)CH$_2$SCH$_3$ |
| 3,5-Br$_2$-4-Cl | CF$_3$ | H | H | C(O)CH$_3$ |
| 3,5-Br$_2$-4-Cl | CF$_3$ | H | Et | C(O)CH$_3$ |
| 3,5-Br$_2$-4-Cl | CF$_3$ | H | H | C(O)Et |
| 3,5-Br$_2$-4-Cl | CF$_3$ | H | H | C(O)Pr-n |
| 3,5-Br$_2$-4-Cl | CF$_3$ | H | H | C(O)Pr-i |
| 3,5-Br$_2$-4-Cl | CF$_3$ | H | H | C(O)Pr-c |
| 3,5-Br$_2$-4-Cl | CF$_3$ | CH$_3$ | H | C(O)Pr-c |
| 3,5-Br$_2$-4-Cl | CF$_3$ | H | H | C(O)Bu-i |
| 3,5-Br$_2$-4-Cl | CF$_3$ | H | H | C(O)CH$_2$Pr-c |
| 3,5-Br$_2$-4-Cl | CF$_3$ | CH$_3$ | H | C(O)CH$_2$Pr-c |
| 3,5-Br$_2$-4-Cl | CF$_3$ | H | H | C(O)CH$_2$CF$_3$ |
| 3,5-Br$_2$-4-Cl | CF$_3$ | CH$_3$ | H | C(O)CH$_2$CF$_3$ |
| 3,5-Br$_2$-4-Cl | CF$_3$ | CH$_3$ | H | C(O)(E4-2a) |
| 3,5-Br$_2$-4-Cl | CF$_3$ | H | H | C(O)CH$_2$SCH$_3$ |
| 3,5-Br$_2$-4-Cl | CF$_3$ | H | CH$_2$C≡CH | C(O)CH$_2$SCH$_3$ |
| 3,5-Br$_2$-4-Cl | CF$_3$ | CH$_3$ | H | C(O)CH$_2$SCH$_3$ |
| 3,5-Br$_2$-4-Cl | CF$_3$ | H | H | C(O)CH$_2$S(O)CH$_3$ |
| 3,5-Br$_2$-4-Cl | CF$_3$ | H | H | C(O)CH$_2$SO$_2$CH$_3$ |

TABLE 3-continued

| (X)$_m$ | R$^3$ | R$^4$ | R$^2$ | R$^1$ |
|---|---|---|---|---|
| 3,5-Br$_2$-4-Cl | CF$_3$ | H | CH$_3$ | C(O)CH$_2$SO$_2$CH$_3$ |
| 3,5-Br$_2$-4-Cl | CF$_3$ | H | H | C(O)CH$_2$SEt |
| 3,5-Br$_2$-4-Cl | CF$_3$ | H | H | C(O)CH$_2$S(O)Et |
| 3,5-Br$_2$-4-Cl | CF$_3$ | H | H | C(O)CH$_2$SO$_2$Et |
| 3,5-Br$_2$-4-Cl | CF$_3$ | H | H | C(O)CH(SCH$_3$)$_2$ |
| 3,5-Br$_2$-4-Cl | CF$_3$ | H | H | C(O)CH[S(O)CH$_3$]$_2$ |
| 3,5-Br$_2$-4-Cl | CF$_3$ | H | H | C(O)NHPr-c |
| 3,5-Br$_2$-4-Cl | CF$_2$Cl | H | H | C(O)CH$_3$ |
| 3,5-Br$_2$-4-Cl | CF$_2$Cl | H | H | C(O)Et |
| 3,5-Br$_2$-4-Cl | CF$_2$Cl | H | H | C(O)Pr-n |
| 3,5-Br$_2$-4-Cl | CF$_2$Cl | H | H | C(O)Pr-c |
| 3,5-Br$_2$-4-Cl | CF$_2$Cl | H | H | C(O)CH$_2$Pr-c |
| 3,5-Br$_2$-4-Cl | CF$_2$Cl | H | H | C(O)CH$_2$CF$_3$ |
| 3,5-Br$_2$-4-Cl | CF$_2$Cl | H | H | C(O)CH$_2$SCH$_3$ |
| 3,5-Br$_2$-4-Cl | CF$_2$Cl | H | H | C(O)CH$_2$S(O)CH$_3$ |
| 3,5-Br$_2$-4-Cl | CF$_2$Cl | H | H | C(O)CH$_2$SO$_2$CH$_3$ |
| 3,5-Br$_2$-4-Cl | CF$_2$Cl | H | H | C(O)CH$_2$SEt |
| 3,5-Br$_2$-4-Cl | CF$_2$Cl | H | H | C(O)CH$_2$S(O)Et |
| 3,5-Br$_2$-4-Cl | CF$_2$Cl | H | H | C(O)CH$_2$SO$_2$Et |
| 3,4,5-Br$_3$ | CF$_3$ | H | H | C(O)CH$_3$ |
| 3,4,5-Br$_3$ | CF$_3$ | H | H | C(O)Et |
| 3,4,5-Br$_3$ | CF$_3$ | H | H | C(O)Pr-n |
| 3,4,5-Br$_3$ | CF$_3$ | H | H | C(O)Pr-c |
| 3,4,5-Br$_3$ | CF$_3$ | H | H | C(O)CH$_2$Pr-c |
| 3,4,5-Br$_3$ | CF$_3$ | CH$_3$ | H | C(O)CH$_2$Pr-c |
| 3,4,5-Br$_3$ | CF$_3$ | H | H | C(O)CH$_2$CF$_3$ |
| 3,4,5-Br$_3$ | CF$_3$ | CH$_3$ | H | C(O)CH$_2$CF$_3$ |
| 3,4,5-Br$_3$ | CF$_3$ | CH$_3$ | H | C(O)(E4-2a) |
| 3,4,5-Br$_3$ | CF$_3$ | H | H | C(O)CH$_2$SCH$_3$ |
| 3,4,5-Br$_3$ | CF$_3$ | H | H | C(O)CH$_2$S(O)CH$_3$ |
| 3,4,5-Br$_3$ | CF$_3$ | H | H | C(O)CH$_2$SO$_2$CH$_3$ |
| 3,4,5-Br$_3$ | CF$_3$ | H | H | C(O)CH$_2$SEt |
| 3,4,5-Br$_3$ | CF$_3$ | H | H | C(O)CH$_2$S(O)Et |
| 3,4,5-Br$_3$ | CF$_3$ | H | H | C(O)CH$_2$SO$_2$Et |
| 3,4,5-Br$_3$ | CF$_3$ | H | H | C(O)CH(SCH$_3$)$_2$ |
| 3,4,5-Br$_3$ | CF$_3$ | H | H | C(O)CH[S(O)CH$_3$]$_2$ |
| 3,4-Cl$_2$-5-CH$_3$ | CF$_3$ | H | H | C(O)CH$_3$ |
| 3,4-Cl$_2$-5-CH$_3$ | CF$_3$ | H | H | C(O)Et |
| 3,4-Cl$_2$-5-CH$_3$ | CF$_3$ | H | H | C(O)Pr-n |
| 3,4-Cl$_2$-5-CH$_3$ | CF$_3$ | H | H | C(O)Pr-c |
| 3,4-Cl$_2$-5-CH$_3$ | CF$_3$ | H | H | C(O)CH$_2$Pr-c |
| 3,4-Cl$_2$-5-CH$_3$ | CF$_3$ | H | H | C(O)CH$_2$CF$_3$ |
| 3,4-Cl$_2$-5-CH$_3$ | CF$_3$ | H | H | C(O)CH$_2$SCH$_3$ |
| 3,4-Cl$_2$-5-CH$_3$ | CF$_3$ | H | H | C(O)CH$_2$S(O)CH$_3$ |
| 3,4-Cl$_2$-5-CH$_3$ | CF$_3$ | H | H | C(O)CH$_2$SO$_2$CH$_3$ |
| 3,4-Cl$_2$-5-CH$_3$ | CF$_3$ | H | H | C(O)CH$_2$SEt |
| 3,4-Cl$_2$-5-CH$_3$ | CF$_3$ | H | H | C(O)CH$_2$S(O)Et |
| 3,4-Cl$_2$-5-CH$_3$ | CF$_3$ | H | H | C(O)CH$_2$SO$_2$Et |
| 3,4-F$_2$-5-CF$_3$ | CHF$_2$ | H | H | C(O)CH$_2$S(O)CH$_3$ |
| 3,4-F$_2$-5-CF$_3$ | CF$_3$ | H | H | C(O)CH$_3$ |
| 3,4-F$_2$-5-CF$_3$ | CF$_3$ | H | Et | C(O)CH$_3$ |
| 3,4-F$_2$-5-CF$_3$ | CF$_3$ | H | CH$_2$OCH$_3$ | C(O)CH$_3$ |
| 3,4-F$_2$-5-CF$_3$ | CF$_3$ | H | CH$_2$CN | C(O)CH$_3$ |
| 3,4-F$_2$-5-CF$_3$ | CF$_3$ | H | CH$_2$C≡CH | C(O)CH$_3$ |
| 3,4-F$_2$-5-CF$_3$ | CF$_3$ | H | H | C(O)Et |
| 3,4-F$_2$-5-CF$_3$ | CF$_3$ | CH$_3$ | H | C(O)Et |
| 3,4-F$_2$-5-CF$_3$ | CF$_3$ | H | H | C(O)Pr-n |
| 3,4-F$_2$-5-CF$_3$ | CF$_3$ | CH$_3$ | H | C(O)Pr-n |
| 3,4-F$_2$-5-CF$_3$ | CF$_3$ | H | H | C(O)Pr-i |
| 3,4-F$_2$-5-CF$_3$ | CF$_3$ | CH$_3$ | H | C(O)Pr-i |
| 3,4-F$_2$-5-CF$_3$ | CF$_3$ | H | H | C(O)Pr-c |
| 3,4-F$_2$-5-CF$_3$ | CF$_3$ | CH$_3$ | H | C(O)Pr-c |
| 3,4-F$_2$-5-CF$_3$ | CF$_3$ | CH$_3$(S) | H | C(O)Pr-c |
| 3,4-F$_2$-5-CF$_3$ | CF$_3$ | H | H | C(O)Bu-i |
| 3,4-F$_2$-5-CF$_3$ | CF$_3$ | H | H | C(O)CH$_2$Pr-c |
| 3,4-F$_2$-5-CF$_3$ | CF$_3$ | CH$_3$ | H | C(O)CH$_2$Pr-c |
| 3,4-F$_2$-5-CF$_3$ | CF$_3$ | CH$_3$(S) | H | C(O)CH$_2$Pr-c |
| 3,4-F$_2$-5-CF$_3$ | CF$_3$ | H | H | C(O)CH$_2$CF$_3$ |
| 3,4-F$_2$-5-CF$_3$ | CF$_3$ | CH$_3$ | H | C(O)CH$_2$CF$_3$ |
| 3,4-F$_2$-5-CF$_3$ | CF$_3$ | CH$_3$(S) | H | C(O)CH$_2$CF$_3$ |
| 3,4-F$_2$-5-CF$_3$ | CF$_3$ | H | H | C(O)(E4-2a) |
| 3,4-F$_2$-5-CF$_3$ | CF$_3$ | CH$_3$ | H | C(O)(E4-2a) |
| 3,4-F$_2$-5-CF$_3$ | CF$_3$ | CH$_3$(S) | H | C(O)(E4-2a) |
| 3,4-F$_2$-5-CF$_3$ | CF$_3$ | H | H | C(O)CH$_2$SCH$_3$ |
| 3,4-F$_2$-5-CF$_3$ | CF$_3$ | H | CH$_2$C≡CH | C(O)CH$_2$SCH$_3$ |
| 3,4-F$_2$-5-CF$_3$ | CF$_3$ | CH$_3$ | H | C(O)CH$_2$SCH$_3$ |
| 3,4-F$_2$-5-CF$_3$ | CF$_3$ | H | H | C(O)CH$_2$S(O)CH$_3$ |
| 3,4-F$_2$-5-CF$_3$ | CF$_3$ | H | H | C(O)CH$_2$SO$_2$CH$_3$ |

TABLE 3-continued

| (X)$_m$ | R$^3$ | R$^4$ | R$^2$ | R$^1$ |
|---|---|---|---|---|
| 3,4-F$_2$-5-CF$_3$ | CF$_3$ | H | CH$_3$ | C(O)CH$_2$SO$_2$CH$_3$ |
| 3,4-F$_2$-5-CF$_3$ | CF$_3$ | H | H | C(O)CH$_2$SEt |
| 3,4-F$_2$-5-CF$_3$ | CF$_3$ | CH$_3$ | H | C(O)CH$_2$SEt |
| 3,4-F$_2$-5-CF$_3$ | CF$_3$ | H | H | C(O)CH$_2$S(O)Et |
| 3,4-F$_2$-5-CF$_3$ | CF$_3$ | H | CH$_3$ | C(O)CH$_2$S(O)Et |
| 3,4-F$_2$-5-CF$_3$ | CF$_3$ | H | H | C(O)CH$_2$SO$_2$Et |
| 3,4-F$_2$-5-CF$_3$ | CF$_3$ | H | CH$_3$ | C(O)CH$_2$SO$_2$Et |
| 3,4-F$_2$-5-CF$_3$ | CF$_3$ | H | H | C(O)CH(CH$_3$)SCH$_3$ |
| 3,4-F$_2$-5-CF$_3$ | CF$_3$ | H | H | C(O)(E5-1a) |
| 3,4-F$_2$-5-CF$_3$ | CF$_3$ | H | H | C(O)CH(SCH$_3$)$_2$ |
| 3,4-F$_2$-5-CF$_3$ | CF$_3$ | H | H | C(O)CH[S(O)CH$_3$]$_2$ |
| 3,4-F$_2$-5-CF$_3$ | CF$_3$ | H | H | C(O)CH(SEt)$_2$ |
| 3,4-F$_2$-5-CF$_3$ | CF$_3$ | H | H | C(O)CH(SEt)S(O)Et |
| 3,4-F$_2$-5-CF$_3$ | CF$_3$ | H | H | C(O)CH(SEt)SO$_2$Et |
| 3,4-F$_2$-5-CF$_3$ | CF$_3$ | H | H | C(O)(D32-2b)Cl |
| 3,4-F$_2$-5-CF$_3$ | CF$_3$ | H | H | C(O)NHEt |
| 3,4-F$_2$-5-CF$_3$ | CF$_3$ | H | H | C(O)NHPr-c |
| 3,4-F$_2$-5-CF$_3$ | CF$_3$ | CH$_3$ | H | C(O)NHPr-c |
| 3,4-F$_2$-5-CF$_3$ | CF$_3$ | CH$_3$ | H | C(O)NHCH$_2$C≡CH |
| 3,4-F$_2$-5-CF$_3$ | CF$_2$Cl | H | H | C(O)CH$_3$ |
| 3,4-F$_2$-5-CF$_3$ | CF$_2$Cl | H | H | C(O)Et |
| 3,4-F$_2$-5-CF$_3$ | CF$_2$Cl | H | H | C(O)Pr-n |
| 3,4-F$_2$-5-CF$_3$ | CF$_2$Cl | H | H | C(O)Pr-c |
| 3,4-F$_2$-5-CF$_3$ | CF$_2$Cl | H | H | C(O)CH$_2$Pr-c |
| 3,4-F$_2$-5-CF$_3$ | CF$_2$Cl | CH$_3$ | H | C(O)CH$_2$Pr-c |
| 3,4-F$_2$-5-CF$_3$ | CF$_2$Cl | H | H | C(O)CH$_2$CF$_3$ |
| 3,4-F$_2$-5-CF$_3$ | CF$_2$Cl | CH$_3$ | H | C(O)CH$_2$CF$_3$ |
| 3,4-F$_2$-5-CF$_3$ | CF$_2$Cl | CH$_3$ | H | C(O)(E4-2a) |
| 3,4-F$_2$-5-CF$_3$ | CF$_2$Cl | H | H | C(O)CH$_2$SCH$_3$ |
| 3,4-F$_2$-5-CF$_3$ | CF$_2$Cl | H | H | C(O)CH$_2$S(O)CH$_3$ |
| 3,4-F$_2$-5-CF$_3$ | CF$_2$Cl | H | H | C(O)CH$_2$SO$_2$CH$_3$ |
| 3,4-F$_2$-5-CF$_3$ | CF$_2$Cl | H | H | C(O)CH$_2$SEt |
| 3,4-F$_2$-5-CF$_3$ | CF$_2$Cl | H | H | C(O)CH$_2$S(O)Et |
| 3,4-F$_2$-5-CF$_3$ | CF$_2$Cl | H | H | C(O)CH$_2$SO$_2$Et |
| 3,4-F$_2$-5-CF$_3$ | CF$_2$Cl | H | H | C(O)CH(SCH$_3$)$_2$ |
| 3,4-F$_2$-5-CF$_3$ | CF$_2$Cl | H | H | C(O)CH[S(O)CH$_3$]$_2$ |
| 3-Cl-4-F-5-CF$_3$ | CHF$_2$ | H | H | C(O)CH$_2$SO$_2$CH$_3$ |
| 3-Cl-4-F-5-CF$_3$ | CF$_3$ | H | H | C(O)CH$_3$ |
| 3-Cl-4-F-5-CF$_3$ | CF$_3$ | H | Et | C(O)CH$_3$ |
| 3-Cl-4-F-5-CF$_3$ | CF$_3$ | H | CH$_2$OCH$_3$ | C(O)CH$_3$ |
| 3-Cl-4-F-5-CF$_3$ | CF$_3$ | H | CH$_2$CN | C(O)CH$_3$ |
| 3-Cl-4-F-5-CF$_3$ | CF$_3$ | H | CH$_2$C≡CH | C(O)CH$_3$ |
| 3-Cl-4-F-5-CF$_3$ | CF$_3$ | H | H | C(O)Et |
| 3-Cl-4-F-5-CF$_3$ | CF$_3$ | CH$_3$ | H | C(O)Et |
| 3-Cl-4-F-5-CF$_3$ | CF$_3$ | H | H | C(O)Pr-n |
| 3-Cl-4-F-5-CF$_3$ | CF$_3$ | CH$_3$ | H | C(O)Pr-n |
| 3-Cl-4-F-5-CF$_3$ | CF$_3$ | H | H | C(O)Pr-i |
| 3-Cl-4-F-5-CF$_3$ | CF$_3$ | CH$_3$ | H | C(O)Pr-i |
| 3-Cl-4-F-5-CF$_3$ | CF$_3$ | H | H | C(O)Pr-c |
| 3-Cl-4-F-5-CF$_3$ | CF$_3$ | CH$_3$ | H | C(O)Pr-c |
| 3-Cl-4-F-5-CF$_3$ | CF$_3$ | CH$_3$(S) | H | C(O)Pr-c |
| 3-Cl-4-F-5-CF$_3$ | CF$_3$ | H | H | C(O)Bu-i |
| 3-Cl-4-F-5-CF$_3$ | CF$_3$ | H | H | C(O)CH$_2$Pr-c |
| 3-Cl-4-F-5-CF$_3$ | CF$_3$ | CH$_3$ | H | C(O)CH$_2$Pr-c |
| 3-Cl-4-F-5-CF$_3$ | CF$_3$ | CH$_3$(S) | H | C(O)CH$_2$Pr-c |
| 3-Cl-4-F-5-CF$_3$ | CF$_3$ | H | H | C(O)CH$_2$CF$_3$ |
| 3-Cl-4-F-5-CF$_3$ | CF$_3$ | CH$_3$ | H | C(O)CH$_2$CF$_3$ |
| 3-Cl-4-F-5-CF$_3$ | CF$_3$ | CH$_3$(S) | H | C(O)CH$_2$CF$_3$ |
| 3-Cl-4-F-5-CF$_3$ | CF$_3$ | H | H | C(O)(E4-2a) |
| 3-Cl-4-F-5-CF$_3$ | CF$_3$ | CH$_3$ | H | C(O)(E4-2a) |
| 3-Cl-4-F-5-CF$_3$ | CF$_3$ | CH$_3$(S) | H | C(O)(E4-2a) |
| 3-Cl-4-F-5-CF$_3$ | CF$_3$ | H | H | C(O)CH$_2$SCH$_3$ |
| 3-Cl-4-F-5-CF$_3$ | CF$_3$ | H | CH$_2$C≡CH | C(O)CH$_2$SCH$_3$ |
| 3-Cl-4-F-5-CF$_3$ | CF$_3$ | CH$_3$ | H | C(O)CH$_2$SCH$_3$ |
| 3-Cl-4-F-5-CF$_3$ | CF$_3$ | H | H | C(O)CH$_2$S(O)CH$_3$ |
| 3-Cl-4-F-5-CF$_3$ | CF$_3$ | H | H | C(O)CH$_2$SO$_2$CH$_3$ |
| 3-Cl-4-F-5-CF$_3$ | CF$_3$ | H | CH$_3$ | C(O)CH$_2$SO$_2$CH$_3$ |
| 3-Cl-4-F-5-CF$_3$ | CF$_3$ | H | H | C(O)CH$_2$SEt |
| 3-Cl-4-F-5-CF$_3$ | CF$_3$ | CH$_3$ | H | C(O)CH$_2$SEt |
| 3-Cl-4-F-5-CF$_3$ | CF$_3$ | H | H | C(O)CH$_2$S(O)Et |
| 3-Cl-4-F-5-CF$_3$ | CF$_3$ | H | CH$_3$ | C(O)CH$_2$S(O)Et |
| 3-Cl-4-F-5-CF$_3$ | CF$_3$ | H | H | C(O)CH$_2$SO$_2$Et |
| 3-Cl-4-F-5-CF$_3$ | CF$_3$ | H | CH$_3$ | C(O)CH$_2$SO$_2$Et |
| 3-Cl-4-F-5-CF$_3$ | CF$_3$ | H | H | C(O)CH(CH$_3$)SCH$_3$ |
| 3-Cl-4-F-5-CF$_3$ | CF$_3$ | H | H | C(O)(E5-1a) |
| 3-Cl-4-F-5-CF$_3$ | CF$_3$ | H | H | C(O)CH(SCH$_3$)$_2$ |
| 3-Cl-4-F-5-CF$_3$ | CF$_3$ | H | H | C(O)CH[S(O)CH$_3$]$_2$ |
| 3-Cl-4-F-5-CF$_3$ | CF$_3$ | H | H | C(O)CH(SEt)$_2$ |

TABLE 3-continued

| (X)$_m$ | R$^3$ | R$^4$ | R$^2$ | R$^1$ |
|---|---|---|---|---|
| 3-Cl-4-F-5-CF$_3$ | CF$_3$ | H | H | C(O)CH(SEt)S(O)Et |
| 3-Cl-4-F-5-CF$_3$ | CF$_3$ | H | H | C(O)CH(SEt)SO$_2$Et |
| 3-Cl-4-F-5-CF$_3$ | CF$_3$ | H | H | C(O)(D32-2b)Cl |
| 3-Cl-4-F-5-CF$_3$ | CF$_3$ | H | H | C(O)NHEt |
| 3-Cl-4-F-5-CF$_3$ | CF$_3$ | H | H | C(O)NHPr-c |
| 3-Cl-4-F-5-CF$_3$ | CF$_3$ | CH$_3$ | H | C(O)NHPr-c |
| 3-Cl-4-F-5-CF$_3$ | CF$_3$ | CH$_3$ | H | C(O)NHCH$_2$C≡CH |
| 3-Cl-4-F-5-CF$_3$ | CF$_2$Cl | H | H | C(O)CH$_3$ |
| 3-Cl-4-F-5-CF$_3$ | CF$_2$Cl | H | H | C(O)Et |
| 3-Cl-4-F-5-CF$_3$ | CF$_2$Cl | H | H | C(O)Pr-n |
| 3-Cl-4-F-5-CF$_3$ | CF$_2$Cl | H | H | C(O)Pr-c |
| 3-Cl-4-F-5-CF$_3$ | CF$_2$Cl | H | H | C(O)CH$_2$Pr-c |
| 3-Cl-4-F-5-CF$_3$ | CF$_2$Cl | CH$_3$ | H | C(O)CH$_2$Pr-c |
| 3-Cl-4-F-5-CF$_3$ | CF$_2$Cl | H | H | C(O)CH$_2$CF$_3$ |
| 3-Cl-4-F-5-CF$_3$ | CF$_2$Cl | CH$_3$ | H | C(O)CH$_2$CF$_3$ |
| 3-Cl-4-F-5-CF$_3$ | CF$_2$Cl | CH$_3$ | H | C(O)(E4-2a) |
| 3-Cl-4-F-5-CF$_3$ | CF$_2$Cl | H | H | C(O)CH$_2$SCH$_3$ |
| 3-Cl-4-F-5-CF$_3$ | CF$_2$Cl | H | H | C(O)CH$_2$S(O)CH$_3$ |
| 3-Cl-4-F-5-CF$_3$ | CF$_2$Cl | H | H | C(O)CH$_2$SO$_2$CH$_3$ |
| 3-Cl-4-F-5-CF$_3$ | CF$_2$Cl | H | H | C(O)CH$_2$SEt |
| 3-Cl-4-F-5-CF$_3$ | CF$_2$Cl | H | H | C(O)CH$_2$S(O)Et |
| 3-Cl-4-F-5-CF$_3$ | CF$_2$Cl | H | H | C(O)CH$_2$SO$_2$Et |
| 3-Cl-4-F-5-CF$_3$ | CF$_2$Cl | H | H | C(O)CH(SCH$_3$)$_2$ |
| 3-Cl-4-F-5-CF$_3$ | CF$_2$Cl | H | H | C(O)CH[S(O)CH$_3$]$_2$ |
| 3,4-Cl$_2$-5-CF$_3$ | CHF$_2$ | H | H | C(O)CH$_2$SEt |
| 3,4-Cl$_2$-5-CF$_3$ | CF$_3$ | H | H | C(O)CH$_3$ |
| 3,4-Cl$_2$-5-CF$_3$ | CF$_3$ | H | Et | C(O)CH$_3$ |
| 3,4-Cl$_2$-5-CF$_3$ | CF$_3$ | H | CH$_2$OCH$_3$ | C(O)CH$_3$ |
| 3,4-Cl$_2$-5-CF$_3$ | CF$_3$ | H | CH$_2$CN | C(O)CH$_3$ |
| 3,4-Cl$_2$-5-CF$_3$ | CF$_3$ | H | CH$_2$C≡CH | C(O)CH$_3$ |
| 3,4-Cl$_2$-5-CF$_3$ | CF$_3$ | H | H | C(O)Et |
| 3,4-Cl$_2$-5-CF$_3$ | CF$_3$ | CH$_3$ | H | C(O)Et |
| 3,4-Cl$_2$-5-CF$_3$ | CF$_3$ | H | H | C(O)Pr-n |
| 3,4-Cl$_2$-5-CF$_3$ | CF$_3$ | CH$_3$ | H | C(O)Pr-n |
| 3,4-Cl$_2$-5-CF$_3$ | CF$_3$ | H | H | C(O)Pr-i |
| 3,4-Cl$_2$-5-CF$_3$ | CF$_3$ | CH$_3$ | H | C(O)Pr-i |
| 3,4-Cl$_2$-5-CF$_3$ | CF$_3$ | H | H | C(O)Pr-c |
| 3,4-Cl$_2$-5-CF$_3$ | CF$_3$ | CH$_3$ | H | C(O)Pr-c |
| 3,4-Cl$_2$-5-CF$_3$ | CF$_3$ | CH$_3$(S) | H | C(O)Pr-c |
| 3,4-Cl$_2$-5-CF$_3$ | CF$_3$ | H | H | C(O)Bu-i |
| 3,4-Cl$_2$-5-CF$_3$ | CF$_3$ | H | H | C(O)CH$_2$Pr-c |
| 3,4-Cl$_2$-5-CF$_3$ | CF$_3$ | CH$_3$ | H | C(O)CH$_2$Pr-c |
| 3,4-Cl$_2$-5-CF$_3$ | CF$_3$ | CH$_3$(S) | H | C(O)CH$_2$Pr-c |
| 3,4-Cl$_2$-5-CF$_3$ | CF$_3$ | H | H | C(O)CH$_2$CF$_3$ |
| 3,4-Cl$_2$-5-CF$_3$ | CF$_3$ | CH$_3$ | H | C(O)CH$_2$CF$_3$ |
| 3,4-Cl$_2$-5-CF$_3$ | CF$_3$ | CH$_3$(S) | H | C(O)CH$_2$CF$_3$ |
| 3,4-Cl$_2$-5-CF$_3$ | CF$_3$ | H | H | C(O)(E4-2a) |
| 3,4-Cl$_2$-5-CF$_3$ | CF$_3$ | CH$_3$ | H | C(O)(E4-2a) |
| 3,4-Cl$_2$-5-CF$_3$ | CF$_3$ | CH$_3$(S) | H | C(O)(E4-2a) |
| 3,4-Cl$_2$-5-CF$_3$ | CF$_3$ | H | H | C(O)CH$_2$SCH$_3$ |
| 3,4-Cl$_2$-5-CF$_3$ | CF$_3$ | H | CH$_2$C≡CH | C(O)CH$_2$SCH$_3$ |
| 3,4-Cl$_2$-5-CF$_3$ | CF$_3$ | CH$_3$ | H | C(O)CH$_2$SCH$_3$ |
| 3,4-Cl$_2$-5-CF$_3$ | CF$_3$ | H | H | C(O)CH$_2$S(O)CH$_3$ |
| 3,4-Cl$_2$-5-CF$_3$ | CF$_3$ | H | H | C(O)CH$_2$SO$_2$CH$_3$ |
| 3,4-Cl$_2$-5-CF$_3$ | CF$_3$ | H | CH$_3$ | C(O)CH$_2$SO$_2$CH$_3$ |
| 3,4-Cl$_2$-5-CF$_3$ | CF$_3$ | H | H | C(O)CH$_2$SEt |
| 3,4-Cl$_2$-5-CF$_3$ | CF$_3$ | CH$_3$ | H | C(O)CH$_2$SEt |
| 3,4-Cl$_2$-5-CF$_3$ | CF$_3$ | H | H | C(O)CH$_2$S(O)Et |
| 3,4-Cl$_2$-5-CF$_3$ | CF$_3$ | H | CH$_3$ | C(O)CH$_2$S(O)Et |
| 3,4-Cl$_2$-5-CF$_3$ | CF$_3$ | H | H | C(O)CH$_2$SO$_2$Et |
| 3,4-Cl$_2$-5-CF$_3$ | CF$_3$ | H | CH$_3$ | C(O)CH$_2$SO$_2$Et |
| 3,4-Cl$_2$-5-CF$_3$ | CF$_3$ | H | H | C(O)CH(CH$_3$)SCH$_3$ |
| 3,4-Cl$_2$-5-CF$_3$ | CF$_3$ | H | H | C(O)(E5-1a) |
| 3,4-Cl$_2$-5-CF$_3$ | CF$_3$ | H | H | C(O)CH(SCH$_3$)$_2$ |
| 3,4-Cl$_2$-5-CF$_3$ | CF$_3$ | H | H | C(O)CH[S(O)CH$_3$]$_2$ |
| 3,4-Cl$_2$-5-CF$_3$ | CF$_3$ | H | H | C(O)CH(SEt)$_2$ |
| 3,4-Cl$_2$-5-CF$_3$ | CF$_3$ | H | H | C(O)CH(SEt)S(O)Et |
| 3,4-Cl$_2$-5-CF$_3$ | CF$_3$ | H | H | C(O)CH(SEt)SO$_2$Et |
| 3,4-Cl$_2$-5-CF$_3$ | CF$_3$ | H | H | C(O)(D32-2b)Cl |
| 3,4-Cl$_2$-5-CF$_3$ | CF$_3$ | H | H | C(O)NHEt |
| 3,4-Cl$_2$-5-CF$_3$ | CF$_3$ | H | H | C(O)NHPr-c |
| 3,4-Cl$_2$-5-CF$_3$ | CF$_3$ | CH$_3$ | H | C(O)NHPr-c |
| 3,4-Cl$_2$-5-CF$_3$ | CF$_3$ | CH$_3$ | H | C(O)NHCH$_2$C≡CH |
| 3,4-Cl$_2$-5-CF$_3$ | CF$_2$Cl | H | H | C(O)CH$_3$ |
| 3,4-Cl$_2$-5-CF$_3$ | CF$_2$Cl | H | H | C(O)Et |
| 3,4-Cl$_2$-5-CF$_3$ | CF$_2$Cl | H | H | C(O)Pr-n |
| 3,4-Cl$_2$-5-CF$_3$ | CF$_2$Cl | H | H | C(O)Pr-c |
| 3,4-Cl$_2$-5-CF$_3$ | CF$_2$Cl | H | H | C(O)CH$_2$Pr-c |

TABLE 3-continued

| $(X)_m$ | $R^3$ | $R^4$ | $R^2$ | $R^1$ |
|---|---|---|---|---|
| 3,4-Cl$_2$-5-CF$_3$ | CF$_2$Cl | CH$_3$ | H | C(O)CH$_2$Pr-c |
| 3,4-Cl$_2$-5-CF$_3$ | CF$_2$Cl | H | H | C(O)CH$_2$CF$_3$ |
| 3,4-Cl$_2$-5-CF$_3$ | CF$_2$Cl | CH$_3$ | H | C(O)CH$_2$CF$_3$ |
| 3,4-Cl$_2$-5-CF$_3$ | CF$_2$Cl | CH$_3$ | H | C(O)(E4-2a) |
| 3,4-Cl$_2$-5-CF$_3$ | CF$_2$Cl | H | H | C(O)CH$_2$SCH$_3$ |
| 3,4-Cl$_2$-5-CF$_3$ | CF$_2$Cl | H | H | C(O)CH$_2$S(O)CH$_3$ |
| 3,4-Cl$_2$-5-CF$_3$ | CF$_2$Cl | H | H | C(O)CH$_2$SO$_2$CH$_3$ |
| 3,4-Cl$_2$-5-CF$_3$ | CF$_2$Cl | H | H | C(O)CH$_2$SEt |
| 3,4-Cl$_2$-5-CF$_3$ | CF$_2$Cl | H | H | C(O)CH$_2$S(O)Et |
| 3,4-Cl$_2$-5-CF$_3$ | CF$_2$Cl | H | H | C(O)CH$_2$SO$_2$Et |
| 3,4-Cl$_2$-5-CF$_3$ | CF$_2$Cl | H | H | C(O)CH(SCH$_3$)$_2$ |
| 3,4-Cl$_2$-5-CF$_3$ | CF$_2$Cl | H | H | C(O)CH[S(O)CH$_3$]$_2$ |
| 3,5-(CF$_3$)$_2$-4-Cl | CHF$_2$ | H | H | C(O)CH$_2$S(O)Et |
| 3,5-(CF$_3$)$_2$-4-Cl | CF$_3$ | H | H | C(O)CH$_3$ |
| 3,5-(CF$_3$)$_2$-4-Cl | CF$_3$ | H | Et | C(O)CH$_3$ |
| 3,5-(CF$_3$)$_2$-4-Cl | CF$_3$ | H | CH$_2$OCH$_3$ | C(O)CH$_3$ |
| 3,5-(CF$_3$)$_2$-4-Cl | CF$_3$ | H | CH$_2$CN | C(O)CH$_3$ |
| 3,5-(CF$_3$)$_2$-4-Cl | CF$_3$ | H | CH$_2$C≡CH | C(O)CH$_3$ |
| 3,5-(CF$_3$)$_2$-4-Cl | CF$_3$ | H | H | C(O)Et |
| 3,5-(CF$_3$)$_2$-4-Cl | CF$_3$ | CH$_3$ | H | C(O)Et |
| 3,5-(CF$_3$)$_2$-4-Cl | CF$_3$ | H | H | C(O)Pr-n |
| 3,5-(CF$_3$)$_2$-4-Cl | CF$_3$ | CH$_3$ | H | C(O)Pr-n |
| 3,5-(CF$_3$)$_2$-4-Cl | CF$_3$ | H | H | C(O)Pr-i |
| 3,5-(CF$_3$)$_2$-4-Cl | CF$_3$ | CH$_3$ | H | C(O)Pr-i |
| 3,5-(CF$_3$)$_2$-4-Cl | CF$_3$ | H | H | C(O)Pr-c |
| 3,5-(CF$_3$)$_2$-4-Cl | CF$_3$ | CH$_3$ | H | C(O)Pr-c |
| 3,5-(CF$_3$)$_2$-4-Cl | CF$_3$ | CH$_3$(S) | H | C(O)Pr-c |
| 3,5-(CF$_3$)$_2$-4-Cl | CF$_3$ | H | H | C(O)Bu-i |
| 3,5-(CF$_3$)$_2$-4-Cl | CF$_3$ | H | H | C(O)CH$_2$Pr-c |
| 3,5-(CF$_3$)$_2$-4-Cl | CF$_3$ | CH$_3$ | H | C(O)CH$_2$Pr-c |
| 3,5-(CF$_3$)$_2$-4-Cl | CF$_3$ | CH$_3$(S) | H | C(O)CH$_2$Pr-c |
| 3,5-(CF$_3$)$_2$-4-Cl | CF$_3$ | H | H | C(O)CH$_2$CF$_3$ |
| 3,5-(CF$_3$)$_2$-4-Cl | CF$_3$ | CH$_3$ | H | C(O)CH$_2$CF$_3$ |
| 3,5-(CF$_3$)$_2$-4-Cl | CF$_3$ | CH$_3$(S) | H | C(O)CH$_2$CF$_3$ |
| 3,5-(CF$_3$)$_2$-4-Cl | CF$_3$ | H | H | C(O)(E4-2a) |
| 3,5-(CF$_3$)$_2$-4-Cl | CF$_3$ | CH$_3$ | H | C(O)(E4-2a) |
| 3,5-(CF$_3$)$_2$-4-Cl | CF$_3$ | CH$_3$(S) | H | C(O)(E4-2a) |
| 3,5-(CF$_3$)$_2$-4-Cl | CF$_3$ | H | H | C(O)CH$_2$SCH$_3$ |
| 3,5-(CF$_3$)$_2$-4-Cl | CF$_3$ | H | CH$_2$C≡CH | C(O)CH$_2$SCH$_3$ |
| 3,5-(CF$_3$)$_2$-4-Cl | CF$_3$ | CH$_3$ | H | C(O)CH$_2$SCH$_3$ |
| 3,5-(CF$_3$)$_2$-4-Cl | CF$_3$ | H | H | C(O)CH$_2$S(O)CH$_3$ |
| 3,5-(CF$_3$)$_2$-4-Cl | CF$_3$ | H | H | C(O)CH$_2$SO$_2$CH$_3$ |
| 3,5-(CF$_3$)$_2$-4-Cl | CF$_3$ | H | CH$_3$ | C(O)CH$_2$SO$_2$CH$_3$ |
| 3,5-(CF$_3$)$_2$-4-Cl | CF$_3$ | H | H | C(O)CH$_2$SEt |
| 3,5-(CF$_3$)$_2$-4-Cl | CF$_3$ | CH$_3$ | H | C(O)CH$_2$SEt |
| 3,5-(CF$_3$)$_2$-4-Cl | CF$_3$ | H | H | C(O)CH$_2$S(O)Et |
| 3,5-(CF$_3$)$_2$-4-Cl | CF$_3$ | H | CH$_3$ | C(O)CH$_2$S(O)Et |
| 3,5-(CF$_3$)$_2$-4-Cl | CF$_3$ | H | H | C(O)CH$_2$SO$_2$Et |
| 3,5-(CF$_3$)$_2$-4-Cl | CF$_3$ | H | CH$_3$ | C(O)CH$_2$SO$_2$Et |
| 3,5-(CF$_3$)$_2$-4-Cl | CF$_3$ | H | H | C(O)CH(CH$_3$)SCH$_3$ |
| 3,5-(CF$_3$)$_2$-4-Cl | CF$_3$ | H | H | C(O)(E5-1a) |
| 3,5-(CF$_3$)$_2$-4-Cl | CF$_3$ | H | H | C(O)CH(SCH$_3$)$_2$ |
| 3,5-(CF$_3$)$_2$-4-Cl | CF$_3$ | H | H | C(O)CH[S(O)CH$_3$]$_2$ |
| 3,5-(CF$_3$)$_2$-4-Cl | CF$_3$ | H | H | C(O)CH(SEt)$_2$ |
| 3,5-(CF$_3$)$_2$-4-Cl | CF$_3$ | H | H | C(O)CH(SEt)S(O)Et |
| 3,5-(CF$_3$)$_2$-4-Cl | CF$_3$ | H | H | C(O)CH(SEt)SO$_2$Et |
| 3,5-(CF$_3$)$_2$-4-Cl | CF$_3$ | H | H | C(O)(D32-2b)Cl |
| 3,5-(CF$_3$)$_2$-4-Cl | CF$_3$ | H | H | C(O)NHEt |
| 3,5-(CF$_3$)$_2$-4-Cl | CF$_3$ | H | H | C(O)NHPr-c |
| 3,5-(CF$_3$)$_2$-4-Cl | CF$_3$ | CH$_3$ | H | C(O)NHPr-c |
| 3,5-(CF$_3$)$_2$-4-Cl | CF$_3$ | CH$_3$ | H | C(O)NHCH$_2$C≡CH |
| 3,5-(CF$_3$)$_2$-4-Cl | CF$_2$Cl | H | H | C(O)CH$_3$ |
| 3,5-(CF$_3$)$_2$-4-Cl | CF$_2$Cl | H | H | C(O)Et |
| 3,5-(CF$_3$)$_2$-4-Cl | CF$_2$Cl | H | H | C(O)Pr-n |
| 3,5-(CF$_3$)$_2$-4-Cl | CF$_2$Cl | H | H | C(O)Pr-c |
| 3,5-(CF$_3$)$_2$-4-Cl | CF$_2$Cl | H | H | C(O)CH$_2$Pr-c |
| 3,5-(CF$_3$)$_2$-4-Cl | CF$_2$Cl | CH$_3$ | H | C(O)CH$_2$Pr-c |
| 3,5-(CF$_3$)$_2$-4-Cl | CF$_2$Cl | H | H | C(O)CH$_2$CF$_3$ |
| 3,5-(CF$_3$)$_2$-4-Cl | CF$_2$Cl | CH$_3$ | H | C(O)CH$_2$CF$_3$ |
| 3,5-(CF$_3$)$_2$-4-Cl | CF$_2$Cl | CH$_3$ | H | C(O)(E4-2a) |
| 3,5-(CF$_3$)$_2$-4-Cl | CF$_2$Cl | H | H | C(O)CH$_2$SCH$_3$ |
| 3,5-(CF$_3$)$_2$-4-Cl | CF$_2$Cl | H | H | C(O)CH$_2$S(O)CH$_3$ |
| 3,5-(CF$_3$)$_2$-4-Cl | CF$_2$Cl | H | H | C(O)CH$_2$SO$_2$CH$_3$ |
| 3,5-(CF$_3$)$_2$-4-Cl | CF$_2$Cl | H | H | C(O)CH$_2$SEt |
| 3,5-(CF$_3$)$_2$-4-Cl | CF$_2$Cl | H | H | C(O)CH$_2$S(O)Et |
| 3,5-(CF$_3$)$_2$-4-Cl | CF$_2$Cl | H | H | C(O)CH$_2$SO$_2$Et |
| 3,5-(CF$_3$)$_2$-4-Cl | CF$_2$Cl | H | H | C(O)CH(SCH$_3$)$_2$ |
| 3,5-(CF$_3$)$_2$-4-Cl | CF$_2$Cl | H | H | C(O)CH[S(O)CH$_3$]$_2$ |

TABLE 3-continued

| (X)$_m$ | R$^3$ | R$^4$ | R$^2$ | R$^1$ |
|---|---|---|---|---|
| 3,5-Cl$_2$-4-OCHF$_2$ | CF$_3$ | H | H | C(O)CH$_3$ |
| 3,5-Cl$_2$-4-OCHF$_2$ | CF$_3$ | H | H | C(O)Et |
| 3,5-Cl$_2$-4-OCHF$_2$ | CF$_3$ | H | H | C(O)Pr-n |
| 3,5-Cl$_2$-4-OCHF$_2$ | CF$_3$ | H | H | C(O)Pr-c |
| 3,5-Cl$_2$-4-OCHF$_2$ | CF$_3$ | H | H | C(O)CH$_2$Pr-c |
| 3,5-Cl$_2$-4-OCHF$_2$ | CF$_3$ | CH$_3$ | H | C(O)CH$_2$Pr-c |
| 3,5-Cl$_2$-4-OCHF$_2$ | CF$_3$ | H | H | C(O)CH$_2$CF$_3$ |
| 3,5-Cl$_2$-4-OCHF$_2$ | CF$_3$ | CH$_3$ | H | C(O)CH$_2$CF$_3$ |
| 3,5-Cl$_2$-4-OCHF$_2$ | CF$_3$ | CH$_3$ | H | C(O)(E4-2a) |
| 3,5-Cl$_2$-4-OCHF$_2$ | CF$_3$ | H | H | C(O)CH$_2$SCH$_3$ |
| 3,5-Cl$_2$-4-OCHF$_2$ | CF$_3$ | H | H | C(O)CH$_2$S(O)CH$_3$ |
| 3,5-Cl$_2$-4-OCHF$_2$ | CF$_3$ | H | H | C(O)CH$_2$SO$_2$CH$_3$ |
| 3,5-Cl$_2$-4-OCHF$_2$ | CF$_3$ | H | H | C(O)CH$_2$SEt |
| 3,5-Cl$_2$-4-OCHF$_2$ | CF$_3$ | H | H | C(O)CH$_2$S(O)Et |
| 3,5-Cl$_2$-4-OCHF$_2$ | CF$_3$ | H | H | C(O)CH$_2$SO$_2$Et |
| 3,5-Cl$_2$-4-OCHF$_2$ | CF$_3$ | H | H | C(O)CH(SCH$_3$)$_2$ |
| 3,5-Cl$_2$-4-OCHF$_2$ | CF$_3$ | H | H | C(O)CH[S(O)CH$_3$]$_2$ |
| 3,5-Br$_2$-4-OCHF$_2$ | CF$_3$ | H | H | C(O)CH$_3$ |
| 3,5-Br$_2$-4-OCHF$_2$ | CF$_3$ | H | H | C(O)Et |
| 3,5-Br$_2$-4-OCHF$_2$ | CF$_3$ | H | H | C(O)Pr-n |
| 3,5-Br$_2$-4-OCHF$_2$ | CF$_3$ | H | H | C(O)Pr-c |
| 3,5-Br$_2$-4-OCHF$_2$ | CF$_3$ | H | H | C(O)CH$_2$Pr-c |
| 3,5-Br$_2$-4-OCHF$_2$ | CF$_3$ | CH$_3$ | H | C(O)CH$_2$Pr-c |
| 3,5-Br$_2$-4-OCHF$_2$ | CF$_3$ | H | H | C(O)CH$_2$CF$_3$ |
| 3,5-Br$_2$-4-OCHF$_2$ | CF$_3$ | CH$_3$ | H | C(O)CH$_2$CF$_3$ |
| 3,5-Br$_2$-4-OCHF$_2$ | CF$_3$ | CH$_3$ | H | C(O)(E4-2a) |
| 3,5-Br$_2$-4-OCHF$_2$ | CF$_3$ | H | H | C(O)CH$_2$SCH$_3$ |
| 3,5-Br$_2$-4-OCHF$_2$ | CF$_3$ | H | H | C(O)CH$_2$S(O)CH$_3$ |
| 3,5-Br$_2$-4-OCHF$_2$ | CF$_3$ | H | H | C(O)CH$_2$SO$_2$CH$_3$ |
| 3,5-Br$_2$-4-OCHF$_2$ | CF$_3$ | H | H | C(O)CH$_2$SEt |
| 3,5-Br$_2$-4-OCHF$_2$ | CF$_3$ | H | H | C(O)CH$_2$S(O)Et |
| 3,5-Br$_2$-4-OCHF$_2$ | CF$_3$ | H | H | C(O)CH$_2$SO$_2$Et |
| 3,5-Br$_2$-4-OCHF$_2$ | CF$_3$ | H | H | C(O)CH(SCH$_3$)$_2$ |
| 3,5-Br$_2$-4-OCHF$_2$ | CF$_3$ | H | H | C(O)CH[S(O)CH$_3$]$_2$ |
| 3,5-Cl$_2$-4-NH$_2$ | CF$_3$ | H | H | C(O)CH$_2$SO$_2$Et |
| 3,5-Br$_2$-4-NH$_2$ | CF$_3$ | H | H | C(O)CH$_3$ |

Compounds of Structural Formulae [1]-1 to [1]-54 having a structure in which G$^2$ is G$^2$-3 to G$^2$-10.

G$^2$-3:

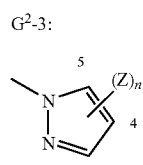

G$^2$-4:

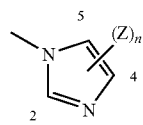

G$^2$-5:

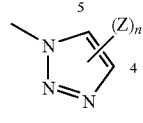

G$^2$-6:

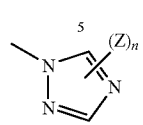

G$^2$-7:

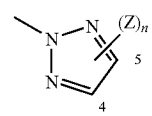

G$^2$-8:

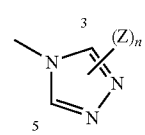

G$^2$-9:

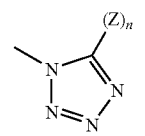

G$^2$-10:

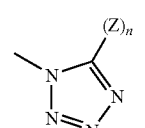

In Table, each of the numbers representing the substituted sites of the substituent (X)$_m$ corresponds to the site indicated by the number in the above Structure Formulae [1]-1 to [1]-54, and each of the numbers representing the substituted sites of the substituent $(Z)_n$ corresponds to the site indicated by the number in the above $G^2$-3 to $G^2$-8. The expression "-" indicates "non-substituted".

| $(X)_m$ | $R^3$ | $G^2$ | $(Z)_n$ |
|---|---|---|---|
| 3-Br | $CF_3$ | $G^2$-6 | — |
| 3-I | $CF_3$ | $G^2$-6 | — |
| 3-I | $CF_3$ | $G^2$-9 | — |
| 3-$CF_3$ | $CF_3$ | $G^2$-6 | — |
| 3-$CF_3$ | $CF_3$ | $G^2$-9 | — |
| 3-$CF_2CF_3$ | $CF_3$ | $G^2$-6 | — |
| 3-$OCF_3$ | $CF_3$ | $G^2$-6 | — |
| 3-$SCF_3$ | $CF_3$ | $G^2$-6 | — |
| 3-$SF_5$ | $CF_3$ | $G^2$-6 | — |
| 3-Cl-4-F | $CF_3$ | $G^2$-6 | — |
| 3-Cl-4-F | $CF_3$ | $G^2$-9 | — |
| 3-F-5-Cl | $CF_3$ | $G^2$-6 | — |
| 3-F-5-Cl | $CF_3$ | $G^2$-9 | — |
| 3,4-$Cl_2$ | $CF_3$ | $G^2$-6 | — |
| 3,4-$Cl_2$ | $CF_3$ | $G^2$-9 | — |
| 3,5-$Cl_2$ | $CF_3$ | $G^2$-3 | 4-C(O)NHCH$_2$CF$_3$ |
| 3,5-$Cl_2$ | $CF_3$ | $G^2$-5 | — |
| 3,5-$Cl_2$ | $CF_3$ | $G^2$-6 | — |
| 3,5-$Cl_2$ | $CF_3$ | $G^2$-8 | — |
| 3,5-$Cl_2$ | $CF_3$ | $G^2$-9 | — |
| 3,5-$Cl_2$ | $CF_3$ | $G^2$-9 | $CH_3$ |
| 3,5-$Cl_2$ | $CF_2Cl$ | $G^2$-6 | — |
| 3-Br-4-F | $CF_3$ | $G^2$-6 | — |
| 3-Br-4-F | $CF_3$ | $G^2$-9 | — |
| 3-F-5-Br | $CF_3$ | $G^2$-6 | — |
| 3-F-5-Br | $CF_3$ | $G^2$-9 | — |
| 3-Br-4-Cl | $CF_3$ | $G^2$-6 | — |
| 3-Cl-4-Br | $CF_3$ | $G^2$-6 | — |
| 3-Cl-5-Br | $CF_3$ | $G^2$-3 | 4-C(O)NHCH$_2$CF$_3$ |
| 3-Cl-5-Br | $CF_3$ | $G^2$-5 | — |
| 3-Cl-5-Br | $CF_3$ | $G^2$-6 | — |
| 3-Cl-5-Br | $CF_3$ | $G^2$-8 | — |
| 3-Cl-5-Br | $CF_3$ | $G^2$-9 | — |
| 3-Cl-5-Br | $CF_3$ | $G^2$-9 | $CH_3$ |
| 3-Cl-5-Br | $CF_2Cl$ | $G^2$-6 | — |
| 3,4-$Br_2$ | $CF_3$ | $G^2$-6 | — |
| 3,5-$Br_2$ | $CF_3$ | $G^2$-3 | 4-C(O)NHCH$_2$CF$_3$ |
| 3,5-$Br_2$ | $CF_3$ | $G^2$-5 | — |
| 3,5-$Br_2$ | $CF_3$ | $G^2$-6 | — |
| 3,5-$Br_2$ | $CF_3$ | $G^2$-8 | — |
| 3,5-$Br_2$ | $CF_3$ | $G^2$-9 | — |
| 3,5-$Br_2$ | $CF_3$ | $G^2$-9 | $CH_3$ |
| 3,5-$Br_2$ | $CF_2Cl$ | $G^2$-6 | — |
| 3-I-4-F | $CF_3$ | $G^2$-6 | — |
| 3-F-5-I | $CF_3$ | $G^2$-6 | — |
| 3-Cl-5-I | $CF_3$ | $G^2$-6 | — |
| 3-Cl-5-I | $CF_3$ | $G^2$-9 | — |
| 3-$CF_3$-4-F | $CF_3$ | $G^2$-6 | — |
| 3-$CF_3$-4-F | $CF_3$ | $G^2$-9 | — |
| 3-F-5-$CF_3$ | $CF_3$ | $G^2$-6 | — |
| 3-F-5-$CF_3$ | $CF_3$ | $G^2$-9 | — |
| 3-$CF_3$-4-Cl | $CF_3$ | $G^2$-6 | — |
| 3-$CF_3$-4-Cl | $CF_3$ | $G^2$-9 | — |
| 3-Cl-5-$CF_3$ | $CF_3$ | $G^2$-3 | — |
| 3-Cl-5-$CF_3$ | $CF_3$ | $G^2$-3 | 4-F |
| 3-Cl-5-$CF_3$ | $CF_3$ | $G^2$-3 | 4-Br |
| 3-Cl-5-$CF_3$ | $CF_3$ | $G^2$-3 | 4-C(O)NHCH$_2$CF$_3$ |
| 3-Cl-5-$CF_3$ | $CF_3$ | $G^2$-3 | 4-NO$_2$ |
| 3-Cl-5-$CF_3$ | $CF_3$ | $G^2$-4 | — |
| 3-Cl-5-$CF_3$ | $CF_3$ | $G^2$-5 | — |
| 3-Cl-5-$CF_3$ | $CF_3$ | $G^2$-6 | — |
| 3-Cl-5-$CF_3$ | $CF_3$ | $G^2$-6 | 3-Br |
| 3-Cl-5-$CF_3$ | $CF_3$ | $G^2$-6 | 5-Br |
| 3-Cl-5-$CF_3$ | $CF_3$ | $G^2$-6 | 3-NH$_2$ |
| 3-Cl-5-$CF_3$ | $CF_3$ | $G^2$-6 | 5-NH$_2$ |
| 3-Cl-5-$CF_3$ | $CF_3$ | $G^2$-7 | — |
| 3-Cl-5-$CF_3$ | $CF_3$ | $G^2$-8 | — |
| 3-Cl-5-$CF_3$ | $CF_3$ | $G^2$-9 | — |
| 3-Cl-5-$CF_3$ | $CF_3$ | $G^2$-9 | $CH_3$ |
| 3-Cl-5-$CF_3$ | $CF_3$ | $G^2$-10 | — |
| 3-Cl-5-$CF_3$ | $CF_2Cl$ | $G^2$-6 | — |
| 3-Cl-5-$CF_3$ | $CF_2Cl$ | $G^2$-9 | — |
| 3-Br-5-$CF_3$ | $CF_3$ | $G^2$-3 | — |
| 3-Br-5-$CF_3$ | $CF_3$ | $G^2$-3 | 4-F |
| 3-Br-5-$CF_3$ | $CF_3$ | $G^2$-3 | 4-Br |
| 3-Br-5-$CF_3$ | $CF_3$ | $G^2$-3 | 4-C(O)NHCH$_2$CF$_3$ |
| 3-Br-5-$CF_3$ | $CF_3$ | $G^2$-3 | 4-NO$_2$ |
| 3-Br-5-$CF_3$ | $CF_3$ | $G^2$-4 | — |
| 3-Br-5-$CF_3$ | $CF_3$ | $G^2$-5 | — |
| 3-Br-5-$CF_3$ | $CF_3$ | $G^2$-6 | — |
| 3-Br-5-$CF_3$ | $CF_3$ | $G^2$-6 | 3-Br |
| 3-Br-5-$CF_3$ | $CF_3$ | $G^2$-6 | 5-Br |
| 3-Br-5-$CF_3$ | $CF_3$ | $G^2$-6 | 3-NH$_2$ |
| 3-Br-5-$CF_3$ | $CF_3$ | $G^2$-6 | 5-NH$_2$ |
| 3-Br-5-$CF_3$ | $CF_3$ | $G^2$-7 | — |
| 3-Br-5-$CF_3$ | $CF_3$ | $G^2$-8 | — |
| 3-Br-5-$CF_3$ | $CF_3$ | $G^2$-9 | — |
| 3-Br-5-$CF_3$ | $CF_3$ | $G^2$-9 | $CH_3$ |
| 3-Br-5-$CF_3$ | $CF_3$ | $G^2$-10 | — |
| 3-Br-5-$CF_3$ | $CF_2Cl$ | $G^2$-6 | — |
| 3-Br-5-$CF_3$ | $CF_2Cl$ | $G^2$-9 | — |
| 3-I-5-$CF_3$ | $CF_3$ | $G^2$-3 | — |
| 3-I-5-$CF_3$ | $CF_3$ | $G^2$-3 | 4-F |
| 3-I-5-$CF_3$ | $CF_3$ | $G^2$-3 | 4-Br |
| 3-I-5-$CF_3$ | $CF_3$ | $G^2$-3 | 4-C(O)NHCH$_2$CF$_3$ |
| 3-I-5-$CF_3$ | $CF_3$ | $G^2$-3 | 4-NO$_2$ |
| 3-I-5-$CF_3$ | $CF_3$ | $G^2$-4 | — |
| 3-I-5-$CF_3$ | $CF_3$ | $G^2$-5 | — |
| 3-I-5-$CF_3$ | $CF_3$ | $G^2$-6 | — |
| 3-I-5-$CF_3$ | $CF_3$ | $G^2$-6 | 3-Br |
| 3-I-5-$CF_3$ | $CF_3$ | $G^2$-6 | 5-Br |
| 3-I-5-$CF_3$ | $CF_3$ | $G^2$-6 | 3-NH$_2$ |
| 3-I-5-$CF_3$ | $CF_3$ | $G^2$-6 | 5-NH$_2$ |
| 3-I-5-$CF_3$ | $CF_3$ | $G^2$-7 | — |
| 3-I-5-$CF_3$ | $CF_3$ | $G^2$-8 | — |
| 3-I-5-$CF_3$ | $CF_3$ | $G^2$-9 | — |
| 3-I-5-$CF_3$ | $CF_3$ | $G^2$-9 | $CH_3$ |
| 3-I-5-$CF_3$ | $CF_3$ | $G^2$-10 | — |
| 3-I-5-$CF_3$ | $CF_2Cl$ | $G^2$-6 | — |
| 3-I-5-$CF_3$ | $CF_2Cl$ | $G^2$-9 | — |
| 3,5-$(CF_3)_2$ | $CF_3$ | $G^2$-3 | — |
| 3,5-$(CF_3)_2$ | $CF_3$ | $G^2$-3 | 4-F |
| 3,5-$(CF_3)_2$ | $CF_3$ | $G^2$-3 | 4-Br |
| 3,5-$(CF_3)_2$ | $CF_3$ | $G^2$-3 | 4-C(O)NHCH$_2$CF$_3$ |
| 3,5-$(CF_3)_2$ | $CF_3$ | $G^2$-3 | 4-NO$_2$ |
| 3,5-$(CF_3)_2$ | $CF_3$ | $G^2$-4 | — |
| 3,5-$(CF_3)_2$ | $CF_3$ | $G^2$-5 | — |
| 3,5-$(CF_3)_2$ | $CF_3$ | $G^2$-6 | — |
| 3,5-$(CF_3)_2$ | $CF_3$ | $G^2$-6 | 3-Br |
| 3,5-$(CF_3)_2$ | $CF_3$ | $G^2$-6 | 5-Br |
| 3,5-$(CF_3)_2$ | $CF_3$ | $G^2$-6 | 3-NH$_2$ |
| 3,5-$(CF_3)_2$ | $CF_3$ | $G^2$-6 | 5-NH$_2$ |
| 3,5-$(CF_3)_2$ | $CF_3$ | $G^2$-7 | — |
| 3,5-$(CF_3)_2$ | $CF_3$ | $G^2$-8 | — |
| 3,5-$(CF_3)_2$ | $CF_3$ | $G^2$-9 | — |
| 3,5-$(CF_3)_2$ | $CF_3$ | $G^2$-9 | $CH_3$ |
| 3,5-$(CF_3)_2$ | $CF_3$ | $G^2$-10 | — |
| 3,5-$(CF_3)_2$ | $CF_2Cl$ | $G^2$-6 | — |
| 3,5-$(CF_3)_2$ | $CF_2Cl$ | $G^2$-9 | — |
| 3-Cl-5-$OCHF_2$ | $CF_3$ | $G^2$-6 | — |
| 3-Cl-5-$OCHF_2$ | $CF_3$ | $G^2$-9 | — |
| 3-Br-5-$OCHF_2$ | $CF_3$ | $G^2$-6 | — |
| 3-$CF_3$-5-$OCHF_2$ | $CF_3$ | $G^2$-6 | — |
| 3-Cl-5-$OCF_3$ | $CF_3$ | $G^2$-6 | — |
| 3-Cl-5-$OCF_3$ | $CF_3$ | $G^2$-9 | — |
| 3-Br-5-$OCF_3$ | $CF_3$ | $G^2$-6 | — |
| 3-$CF_3$-5-$OCF_3$ | $CF_3$ | $G^2$-6 | — |
| 3-Cl-5-$SCF_3$ | $CF_3$ | $G^2$-6 | — |
| 3-Cl-5-$SCF_3$ | $CF_3$ | $G^2$-9 | — |
| 3-Br-5-$SCF_3$ | $CF_3$ | $G^2$-6 | — |
| 3-$CF_3$-5-CN | $CF_3$ | $G^2$-6 | — |
| 3,4,5-$F_3$ | $CF_3$ | $G^2$-6 | — |
| 3,5-$Cl_2$-4-F | $CF_3$ | $G^2$-3 | 4-C(O)NHCH$_2$CF$_3$ |
| 3,5-$Cl_2$-4-F | $CF_3$ | $G^2$-5 | — |
| 3,5-$Cl_2$-4-F | $CF_3$ | $G^2$-6 | — |
| 3,5-$Cl_2$-4-F | $CF_3$ | $G^2$-8 | — |
| 3,5-$Cl_2$-4-F | $CF_3$ | $G^2$-9 | — |
| 3,5-$Cl_2$-4-F | $CF_3$ | $G^2$-9 | $CH_3$ |
| 3,5-$Cl_2$-4-F | $CF_2Cl$ | $G^2$-6 | — |
| 3,4,5-$Cl_3$ | $CF_3$ | $G^2$-3 | 4-C(O)NHCH$_2$CF$_3$ |
| 3,4,5-$Cl_3$ | $CF_3$ | $G^2$-5 | — |

-continued

| $(X)_m$ | $R^3$ | $G^2$ | $(Z)_n$ |
|---|---|---|---|
| 3,4,5-Cl$_3$ | CF$_3$ | G$^2$-6 | — |
| 3,4,5-Cl$_3$ | CF$_3$ | G$^2$-8 | — |
| 3,4,5-Cl$_3$ | CF$_3$ | G$^2$-9 | — |
| 3,4,5-Cl$_3$ | CF$_3$ | G$^2$-9 | CH$_3$ |
| 3,4,5-Cl$_3$ | CF$_2$Cl | G$^2$-6 | — |
| 3,5-Br$_2$-4-F | CF$_3$ | G$^2$-3 | — |
| 3,5-Br$_2$-4-F | CF$_3$ | G$^2$-3 | 4-F |
| 3,5-Br$_2$-4-F | CF$_3$ | G$^2$-3 | 4-Br |
| 3,5-Br$_2$-4-F | CF$_3$ | G$^2$-3 | 4-C(O)NHCH$_2$CF$_3$ |
| 3,5-Br$_2$-4-F | CF$_3$ | G$^2$-3 | 4-NO$_2$ |
| 3,5-Br$_2$-4-F | CF$_3$ | G$^2$-4 | — |
| 3,5-Br$_2$-4-F | CF$_3$ | G$^2$-5 | — |
| 3,5-Br$_2$-4-F | CF$_3$ | G$^2$-6 | — |
| 3,5-Br$_2$-4-F | CF$_3$ | G$^2$-6 | 3-Br |
| 3,5-Br$_2$-4-F | CF$_3$ | G$^2$-6 | 5-Br |
| 3,5-Br$_2$-4-F | CF$_3$ | G$^2$-6 | 3-NH$_2$ |
| 3,5-Br$_2$-4-F | CF$_3$ | G$^2$-6 | 5-NH$_2$ |
| 3,5-Br$_2$-4-F | CF$_3$ | G$^2$-7 | — |
| 3,5-Br$_2$-4-F | CF$_3$ | G$^2$-8 | — |
| 3,5-Br$_2$-4-F | CF$_3$ | G$^2$-9 | — |
| 3,5-Br$_2$-4-F | CF$_3$ | G$^2$-9 | CH$_3$ |
| 3,5-Br$_2$-4-F | CF$_3$ | G$^2$-10 | — |
| 3,5-Br$_2$-4-F | CF$_2$Cl | G$^2$-6 | — |
| 3,5-Br$_2$-4-F | CF$_2$Cl | G$^2$-9 | — |
| 3,5-Br$_2$-4-Cl | CF$_3$ | G$^2$-6 | — |
| 3,4,5-Br$_3$ | CF$_3$ | G$^2$-6 | — |
| 3,4-F$_2$-5-CF$_3$ | CF$_3$ | G$^2$-3 | 4-C(O)NHCH$_2$CF$_3$ |
| 3,4-F$_2$-5-CF$_3$ | CF$_3$ | G$^2$-5 | — |
| 3,4-F$_2$-5-CF$_3$ | CF$_3$ | G$^2$-6 | — |
| 3,4-F$_2$-5-CF$_3$ | CF$_3$ | G$^2$-8 | — |
| 3,4-F$_2$-5-CF$_3$ | CF$_3$ | G$^2$-9 | — |
| 3,4-F$_2$-5-CF$_3$ | CF$_3$ | G$^2$-9 | CH$_3$ |
| 3,4-F$_2$-5-CF$_3$ | CF$_2$Cl | G$^2$-6 | — |
| 3-Cl-4-F-5-CF$_3$ | CF$_3$ | G$^2$-3 | 4-C(O)NHCH$_2$CF$_3$ |
| 3-Cl-4-F-5-CF$_3$ | CF$_3$ | G$^2$-5 | — |
| 3-Cl-4-F-5-CF$_3$ | CF$_3$ | G$^2$-6 | — |
| 3-Cl-4-F-5-CF$_3$ | CF$_3$ | G$^2$-8 | — |
| 3-Cl-4-F-5-CF$_3$ | CF$_3$ | G$^2$-9 | — |
| 3-Cl-4-F-5-CF$_3$ | CF$_3$ | G$^2$-9 | CH$_3$ |
| 3-Cl-4-F-5-CF$_3$ | CF$_2$Cl | G$^2$-6 | — |
| 3,4-Cl$_2$-5-CF$_3$ | CF$_3$ | G$^2$-3 | 4-C(O)NHCH$_2$CF$_3$ |
| 3,4-Cl$_2$-5-CF$_3$ | CF$_3$ | G$^2$-5 | — |
| 3,4-Cl$_2$-5-CF$_3$ | CF$_3$ | G$^2$-6 | — |
| 3,4-Cl$_2$-5-CF$_3$ | CF$_3$ | G$^2$-8 | — |
| 3,4-Cl$_2$-5-CF$_3$ | CF$_3$ | G$^2$-9 | — |
| 3,4-Cl$_2$-5-CF$_3$ | CF$_3$ | G$^2$-9 | CH$_3$ |
| 3,4-Cl$_2$-5-CF$_3$ | CF$_2$Cl | G$^2$-6 | — |
| 3,5-(CF$_3$)$_2$-4-Cl | CF$_3$ | G$^2$-3 | 4-C(O)NHCH$_2$CF$_3$ |
| 3,5-(CF$_3$)$_2$-4-Cl | CF$_3$ | G$^2$-5 | — |
| 3,5-(CF$_3$)$_2$-4-Cl | CF$_3$ | G$^2$-6 | — |
| 3,5-(CF$_3$)$_2$-4-Cl | CF$_3$ | G$^2$-8 | — |
| 3,5-(CF$_3$)$_2$-4-Cl | CF$_3$ | G$^2$-9 | — |
| 3,5-(CF$_3$)$_2$-4-Cl | CF$_3$ | G$^2$-9 | CH$_3$ |
| 3,5-(CF$_3$)$_2$-4-Cl | CF$_2$Cl | G$^2$-6 | — |
| 3,5-Cl$_2$-4-OCHF$_2$ | CF$_3$ | G$^2$-6 | — |
| 3,5-Br$_2$-4-OCHF$_2$ | CF$_3$ | G$^2$-6 | — |

The compound of the present invention can effectively control with a low concentration thereof, any pests such as insects including so-called agricultural insect pests damaging agricultural or horticultural crops and trees, so-called domestic animal insect pests being parasitic in domestic animals/fowls, so-called sanitary insects adversely effecting in various manners, the living environment of the human such as the house, and so-called stored grain insect pests damaging grains and the like stored in a warehouse; and mites, Crustacea, Mollusc and Nematoda which are generated to cause damages in situations similar to those in the case of the insects.

Specific examples of the insects, the mites, the Crustacea, the Mollusc and the Nematoda capable of being controlled using the compound of the present invention include:

Lepidopteran insects such as *Adoxophyes honmai, Adoxophyes orana faciata, Archips breviplicanus, Archips fuscocupreanus, Grapholita molesta, Homona magnanima, Leguminivora glycinivorella, Matsumuraeses phaseoli, Pandemis heparana, Bucculatrix pyrivorella, Lyonetia clerkella, Lyonetia prunifoliella malinella, Caloptilia theivora, Phyllonorycter ringoniella, Phyllocnistis citrella, Acrolepiopsis sapporensis, Acrolepiopsis suzukiella, Plutella xylostella, Stathmopoda masinissa, Helcystogramma triannulella, Pectinophora gossypiella, Carposina sasakii, Cydla pomonella, Chilo suppressalis, Cnaphalocrocis medinalis, Conogethes punctiferalis, Diaphania indica, Etiella zinckenella, Glyphodes pyloalis, Hellula undalis, Ostrinia furnacalis, Ostrinia scapulalis, Ostrinia nubilalis, Parapediasia teterrella, Parnara guttata, Pieris brassicae, Pieris rapae crucivora, Ascotis selenaria, Pseudoplusia includens, Euproctis pseudoconspersa, Lymantria dispar, Orgyia thyellina, Hyphantria cunea, Lemyra imparilis, Adris tyrannus, Aedia leucomelas, Agrotis ipsilon, Agrotis segetum, Autographa nigrisigna, Ctenoplusia agnata, Helicoverpa armigera, Helicoverpa assulta, Helicoverpa zea, Heliothis virescens, Mamestra brassicae, Mythimna separata, Naranga aenescens, Spodoptera eridania, Spodoptera exigua, Spodoptera frugiperda, Spodoptera littoralis, Spodoptera litura, Spodoptera depravata, Trichoplusia ni, Endopiza viteana, Manduca quinquemaculata* and *Manduca sexta*;

Thysanoptera insects such as *Frankliniella intonsa, Frankliniella occidentalis, Heliothrips haemorrhoidalis, Scirtothrips dorsalis, Thrips palmi, Thrips tabaci* and *Ponticulothrips diospyrosi*;

Hemiptera insects such as *Dolycoris baccarum, Eurydema rugosum, Eysarcoris aeneus, Eysarcoris lewisi, Eysarcoris ventralis, Glaucias subpunctatus, Halyomorpha halys, Nezara antennata, Nezara viridula, Piezodorus hybneri, Plautia crossota, Scotinophora lurida, Cletus punctiger, Leptocorisa chinensis, Riptortus clavatus, Rhopalus msculatus, Cavelerius saccharivorus, Togo hemipterus, Dysdercus cingulatus, Stephanitis pyrioides, Halticus insularis, Lygus lineolaris, Stenodema sibiricum, Stenotus rubrovittatus, Trigonotylus caelestialium, Arboridia apicalis, Balclutha saltuella, Epiacanthus stramineus, Empoasca fabae, Empoasca nipponica, Empoasca onukii, Empoasca sakaii, Macrosteles striifrons, Nephotettix cinctinceps, Psuedatomoscelis seriatus, Laodelphax striatella, Nilaparvata lugens, Sogatella furcifera, Diaphorina citri, Psylla pyrisuga, Aleurocanthus spiniferus, Bemisia argentifolii, Bemisia tabaci, Dialeurodes citri, Trialeurodes vaporariorum, Viteus vitifolii, Aphis gossypii, Aphis spiraecola, Myzus persicae, Toxoptera aurantii, Drosicha corpulenta, Icerya purchasi, Phenacoccus solani, Planococcus citri, Planococcus kuraunhiae, Pseudococcus comstocki, Ceroplastes ceriferus, Ceroplastes rubens, Aonidiella aurantii, Comstockaspis perniciosa, Fiorinia theae, Pseudaonidia paeoniae, Pseudaulacaspis pentagona, Pseudaulacaspis prunicola, Unaspis euonymi, Unaspis yanonensis* and *Cimex lectularius*;

Coleoptera insects such as *Anomala cuprea, Anomala rufocuprea, Gametis jucunda, Heptophylla picea, Popillia japonica, Lepinotarsa decemlineata, Melanotus fortnumi, Melanotus tamsuyensis, Lasioderma serricorne, Epuraea domina, Epilachna varivestis, Epilachna vigintioctopunctata, Tenebrio molitor, Tribolium castaneum, Anoplophora malasiaca, Monochamus alternatus, Psacothea hilaris, Xylotrechus pyrrhoderus, Callosobruchus chinensis, Aulacophora femoralis, Chaetocnema concinna, Diabrotica undecimpunctata, Diabrotica virgifera, Diabrotica barberi, Oulema oryzae, Phyllotreta striolata, Psylliodes angusticollis, Rhynchites heros, Cylas formicarius, Anthonomus grandis, Echinocnemus squameus, Euscepes postfasciatus, Hypera postica, Lissohoptrus oryzophilus, Otiorhynchus sul-* catus, Sitophilus granarius, Sitophilus zeamais, Sphenophorus venatus vestitus and Paederus fuscipes;

Diptera insects such as Asphondylia yushimai, Sitodiplosis mosellana, Bactrocera cucurbitae, Bactrocera dorsalis, Ceratitis capitata, Hydrellia griseola, Drosophila suzukii, Agromyza oryzae, Chromatomyia horticola, Liriomyza bryoniae, Liriomyza chinensis, Liriomyza sativae, Liriomyza trifolii, Delia platura, Pegomya cunicularia, Rhagoletis pomonella, Mayetiola destructor, Musca domestica, Stomoxys calcitrans, Melophagus ovinus, Hypoderma bovis, Hypoderma lineatum, Oestrus ovis, Glossina palpalis (Glossina morsitans), Prosimulium yezoensis, Tabanus trigonus, Telmatoscopus albipunctatus, Leptoconops nipponensis, Culex pipiens pallens, Aedes aegypti, Aedes albopicutus and Anopheles hyracanus sinesis;

Hymenoptera insects such as Apethymus kuri, Athalia rosae, Arge pagana, Neodiprion sertifer, Dryocosmus kuriphilus, Eciton burchelli (Eciton schmitti), Camponotus japonicus, Vespa mandarina, Myrmecia spp., Solenopsis spp. and Monomorium pharaonis;

Orthoptera insects such as Teleogryllus emma, Gryllotalpa orientalis, Locusta migratoria, Oxya yezoensis and Schistocerca gregaria;

Collembolan insects such as Onychiurus folsomi, Onychiurus sibiricus and Bourletiella hortensis;

Dictyoptera insects such as Periplaneta fuliginosa, Periplaneta japonica and Blattella germanica;

Isoptera insects such as Coptotermes formosanus, Reticulitermes speratus and Odontotermes formosanus;

Isoptera insects such as Ctenocephalidae felis, Ctenocephalides canis, Echidnophaga gallinacea, Pulex irritans and Xenopsylla cheopis;

Mallophaga insects such as Menacanthus stramineus and Bovicola bovis;

Anoplura insects such as Haematopinus eurysternus, Haematopinus suis, Linognathus vituli and Solenopotes capillatus;

Tarsonemidae such as Phytonemus pallidus, Polyphagotarsonemus latus and Tarsonemus bilobatus;

Eupodidae such as Penthaleus erythrocephalus and Penthaleus major;

Tetranychidae such as Oligonychus shinkajii, Panonychus citri, Panonychus mori, Panonychus ulmi, Tetranychus kanzawai and Tetranychus urticae;

Eriophydae such as Acaphylla theavagrans, Aceria tulipae, Aculops lycopersici, Aculops pelekassi, Aculus schlechtendali, Eriophyes chibaensis and Phyllocoptruta oleivora;

Acaridae such as Rhizoglyphus robini, Tyrophagus putrescentiae and Tyrophagus similis;

Varroa destructor such as Varroa jacobsoni;

Ixodidae such as Boophilus microplus, Rhipicephalus sanguineus, Haemaphysalis longicornis, Haemophysalis flava, Haemophysalis campanulata, Ixodes ovatus, Ixodes persulcatus, Amblyomma spp. and Dermacentor spp.

Cheyletidae such as Cheyletiella yasguri and Cheyletiella blakei;

Demodicidae such as Demodex canis and Demodex cati;

Psoroptidae such as Psoroptes ovis;

Sarcoptidae such as Sarcoptes scabiei, Notoedres cati and Knemidocoptes spp.;

Crustacea such as Armadillidium vulgare;

Gastropoda such as Pomacea canaliculata, Achatina fulica, Meghimatium bilineatum, Limax Valentiana, Acusta despecta sieboldiana and Euhadra peliomphala; and Nematoda such as Prathylenchus coffeae, Prathylenchus penetrans, Prathylenchus vulnus, Globodera rostochiensis, Heterodera glycines, Meloidogyne hapla, Meloidogyne incognita, Aphelenchoides besseyi and Bursaphelenchus xylophilus, which should not be construed as limiting the scope of the present invention.

In addition, specific examples of the internal parasites of domestic animals, fowls, pet animals or the like capable of being controlled using the compound of the present invention include:

Nematoda such as Haemonchus, Trichostrongylus, Ostertagia, Nematodirus, Cooperia, Ascaris, Bunostomum, Oesophagostomum, Chabertia, Trichuris, Storongylus, Trichonema, Dictyocaulus, Capillaria, Heterakis, Toxocara, Ascaridia, Oxyuris, Ancylostoma, Uncinaria, Toxascaris and Parascaris;

Nematoda, Filariidae such as Wuchereria, Brugia, Onchoceca, Dirofilaria and Loa;

Nematoda, Dracunculidae such as Deacunculus;

Cestoda such as Dipylidium caninum, Taenia taeniaeformis, Taenia solium, Taenia saginata, Hymenolepis diminuta, Moniezia benedeni, Diphyllobothrium latum, Diphyllobothrium erinacei, Echinococcus granulosus and Echinococcus multilocularis;

Trematoda such as Fasciola hepatica and F. gigantica, Paragonimus westermanii, Fasciolopsic bruski, Eurytrema pancreaticum and E. coelomaticum, Clonorchis sinensis, Schistosoma japonicum, Schistosoma haematobium and Schistosoma mansoni;

Eimeria spp. such as Eimeria tenella, Eimeria acervulina, Eimeria brunetti, Eimeria maxima, Eimeria necatrix, Eimeria bovis and Eimeria ovinoidalis;

Trypanosomsa cruzi; Leishmania spp.; Plasmodium spp.; Babesis spp.; Trichomonadidae spp.; Histomanas spp.; Giardia spp.; Toxoplasma spp.; Entamoeba histolytica and Theileria spp, which should not be construed as limiting the scope of the present invention.

Furthermore, the compound of the present invention is effective against pests which have developed the resistance to the related art insecticides such as organic phosphorus-based compounds, carbamate-based compounds or pyrethroid-based compounds.

That is, the compound of the present invention can effectively control pests belonging to insects such as Collembola, Dictyoptera (Blattaria), Orthoptera, Isoptera, Thysanoptera, Hemiptera (Heteroptera and Homoptera), Lepidoptera, Coleoptera, Hymenoptera, Diptera, Isoptera (Siphonaptera) and Phthiraptera; mites; Gastropoda; and Nematoda with a low concentration. On the other hand, the compound of the present invention has an extremely useful characteristic of having substantially no adverse effect on mammals, fish, Crustacea and beneficial insects (useful insects such as Apidae and Bombus, and natural enemies such as Aphelinidae, Aphidiidae, Tachinidae, Orius and Amblyseius).

For using the compound of the present invention, the compound can be put to practical use as a preparation in any formulation such as a soluble concentrate, an emulsifiable concentrate, a wettable powder, a water soluble powder, a water dispersible granule, a water soluble granule, a suspension concentrate, a concentrated emulsion, a suspoemulsion, a microemulsion, a dustable powder, a granule, a tablet and an emulsifiable gel, typically by mixing the compound with an appropriate solid carrier or liquid carrier, further if desired by adding to the resultant mixture, a surfactant, a penetrant, a spreader, a thickener, an antifreezing agent, a binder, an anti-caking agent, a disintegrant, an antifoamer, an antiseptic or a stabilizer. In addition, from the viewpoint of laborsaving and safety-enhancing, the compound can be put to use by encapsulating the above preparation in any dosage form in a water soluble packaging material such as a water soluble capsule and a bag of water soluble film.

Examples of the solid carrier include: natural mineral matters such as quartz, calcite, sepiolite, dolomite, chalk, kaolinite, pyrophyllite, sericite, halloysite, methahalloysite, kibushi clay, gairome clay, pottery stone, zeeklite, allophane, Shirasu, mica, talc, bentonite, activated clay, acid clay, pumice, attapulgite, zeolite and diatom earth; burned products of natural mineral matters such as burned clay, perlite, Shirasu balloon, vermiculite, attapulgous clay and burned diatom earth; inorganic salts such as magnesium carbonate, calcium carbonate, sodium carbonate, sodium hydrogen carbonate, ammonium sulfate, sodium sulfate, magnesium sulfate, diammonium hydrogen phosphate, ammonium dihydrogen phosphate and potassium chloride; saccharides such as glucose, fructose, sucrose and lactose; polysaccharides such as starch, powdered cellulose and dextrin; organic substances such as urea, urea derivatives, benzoic acid and salts of benzoic acid; plants such as wood flour, cork flour, corncob, walnut shell and tobacco stem; fly ash; white carbon (such as hydrous synthetic silica, anhydrous synthetic silica and hydrous synthetic silicate); and fertilizers.

Examples of the liquid carrier include: aromatic hydrocarbons such as xylene, alkyl ($C_9$, $C_{10}$, or the like) benzene, phenylxylylethane and alkyl ($C_1$, $C_3$, or the like) naphthalene; aliphatic hydrocarbons such as machine oil, n-paraffin, isoparaffin and naphthene; a mixture of aromatic hydrocarbons and aliphatic hydrocarbons such as kerosene; alcohols such as ethanol, isopropanol, cyclohexanol, phenoxyethanol and benzyl alcohol; polyalcohols such as ethylene glycol, propylene glycol, diethylene glycol, hexylene glycol, polyethylene glycol and polypropylene glycol; ethers such as propyl cellosolve, butyl cellosolve, phenyl cellosolve, propylene glycol monomethyl ether, propylene glycol monoethyl ether, propylene glycol monopropyl ether, propylene glycol monobutyl ether and propylene glycol monophenyl ether; ketones such as acetophenone, cyclohexanone and γ-butyro lactone; esters such as aliphatic acid methyl esters, succinic acid dialkyl esters, glutamic acid dialkyl esters, dialkyl adipate esters, and dialkyl phthalate esters; acid amides such as N-alkyl ($C_1$, $C_8$, $C_{12}$, or the like) pyrrolidone; oils and fats such as soybean oil, linseed oil, rapeseed oil, coconut oil, cottonseed oil and castor oil; dimethyl sulfoxide; and water.

These solid or liquid carriers may be used individually or in combination of two or more types thereof.

Examples of the surfactant include: nonionic surfactants such as polyoxyethylene alkyl ethers, polyoxyethylene alkyl (mono- or di-)phenyl ethers, polyoxyethylene (mono-, di- or tri-)stylyl phenyl ethers, polyoxyethylene-polyoxypropylene block copolymers, polyoxyethylene aliphatic acid (mono- or di-) esters, sorbitan aliphatic acid esters, polyoxyethylene sorbitan aliphatic acid esters, castor oil ethylene-oxide adducts, acetylene glycol, acetylene alcohols, acetylene glycol ethylene-oxide adducts, acetylene alcohol ethylene-oxide adducts and alkylglucosides; anionic surfactants such as alkyl sulfate ester salts, alkylbenzene sulfonates, lignin sulfonates, alkyl sulfosuccinates, naphthalene sulfonates, alkylnaphthalene sulfonates, salts of naphthalene sulfonate formalin condensate, salts of alkylnaphthalene sulfonate formalin condensate, polyoxyethylenealkylether sulfate or phosphate esters, polyoxyethylene (mono- or di-)alkylphenyl ether sulfate or phosphate esters, polyoxyethylene (mono-, di- or tri-)stylylphenyl ether sulfate or phosphate esters, polycarboxylic acid salts (such as polyacrylic acid salts, polymaleic acid salts and maleic acid-olefin copolymer) and polystylene sulfonates; cationic surfactants such as alkylamine salts and alkyl quaternary ammonium salts; amphoteric surfactants such as amino acid-type surfactants and betaine-type surfactants; silicone-based surfactants; and fluorinated surfactants.

Although the content of these surfactants is not particularly limited, it is desirably in a range of usually 0.05 to 20 parts by weight, relative to 100 parts by weight of the preparation of the present invention. In addition, these surfactants may be used individually or in combination of two or more types thereof.

Although the application dosage of the compound of the present invention varies depending on the application situation, the application period, the application method, the cultivated crop and the like, it is generally appropriate to be around 0.005 to 50 kg per hectare (ha) as an active ingredient amount.

On the other hand, in using the compound of the present invention for controlling external or internal parasites of mammals and birds as domestic animals and pet animals, an effective amount of the compound of the present invention can be administered together with additives for the preparation by: oral administration and parenteral administration such as injections (intramuscular, subcutaneous, intravenous and intraperitoneal injections); a percutaneous administration such as immersing, spraying, bathing, cleaning, pouring-on and spotting-on, and dusting; and transnasal administration. The compound of the present invention can be administered also as a molded product using a strip, a plate, a band, a collar, an ear mark, a limb band and an indicator. For the administration of the compound of the present invention, the compound can be prepared in any dosage form suitable for an administration route.

Examples of the dosage form to be prepared include solid preparations such as dustable powders, granules, wettable powders, pellets, tablets, boluses, capsules and molded products containing activated compounds; soluble concentrates for injection, soluble concentrates for oral administration and soluble concentrates used on the skin or in the body cavity; solution preparations such as pour-on drugs, spot-on drugs, flowable drugs and emulsifiable concentrates; and semisolid preparations such as ointments and gels.

The solid preparation can be mainly used for oral administration, percutaneous administration of the preparation diluted with water, or an environmental treatment. The solid preparation can be prepared by mixing an activated compound with an appropriate excipient, if necessary together with an adjuvant, and converting the resultant mixture into a desired form. Examples of the appropriate excipient include: inorganic substances such as carbonate salts, hydrogen carbonate salts, phosphate salts, aluminum oxide, silica and clay; and organic substances such as saccharides, celluloses, ground grains and starch.

The soluble concentrate for injection can be prepared by dissolving an activated compound capable of being administered intravenously, intramuscularly or subcutaneously in an appropriate solvent, and if necessary by adding to the resultant solution, additives such as solubilizers, acids, bases, buffering salts, antioxidants and protective agents. Examples of the appropriate solvent include water, ethanol, butanol, benzyl alcohol, glycerin, propylene glycol, polyethylene glycol, N-methylpyrrolidone, mixtures thereof, physiologically acceptable vegetable oils and synthetic oils suitable for injection. Examples of the solubilizer include polyvinylpyrrolidone, polyoxyethylated castor oil and polyoxyethylated sorbitan esters. Examples of the protective agents include benzyl alcohol, trichlorobutanol, p-hydroxybenzoic acid esters and n-butanol.

The soluble concentrate for oral administration can be administered directly or as a diluted soluble concentrate and can be prepared in substantially the same manner as in the case of the soluble concentrate for injection.

The flowable drug, the emulsifiable concentrate and the like can be administered percutaneously directly or as a diluted drug, or through an environmental treatment.

The soluble concentrate used on the skin can be administrated by dropping, spreading, rubbing, spraying, dusting or immersing (immersing, bathing or cleaning) to apply the drug on the skin. These soluble concentrates can be prepared in substantially the same manner as that in the case of the soluble concentrate for injection.

The pour-on drug and the spot-on drug are dropped or sprayed on a limited range of the skin, so that these drugs can immerse activated compounds thereof into the skin to obtain the systemic effect. The pour-on drug and the spot-on drug can be prepared by dissolving, suspending or emulsifying an active ingredient in an appropriate skin-adaptable solvent or solvent mixture. If necessary, in these drugs, an adjuvant such as a surfactant, a colorant, an absorption-accelerating substance, an antioxidant, a light stabilizer and an adhesive can be incorporated.

Examples of the appropriate solvent include water, alkanol, glycol, polyethylene glycol, polypropylene glycol, glycerin, benzyl alcohol, phenylethanol, phenoxyethanol, ethyl acetate, butyl acetate, benzyl benzoate, dipropylene glycol monomethyl ether, diethylene glycol monobutyl ether, acetone, methyl ethyl ketone, aromatic and/or aliphatic hydrocarbons, vegetable or synthetic oils, DMF, liquid paraffin, light liquid paraffin, silicone, dimethylacetoamide, N-methylpyrrolidone or 2,2-dimethyl-4-oxy-methylene-1,3-dioxolane. Examples of the absorption accelerating substance include DMSO, isopropyl myristate, dipropylene glycol pelargonate, silicone oil, aliphatic esters, triglycerides and aliphatic alcohols. Examples of the antioxidant include sulfites, metabisulfites, ascorbic acid, butylhydroxytoluene, butylated hydroxyanisole and tocopherol.

The emulsifiable concentrate can be administered by an oral administration, a percutaneous administration or an injection. The emulsifiable concentrate can be prepared by dissolving an active ingredient in a hydrophobic phase or a hydrophilic phase and homogenizing the resultant solution with a solvent of another type of phase using an appropriate emulsifier, if necessary further together with an adjuvant such as a colorant, an absorption accelerating substance, a protective agent, an antioxidant, a sunscreen and a thickener substance.

Examples of the hydrophobic phase (oil) include paraffin oil, silicone oil, sesame oil, almond oil, castor oil, synthetic triglyceride, ethyl stearate, di-n-butyryl adipate, hexyl laurate, dipropylene glycol pelargonate, an ester of a branched aliphatic acid having a short chain length with a saturated aliphatic acid having a chain length of C16 to C18, isopropyl myristate, isopropyl palmitate, caprylate/caprate esters of a saturated aliphatic alcohol having a chain length of C12 to C18, isopropyl stearate, oleyl oleate, decyl oleate, ethyl oleate, ethyl lactate, a wax-like aliphatic acid ester, dibutyl phthalate, diisopropyl adipate, isotridecyl alcohol, 2-octyl dodecanol, cetylstearyl alcohol and oleyl alcohol.

Examples of the hydrophilic phase include water, propylene glycol, glycerin and sorbitol.

Examples of the emulsifier include: nonionic surfactants such as polyoxyethylated castor oil, polyoxyethylated monoolefin acid sorbitan, sorbitan monostearate, glycerin monostearate, polyoxyethyl stearate and alkylphenol polyglycol ether; amphoteric surfactants such as disodium N-lauryl-β-iminodipropionateand lecithin; anionic surfactants such as sodium laurylsulfate, aliphatic alcohol sulfate ether and mono-/di-alkyl polyglycol orthophosphate ester monoethanolamine salt; and cationic surfactants such as cetyltrimethylammonium chloride.

Examples of the other adjuvants include carboxymethyl cellulose, methyl cellulose, polyacrylate, alginate, gelatin, gum Arabic, polyvinylpyrrolidone, polyvinyl alcohol, methyl vinyl ether, copolymers of maleic anhydride, polyethylene glycol, wax and colloidal silica.

The semisolid preparation can be administered by applying or spreading the preparation on the skin or by introducing the preparation into a body cavity. The gel can be prepared by adding to a solution prepared as described above with respect to the soluble concentrate for injection, a thickener in an amount sufficient for generating an ointment-like transparent substance having viscosity.

Next, examples of the formulation of the preparation in the case of using the compound of the present invention are described, with the proviso that the formulation examples of the present invention are not limited to these examples. Here, in the following formulation examples, "part" represents a part by weight.

(Wettable Powder)

| | |
|---|---|
| Compound of the present invention | 0.1 to 80 parts |
| Solid carrier | 5 to 98.9 parts |
| Surfactant | 1 to 10 part(s) |
| Others | 0 to 5 parts |

Examples of the others include an anticaking agent and a stabilizer.

(Emulsifiable Concentrate)

| | |
|---|---|
| Compound of the present invention | 0.1 to 30 parts |
| Liquid carrier | 45 to 95 parts |
| Surfactant | 4.9 to 15 parts |
| Others | 0 to 10 parts |

Examples of the others include a spreader and a stabilizer.

(Suspension Concentrate)

| | |
|---|---|
| Compound of the present invention | 0.1 to 70 parts |
| Liquid carrier | 15 to 98.89 parts |
| Surfactant | 1 to 12 part(s) |
| Others | 0.01 to 30 parts |

Examples of the others include an antifreezing agent and a thickener.

(Water Dispersible Granule)

| | |
|---|---|
| Compound of the present invention | 0.1 to 90 parts |
| Solid carrier | 0 to 98.9 parts |
| Surfactant | 1 to 20 part(s) |
| Others | 0 to 10 parts |

Examples of the others include a binder and a stabilizer.

(Soluble Concentrate)

| Compound of the present invention | 0.01 to 70 parts |
|---|---|
| Liquid carrier | 20 to 99.99 parts |
| Others | 0 to 10 parts |

Examples of the others include an antifreezing agent and a spreader.

(Granule)

| Compound of the present invention | 0.01 to 80 parts |
|---|---|
| Solid carrier | 10 to 99.99 parts |
| Others | 0 to 10 parts |

Examples of the others include a binder and a stabilizer.

(Dustable Powder)

| Compound of the present invention | 0.01 to 30 parts |
|---|---|
| Solid carrier | 65 to 99.99 parts |
| Others | 0 to 5 parts |

Examples of the others include an antidrift agent and a stabilizer.

Next, examples of the preparation containing the compound of the present invention as an active ingredient are more specifically described. However, the examples should not be construed as limiting the scope of the present invention.

Here, in the following formulation examples, "parts" represents parts by weight.

Formulation Example 1

Wettable Powder prepared by homogeneously mixing and grinding a composition containing:

| compound of the present invention No. 1-001 | 20 parts; |
|---|---|
| pyrophyllite | 74 parts; |
| SORPOL 5039 | 4 parts |
| (trade name; manufactured by TOHO Chemical Industry Co., LTD.; mixture of nonionic surfactant and anionic surfactant); and | |
| CARPLEX #80D | 2 parts |
| (trade name; manufactured by Shionogi & Co., Ltd.; synthetic hydrous silicic acid). | |

Formulation Example 2

Emulsifiable Concentrate prepared by homogeneously mixing a composition containing:

| compound of the present invention No. 1-001 | 5 parts; |
|---|---|
| xylene | 75 parts; |
| N-methylpyrrolidone | 15 parts; and |
| SORPOL 2680 | 5 parts |
| (trade name; manufactured by TOHO Chemical Industry Co., LTD.; mixture of nonionic surfactant and anionic surfactant). | |

Formulation Example 3

Emulsifiable Concentrate prepared by homogeneously mixing a composition containing:

| compound of the present invention No. 1-001 | 4 parts; |
|---|---|
| DBE | 36 parts |
| (trade name; manufactured by INVISTA; mixture of dimethyl adipate, dimethyl glutarate, and dimethyl succinate); | |
| diisobutyl adipate | 30 parts; |
| N-methylpyrrolidone | 10 parts; |
| SOPROPHOR BSU | 14 parts; and |
| (trade name; manufactured by Rhodia; mixture of nonionic surfactant) | |
| RHODACAL 70BC | 6 parts |
| (trade name; manufactured by Rhodia; mixture of anionic surfactant). | |

Formulation Example 4

Emulsifiable Concentrate prepared by homogeneously mixing a composition containing:

| compound of the present invention No. 1-001 | 4 parts; |
|---|---|
| DBE | 11 parts |
| (trade name; manufactured by INVISTA; mixture of dimethyl adipate, dimethyl glutarate, and dimethyl succinate); | |
| diisobutyl adipate | 30 parts; |
| N-methylpyrrolidone | 5 parts; |
| SOPROPHOR BSU | 14 parts; |
| (trade name; manufactured by Rhodia; mixture of nonionic surfactant) | |
| RHODACAL 70BC | 6 parts |
| (trade name; manufactured by Rhodia; mixture of anonionic surfactant). | |
| propylene glycol | 10 parts; and |
| water | 20 parts. |

Formulation Example 5

Suspension Concentrate prepared by homogeneously mixing a composition containing:

| compound of the present invention No. 1-001 | 25 parts; |
|---|---|
| AGRISOL S-710 | 10 parts |
| (trade name; manufactured by Kao Corporation; nonionic surfactant); | |
| LUNOX 1000C | 0.5 parts |
| (trade name; manufactured by TOHO Chemical Industry Co., LTD.; anionic surfactant); | |

-continued

| | |
|---|---|
| xanthan gum | 0.2 parts; and |
| water | 64.3 parts, | and then wet-grinding the resultant mixture.

Formulation Example 6

Water Dispersible Granule prepared by homogeneously mixing and grinding a composition containing:

| | |
|---|---|
| compound of the present invention No. 1-001 | 75 parts; |
| HITENOL NE-15 | 5 parts; |
| (trade name; manufactured by Dai-ichi Kogyo Seiyaku Co., Ltd.; anionic surfactant); | |
| VANILLEX N | 10 parts |
| (trade name; manufactured by Nippon Paper Industries Co., Ltd.; anionic surfactant); and | |
| CARPLEX #80D | 10 parts |
| (trade name; manufactured by Shionogi & Co., Ltd.; synthetic hydrous silicic acid), then adding a small amount of water to the resultant mixture to stir and mix the mixture, granulating the mixture with an extrusion granulator, and drying the resultant granules. | |

Formulation Example 7

Granule prepared by homogeneously mixing and grinding a composition containing:

| | |
|---|---|
| compound of the present invention No. 1-001 | 5 parts; |
| bentonite | 50 parts; and |
| talc | 45 parts, |
| then adding a small amount of water to the resultant mixture to stir and mix the mixture, granulating the mixture with an extrusion granulator, and drying the resultant granules. | |

Formulation Example 8

Dustable Powder prepared by homogeneously mixing and grinding a composition containing:

| | |
|---|---|
| compound of the present invention No. 1-001 | 3 parts; |
| CARPLEX #80D | 0.5 parts |
| (trade name; manufactured by Shionogi & Co., Ltd.; synthetic hydrous silicic acid); | |
| kaolinite | 95 parts; and |
| diisopropyl phosphate | 1.5 parts. |

For using the preparation, the preparation is diluted with water by 1 to 10,000 time(s) to be directly dusted or is directly dusted without dilution.

Formulation Example 9

Wettable Powder Preparation

| | |
|---|---|
| compound of the present invention No. 1-004 | 25 parts |
| sodium diisobutylnaphthalenesulfonate | 1 part |
| calcium n-dodecylbenzenesulfonate | 10 parts |
| alkylaryl polyglycol ether | 12 parts |
| sodium salt of naphthalenesulfonic acid formalin condensate | 3 parts |
| emulsion-type silicone | 1 part |
| silicon dioxide | 3 parts |
| kaolin | 45 parts |

Formulation Example 10

Water Soluble Thickener Preparation

| | |
|---|---|
| compound of the present invention No. 1-004 | 20 parts |
| polyoxyethylene lauryl ether | 3 parts |
| sodium dioctylsulfosuccinate | 3.5 parts |
| dimethylsulfoxide | 37 parts |
| 2-propanol | 36.5 parts |

Formulation Example 11

Soluble Concentrate for Spraying

| | |
|---|---|
| compound of the present invention No. 1-004 | 2 parts |
| dimethylsulfoxide | 10 parts |
| 2-propanol | 35 parts |
| acetone | 53 parts |

Formulation Example 12

Soluble Concentrate for Percutaneous Administration

| | |
|---|---|
| compound of the present invention No. 1-004 | 5 parts |
| hexylene glycol | 50 parts |
| isopropanol | 45 parts |

Formulation Example 13

Soluble Concentrate for Percutaneous Administration

| | |
|---|---|
| compound of the present invention No. 1-004 | 5 parts |
| propylene glycol monomethyl ether | 50 parts |
| dipropylene glycol | 45 parts |

Formulation Example 14

Soluble Concentrate for Percutaneous Administration (Dropping)

| | |
|---|---|
| compound of the present invention No. 1-004 | 2 parts |
| light liquid paraffin | 98 parts |

Formulation Example 15

Soluble Concentrate for Percutaneous Administration (Dropping)

| | |
|---|---|
| compound of the present invention No. 1-004 | 2 parts |
| light liquid paraffin | 58 parts |
| olive oil | 30 parts |
| ODO-H | 9 parts |
| Shin-Etsu silicone | 1 part |

In addition, when the compound of the present invention is used as an agricultural chemical, if necessary the compound may be mixed with another type of herbicide, various insecticides, a miticide, a nematicide, a fungicide, a plant growth regulator, a synergist, a fertilizer or a soil conditioner to be applied during the preparation or the dusting.

Particularly, by applying the compound mixed with other agricultural chemicals or phytohormones, a cost reduction by reducing the application dose, an enlargement of the insecticidal spectrum by a synergism of a mixed drug, and a higher pest control effect can be expected. In this case, it is possible to combine simultaneously a plurality of publicly-known agricultural chemicals. Examples of types of agricultural chemicals to be mixed with the compound of the present invention to be used include compounds described in "The Pesticide Manual, vol. 14 (2006)". Specific examples of the general names include the following names, to which the examples are not limited.

Fungicides: acibenzolar-S-methyl, acylaminobenzamide, acypetacs, aldimorph, amisulbrom, amobam, ampropylos, anilazine, azaconazole, azithiram, azoxystrobin, barium polysulfide, benalaxyl, benodanil, benomyl, benquinox, bentaluron, benthiavalicarb, benthiazole, benzamacril, benzamorf, bethoxazine, binapacryl, biphenyl, bitertanol, blasticidin-S, bordeaux mixture, boscalid, bromoconazole, bupirimate, buthiobate, calcium polysulfide, captafol, captan, carpropamid, carbamorph, carbendazim, carboxin, carvone, cheshunt mixture, chinomethionat, chlobenthiazone, chloraniformethane, chloranil, chlorfenazol, chloroneb, chloropicrin, chlorothalonil, chloroquinox, chlozolinate, climbazole, clotrimazole, copper acetate, copper carbonate basic, copper hydroxide, copper naphthenate, copper oleate, copper oxychloride, copper sulfate, copper sulfate basic, copper zinc chromate, cufraneb, cuprobam, cyazofamid, cyclafuramid, cycloheximide, cyflufenamid, cymoxanil, cypendazole, cyproconazol, cyprodinil, cyprofuram, dazomet, debacarb, decafentin, dehydroacetic acid, dichlofluanid, dichlone, dichlorophen, dichlozoline, dichlobutrazol, diclocymet, diclomedine, dicloran, diethofencarb, difenoconazole, diflumetorim, dimethirimol, dimethomorph, dimoxystrobin, diniconazole, diniconazole-M, dinobuton, dinocap, dinocap-4, dinocap-6, dinocton, dinosulfon, dinoterbon, diphenylamine, dipyrithione, ditalimfos, dithianon, dodemorph, dodine, drazoxolon, edifenphos, epoxiconazole, etaconazole, etem, ethirimol, ethoxyquin, etridiazole, famoxadone, fenarimol, febuconazole, fenamidone, fenaminosulf, fenapanil, fendazosulam, fenfuram, fenhexamid, fenitropan, fenoxanil, fenpiclonil, fenpropidin, fenpropimorph, fentin, ferbam, ferimzone, fluazinam, fludioxonil, flumetover, flumorph, fluopicolide, fluoroimide, fluotrimazole, fluoxastrobin, fluquinconazole, flusilazole, flusulfamide, flutolanil, flutriafol, folpet, fosetyl-aluminium, fuberidazole, furalaxyl, furametpyr, furcarbanil, furconazole, fluconazole-cis, furmecyclox, furphanate, glyodin, griseofulvin, guazatine, halacrinate, hexachlorobenzene, hexaconazole, hexylthiofos, 8-hydroxyquinoline sulfate, hymexazol, imazalil, imibenconazole, iminoctadine, ipconazole, iprobenfos, iprodione, iprovalicarb, isoprothiolane, isovaledione, kasugamycin, kresoxim-methyl, mancopper, mancozeb, mandipropamid, maneb, mebenil, mecarbinzid, mepanipyrim, mepronil, metalaxyl, metalaxyl-M, metam, metazoxolon, metconazole, methasulfocarb, methfuroxam, methyl isothiocyanate, metiram, metominostrobin, metrafenone, metsulfovax, milneb, myclobutanil, myclozolin, nabam, natamycin, nickel bis(dimethyldithiocarbamate), nitrostyrene, nitrothal-isopropyl, nuarimol, OCH, octhilinone, ofurace, orysastrobin, oxadixyl, oxine copper, oxycarboxin, oxpoconazole fumarate, pefurzoate, penconazole, pencycuron, penthiopyrad, o-phenylphenol, phosdiphen, phthalide, picoxystrobin, piperalin, polycarbamate, polyoxins, polyoxorim, potassium azide, potassium hydrogen carbonate, proquinazid, probenazole, prochloraz, procymidone, propamocarb hydrochloride, propiconazole, propineb, prothiocarb, prothioconazole, pyracarbolid, pyraclostrobin, pyrazophos, pyridinitril, pyrifenox, pyrimethanil, pyroquilon, pyroxychlor, pyroxyfur, quinomethionate, quinoxyfen, quintozene, quinacetol-sulfate, quinazamid, quinconazole, rabenzazole, sodium azide, sodium hydrogen carbonate, sodium hypochlorite, sulfur, spiroxamine, salycylanilide, silthiofam, simeconazole, tebuconazole, tecnazene, tecoram, tetraconazole, thiabendazole, thiadifluor, thicyofen, thifluzamide, thiochlorfenphim, thiophanate, thiophanate-methyl, thioquinox, thiram, tiadinil, tioxymid, tolclofos-methyl, tolylfluanid, triadimefon, toriadimenol, triamiphos, triarimol, triazoxide, triazbutil, tributyltin oxide, trichlamide, tricyclazole, tridemorph, trifloxystrobin, triflumizole, triforine, triticonazole, validamycin, vinclozolin, zarilamide, zinc sulfate, zineb, ziram, zoxamide, siitake mushroom mycelia extract, and the like.

Bactericides: benzalkonium chloride, bithionol, bronopol, cresol, formaldehyde, nitrapyrin, oxolinic acid, oxyterracycline, streptomycin, tecloftalam, and the like.

Nematicides: aldoxycarb, cadusafos, DBCP, dichlofenthion, DSP, ethoprophos, fenamiphos, fensulfothion, fosthiazate, fosthietan, imicyafos, isamidofos, isazofos, oxamyl, thionazin, and the like.

Miticides: acequinocyl, acrinathrin, amitraz, BCI-033 (test name), bifenazate, bromopropylate, chinomethionat, chlorobenzilate, clofentezine, cyenopyrafen, cyflumetofen, cyhexatine, dicofol, dienochlor, DNOC, etoxazole, fenazaquin, fenbutatin oxide, fenothiocarb, fenpropathrin, fenpyroximate, fluacrypyrim, halfenprox, hexythiazox, milbemectin, propargite, pyridaben, pyrimidifen, S-1870 (test name), spirodiclofen, spyromesifen, tebufenpyrad, and the like.

Insecticides: abamectin, acephate, acetamipirid, alanycarb, aldicarb, allethrin, azinphos-methyl, *bacillus thuringiensis*, bendiocarb, benfuracarb, bensultap, bifenthrin, buprofezin, butocarboxim, carbaryl, carbofuran, carbosulfan, cartap, chlorantraniliprole, chlorfenapyr, chlorfenvinphos, chlorfluazuron, chlorpyrifos, chlorpyrifos-methyl, chlromafenozide, clothianidin, cyazypyr cycloprothrin, cyflumetofen, cyfluthrin, beta-cyfluthrin, cyhalothrin, lambda-cyhalothrin, cypermethrin, cyromazine, deltamethrin, diacloden, diafenthiuron, diazinon, dichlorvos, diflubenzuron, dimethylvinphos, dinotefuran, diofenolan, disulfoton, dimethoate, emamectin-benzoate, EPN, esfenvalerate, ethiofencarb, ethiprole, etofenprox, etrimfos, fenitrothion, fenobucarb, fenoxycarb, fenpropathrin, fenthion, fenvalerate, fipronil, flonicamid, flubendiamide, flucythrinate, flufenerim, flufenoxuron, flufenprox, fluvalinate, tau-fluvalinate, fonophos, formetanate, formothion, furathiocarb, halofenozide, hexaflumuron, hydramethylnon, imidacloprid, isofenphos, indoxacarb, isoprocarb, isoxathion, lepimectin, lufenuron, malathion, metaldehyde, methamidophos, methidathion, methacrifos, metaflumizone, metalcarb, methomyl, methoprene, methoxychlor, methoxyfenozide, methyl bromide, monocrotophos, muscalure, nitenpyram, novaluron, omethoate, oxamyl, oxydemeton-methyl, oxydeprofos, parathion, parathion-methyl, pentachlorophenol (PCP), permethrin, phenthoate, phoxim, phorate, phosalone, phosmet, phosphamidon, pirimicarb, pirimiphos-methyl, profenofos, prothiofos, propaphos, protrifenbute, pymetrozine, pyraclofos, pyridalyl, pyrifluquinazon, pyriproxyfen, rotenone, SI-0405 (test name), sulprofos, silafluofen, spinetoram, spinosad, spirotetramat, sulfotep, SYJ-159 (test name), tebfenozide, teflubenzuron, tefluthorin, terbufos, tetrachlorvinphos, thiacloprid, thiocyclam, thiodicarb, thiamethoxam, thiofanox, thiometon, tolfenpyrad, tralomethrin, trichlorfon, triazuron, triflumuron, vamidothion, and the like.

EXAMPLES

Hereinafter, the present invention is described more in detail referring specifically to Synthetic Examples and Test Examples of the compound of the present invention as Examples, which should not be construed as limiting the scope of the present invention.

Synthetic Examples

Synthetic Example 1

2-bromo-N-cyclopropylcarbonyl-4-[4-(3,5-dichlorophenyl)-4-trifluoromethyl-4,5-dihydro-3H-pyrrole-2-yl] benzylamine (compound of the present invention No. 1-001)

Process 1; Production of 1-(3-bromo-4-methylphenyl)-3-(3,5-dichlorophenyl)-4,4,4-trifluoro-3-hydroxybutane-1-one To a solution of 3.42 g of 3',5'-dichloro-2,2,2-trifluoroacetophenone and 3.00 g of 3'-bromo-4'-methylacetophenone in 5 mL of heptane, 0.71 g of triethylamine was added and the resultant reaction mixture was stirred at 60° C. for 8 hours. After the completion of the reaction, the reaction mixture was left to be cooled down to room temperature. A deposited solid was separated off and was washed with 3 mL of hexane to obtain 6.16 g of the objective substance as a white crystal.

Melting point: 141.0 to 142.0° C.

$^1$H NMR (CDCl$_3$, Me$_4$Si, 400 MHz) δ 8.08 (d, J=2.0 Hz, 1H), 7.77 (dd, J=7.6, 2.0 Hz, 1H), 7.49 (d, J=1.8 Hz, 2H), 7.38 (d, J=7.6 Hz, 1H), 7.35 (t, J=1.8 Hz, 1H), 5.69 (s, 1H), 3.80 (d, J=17.6 Hz, 1H), 3.64 (d, J=17.6 Hz, 1H), 2.49 (s, 3H).

Process 2; Production of 1-(3-bromo-4-methylphenyl)-3-(3,5-dichlorophenyl)-4,4,4-trifluoro-2-butene-1-one To a solution of 6.00 g of 1-(3-bromo-4-methylphenyl)-3-(3,5-dichlorophenyl)-4,4,4-trifluoro-3-hydroxybutane-1-one and 4.70 g of thionyl chloride in 30 mL of toluene, 3.12 g of pyridine was added while heating and stirring the solution at 80° C. and the resultant reaction mixture was continued to be stirred at the same temperature further for 2 hours. After the completion of the reaction, the reaction mixture was left to be cooled down to room temperature and was diluted with 30 mL of toluene, and the diluted reaction mixture was washed with water (30 mL×1). Subsequently, the washed reaction mixture was dehydrated and dried over a saturated brine and anhydrous magnesium sulfate in this order and the solvent was distilled off under reduced pressure to obtain 6.04 g of the objective substance as a yellow oily substance.

$^1$H NMR (CDCl$_3$, Me$_4$Si, 300 MHz) δ 7.97 (d, J=1.8 Hz, 1H), 7.65 (dd, J=7.8, 1.8 Hz, 1H), 7.3-7.45 (m, 3H), 7.15 (d, J=1.8 Hz, 2H), 2.45 (s, 3H).

Process 3; Production of N-[2-bromo-4-[3-(3,5-dichlorophenyl)-4,4,4-trifluoro-2-butenoyl]phenylmethyl]phthalimide To a solution of 2.00 g of 1-(3-bromo-4-methylphenyl)-3-(3,5-dichlorophenyl)-4,4,4-trifluoro-2-butene-1-one in 15 mL of 1,2-dichloroethane, 0.98 g of N-bromosuccinimide and 0.06 g of α,α'-azobisisobutyronitrile were added, and the resultant reaction mixture was stirred while heating the reaction mixture to reflux for 1 hour. Next, to the reaction mixture, 0.61 g of N-bromosuccinimide and 0.05 g of α,α'-azobisisobutyronitrile were added and the reaction mixture was continued to be stirred at the same temperature further for 2 hours. After the completion of the reaction, the reaction mixture was left to be cooled down to room temperature and was diluted with 50 mL of chloroform. Subsequently, the diluted reaction mixture was washed with water (30 mL×2) and then dehydrated and dried over a saturated brine and anhydrous sodium sulfate in this order, and the solvent was distilled off under reduced pressure. The resultant residue was dissolved in 10 mL of N,N-dimethylformamide, and 0.85 g of phthalimide potassium was added to the resultant solution, followed by stirring the resultant reaction mixture at room temperature for 13 hours. After the completion of the reaction, 30 mL of water was added to the reaction mixture and the resultant reaction mixture was extracted with ethyl acetate (50 mL×1). The organic phase was dehydrated and dried over a saturated brine and anhydrous magnesium sulfate in this order and the solvent was distilled off under reduced pressure. The resultant residue was purified by silica gel column chromatography eluting with ethyl acetate-hexane (1:1) to obtain 1.67 g of the objective substance as a yellow crystal.

Melting point: 99.0 to 103.0° C.

$^1$H NMR (CDCl$_3$, Me$_4$Si, 300 MHz) δ 8.00 (d, J=1.8 Hz, 1H), 7.85-7.95 (m, 2H), 7.75-7.85 (m, 2H), 7.66 (dd, J=8.1-1.8 Hz, 1H), 7.15-7.4 (m, 3H), 7.11 (d, J=1.8 Hz, 2H), 4.98 (s, 2H).

Process 4; Production of N-[2-bromo-4-[3-(3,5-dichlorophenyl)-4,4,4-trifluoro-3-(nitromethyl)butanoyl]phenylmethyl]phthalimide To a solution of 0.80 g of N-[2-bromo-4-[3-(3,5-dichlorophenyl)-4,4,4-trifluoro-2-butenoyl]phenylmethyl]phthalimide and 0.12 g of nitromethane in 10 mL of acetonitrile, 0.23 g of 1,8-diazabicyclo[5,4,0]-7-undecene was added and the resultant reaction mixture was stirred at room temperature for 15 hours. After the completion of the reaction, 20 mL of water was added to the reaction mixture and the resultant reaction mixture was extracted with ethyl acetate (30 mL×2). The organic phase was dehydrated and dried over a saturated brine and anhydrous magnesium sulfate in this order and the solvent was distilled off under reduced pressure to obtain 0.90 g of the objective substance as a yellow resinoid.

$^1$H NMR (CDCl$_3$, Me$_4$Si, 300 MHz) δ 8.15 (d, J=1.8 Hz, 1H), 7.85-7.95 (m, 2H), 7.75-7.85 (m, 3H), 7.40 (t, J=1.7 Hz, 1H), 7.28 (d, J=8.4 Hz, 1H), 7.17 (d, J=1.7 Hz, 2H), 5.56 (d, J=12.7 Hz, 1H), 5.44 (d, J=12.7 Hz, 1H), 5.02 (s, 2H), 4.09 (d, J=18.9 Hz, 1H), 3.92 (d, J=18.9 Hz, 1H):

Process 5; Production of N-[2-bromo-4-[4-(3,5-dichlorophenyl)-4-trifluoromethyl-4,5-dihydro-3H-pyrrole-2-yl]phenylmethyl]phthalimide To a solution of 0.70 g of N-[2-bromo-4-[3-(3,5-dichlorophenyl)-4,4,4-trifluoro-3-(nitromethyl) butanoyl]phenylmethyl]phthalimide and 1.03 g of ammonium formate in 20 mL of tetrahydrofuran, 1.07 g of zinc powder was added and the resultant reaction mixture was stirred while heating the mixture to reflux for 1 hour. After the completion of the reaction, the reaction mixture was left to be cooled down to room temperature, and 100 mL of ethyl acetate and 50 mL of water were added to the reaction mixture, followed by filtering the reaction mixture with Celite. Subsequently, the organic phase was separated off and was dehydrated and dried over a saturated brine and anhydrous magnesium sulfate in this order, and the solvent was distilled off under reduced pressure. The resultant residue was purified by silica gel column chromatography eluting with chloroform to obtain 0.18 g of the objective substance as a white crystal.

Melting point: 199.0 to 203.0° C.

$^1$H NMR (CDCl$_3$, Me$_4$Si, 300 MHz) δ 8.07 (d, J=1.5 Hz, 1H), 7.85-7.95 (m, 2H), 7.75-7.85 (m, 2H), 7.70 (dd, J=8.1, 1.5 Hz, 1H), 7.37 (t, J=1.8 Hz, 1H), 7.2-7.3 (m, 3H), 5.00 (s, 2H), 4.87 (dd, J=17.4, 1.8 Hz, 1H), 4.43 (d, J=17.4 Hz, 1H), 3.73 (dd, J=17.4, 1.8 Hz, 1H), 3.39 (d, J=17.4 Hz, 1H).

Process 6; Production of 2-(4-aminomethyl-3-bromophenyl)-4-(3,5-dichlorophenyl)-4-trifluoromethyl-4,5-dihydro-3H-pyrrole To a solution of 0.22 g of N-[2-bromo-4-[4-(3,5-dichlorophenyl)-4-trifluoromethyl-4,5-dihydro-3H-pyrrole-2-yl]phenylmethyl]phthalimide in 5 mL of ethanol, 0.074 g of hydrazine monohydrate was added and the resultant reaction mixture was stirred while heating the mixture to reflux for 2 hours. After the completion of the reaction, the reaction mixture was left to be cooled down to room temperature and deposited insoluble substances were filtered off, followed by distilling off the solvent under reduced pressure. To the resultant residue, 20 mL of chloroform was added and insoluble substances were filtered off, followed by washing the filtrate with water (20 mL×1). Subsequently, the filtrate was dehydrated and dried over a saturated brine and anhydrous sodium sulfate in this order and the solvent was distilled off under reduced pressure to obtain 0.18 g of the objective substance as a yellow resinoid.

$^1$H NMR (CDCl$_3$, Me$_4$Si, 300 MHz) δ 8.05 (d, J=1.5 Hz, 1H), 7.77 (dd, J=7.8, 1.5 Hz, 1H), 7.49 (d, J=7.8 Hz, 1H), 7.38 (t, J=1.8 Hz, 1H), 7.2-7.3 (m, 2H), 4.89 (dd, J=17.1, 1.8 Hz, 1H), 4.44 (d, J=17.1 Hz, 1H), 3.96 (s, 2H), 3.77 (dd, J=17.4, 1.8 Hz, 1H), 3.43 (d, J=17.4 Hz, 1H), 1.5-1.7 (bs, 2H).

Process 7; Production of 2-bromo-N-cyclopropylcarbonyl-4-[4-(3,5-dichlorophenyl)-4-trifluoromethyl-4,5-dihydro-3H-pyrrole-2-yl]benzylamine Into a solution of 0.18 g of 2-(4-aminomethyl-3-bromophenyl)-4-(3,5-dichlorophenyl)-4-trifluoromethyl-4,5-dihydro-3H-pyrrole and 0.056 g of triethylamine in 3 mL of dichloromethane, 0.046 g of cyclopropanecarbonyl=chloride was dropped while ice-cooling and stirring the solution, and after the completion of the dropping, the resultant reaction mixture was continued to be stirred at room temperature further for 20 minutes. After the completion of the reaction, 20 mL of chloroform was added to the reaction mixture, and the reaction mixture was washed with 10 mL of a 3N hydrochloric acid aqueous solution and 10 mL of a saturated sodium hydrogen carbonate aqueous solution, and was dehydrated and dried over a saturated brine and anhydrous sodium sulfate in this order. Then, the solvent was distilled off under reduced pressure. The resultant residue was purified by silica gel column chromatography eluting with ethyl acetate-hexane (1:1) to obtain 0.054 g of the objective substance as a white crystal.

Melting point: 204.0 to 207.0° C.

$^1$H NMR (CDCl$_3$, Me$_4$Si, 300 MHz) δ 8.06 (d, J=1.8 Hz, 1H), 7.72 (dd, J=8.4, 1.8 Hz, 1H), 7.47 (d, J=8.4 Hz, 1H), 7.37 (t, J=1.7 Hz, 1H), 7.2-7.3 (m, 2H), 6.25 (t, J=6.0 Hz, 1H), 4.88 (dd, J=17.1, 1.5 Hz, 1H), 4.56 (d, J=6.0 Hz, 2H), 4.43 (d, J=17.1 Hz, 1H), 3.75 (dd, J=18.0, 1.5 Hz, 1H), 3.41 (d, J=18.0 Hz, 1H), 1.3-1.45 (m, 1H), 0.95-1.1 (m, 2H), 0.7-0.85 (m 2H).

Synthetic Example 2

4-(3,5-dichlorophenyl)-2-[4-(1,2,4-triazole-1-yl)phenyl]-4-trifluoromethyl-4,5-dihydro-3H-pyrrole (compound of the present invention No. 3-001)

Process 1; Production of 3,5-dichloro-1-(1-trifluoromethylethenyl)benzene

To a solution of 25.0 g of 3,5-dichlorophenyl boronic acid in 200 mL of tetrahydrofuran and 100 mL of water, 27.5 g of 2-bromo-3,3,3-trifluoropropene, 38.0 g of potassium carbonate and 1.84 g of dichlorobis(triphenylphosphine) palladium (II) were added, and the resultant reaction mixture was stirred while heating the mixture to reflux for 3 hours. After the completion of the reaction, the reaction mixture was left to be cooled down to room temperature and 500 mL of ice water was added to the reaction mixture, followed by extracting the reaction mixture with ethyl acetate (500 mL×1). Subsequently, the organic phase was washed with water and was dried over anhydrous sodium sulfate, and the solvent was distilled off under reduced pressure. The resultant residue was purified by silica gel column chromatography eluting with hexane to obtain 25.7 g of the objective substance as a colorless oily substance.

$^1$H NMR (CDCl$_3$, Me$_4$Si, 400 MHz) δ 7.41 (t, J=2.0 Hz, 1H), 7.3-7.35 (m, 2H), 6.05 (q, J=3.2 Hz, 1H), 5.82 (q, J=3.2 Hz, 1H).

Process 2; Production of N-(4-bromobenzyl) formamide

Into a mixture of 9.87 g of 4-bromobenzylamine hydrochloride and 5.04 g of triethylamine, 20 mL of a formic acid solution was dropped and the resultant reaction mixture was stirred at 80° C. for 3.5 hours. After the completion of the reaction, the reaction mixture was charged into 100 mL of ice water and the resultant reaction mixture was extracted with ethyl acetate (30 mL×2). The organic phase was dehydrated and dried over a saturated brine and anhydrous sodium sulfate in this order and the solvent was distilled off under reduced pressure. The residual solid was washed with hexane to obtain 9.29 g of the objective substance as a white crystal.

Melting point: 120.0 to 123.0° C.

$^1$H NMR (CDCl$_3$, Me$_4$Si, 400 MHz) δ 8.28 (s, 1H), 7.47 (d, J=8.4 Hz, 2H), 7.18 (d, J=8.4 Hz, 2H), 5.85 (bs, 1H), 4.25 (d, J=6.0 Hz, 2H).

Process 3; Production of 2-(4-bromophenyl)-4-(3,5-dichlorophenyl)-4-trifluoromethyl-4,5-dihydro-3H-pyrrole Into a solution of 1.47 g of N-(4-bromobenzyl) formamide and 2.08 g of triethylamine in 15 mL of toluene, 1.12 g of phosphorus oxychloride was dropped while ice-cooling and stirring the solution, and after the completion of the dropping, the resultant reaction mixture was gradually heated to room temperature and was continued to be stirred at room temperature further for 1 hour. After the completion of the reaction, the reaction mixture was carefully charged into 50 mL of water and was neutralized by adding a saturated sodium carbonate aqueous solution thereto, followed by extracting the neutralized reaction mixture with ethyl acetate (30 mL×2). Subsequently, the organic phase was dehydrated and dried over a saturated brine and anhydrous sodium sulfate in this order and the solvent was distilled off under reduced pressure. The resultant residue was dissolved in 35 mL of toluene and to the resultant solution, 1.69 g of 3,5-dichloro-1-(1-trifluoromethylethenyl)benzene synthesized in Process 1 and 0.09 g of copper (II) oxide were added, followed by stirring the resultant reaction mixture while heating the mixture to reflux for 4 days. After the completion of the reaction, a solid was removed by Celite filtration and the filtrate was washed with 30 mL of water and was dehydrated and dried over a saturated brine and anhydrous sodium sulfate in this order, followed by distilling off the solvent under reduced pressure to obtain a crude 5-(4-bromophenyl)-3-(3,5-dichlorophenyl)-3-trifluoromethyl-4,5-dihydro-3H-pyrrole.

The obtained crude 5-(4-bromophenyl)-3-(3,5-dichlorophenyl)-3-trifluoromethyl-4,5-dihydro-3H-pyrrole was dissolved in 35 mL of tetrahydrofuran, and to the resultant solution, 0.78 g of potassium tert-butoxide was added while ice-cooling and stirring the solution, followed by stirring the resultant reaction mixture at room temperature for 16 hours. After the completion of the reaction, the reaction mixture was charged into 150 mL of water and the resultant reaction mixture was extracted with ethyl acetate (30 mL×2). The organic phase was dehydrated and dried over a saturated brine and anhydrous sodium sulfate in this order and the solvent was distilled off under reduced pressure. The resultant residue was purified by silica gel column chromatography eluting with ethyl acetate-hexane (1:5) to obtain 1.60 g of the objective substance as a colorless oily substance.

$^1$H NMR (CDCl$_3$, Me$_4$Si, 400 MHz) δ 7.74 (s, 2H), 7.62 (s, 2H), 7.40 (s, 1H), 7.26 (s, 2H), 4.89 (d, J=21.6 Hz, 1H), 4.42 (d, J=21.6 Hz, 1H), 3.77 (d, J=21.6 Hz, 1H), 3.46 (d, J=21.6 Hz, 1H).

Process 4; Production of 4-(3,5-dichlorophenyl)-2-[4-(1,2,4-triazole-1-yl)phenyl]-4-trifluoromethyl-4,5-dihydro-3H-pyrrole To a suspension of 1.60 g of 2-(4-bromophenyl)-4-(3,5-dichlorophenyl)-4-trifluoromethyl-4,5-dihydro-3H-pyrrole, 0.53 g of 1,2,4-triazole, 1.01 g of potassium carbonate and 1.25 g of potassium iodide in 20 mL of N-methylpyrrolidone, 0.21 g of copper iodide was added and the resultant reaction mixture was stirred at 190° C. for 1 hour. After the completion of the reaction, the reaction mixture was left to be cooled down to room temperature and was poured carefully into 50 mL of water, followed by extracting the reaction mixture with ethyl acetate (30 mL×2). The organic phase was dehydrated and dried over a saturated brine and anhydrous sodium sulfate in this order and the solvent was distilled off under reduced pressure. The resultant residue was purified by silica gel column chromatography eluting with ethyl acetate-hexane (3:2) to obtain 0.27 g of the objective substance as a white crystal.

Melting point: 197.0 to 198.0° C.

$^1$H NMR (CDCl$_3$, Me$_4$Si, 400 MHz) δ 8.65 (s, 1H), 8.15 (s, 1H), 8.04 (d, J=8.4 Hz, 2H), 7.82 (d, J=8.4 Hz, 2H), 7.40 (s, 1H), 7.28 (s, 2H), 4.93 (d, J=17.2 Hz, 1H), 4.49 (d, J=16.8 Hz, 1H), 3.85 (d, J=17.6 Hz, 1H), 3.51 (d, J=18.0 Hz, 1H).

The compound of the present invention can be produced according to the above Production Methods and Examples. Examples of the compound of the present invention produced in substantially the same manner as those in Synthetic Example 1 and Synthetic Example 2 are shown in Table 4 to Table 6, which should not be construed as limiting the scope of the present invention.

Here, in Tables, c-Pr is a cyclopropyl group and Ph is a phenyl group.

In Tables, a heterocycle of G$^2$-6 is the following structure:

In addition, in Tables, each of the numbers representing the substituted sites of the substituents (X)$_m$ and (Z)$_n$ corresponds to the site indicated by the number in the above and the below Structure Formulae, and the expression "-" indicates "non-substituted".

Furthermore, in Tables, "*1" means "resinous".

TABLE 4

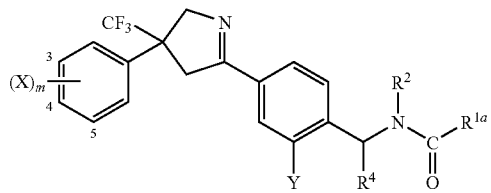

| No. | (X)$_m$ | Y | R$^4$ | R$^2$ | R$^{1a}$ | m.p. (° C.) |
|---|---|---|---|---|---|---|
| 1-001 | 3,5-Cl$_2$ | Br | H | H | c-Pr | 204.0-207.0 |
| 1-002 | 3,5-Cl$_2$ | Br | H | H | Ph-2,4,6-F$_3$ | 114.5-118.0 |
| 1-003 | 3,5-Cl$_2$ | H | CH$_3$ | H | c-Pr | *1 |
| 1-004 | 3,5-Cl$_2$ | H | CH$_3$ | H | CH$_2$CF$_3$ | *1 |

TABLE 5

[Structure: pyrrolidine N-oxide with CF3 group, phenyl with (X)m substituents at 3,4,5 positions, connected to phenyl with Y substituent, then CH(R4)-N(R2)-C(=O)-R1a]

| No. | (X)$_m$ | Y | R$^4$ | R$^2$ | R$^{1a}$ | m.p. (° C.) |
|---|---|---|---|---|---|---|
| 2-001 | 3,5-Cl$_2$ | H | CH$_3$ | H | CH$_2$CF$_3$ | 99.5-103.0 |

TABLE 6

[Structure: pyrroline with CF3, phenyl with (X)m, connected to phenyl with Y and G² substituent with (Z)n]

| No. | (X)$_m$ | Y | G$^2$ | (Z)$_n$ | m. p. (° C.) |
|---|---|---|---|---|---|
| 3-001 | 3,5-Cl$_2$ | H | G$^2$-6 | — | 197.0-198.0 |

TABLE 7

[Structure: CF3-C(CH2NO2)-phenyl(X)m bonded via CH2-C(=O) to phenyl(Y)-CH(R4)-phthalimide]

| No. | (X)$_m$ | Y | R$^4$ | m.p. (° C.) |
|---|---|---|---|---|
| 4-001 | 3,5-Cl$_2$ | Br | H | *1 |

TABLE 8

[Structure: CF3-C=C(C=O)-phenyl(X)m connected to phenyl(Y)-CH(R4)-phthalimide]

| No. | (X)$_m$ | Y | R$^4$ | m.p. (° C.) |
|---|---|---|---|---|
| 5-001 | 3,5-Cl$_2$ | H | CH$_3$ | 112.0-115.0 |
| 5-002 | 3,5-Cl$_2$ | Br | H | 99.0-103.0 |

TABLE 9

[Structure: CF3-C(OH)-phenyl(X)m connected via CH2-C(=O) to phenyl(Y)-CH(R4)-phthalimide]

| No. | (X)$_m$ | Y | R$^4$ | m. p. (° C.) |
|---|---|---|---|---|
| 6-001 | 3,5-Cl$_2$ | Br | H | *1 |

Among the compounds of the present invention, $^1$H NMR data of the compound of which the melting point is not described is shown in Table 10.

TABLE 10

| No. | $^1$H NMR (CDCl$_3$, Me$_4$Si, 300 MHz) |
|---|---|
| 1-003 | δ 7.82 (d, J = 8.4 Hz, 2H), 7.40 (d, J = 8.4 Hz, 2H), 7.36 (d, J = 1.7 Hz, 1H), 7.2-7.3 (m, 2H), 5.87 (d, J = 7.2 Hz, 1H), 5.1-5.25 (m, 1H), 4.87 (d, J = 17.0 Hz, 1H), 4.43 (d, J = 17.0 Hz, 1H), 3.78 (d, J = 17.8 Hz, 1H), 3.43 (d, J = 17.8 Hz, 1H), 1.51 (d, J = 7.2 Hz, 3H), 1.3-1.45 (m, 1H), 0.9-1.1 (m, 2H), 1.65-1.85 (m, 2H). |
| 1-004 | δ 7.83 (d, J = 8.3 Hz, 2H), 7.35-7.45 (m, 3H), 7.27 (s, 2H), 6.08 (d, J = 7.9 Hz, 1H), 5.1-5.25 (m, 1H), 4.87 (d, J = 17.0 Hz, 1H), 4.43 (d, J = 17.0 Hz, 1H), 3.78 (d, J = 17.8 Hz, 1H), 3.43 (d, J = 17.8 Hz, 1H), 3.08 (q, J = 11.0 Hz, 2H), 1.53 (d, J = 7.2 Hz, 3H). |

Test Examples

Next, the usefulness of the compound of the present invention as a pest control agent is more specifically described in the following Test Examples, which should not be construed as limiting the scope of the present invention.

Test Example 1

Mortality Test for *Plutella xylostella*

A 10% emulsifiable concentrate of the compound of the present invention (depending on the type of the compound, a 10% wettable powder was subjected to the test) was diluted with water containing a spreader to prepare a drug solution in a concentration of 10 ppm. In this drug solution, a leaf of cabbage was immersed for about 10 seconds and was air-dried and then put into a petri dish. In the petri dish, five 2 instar larvae of *Plutella xylostella* per petri dish were released and the petri dish was capped and stored in a thermostatic room of 25° C. The number of killed larvae after 6 days was counted and the mortality was calculated from the following calculation formula:

Mortality (%)=(number of killed insects/number of released insects)×100.

Here, the test was carried out in two replications.

As the results of the test, among the compounds subjected to the test, the following compounds exhibited the mortality of 80% or more.

The compounds of the present invention: Nos. 1-001 to 1-004, 2-001*, and 3-001*.

Here, the mark "*" indicates that the mortality test was performed using a drug solution of 100 ppm concentration.

Test Example 2

Mortality Test for *Spodoptera litura*

A 10% emulsifiable concentrate of the compound of the present invention (depending on the type of the compound, a 10% wettable powder was subjected to the test) was diluted with water containing a spreader to prepare a drug solution in a concentration of 10 ppm. In this drug solution, a leaf of cabbage was immersed for about 10 seconds and was air-dried and then put into a petri dish. In the petri dish, five 2 instar larvae of *Spodoptera litura* per petri dish were released and the petri dish was capped and stored in a thermostatic room of 25° C. The number of killed larvae after 6 days was counted and the mortality was calculated from the same calculation formula as that in Test Example 1. Here, the test was carried out in two replications.

As the results of the test, among the compounds subjected to the test, the following compounds exhibited the mortality of 80% or more. The compounds of the present invention: Nos. 1-001 to 1-004, and 2-001*.

Here, the mark "*" indicates that the mortality test was performed using a drug solution of 100 ppm concentration.

Test Example 3

Mortality Test for Homona Magnanima

A 10% emulsifiable concentrate of the compound of the present invention (depending on the type of the compound, a 10% wettable powder was subjected to the test) was diluted with water containing a spreader to prepare a drug solution in a concentration of 100 ppm. In this drug solution, a leaf of cabbage was immersed for about 10 seconds and was air-dried and then put into a petri dish. In the petri dish, five 2 instar larvae of *Homona magnanima* per petri dish were released and the petri dish was capped and stored in a thermostatic room of 25° C. The number of killed larvae after 6 days was counted and the mortality was calculated from the same calculation formula as that in Test Example 1. Here, the test was carried out in two replications.

As the results of the test, among the compounds subjected to the test, the following compound exhibited the mortality of 80% or more.
The compounds of the present invention: No. 1-003.

Test Example 4

Mortality Test for *Helicoverpa armigera*

A 10% emulsifiable concentrate of the compound of the present invention (depending on the type of the compound, a 10% wettable powder was subjected to the test) was diluted with water containing a spreader to prepare a drug solution in a concentration of 100 ppm. In this drug solution, a leaf of cabbage was immersed for about 10 seconds and was air-dried and then put into a petri dish. In the petri dish, one 2 instar larva of *Helicoverpa armigera* per petri dish was released and the petri dish was capped and stored in a thermostatic room of 25° C. The number of killed larvae after 6 days was counted and the mortality was calculated from the same calculation formula as that in Test Example 1. Here, the test was carried out in 12 replications.

As the results of the test, among the compounds subjected to the test, the following compounds exhibited the mortality of 80% or more.
The compounds of the present invention: Nos. 1-001, 1-003, and 1-004.

Test Example 5

Mortality Test for *Frankliniella occidentalis*

In a styrol cup having an inner diameter of 7 cm, a wet filtration paper was laid, and on the paper, a leaf of kidney bean cut out so as to have the same diameter as the inner diameter of the cup was laid, followed by inoculating the leaf with ten 1 instar larvae of *Frankliniella occidentalis* per leaf. A 10% emulsifiable concentrate of the compound of the present invention (depending on the type of the compound, a 10% wettable powder was subjected to the test) was diluted with water containing a spreader to prepare a drug solution in a concentration of 500 ppm. The drug solution was sprayed using a rotary spray tower in an amount of 2.5 mL per styrol cup and the cup was capped and stored in a thermostatic room of 25° C. The number of killed larvae after 2 days was counted and the mortality was calculated from the same calculation formula as that in Test Example 1. Here, the test was carried out in two replications.

As the results of the test, among the compounds subjected to the test, the following compounds exhibited the mortality of 80% or more.
The compounds of the present invention: Nos. 1-003 and 3-001.

Test Example 6

Mortality Test for *Thrips Palmi*

In a styrol cup having an inner diameter of 7 cm, a wet filtration paper was laid, and on the paper, a leaf of kidney bean cut out so as to have the same diameter as the inner diameter of the cup was laid, followed by inoculating the leaf with ten imagines of *Thrips palmi* per leaf. A 10% emulsifiable concentrate of the compound of the present invention (depending on the type of the compound, a 10% wettable powder was subjected to the test) was diluted with water containing a spreader to prepare a drug solution in a concentration of 100 ppm. The drug solution was sprayed using a rotary spray tower in an amount of 2.5 mL per styrol cup and the cup was capped and stored in a thermostatic room of 25° C. The number of killed imagines after 2 days was counted and the mortality was calculated from the same calculation formula as that in Test Example 1. Here, the test was carried out in two replications.

As the results of the test, among the compounds subjected to the test, the following compounds exhibited the mortality of 80% or more.
The compounds of the present invention: Nos. 1-003.

Test Example 7

Mortality Test for *Nilaparvata lugens*

A 10% emulsifiable concentrate of the compound of the present invention (depending on the type of the compound, a 10% wettable powder was subjected to the test) was diluted with water containing a spreader to prepare a drug solution in a concentration of 500 ppm. In this drug solution, a leaf sheath of rice was immersed for about 10 seconds and was air-dried and then put into a test tube. In the test tube, five 2 instar larvae of *Nilaparvata lugens* per test tube were released and the test tube was capped with a sponge and stored in a thermostatic room of 25° C. The number of killed larvae after 6 days was counted and the mortality was calculated from the same calculation formula as that in Test Example 1. Here, the test was carried out in two replications.

As the results of the test, among the compounds subjected to the test, the following compounds exhibited the mortality of 80% or more.
The compounds of the present invention: Nos. 1-002 and 1-003.

Test Example 8

Mortality Test for *Bemisia* Argentifolii

In a styrol cup having an inner diameter of 7 cm, a wet filtration paper was laid, and on the paper, a cut-out leaf of tomato on which *Bemisia argentifolii* laid eggs (10 eggs/leaf) was laid. A 10% emulsifiable concentrate of the compound of the present invention (depending on the type of the compound, a 10% wettable powder was subjected to the test) was diluted with water containing a spreader to prepare a drug solution in a concentration of 500 ppm. The drug solution was sprayed using a rotary spray tower in an amount of 2.5 mL per styrol cup and the cup was capped and stored in a thermostatic room of 25° C. The number of killed larvae after 6 days was counted and the mortality was calculated from the same calculation formula as that in Test Example 1. Here, the test was carried out in two replications.

As the results of the test, among the compounds subjected to the test, the following compounds exhibited the mortality of 80% or more.
The compounds of the present invention: Nos. 1-003 and 3-001.

Test Example 9

Mortality Test for *Myzus persicae*

In a glass petri dish having an inner diameter of 3 cm, a wet absorbent cotton was laid, and on the cotton, a leaf of cabbage cut out so as to have the same diameter as the inner diameter of the petri dish was laid, followed by releasing four apterous imagines of *Myzus persicae* on the leaf. After one day, a 10% emulsifiable concentrate of the compound of the present invention (depending on the type of the compound, a 10% wettable powder was subjected to the test) was diluted with water containing a spreader to prepare a drug solution in a concentration of 500 ppm. The drug solution was sprayed using a rotary spray tower (2.5 mg/cm$^2$), and the petri dish was capped and stored in a thermostatic room of 25° C. The number of killed imagines after 6 days was counted and the mortality was calculated from the same calculation formula as that in Test Example 1. Here, the test was carried out in two replications.

As the results of the test, among the compounds subjected to the test, the following compound exhibited the mortality of 80% or more.
The compounds of the present invention: No. 1-003.

Test Example 10

Mortality Test for *Planococcus kraunhiae*

In a styrol cup having an inner diameter of 7 cm, a wet filtration paper was laid, and on the paper, a leaf of kidney bean cut out so as to have the same diameter as the inner diameter of the cup was laid, followed by inoculating the leaf with ten 1 instar larvae of *Planococcus kraunhiae* per leaf. A 10% emulsifiable concentrate of the compound of the present invention (depending on the type of the compound, a 10% wettable powder was subjected to the test) was diluted with water containing a spreader to prepare a drug solution in a concentration of 500 ppm. The drug solution was sprayed using a rotary spray tower in an amount of 2.5 mL per styrol cup and the cup was capped and stored in a thermostatic room of 25° C. The number of killed larvae after 6 days was counted and the mortality was calculated from the same calculation formula as that in Test Example 1. Here, the test was carried out in two replications.

As the results of the test, among the compounds subjected to the test, the following compounds exhibited the mortality of 80% or more.
The compounds of the present invention: No. 3-001.

Test Example 11

Mortality Test for *Aulacophora femoralis*

A 10% emulsifiable concentrate of the compound of the present invention (depending on the type of the compound, a 10% wettable powder was subjected to the test) was diluted with water containing a spreader to prepare a drug solution in a concentration of 500 ppm. In this drug solution, a leaf of cucumber was immersed for about 10 seconds and was air-dried and then put into a petri dish. In the petri dish, five 2 instar larvae of *Aulacophora femoralis* per petri dish were released and the petri dish was capped and stored in a thermostatic room of 25° C. The number of killed larvae after 6 days was counted and the mortality was calculated from the same calculation formula as that in Test Example 1. Here, the test was carried out in two replications.

As the results of the test, among the compounds subjected to the test, the following compound exhibited the mortality of 80% or more.
The compounds of the present invention: No. 3-001.

Test Example 12

Mortality Test for *Liriomyza trifolii*

A 10% emulsifiable concentrate of the compound of the present invention (depending on the type of the compound, a 10% wettable powder was subjected to the test) was diluted with water containing a spreader to prepare a drug solution in a concentration of 500 ppm. In this drug solution, a leaf of kidney bean which was cut out to a diameter of 7 cm, on which *Liriomyza trifolii* laid eggs (10 eggs/leaf) was immersed for about 10 seconds and was air-dried and then laid on a wet filtration paper laid in a styrol cup having an inner diameter of 7 cm. The styrol cup was capped and stored in a thermostatic room of 25° C. The number of killed larvae after 6 days was counted and the mortality was calculated from the same calculation formula as that in Test Example 1. Here, the test was carried out in two replications.

As the results of the test, among the compounds subjected to the test, the following compound exhibited the mortality of 80% or more.
The compounds of the present invention: No. 3-001.

Test Example 13

Mortality Test for *Tetranychus urticae*

In a styrol cup having an inner diameter of 7 cm, a wet filtration paper was laid, and on the paper, a leaf of kidney bean cut out so as to have the same diameter as the inner diameter of the cup was laid, followed by inoculating the leaf with ten larvae of *Tetranychus urticae* per leaf. A 10% emulsifiable concentrate of the compound of the present invention (depending on the type of the compound, a 10% wettable powder was subjected to the test) was diluted with water containing a spreader to prepare a drug solution in a concentration of 500 ppm. The drug solution was sprayed using a rotary spray tower in an amount of 2.5 mL per styrol cup and the cup was capped and stored in a thermostatic room of 25° C. The number of killed larvae after 6 days was counted and the mortality was calculated from the same calculation formula as that in Test Example 1. Here, the test was carried out in two replications.

As the results of the test, among the compounds subjected to the test, the following compounds exhibited the mortality of 80% or more.
The compounds of the present invention: Nos. 1-002, 1-003, and 3-001.

Test Example 14

Mortality Test for Cat Flea

To the bottom surface and the side surface of a petri dish having an inner diameter of 5.3 cm, 400 μL of an acetone solution in which 4 mg of the compound of the present invention was dissolved in 40 mL of acetone (concentration: 100 ppm) was applied, and then acetone was volatilized to form a thin film of the compound of the present invention on the inner wall of the petri dish. The inner wall of the used petri dish had an area of 40 cm², so that the amount of the applied drug became 1.0 μg/cm². In the petri dish, ten *Ctenocephalides felis* imagines (male and female were mixed) were released and the petri dish was capped and stored in a thermostat room of 25° C. The number of killed imagines after 4 days was counted and the mortality was calculated from the same calculation formula as that in Test Example 1. Here, the test was carried out on the single sample.

As the results of the test, among the compounds subjected to the test, the following compound exhibited the mortality of 80% or more.
The compounds of the present invention: No. 1-004.

Test Example 15

Mortality Test for American Dog Tick

To the bottom surface and the side surface of two petri dishes having an inner diameter of 5.3 cm, 400 μL of an acetone solution in which 4 mg of the compound of the present invention was dissolved in 40 mL of acetone (concentration: 100 ppm) was applied, and then acetone was volatilized to form a thin film of the compound of the present invention on the inner wall of the petri dishes. The inner wall of each of the used petri dishes had an area of 40 cm², so that the amount of the applied drug became 0.1 μg/cm². In one of the petri dishes, ten American dog tick (*Dermacentor variabilis*) protonymphs (male and female were mixed) were released, and the petri dish was capped with the other petri dish. The seam of the two petri dishes was sealed with tape so that the protonymphs did not escape, and the petri dishes were stored in a thermostat room of 25° C. The number of killed protonymphs after 4 days was counted and the mortality was calculated from the same calculation formula as that in Test Example 1. Here, the test was carried out on the single sample.

As the results of the test, among the compounds subjected to the test, the following compound exhibited the mortality of 80% or more.
The compounds of the present invention: No. 1-004.

INDUSTRIAL APPLICABILITY

The substituted dihydroazole compound according to the present invention is an extremely useful compound exhibiting excellent pest control activity, particularly excellent insecticidal and miticidal activity and having substantially no adverse effect on non-target organisms such as mammals, fish and beneficial insects.

The invention claimed is:
1. A substituted dihydroazole compound of Formula (1) or a salt of the substituted dihydroazole compound:

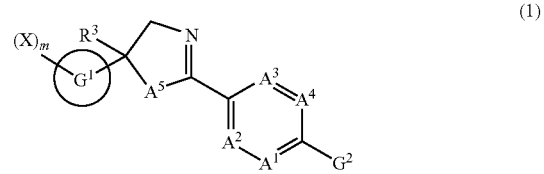

where $A^1$, $A^2$, $A^3$ and $A^4$ are independently C—Y or N,
$A^5$ is —CH($R^{3a}$)—, O or S,
$G^1$ is a benzene ring, a nitrogen-containing 6-membered aromatic heterocycle, a furan ring, a thiophene ring or a 5-membered aromatic heterocycle containing two or more hetero atoms selected from an oxygen atom, a sulfur atom and a nitrogen atom,
$G^2$ is a structure of $G^2$-1 to $G^2$-10:

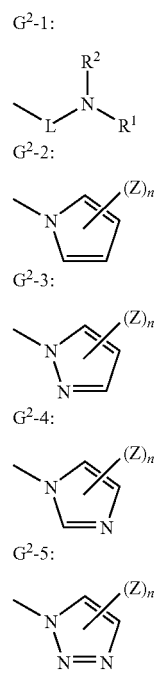

-continued

G²-6:
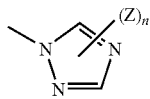

G²-7:
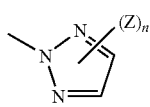

G²-8:
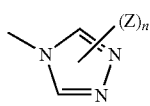

G²-9:
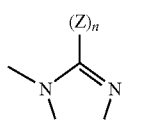

G²-10:
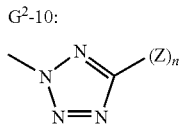

L is —C($R^4$)($R^{4a}$)—, —C($R^4$)($R^{4a}$)CH$_2$—, —CH$_2$C($R^4$)($R^{4a}$)—, —N($R^{4b}$)—, —C($R^4$)($R^{4a}$)N($R^{4b}$)— or a single bond, X is a halogen atom, cyano, nitro, azide, —SCN, —SF$_5$, $C_{1-6}$ alkyl, ($C_{1-6}$) alkyl optionally substituted with $R^5$, $C_{3-8}$ cycloalkyl, ($C_{3-8}$) cycloalkyl optionally substituted with $R^5$, E1 to E19, $C_{2-6}$ alkenyl, ($C_{2-6}$) alkenyl optionally substituted with $R^5$, $C_{5-10}$ cycloalkenyl, $C_{5-10}$halocycloalkenyl, $C_{2-6}$ alkynyl, ($C_{2-6}$) alkynyl optionally substituted with $R^5$, —OH, —$OR^6$, —OS(O)$_2R^6$, —SH, —S(O)$_rR^6$, —N($R^8$)$R^7$, —N=C($R^{8a}$)$R^{7a}$, —C(O)$R^9$, —C($R^9$)=NOH, —C($R^9$)=NOR$^{10}$, M3, M13, M30, —C(O)OR$^{10}$, —C(O)SR$^{10}$, —C(O)N($R^{12}$)$R^{11}$, —C(S)OR$^{10}$, —C(S)SR$^{10}$, —C(S)N($R^{12}$)$R^{11}$, M23 to M26, M28, M29, —S(O)$_2$OR$^{10}$, —S(O)$_2$N($R^{12}$)$R^{11}$, —Si($R^{13a}$)($R^{13b}$)$R^{13}$, phenyl, phenyl substituted with ($Z^a$)$_{p1}$ or D1 to D38, when m is an integer of 2 or more, Xs are optionally the same as or different from each other, and further, when two Xs are adjacent to each other, the two adjacent Xs optionally form —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —CH$_2$CH$_2$N($R^{14}$)—, —CH$_2$N($R^{14}$)CH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —CH$_2$CH=CH—, —OCH=CH—, —SCH=CH—, —N($R^{14}$)CH=CH—, —OCH=N—, —SCH=N—, —N($R^{14}$)CH=N—, —N($R^{14}$)N=CH—, —CH=CHCH=CH—, —OCH$_2$CH=CH—, —N=CHCH=CH—, —N=CHCH=N— or —N=CHN=CH— to form together with carbon atoms to which each of the two Xs is bonded, a 5-membered ring or a 6-membered ring, and in this case, hydrogen atoms bonded to each carbon atom forming the ring is optionally substituted with $Z^a$s, and further when hydrogen atoms are substituted simultaneously with 2 or more $Z^a$s, such $Z^a$s are optionally the same as or different from each other, Y is a hydrogen atom, a halogen atom, cyano, nitro, azide, —SCN, —SF$_5$, $C_{1-6}$ alkyl, ($C_{1-6}$) alkyl optionally substituted with $R^5$, $C_{3-8}$ cycloalkyl, ($C_{3-8}$) cycloalkyl optionally substituted with $R^5$, E1 to E19, $C_{2-6}$ alkenyl, ($C_{2-6}$) alkenyl optionally substituted with $R^5$, $C_{2-6}$ alkynyl, ($C_{2-6}$) alkynyl optionally substituted with $R^5$, —OH, —$OR^6$, —OS(O)$_2R^6$, —SH, —S(O)$_rR^6$, —N($R^8$)$R^7$, —N($R^8$)C(O)$R^{9a}$, —N=C($R^{8a}$)$R^{7a}$, —C(O)N($R^{12}$)$R^{11}$, —C(S)N($R^{12}$)$R^{11}$, —Si($R^{13a}$)($R^{13b}$)$R^{13}$, phenyl, phenyl substituted with ($Z^a$)$_{p1}$ or D1 to D38, when two or more Ys exist simultaneously, the Ys are optionally the same as or different from each other, and further, when two Ys are adjacent to each other, the two adjacent Ys optionally form —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —SCH$_2$S—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —SCH$_2$CH$_2$S—, —OCH=N—, —SCH=N—, —CH=CHCH=CH—, —CH=CHCH=N—, —CH=CHN=CH—, —CH=NCH=CH— or —N=CHCH=CH— to form together with carbon atoms to which each of the two Ys is bonded, a 5-membered ring or a 6-membered ring, and in this case, hydrogen atoms bonded to each carbon atom forming the ring is optionally substituted with $Z^a$s, and further when hydrogen atoms are substituted simultaneously with two or more $Z^a$s, such $Z^a$s are optionally the same as or different from each other, Z is a halogen atom, cyano, nitro, $C_{1-6}$ alkyl, ($C_{1-6}$) alkyl optionally substituted with $R^5$, —OH, —$OR^6$, —OS(O)$_2R^6$, —SH, —S(O)$_rR^6$, —N($R^8$)$R^7$, —C(O)$R^9$, —C($R^9$)=NOH, —C($R^9$)=NOR$^{10}$, M3, M13, M30, —C(O)OR$^{10}$, —C(O)SR$^{10}$, —C(O)N($R^{12a}$)$R^{11a}$, —C(S)OR$^{10}$, —C(S)SR$^{10}$, —C(S)N($R^{12a}$)$R^{11a}$, M23 to M26, M28, M29, —S(O)$_2$OR$^{10}$, —S(O)$_2$N($R^{12}$)$R^{11}$, —Si($R^{13a}$)($R^{13b}$)$R^{13}$, phenyl or phenyl substituted with ($Z^a$)$_{p1}$, when n is an integer of 2 or more, Zs are optionally the same as or different from each other, and further, when two Zs are adjacent to each other, the two adjacent Zs optionally form —CH=CH—CH=CH— to form a condensed-ring, and in this case, hydrogen atoms bonded to each carbon atom forming the ring is optionally substituted with a halogen atom, a cyano group, a nitro group, a $C_{1-4}$ alkyl group, a $C_{1-4}$ haloalkyl group, a $C_{1-4}$ alkoxy group or a $C_{1-4}$ alkylthio group, $Z^a$ is a halogen atom, cyano, nitro, $C_{1-6}$ alkyl, $C_{1-6}$ haloalkyl, $C_{1-4}$ alkoxy($C_{1-4}$) alkyl, $C_{1-4}$ haloalkoxy($C_{1-4}$) alkyl, $C_{1-4}$ alkylthio($C_{1-4}$) alkyl, $C_{1-4}$ haloalkylthio($C_{1-4}$) alkyl, $C_{1-4}$ alkylsulfinyl($C_{1-4}$) alkyl, $C_{1-4}$ haloalkylsulfinyl($C_{1-4}$) alkyl, $C_{1-4}$ alkylsulfonyl($C_{1-4}$) alkyl, $C_{1-4}$ haloalkylsulfonyl($C_{1-4}$) alkyl, $C_{3-6}$ cycloalkyl, $C_{3-6}$ halocycloalkyl, —OH, $C_{1-6}$ alkoxy, $C_{1-6}$ haloalkoxy, $C_{1-6}$ alkyl sulfonyloxy, $C_{1-6}$ haloalkylsulfonyloxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, —NH$_2$, $C_{1-6}$ alkylamino, di($C_{1-6}$ alkyl)amino, $C_{1-6}$ alkoxycarbonyl, $C_{1-6}$ haloalkoxycarbonyl, —C(O)NH$_2$, $C_{1-6}$ alkylaminocarbonyl, $C_{1-6}$ haloalkylaminocarbonyl, di($C_{1-6}$ alkyl)aminocarbonyl, —C(S)NH$_2$, —S(O)$_2$NH$_2$, $C_{1-6}$ alkylaminosulfonyl, di($C_{1-6}$ alkyl)aminosulfonyl or phenyl, when p or p1 is an integer of 2 or more, $Z^a$s are optionally the same as or different from each other, and further, when two $Z^a$s are adjacent to each other, the two adjacent $Z^a$s optionally form —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —CH$_2$CH$_2$CH$_2$S—, —OCH$_2$CH$_2$S— or —CH═CH—CH═CH— to form together with carbon atoms to which each of the two $Z^a$s is bonded, a 5-membered ring or a 6-membered ring, and in this case, hydrogen atoms bonded to each carbon atom forming the ring is optionally substituted with a halogen atom, a cyano group, a nitro group, a $C_{1-4}$ alkyl group, a $C_{1-4}$ haloalkyl group, a $C_{1-4}$ alkoxy group or a $C_{1-4}$ alkylthio group, $R^1$ is a hydrogen atom, —C(O)$R^{1a}$, —C(O)O$R^{1b}$, —C(O)S$R^{1b}$, —C(O)N($R^{1d}$)$R^{1c}$, —C(S)$R^{1a}$, —C(S)O$R^{1b}$, —C(S)S$R^{1b}$, —C(S)N($R^{1d}$)$R^{1c}$, —S(O)$_2R^{1b}$ or —S(O)$_2$N($R^{1d}$)$R^{1c}$, $R^{1a}$ is a hydrogen atom, $C_{1-12}$ alkyl, ($C_{1-12}$) alkyl optionally substituted with $R^{15}$, $C_{3-12}$ cycloalkyl, ($C_{3-12}$) cycloalkyl optionally substituted with $R^{15}$, E1 to E21, $C_{2-12}$ alkenyl, ($C_{2-12}$) alkenyl optionally substituted with $R^{15}$, $C_{5-12}$ cycloalkenyl, $C_{5-12}$ halocycloalkenyl, $C_{2-12}$ alkynyl, ($C_{2-12}$) alkynyl optionally substituted with $R^{15}$, —C(O)$R^9$, —C(O)$R^{9a}$, —C($R^9$)═NOH, —C($R^9$)═NO$R^{10}$, —C($R^9$)═NN($R^{17}$)$R^{16}$, —C(O)O$R^{10}$, —C(O)N($R^{12}$)$R^{11}$, M4, phenyl, phenyl substituted with $(Z^a)_{p1}$ or D-1 to D-38, $R^{1b}$ is $C_{1-12}$ alkyl, ($C_{1-12}$) alkyl optionally substituted with $R^{15}$, $C_{3-12}$ cycloalkyl, ($C_{3-12}$) cycloalkyl optionally substituted with $R^{15}$, E2 to E6, E12 to E19, $C_{2-12}$ alkenyl, $C_{2-12}$ haloalkenyl, $C_{3-12}$ alkynyl, $C_{3-12}$ haloalkynyl, phenyl, phenyl substituted with $(Z^a)_{p1}$, D1, D2, D4 to D6, D8 to D10, D12 to D19, D21, D23, D25, D27 or D30 to D38, $R^{1c}$ is a hydrogen atom, $C_{1-12}$ alkyl, ($C_{1-12}$) alkyl optionally substituted with $R^{15}$, $C_{3-12}$ cycloalkyl, ($C_{3-12}$) cycloalkyl optionally substituted with $R^{15}$, E2 to E6, E12 to E19, $C_{2-12}$ alkenyl, $C_{2-12}$ haloalkenyl, $C_{3-12}$ alkynyl, $C_{3-12}$ haloalkynyl, —C(O)$R^9$, —C(O)$R^{9a}$, —C($R^9$)═NOR$^{10}$, C(O)O$R^{10}$, —C(O)S$R^{10}$, —C(O)N($R^{12}$)$R^{11}$, M7, M17, —C(S)$R^9$, —C(S)O$R^{10}$, —C(S)S$R^{10}$, —C(S)N($R^{12}$)$R^{11}$, M9, M19, —O$R^{10}$, —S(O)$_2R^{10}$, —S(O)$_2$N($R^{12}$)$R^{11}$, —N($R^{17}$)$R^{16}$, phenyl, phenyl substituted with $(Z^a)_{p1}$, D1 to D25 or D27 to D38, $R^{1d}$ is a hydrogen atom, $C_{1-6}$ alkyl, $C_{1-6}$ haloalkyl, $C_{3-6}$ cycloalkyl($C_{1-4}$) alkyl, $C_{1-6}$ alkoxy($C_{1-4}$) alkyl, $C_{1-6}$ alkylthio($C_{1-4}$) alkyl, cyano($C_{1-6}$) alkyl, phenyl($C_{1-4}$) alkyl, $C_{3-6}$ alkenyl or $C_{3-6}$ alkynyl, or $R^{1d}$ together with $R^{1c}$ optionally forms $C_{2-6}$ alkylene chain to form together with a nitrogen atom to which $R^{1c}$ and $R^{1d}$ are bonded, a 3- to 7-membered ring, and in this case, the alkylene chain optionally contains one oxygen atom, sulfur atom or nitrogen atom and is optionally substituted with a $C_{1-6}$ alkyl group, a —CHO group, a $C_{1-6}$ alkylcarbonyl group, a $C_{1-6}$ alkoxycarbonyl group, a $C_{1-6}$ alkylaminocarbonyl group, a $C_{1-6}$ haloalkylaminocarbonyl group, a di($C_{1-6}$ alkyl)aminocarbonyl group, an oxo group or a thioxo group, $R^2$ is a hydrogen atom, cyano, $C_{1-12}$ alkyl, ($C_{1-12}$) alkyl optionally substituted with $R^{15a}$, $C_{3-12}$ cycloalkyl, $C_{3-12}$ alkenyl, $C_{3-12}$ haloalkenyl, $C_{3-12}$ alkynyl, $C_{3-12}$ haloalkynyl, —C(O)$R^9$, —C(O)$R^{9a}$, —C(O)O$R^{10}$, —C(O)S$R^{10}$, —C(O)N($R^{12}$)$R^{11}$, —C(O)C(O)O$R^{10}$, —C(S)O$R^{10}$, —C(S)S$R^{10}$, —C(S)N($R^{12}$)$R^{11}$, $C_{1-12}$alkoxy, $C_{1-12}$ haloalkoxy, —S$R^{10}$, —S(O)$_2R^{10}$, —SN($R^{17a}$)$R^{16a}$, phenyl, phenyl substituted with $(Z^a)_{p1}$ or D32, or $R^2$ together with $R^1$ optionally forms a $C_{4-6}$ alkylene chain to form together with a nitrogen atom to which $R^1$ and $R^2$ are bonded, a 5- to 7-membered ring, and in this case, the alkylene chain optionally contains one oxygen atom, sulfur atom or nitrogen atom and is optionally substituted with a $C_{1-6}$ alkyl group, a $C_{1-6}$ alkylidene group, a —CHO group, a $C_{1-6}$ alkylcarbonyl group, a $C_{1-6}$ haloalkylcarbonyl group, a $C_{1-6}$ alkoxycarbonyl group, a $C_{1-6}$ haloalkoxycarbonyl group, a $C_{1-6}$ alkylaminocarbonyl group, a $C_{1-6}$ haloalkylaminocarbonyl group, a di($C_{1-6}$ alkyl)aminocarbonyl group, a phenyl group, a D32 group, a D34 group, an oxo group or a thioxo group, $R^3$ is a halogen atom, cyano, $C_{1-6}$ alkyl, ($C_{1-6}$) alkyl optionally substituted with $R^5$, $C_{3-8}$ cycloalkyl, ($C_{3-8}$) cycloalkyl optionally substituted with $R^5$, E1 to E19, $C_{3-6}$ alkenyl, ($C_{2-6}$) alkenyl optionally substituted with $R^5$, $C_{3-6}$ alkynyl, ($C_{2-6}$) alkynyl optionally substituted with $R^5$, —O$R^6$, —S(O)$_rR^6$, —N($R^{12}$)$R^{11}$, —C(O)$R^9$, —C($R^9$)═NOH, —C($R^9$)═NO$R^{10}$, M3, M13, M30, —C(O)O$R^{10}$, —C(O)S$R^{10}$, —C(O)N($R^{12}$)$R^{11}$, —C(S)O$R^{10}$, —C(S)S$R^{10}$, —C(S)N($R^{12}$)$R^{11}$, —Si($R^{13a}$)($R^{13b}$)$R^{13}$, —P(O)(O$R^{18}$)$_2$, phenyl, phenyl substituted with $(Z^a)_{p1}$ or D1 to D38, $R^{3a}$ is a hydrogen atom, $C_{1-6}$ alkyl or $C_{1-6}$ haloalkyl, $R^4$ is a hydrogen atom, cyano, $C_{1-6}$ alkyl, $C_{1-6}$ haloalkyl, $C_{3-6}$ cycloalkyl, $C_{2-6}$ alkenyl, $C_{2-6}$ alkynyl, $C_{1-6}$ alkoxycarbonyl, —C(O)NH$_2$, —C(S)NH$_2$, phenyl, phenyl substituted with $(Z^a)_{p1}$, D1, D2, D9, D10 or D32, $R^{4a}$ is a hydrogen atom or $C_{1-6}$ alkyl, or $R^{4a}$ together with $R^4$ optionally forms a $C_{2-5}$ alkylene chain to form together with a carbon atom to which $R^4$ and $R^{4a}$ are bonded, a 3- to 6-membered ring, and in this case, the alkylene chain optionally contains one oxygen atom, sulfur atom or nitrogen atom and is optionally substituted with a $C_{1-4}$ alkyl group, a —CHO group, a $C_{1-4}$ alkylcarbonyl group, a $C_{1-4}$ alkoxycarbonyl group, a $C_{1-4}$ alkylaminocarbonyl group, a $C_{1-4}$ haloalkylaminocarbonyl group, a di($C_{1-4}$ alkyl)aminocarbonyl group or a phenyl group, $R^{4b}$ is a hydrogen atom, $C_{1-6}$ alkyl, $C_{1-6}$ haloalkyl, $C_{1-6}$ alkylcarbonyl, $C_{1-6}$ haloalkylcarbonyl, $C_{3-6}$ cycloalkylcarbonyl, $C_{3-6}$ halocycloalkylcarbonyl, $C_{1-6}$ alkoxycarbonyl or $C_{1-6}$ haloalkoxycarbonyl, D1 to D38 are individually an aromatic heterocycle of Structural Formulae below:

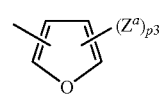

D1

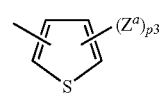

D2

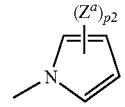

D3

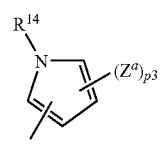

D4

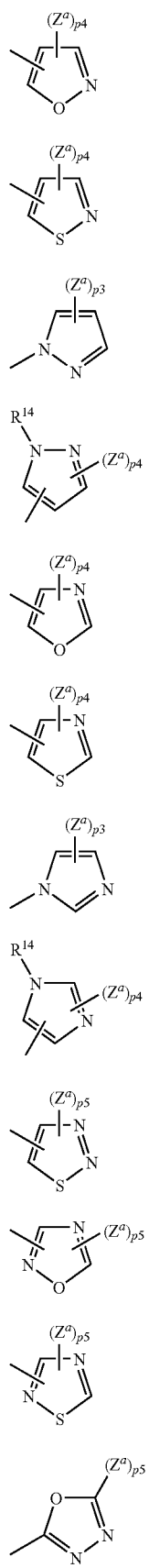
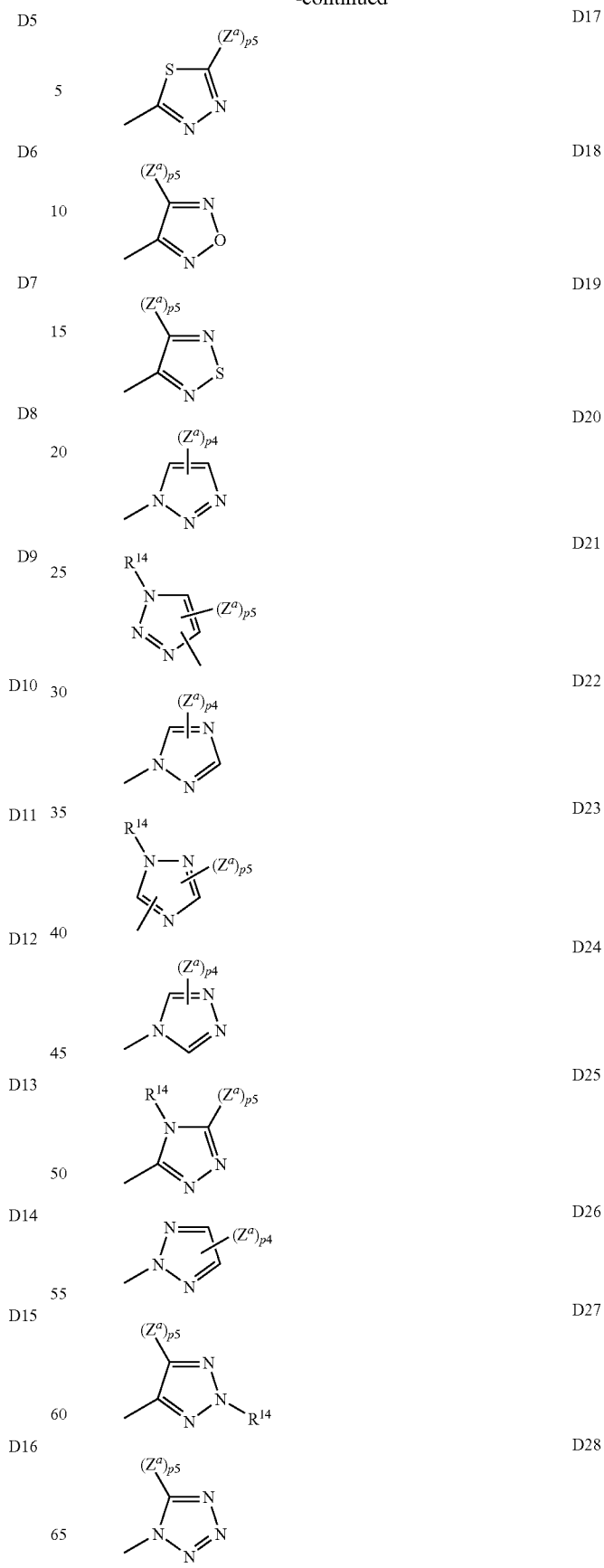

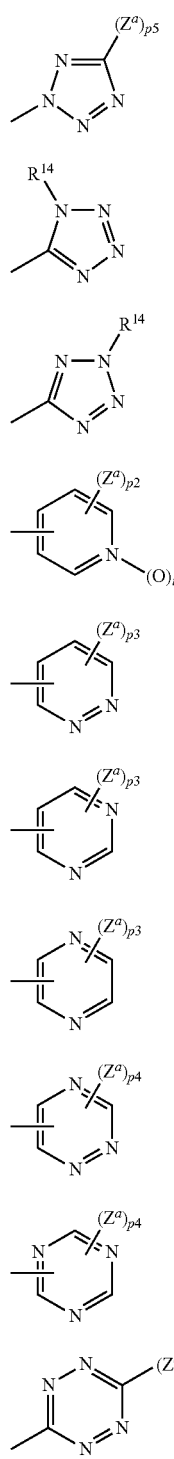

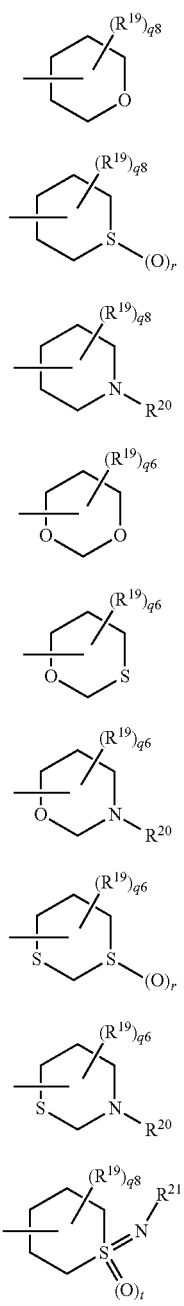

E12, E13, E14, E153, E16, E17, E18, E19, E21

$R^5$ is a halogen atom, cyano, $C_{3-8}$ cycloalkyl, $C_{3-8}$ halocycloalkyl, E1 to E19, —OH, —OR$^6$, —SH, —S(O)$_r$R$^6$, —N(R$^8$)R$^7$, —N(R$^8$)C(O)R$^{9a}$, —C(O)OR$^{10}$, —C(O)N(R$^{12}$)R$^{11}$, —Si(R$^{13a}$)(R$^{13b}$)R$^{13}$, phenyl, phenyl substituted with $(Z^a)_{p1}$ or D1 to D38, $R^6$ is $C_{1-6}$ alkyl, $(C_{1-6})$ alkyl optionally substituted with $R^{22}$, $C_{3-8}$ cycloalkyl, $(C_{3-8})$ cycloalkyl optionally substituted with $R^{22}$, E2 to E6, E12 to E15, E18, $C_{2-6}$ alkenyl, $(C_{2-6})$ alkenyl optionally substituted with $R^{22}$, $C_{5-10}$ cycloalkenyl, $C_{5-10}$ halocycloalkenyl, $C_{3-6}$ alkynyl, $(C_{3-6})$ alkynyl optionally substituted with $R^{22}$, $C_{1-6}$ alkylcarbonyl, $C_{1-6}$ alkoxycarbonyl, phenyl, phenyl substituted with $(Z^a)_{p1}$, D1, D2, D4 to D6, D8 to D10, D12 to D19, D21, D23, D25, D27 or D30 to D38, $R^7$ is a hydrogen atom, $C_{1-6}$ alkyl, $(C_{1-6})$ alkyl optionally substituted with $R^{22}$, $C_{3-8}$ cycloalkyl, $C_{3-8}$ halocycloalkyl, $C_{3-6}$ alkenyl, $C_{3-6}$ haloalkenyl, $C_{3-6}$ alkynyl, $C_{3-6}$ haloalkynyl, —C(O)R$^9$, —C(O)OR$^{10}$, —C(O)SR$^{10}$, —C(O)N(R$^{12}$)R$^{11}$, —C(S)OR$^{10}$, —C(S)SR$^{10}$, —C(S)N(R$^{12}$)R$^{11}$, —C(O)C(O)R$^{10}$, —C(O)C(O)OR$^{10}$, —OH, —S(O)$_2$R$^{10}$, —S(O)$_2$N(R$^{12}$)R$^{11}$, —P(O)(OR$^{18}$)$_2$ or —P(S)(OR$^{18}$)$_2$, $R^8$ is a hydrogen atom, $C_{1-6}$ alkyl, $(C_{1-6})$ alkyl optionally substituted with $R^{22}$, $C_{3-8}$ cycloalkyl, $C_{3-6}$ alkenyl, $C_{3-6}$ haloalkenyl, $C_{3-6}$ alkynyl, $C_{3-6}$ haloalkynyl, —CHO, $C_{1-6}$ alkylcarbonyl, $C_{1-6}$ haloalkylcarbonyl or $C_{1-6}$ alkoxycarbonyl, or $R^8$ together with $R^7$ optionally forms a $C_{2-6}$ alkylene chain to form together with a nitrogen atom to which $R^7$ and $R^8$ are bonded, a 3- to 7-membered ring, and in this case, the alkylene chain optionally contains one oxygen atom, sulfur atom or nitrogen atom and is optionally substituted with a halogen atom, a $C_{1-4}$ alkyl group, a $C_{1-4}$ haloalkyl group, an oxo group or a thioxo group, $R^{7a}$ is $C_{1-6}$ alkyl, $C_{1-6}$ alkoxy, $C_{1-6}$ haloalkoxy, $C_{3-6}$ alkenyloxy, phenoxy or phenoxy substituted with $(Z^a)_{p1}$, $R^{8a}$ is a hydrogen atom, $C_{1-6}$ alkyl, $C_{1-6}$ haloalkyl, $C_{3-6}$ alkenyl, phenyl, phenyl substituted with $(Z^a)_{p1}$, or $R^{8a}$ together with $R^{7a}$ optionally forms a $C_{4-6}$ alkylene chain to form together with a carbon atom to which $R^{7a}$ and $R^{8a}$ are bonded, a 5- to 7-membered ring, and in this case, the alkylene chain optionally contains one oxygen atom or sulfur atom, $R^9$ is a hydrogen atom, $C_{1-6}$ alkyl, $(C_{1-6})$ alkyl optionally substituted with $R^{22}$, $C_{3-8}$ cycloalkyl, $C_{3-8}$ halocycloalkyl, E4 to E6, E12 to E14, $C_{2-6}$ alkenyl, $C_{2-6}$ haloalkenyl, $C_{5-10}$ cycloalkenyl, $C_{5-10}$ halocycloalkenyl, $C_{2-6}$ alkynyl or $C_{2-6}$ haloalkynyl, $R^{9a}$ is phenyl, phenyl substituted with $(Z^a)_{p1}$, naphthyl or D1 to D38, $R^{10}$ is $C_{1-6}$ alkyl, $(C_{1-6})$ alkyl optionally substituted with $R^{22}$, $C_{3-8}$ cycloalkyl, $C_{3-8}$ halocycloalkyl, E2 to E6, E12 to E19, $C_{2-6}$ alkenyl, $C_{2-6}$ haloalkenyl, $C_{5-10}$ cycloalkenyl, $C_{5-10}$ halocycloalkenyl, $C_{3-6}$ alkynyl, $C_{3-6}$ haloalkynyl, phenyl, phenyl substituted with $(Z^a)_{p1}$, D1, D2, D4 to D6, D8 to D10, D12 to D19, D21, D23, D25, D27 or D30 to D38, $R^{11}$ is a hydrogen atom, $C_{1-6}$ alkyl, $(C_{1-6})$ alkyl optionally substituted with $R^{22}$, $C_{3-8}$ cycloalkyl, $C_{3-8}$ halocycloalkyl, E2 to E6, E12 to E19, $C_{2-6}$ alkenyl, $C_{2-6}$ haloalkenyl, $C_{3-6}$ alkynyl, $C_{3-6}$ haloalkynyl, phenyl, phenyl substituted with $(Z^a)_{p1}$, D1 to D25 or D27 to D38, $R^{12}$ is a hydrogen atom, $C_{1-6}$ alkyl, $C_{1-6}$ haloalkyl, $C_{3-6}$ cycloalkyl($C_{1-4}$) alkyl, $C_{1-4}$ alkoxy($C_{1-4}$) alkyl, $C_{1-4}$ alkylthio($C_{1-4}$) alkyl, cyano($C_{1-4}$) alkyl, $C_{3-6}$ alkenyl or $C_{3-6}$ alkynyl, or $R^{12}$ together with $R^{11}$ optionally forms a $C_{2-6}$ alkylene chain to form together with a nitrogen atom to which $R^{11}$ and $R^{12}$ are bonded, a 3- to 7-membered ring, and in this case, the alkylene chain optionally contains one oxygen atom, sulfur atom or nitrogen atom and is optionally substituted with a halogen atom, a $C_{1-4}$ alkyl group, a $C_{1-4}$ alkoxy group, a —CHO group, a $C_{1-4}$ alkylcarbonyl group or a $C_{1-4}$ alkoxycarbonyl group, $R^{11a}$ is a hydrogen atom, $C_{1-6}$ alkyl, $(C_{1-6})$ alkyl optionally substituted with $R^{22}$, $C_{3-4}$ cycloalkyl, cyclopropyl substituted with $R^{22}$, E4, E5, $C_{3-6}$ alkenyl, $C_{3-6}$ haloalkenyl, —CH=NOR$^{10}$, —C(O)OR$^{10}$, —C(O)N(R$^{12}$)R$^{11}$, —C(S)OR$^{10}$, —N(R$^{12b}$)R$^{11b}$, D34 or D35, $R^{12a}$ is a hydrogen atom, $C_{1-6}$ alkyl, $(C_{1-4})$ alkyl substituted with $R^{22a}$, $C_{3-6}$ alkynyl, —C(O)$R^9$, —C(O)O$R^{10}$ or $C_{1-6}$ haloalkylthio, or $R^{12a}$ together with $R^{11a}$ optionally forms =C($R^{12c}$)$R^{11c}$, $R^{11b}$ is phenyl, D32 or D34, $R^{12b}$ is a hydrogen atom, $C_{1-4}$ alkyl, $C_{3-4}$ alkenyl or $C_{3-4}$ alkynyl, $R^{11c}$ is $C_{1-4}$ alkoxy or $C_{1-4}$ alkylthio, $R^{12c}$ is —NH$_2$ or $C_{1-4}$ alkylamino, $R^{13}$ is $C_{1-6}$ alkyl, $C_{1-6}$ haloalkyl, $C_{1-6}$ alkoxy, phenyl, phenyl substituted with $(Z^a)_{p1}$, $R^{13a}$ and $R^{13b}$ are independently $C_{1-6}$ alkyl, $C_{1-6}$ haloalkyl or $C_{1-6}$ alkoxy, $R^{14}$ is a hydrogen atom, $C_{1-6}$ alkyl, $C_{1-6}$ haloalkyl, $C_{1-4}$ alkoxycarbonyl($C_{1-4}$) alkyl, $C_{1-4}$ haloalkoxycarbonyl ($C_{1-4}$) alkyl, phenyl($C_{1-4}$) alkyl, phenyl($C_{1-4}$) alkyl substituted with $(Z^a)_{p1}$, $C_{2-6}$ alkenyl, $C_{2-6}$ haloalkenyl, $C_{3-6}$ alkynyl, $C_{3-6}$ haloalkynyl, $C_{1-6}$ alkoxy, $C_{1-6}$ alkoxycarbonyl, $C_{1-6}$ haloalkoxycarbonyl, phenyl or phenyl substituted with $(Z^a)_{p1}$, and further, when $Z^a$ is present adjacent to $R^{14}$, $R^{14}$ and $Z^a$ adjacent to each other optionally form —CH$_2$CH$_2$CH$_2$CH$_2$—, —CH=CH—CH=CH—, —N=CH—CH=CH—, —CH=N—CH=CH—, —CH=CH—N=CH— or —CH=CH—CH=N— to form together with atoms to which each of $R^{14}$ and $Z^a$ is bonded, a 6-membered ring, and in this case, hydrogen atoms bonded to each carbon atom forming the ring is optionally substituted with a halogen atom, a $C_{1-4}$ alkyl group or a $C_{1-4}$ haloalkyl group, $R^{15}$ is a halogen atom, cyano, nitro, $C_{3-8}$ cycloalkyl, $C_{3-8}$ halocycloalkyl, hydroxy($C_{3-8}$) cycloalkyl, $C_{1-4}$ alkoxy ($C_{3-8}$) cycloalkyl, E1 to E 21, $C_{5-10}$ cycloalkenyl, $C_{5-10}$ halocycloalkenyl, —O$R^{23}$, —N($R^{24}$)$R^{23}$, —SH, —S(O)$_r R^{25}$, —S(O)$_t (R^{25})$=N$R^{21}$, —C(O)$R^{26}$, —C($R^{26}$)=NOH, —C($R^{26}$)=NO$R^{27}$, —C(O)OH, —C(O)O$R^{27}$, —C(O)S$R^{27}$, —C(O)N($R^{29}$)$R^{28}$, —C(O)N($R^{29}$)O$R^{27}$, —C(O)N($R^{29}$)N($R^{28a}$)$R^{28}$, —C(O)C(O)O$R^{27}$, —C(S)O$R^{27}$, —C(S)S$R^{27}$, —C(S)N($R^{29}$)$R^{28}$, —C(=N$R^{28}$)O$R^{27}$, —C(=N$R^{28}$)S$R^{27}$, —C(=N$R^{29}$)N($R^{28a}$)$R^{28}$, —C(=NO$R^{27}$)N($R^{29}$)$R^{28}$, —S(O)$_2$OH, —S(O)$_2$O$R^{27}$, —S(O)$_2$N($R^{29}$)$R^{28}$, —Si($R^{13a}$)($R^{13b}$)$R^{13}$, —P(O)(O$R^{18}$)$_2$, —P(S)(O$R^{18}$)$_2$, —P(phenyl)$_2$, —P(O)(phenyl)$_2$, M1 to M30, phenyl, phenyl substituted with $(Z^a)_{p1}$, naphthyl or D1 to D38, M1 to M30 are individually a partially saturated heterocycle of Structural Formulae below:

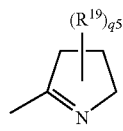

M1

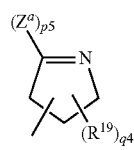

M2

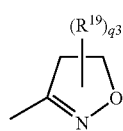

M3

-continued

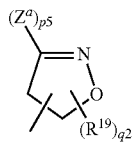

M4

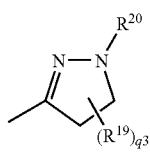

M5

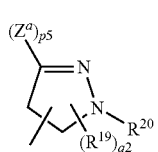

M6

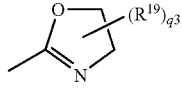

M7

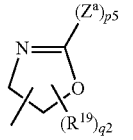

M8

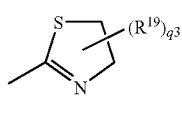

M9

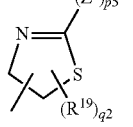

M10

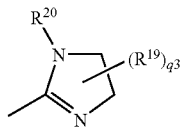

M11

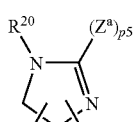

M12

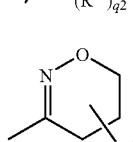

M13

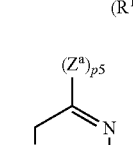

M14

M15 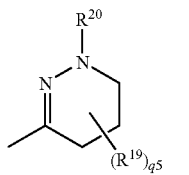

M16 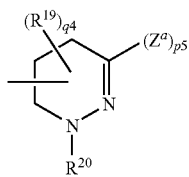

M17 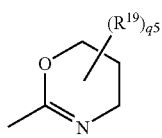

M18 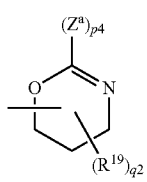

M19 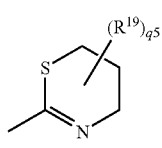

M20 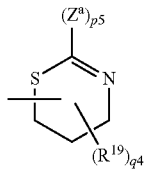

M21 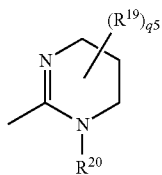

M22 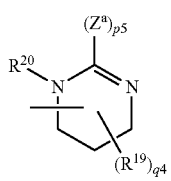

M23 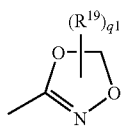

M24 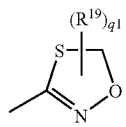

M25 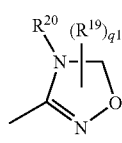

M26 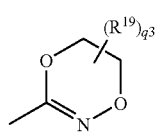

M27 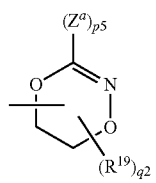

M28 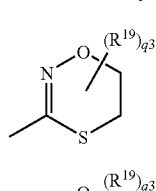

M29 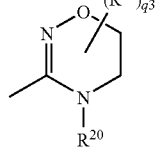

M30 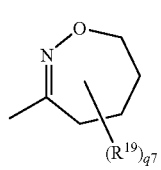

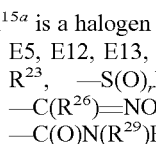

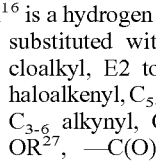

$R^{15a}$ is a halogen atom, cyano, nitro, $C_{3-8}$ cycloalkyl, E4, E5, E12, E13, $C_{5-10}$ cycloalkenyl, —$OR^{23}$, —$N(R^{24})R^{23}$, —$S(O)_rR^{25}$, —$C(O)R^{26}$, —$C(R^{26})$=NOH, —$C(R^{26})$=$NOR^{27}$, M3, —$C(O)OR^{27}$, —$C(O)SR^{27}$, —$C(O)N(R^{29})R^{28}$, M7, M17, —$C(S)OR^{27}$, —$C(S)SR^{27}$, —$C(S)N(R^{29})R^{28}$, M9, M19, —$C(O)C(O)OR^{27}$, —$S(O)_2N(R^{29})R^{28}$, —$Si(R^{13a})(R^{13b})R^{13}$, —$P(O)(OR^{18})_2$, —$P(S)(OR^{18})_2$, phenyl, phenyl substituted with $(Z^a)_{p1}$, D1 to D3, D7, D10, D11, D22 or D32 to D35, $R^{16}$ is a hydrogen atom, $C_{1-6}$ alkyl, $(C_{1-6})$ alkyl optionally substituted with $R^{30}$, $C_{3-8}$ cycloalkyl, $C_{3-8}$ halocycloalkyl, E2 to E6, E12 to E19, $C_{2-6}$ alkenyl, $C_{2-6}$ haloalkenyl, $C_{5-10}$ cycloalkenyl, $C_{5-10}$ halocycloalkenyl, $C_{3-6}$ alkynyl, $C_{3-6}$ haloalkynyl, —$C(O)R^{26}$, —$C(O)OR^{27}$, —$C(O)SR^{27}$, —$C(O)N(R^{29})R^{28}$, —$C(S)R^{26}$, —$C(S)OR^{27}$, —$C(S)SR^{27}$, —$C(S)N(R^{29})R^{28}$, —$S(O)_2OR^{27}$, —$S(O)_2N(R^{29})R^{28}$, —$P(O)(OR^{18})_2$, —$P(S)(OR^{18})_2$, phenyl, phenyl substituted with $(Z^a)_{p1}$, D1 to D25 or D27 to D38, $R^{17}$ is a hydrogen atom, $C_{1-6}$ alkyl, $C_{1-6}$ haloalkyl, $C_{3-6}$ cycloalkyl$(C_{1-4})$ alkyl, $C_{1-4}$ alkoxy$(C_{1-4})$ alkyl, $C_{1-4}$ haloalkoxy($C_{1-4}$) alkyl, $C_{1-4}$ alkylthio($C_{1-4}$) alkyl, $C_{1-4}$ haloalkylthio($C_{1-4}$) alkyl, $C_{1-4}$ alkylsulfonyl($C_{1-4}$) alkyl, $C_{1-4}$ haloalkylsulfonyl($C_{1-4}$) alkyl, cyano($C_{1-4}$) alkyl, $C_{1-4}$ alkoxycarbonyl($C_{1-4}$) alkyl, phenyl($C_{1-4}$) alkyl, $C_{2-6}$ alkenyl, $C_{2-6}$ haloalkenyl, $C_{3-6}$ alkynyl or $C_{3-6}$ haloalkynyl, or $R^{17}$ together with $R^{16}$ optionally forms a $C_{2-6}$ alkylene chain to form together with a nitrogen atom to which $R^{16}$ and $R^{17}$ are bonded, a 3- to 7-membered ring, and in this case, the alkylene chain optionally contains one oxygen atom, sulfur atom or nitrogen atom and is optionally substituted with a halogen atom, a $C_{1-4}$ alkyl group, a $C_{1-2}$ alkoxy($C_{1-2}$) alkyl group, a $C_{1-4}$ alkoxy group, a —CHO group, a $C_{1-4}$ alkylcarbonyl group or a $C_{1-4}$ alkoxycarbonyl group, $R^{16a}$ is $C_{1-12}$ alkyl, $C_{1-12}$ haloalkyl, $C_{1-12}$ alkoxy($C_{1-12}$) alkyl, cyano($C_{1-12}$) alkyl, $C_{1-12}$ alkoxycarbonyl($C_{1-12}$) alkyl, phenyl($C_{1-4}$) alkyl, phenyl ($C_{1-4}$) alkyl substituted with $(Z^a)_{p1}$, $C_{3-12}$ alkenyl, $C_{3-12}$ haloalkenyl, $C_{3-12}$ alkynyl, $C_{3-12}$ haloalkynyl, $C_{1-12}$ alkylcarbonyl, $C_{1-12}$ alkoxycarbonyl, —C(O)ON=C(CH$_3$)SCH$_3$, —C(O)ON=C(SCH$_3$)C(O)N(CH$_3$)$_2$, phenyl or phenyl substituted with $(Z^a)_{p1}$, $R^{17a}$ is $C_{1-12}$ alkyl, $C_{1-12}$ haloalkyl, $C_{1-12}$ alkoxy($C_{1-12}$) alkyl, cyano($C_{1-12}$) alkyl, $C_{1-12}$ alkoxycarbonyl($C_{1-12}$) alkyl, phenyl($C_{1-4}$) alkyl, phenyl ($C_{1-4}$) alkyl substituted with $(Z^a)_{p1}$, $C_{3-12}$ alkenyl, $C_{3-12}$ haloalkenyl, $C_{3-12}$ alkynyl, $C_{3-12}$ haloalkynyl, phenyl or phenyl substituted with $(Z^a)_{p1}$, or $R^{17a}$ together with $R^{16a}$ optionally forms a $C_{4-7}$ alkylene chain to form together with a nitrogen atom to which $R^{16a}$ and $R^{17a}$ are bonded, a 5- to 8-membered ring, and in this case, the alkylene chain optionally contains one oxygen atom or sulfur atom and is optionally substituted with a $C_{1-4}$ alkyl group or a $C_{1-4}$ alkoxy group, $R^{18}$ is $C_{1-6}$ alkyl or $C_{1-6}$ haloalkyl, $R^{19}$ is a halogen atom, cyano, $C_{1-6}$ alkyl, $C_{1-6}$ haloalkyl, hydroxy($C_{1-4}$) alkyl, $C_{1-4}$ alkoxy($C_{1-4}$) alkyl, $C_{1-4}$ alkoxycarbonyl($C_{1-4}$alkyl, $C_{1-6}$ alkoxy, $C_{1-6}$ alkylthio, $C_{1-6}$ alkylamino, di($C_{1-6}$ alkyl)amino, $C_{1-6}$ alkoxycarbonyl, phenyl or phenyl substituted with $(Z^a)_{p1}$, when q1 to q8 are an integer of 2 or more, $R^{19}$s are optionally the same as or different from each other, and further when two $R^{19}$s are substituents on the same carbon atom, the two $R^{19}$s together optionally form oxo, thioxo, imino, $C_{1-4}$ alkylimino, $C_{1-4}$ alkoxyimino or $C_{1-4}$ alkylidene, $R^{20}$ is a hydrogen atom, $C_{1-6}$ alkyl, ($C_{1-6}$) alkyl optionally substituted with $R^{30}$, $C_{3-6}$ cycloalkyl, $C_{3-6}$ alkenyl, $C_{3-6}$ haloalkenyl, $C_{3-6}$ alkynyl, —OH, benzyloxy, —C(O)R$^{31}$, —C(O)OR$^{32}$, —C(O)SR$^{32}$, —C(O)N(R$^{34}$)R$^{33}$, —C(S)N(R$^{34}$)R$^{33}$, —S(O)$_2$R$^{32}$, —P(O)(OR$^{18}$)$_2$, —P(S)(OR$^{18}$)$_2$, phenyl, phenyl substituted with $(Z^a)_{p1}$ or D3, $R^{21}$ is a hydrogen atom, cyano, nitro, $C_{1-6}$ alkyl, $C_{1-6}$ haloalkyl, $C_{1-6}$ alkylcarbonyl, $C_{1-6}$ haloalkylcarbonyl, $C_{1-6}$ alkoxycarbonyl, $C_{1-6}$ haloalkoxycarbonyl, $C_{1-6}$ alkylsulfonyl or $C_{1-6}$ haloalkylsulfonyl, $R^{22}$ is a halogen atom, cyano, $C_{3-8}$ cycloalkyl, $C_{3-8}$ halocycloalkyl, E1 to E19, —OR$^{23}$, $C_{1-6}$ alkylthio, $C_{1-6}$ haloalkylthio, $C_{1-6}$ alkylsulfonyl, $C_{1-6}$ haloalkylsulfonyl, —N(R$^{24}$)R$^{23}$, —C(O)R$^{26}$, —C(R$^{26}$)=NOR$^{27}$, —C(O)OR$^{27}$, —C(O)N(R$^{29}$)R$^{28}$, phenyl, phenyl substituted with $(Z^a)_{p1}$ or D1 to D38, $R^{22a}$ is cyano, $C_{3-6}$ cycloalkyl, —OR$^{23}$ or $C_{1-6}$ alkylthio, $R^{23}$ is a hydrogen atom, $C_{1-8}$ alkyl, ($C_{1-8}$) alkyl optionally substituted with $R^{30}$, $C_{3-8}$ cycloalkyl, ($C_{3-8}$) cycloalkyl optionally substituted with $R^{30}$, E2 to E6, E12 to E19, $C_{3-8}$ alkenyl, ($C_{3-8}$) alkenyl optionally substituted with $R^{30}$, $C_{3-8}$ alkynyl, ($C_{3-8}$) alkynyl optionally substituted with $R^{30}$, —C(O)R$^{31}$, —C(O)OR$^{32}$, —C(O)SR$^{32}$, —C(O)N(R$^{34}$)R$^{33}$, —C(O)C(O)R$^{32}$, —C(O)C(O)OR$^{32}$, —C(O)C(O)OR$^{32}$, —C(S)R$^{31}$, —C(S)OR$^{32}$, —C(S)SR$^{32}$, —C(S)N(R$^{34}$)R$^{33}$, —S(O)$_2$R$^{32}$, —S(O)$_2$N(R$^{34}$)R$^{33}$, —Si—P(O)(OR$^{18}$)$_2$, —P(S)(OR$^{18}$)$_2$, phenyl, phenyl substituted with $(Z^a)_{p1}$, D1, D2, D4 to D6, D8 to D10, D12 to D19, D21, D23, D25, D27 or D30 to D38, $R^{24}$ is a hydrogen atom, $C_{1-6}$ alkyl, $C_{1-6}$ haloalkyl, $C_{3-4}$ cycloalkyl($C_{1-4}$) alkyl, $C_{1-4}$ alkoxy($C_{1-4}$) alkyl, $C_{1-4}$ alkylthio($C_{1-4}$) alkyl, cyano($C_{1-4}$) alkyl, $C_{3-6}$ cycloalkyl, $C_{3-6}$ alkenyl, $C_{3-6}$ alkynyl, $C_{1-6}$ alkoxy, $C_{1-6}$ haloalkylcarbonyl, $C_{1-6}$ alkoxycarbonyl, $C_{1-6}$ alkylsulfonyl, phenyl or phenyl substituted with $(Z^a)_{p1}$, or $R^{24}$ together with $R^{23}$ optionally forms a $C_{2-5}$ alkylene chain to form together with a nitrogen atom to which $R^{23}$ and $R^{24}$ are bonded, a 3- to 6-membered ring, and in this case, the alkylene chain optionally contains one oxygen atom, sulfur atom or nitrogen atom and is optionally substituted with a halogen atom, a $C_{1-4}$ alkyl group, a $C_{1-4}$ haloalkyl group, a $C_{1-4}$ alkoxy group, a —CHO group, a $C_{1-4}$ alkylcarbonyl group, a $C_{1-4}$ alkoxycarbonyl group, a phenyl group, a phenyl group substituted with $(Z^a)_{p1}$, an oxo group or a thioxo group, $R^{25}$ is $C_{1-8}$ alkyl, ($C_{1-8}$) alkyl optionally substituted with $R^{30}$, $C_{3-8}$ cycloalkyl, ($C_{3-8}$) cycloalkyl optionally substituted with $R^{30}$, E2 to E6, E12 to E19, $C_{3-8}$ alkenyl, ($C_{3-8}$) alkenyl optionally substituted with $R^{30}$, $C_{3-8}$ alkynyl, ($C_{3-8}$) alkynyl optionally substituted with $R^{30}$, —C(O)R$^{31}$, —C(O)OR$^{32}$, —C(O)SR$^{32}$, —C(O)N(R$^{34}$)R$^{33}$, —C(O)C(O)R$^{32}$, —C(O)C(O)OR$^{32}$, —C(S)R$^{31}$, —C(S)OR$^{32}$, —C(S)SR$^{32}$, —C(S)N(R$^{34}$)R$^{33}$, —SH, $C_{1-6}$ alkylthio, $C_{1-6}$ haloalkylthio, phenylthio, phenylthio substituted with $(Z^a)_{p1}$, —P(O)(OR$^{18}$)$_2$, —P(S)(OR$^{18}$)$_2$, phenyl, phenyl substituted with $(Z^a)_{p1}$, D9, D10, D12, D14 to D17, D30 or D32 to D35, $R^{26}$ is a hydrogen atom, $C_{1-6}$ alkyl, $C_{1-6}$ haloalkyl, $C_{3-6}$ cycloalkyl($C_{1-4}$) alkyl, $C_{1-6}$ alkoxy($C_{1-4}$) alkyl, $C_{1-6}$ haloalkoxy($C_{1-4}$) alkyl, $C_{1-6}$ alkylthio($C_{1-4}$) alkyl, $C_{1-6}$ haloalkylthio($C_{1-4}$) alkyl, $C_{1-6}$ alkylsulfonyl($C_{1-4}$) alkyl, $C_{1-6}$ haloalkylsulfonyl($C_{1-4}$) alkyl, phenyl($C_{1-4}$) alkyl, phenyl ($C_{1-4}$) alkyl substituted with $(Z^a)_{p1}$, $C_{3-6}$ cycloalkyl, phenyl or phenyl substituted with $(Z^a)_{p1}$, $R^{27}$ is $C_{1-6}$ alkyl, ($C_{1-6}$) alkyl optionally substituted with $R^{30}$, $C_{3-8}$ cycloalkyl, ($C_{3-8}$) cycloalkyl optionally substituted with $R^{30}$, E2 to E6, E12 to E19, $C_{2-6}$ alkenyl, ($C_{2-6}$) alkenyl optionally substituted with $R^{30}$, $C_{3-6}$ alkynyl, ($C_{3-6}$) alkynyl optionally substituted with $R^{30}$, phenyl, phenyl substituted with $(Z^a)_{p1}$, D1, D2, D4 to D6, D8 to D10, D12 to D19, D21, D23, D25, D27 or D30 to D38, $R^{28}$ is a hydrogen atom, $C_{1-6}$ alkyl, ($C_{1-6}$) alkyl optionally substituted with $R^{30}$, $C_{3-8}$ cycloalkyl, ($C_{3-8}$) cycloalkyl optionally substituted with $R^{30}$, E1 to E6, E12 to E19, $C_{2-6}$ alkenyl, ($C_{2-6}$) alkenyl optionally substituted with $R^{30}$, $C_{3-8}$ alkynyl, ($C_{3-6}$) alkynyl optionally substituted with $R^{30}$, phenyl, phenyl substituted with $(Z^a)_{p1}$, D1 to D25 or D27 to D38, $R^{28a}$ is a hydrogen atom or $C_{1-4}$ alkyl, $R^{29}$ is a hydrogen atom, $C_{1-6}$ alkyl, ($C_{1-6}$) alkyl optionally substituted with $R^{30}$, $C_{3-6}$ alkenyl, $C_{3-6}$ haloalkenyl, $C_{3-6}$ alkynyl, $C_{3-6}$ haloalkynyl, phenyl or phenyl substituted with $(Z^a)_{p1}$, or $R^{29}$ together with $R^{28}$ optionally forms a $C_{2-5}$ alkylene chain to form together with a nitrogen atom to which $R^{28}$ and $R^{29}$ are bonded, a 3- to 6-membered ring, and in this case, the alkylene chain optionally contains one oxygen atom, sulfur atom or nitrogen atom and is optionally substituted with a halogen atom, a $C_{1-4}$ alkyl group, a $C_{1-4}$ alkoxy group, a —CHO group, a $C_{1-4}$ alkylcarbonyl group, a $C_{1-4}$ alkoxycarbonyl group, a phenyl group, a phenyl group substituted with $(Z^a)_{p1}$ or an oxo group, $R^{30}$ is a halogen atom, cyano, nitro, $C_{3-8}$ cycloalkyl, $C_{3-8}$ halocycloalkyl, E4, E5, E7, E8, E10, E12, E13, E15, E16, E18, $C_{2-6}$ alkenyl, $C_{2-6}$ haloalkenyl, —OH, —OR$^{32}$, —OC(O)R$^{31}$, —OC(O)OR$^{32}$, —OC(O)N(R$^{34}$)R$^{33}$, —OC(S)N(R$^{34}$)R$^{33}$, —SH, —S(O)$_r$R$^{32}$, —SC(O)R$^{31}$, —SC(O)OR$^{32}$, —SC(O)N(R$^{34}$)R$^{33}$, —SC(S)N(R$^{34}$)R$^{33}$, —N(R$^{34}$)R$^{33}$, —N(R$^{34}$)CHO, —N(R$^{34}$)C(O)R$^{31}$, —N(R$^{34}$)C(O)OR$^{32}$, —N(R$^{34}$)C(O)N(R$^{34}$)R$^{33}$, —N(R$^{34}$)C(S)N(R$^{34}$)R$^{33}$, —N(R$^{34}$)S(O)$_2$R$^{32}$, —C(O)R$^{31}$, —C(O)OH, —C(O)OR$^{32}$, —C(O)SR$^{32}$, —C(O)N(R$^{34}$)R$^{33}$, —C(O)C(O)OR$^{32}$, —Si(R$^{13a}$)(R$^{13b}$)R$^{13}$, —P(O)(OR$^{18}$)$_2$, —P(S)(OR$^{18}$)$_2$, —P(phenyl)$_2$, —P(O)(phenyl)$_2$, phenyl, phenyl substituted with $(Z^a)_{p1}$ or D1 to D38, $R^{31}$ is a hydrogen atom, $C_{1-6}$ alkyl, $C_{1-6}$ haloalkyl, $(C_{1-4})$ alkyl optionally substituted with $R^{35}$, $C_{3-6}$ cycloalkyl, $C_{3-6}$ halocycloalkyl, E4, E5, E12, E13, $C_{2-8}$ alkenyl, $C_{2-8}$ haloalkenyl, $C_{5-10}$ cycloalkenyl, $C_{5-10}$ halocycloalkenyl, $C_{2-4}$ alkynyl, $C_{2-8}$ haloalkynyl, phenyl, phenyl substituted with $(Z^a)_{p1}$ or D1 to D38, $R^{32}$ is $C_{1-6}$ alkyl, $C_{1-6}$ haloalkyl, $(C_{1-4})$ alkyl optionally substituted with $R^{35}$, $C_{3-6}$ cycloalkyl, E4, E5, $C_{2-8}$ alkenyl, $C_{2-4}$ haloalkenyl, $C_{3-8}$ alkynyl or phenyl, $R^{33}$ is $C_{1-6}$ alkyl, $C_{1-6}$ haloalkyl, $(C_{1-4})$ alkyl optionally substituted with $R^{35}$, $C_{3-6}$ cycloalkyl, E4, E5, E12, $C_{2-8}$ alkenyl, $C_{2-8}$ haloalkenyl, $C_{3-8}$ alkynyl, phenyl, phenyl substituted with $(Z^a)_{p1}$, D1 to D25 or D27 to D38, $R^{34}$ is a hydrogen atom, $C_{1-6}$ alkyl, $C_{1-6}$ haloalkyl, $C_{3-8}$ cycloalkyl, $C_{3-6}$ alkenyl or $C_{3-6}$ alkynyl, or $R^{34}$ together with $R^{33}$ optionally forms a $C_{2-5}$ alkylene chain to form together with a nitrogen atom to which $R^{33}$ and $R^{34}$ are bonded, a 3- to 6-membered ring, and in this case, the alkylene chain optionally contains one oxygen atom, sulfur atom or nitrogen atom and is optionally substituted with a halogen atom, a $C_{1-4}$ alkyl group, a $C_{1-4}$ alkoxy group, a —CHO group, a $C_{1-4}$ alkylcarbonyl group, a $C_{1-4}$ alkoxycarbonyl group, a phenyl group or a phenyl group substituted with $(Z^a)_{p1}$, $R^{35}$ is cyano, $C_{3-6}$ cycloalkyl, $C_{3-6}$ halocycloalkyl, E4, E5, E12, E13, $C_{1-4}$ alkoxy, $C_{1-4}$ haloalkoxy, phenoxy, phenoxy substituted with $(Z^a)_{p1}$, $C_{1-4}$ alkylthio, $C_{1-4}$ haloalkylthio, phenylthio, phenylthio substituted with $(Z^a)_{p1}$, $C_{1-4}$ alkylsulfonyl, $C_{1-4}$ haloalkylsulfonyl, phenylsulfonyl, phenylsulfonyl substituted with $(Z^a)_{p1}$, —N(R$^{37}$)R$^{36}$, $C_{1-6}$ alkylcarbonyl, $C_{1-6}$ haloalkylcarbonyl, $C_{1-6}$ alkoxycarbonyl, di($C_{1-6}$ alkyl)aminocarbonyl, tri($C_{1-4}$ alkyl) silyl, phenyl, phenyl substituted with $(Z^a)_{p1}$, naphthyl or D1 to D38, $R^{36}$ is a hydrogen atom, $C_{1-6}$ alkyl, $C_{1-6}$ alkylcarbonyl, $C_{1-6}$ haloalkylcarbonyl, $C_{1-6}$ alkoxycarbonyl, phenylcarbonyl or phenylcarbonyl substituted with $(Z^a)_{p1}$, $R^{37}$ is a hydrogen atom or $C_{1-6}$ alkyl, m is an integer of 0 to 5,
n is an integer of 0 to 4,
p1 is an integer of 1 to 5,
p2 is an integer of 0 to 4,
p3 is an integer of 0 to 3,
p4 is an integer of 0 to 2,
p5 is an integer of 0 or 1,
q1 is an integer of 0 to 2,
q2 is an integer of 0 to 3,
q3 is an integer of 0 to 4,
q4 is an integer of 0 to 5,
q5 is an integer of 0 to 6,
q6 is an integer of 0 to 7,
q7 is an integer of 0 to 8,
q8 is an integer of 0 to 9,
r is an integer of 0 to 2, and
t is an integer of 0 or 1.

2. The substituted dihydroazole compound or the salt of the substituted dihydroazole compound according to claim 1, wherein $A^1$, $A^2$ and $A^4$ are independently C—Y or N,
$A^3$ is C—H or N,
$G^1$ is a benzene ring,
$G^2$ is a structure of $G^2$-1, $G^2$-3, $G^2$-5, $G^2$-6, $G^2$-8 or $G^2$-9,
L is —C(R$^4$)(R$^{4a}$)—, —C(R$^4$)(R$^{4a}$)CH$_2$—, —N(R$^{4b}$)— or —C(R$^4$)(R$^{4a}$)N(R$^{4b}$)—, X is a halogen atom, cyano, nitro, —SF$_5$, $C_{1-6}$ alkyl, $C_{1-6}$ haloalkyl, hydroxy($C_{1-4}$) haloalkyl, $C_{1-4}$ alkoxy($C_{1-4}$) haloalkyl, —OR$^6$, —S(O)$_r$R$^6$ or —NH$_2$, and when m is an integer of 2 or more, Xs are optionally the same as or different from each other, and further, when two Xs are adjacent to each other, the two adjacent Xs optionally form —CF$_2$OCF$_2$—, —OCF$_2$O—, —CF$_2$OCF$_2$O— or —OCF$_2$CF$_2$O— to form together with carbon atoms to which each of the two Xs is bonded, a 5-membered ring or a 6-membered ring, Y is a hydrogen atom, a halogen atom, cyano, nitro, $C_{1-6}$ alkyl, $C_{1-6}$ haloalkyl, $(C_{1-4})$ alkyl substituted with $R^5$, $C_{2-6}$ alkenyl, $C_{2-6}$ alkynyl, —OR$^6$, —S(O)$_r$R$^6$, —N(R$^8$)R$^7$, —C(S)NH$_2$, D1 to D3, D7, D11 or D22, when two or more Ys exist, the Ys are optionally the same as or different from each other, and further, when two Ys are adjacent to each other, the two adjacent Ys optionally form —CH=CHCH=CH— to form together with carbon atoms to which each of the two Ys is bonded, a 6-membered ring, Z is a halogen atom, cyano, nitro, $C_{1-6}$ alkyl, $C_{1-6}$ haloalkyl, —OR$^6$, —S(O)$_r$R$^6$, —NH$_2$, —C(O)N(R$^{12a}$)R$^{11a}$ or —C(S)N(R$^{12a}$)R$^{11a}$, $R^1$ is a hydrogen atom, —C(O)R$^{1a}$, —C(O)OR$^{1b}$, —C(O)SR$^{1b}$, —C(O)N(R$^{1d}$)R$^{1c}$, —C(S)R$^{1a}$ or —C(S)N(R$^{1d}$)R$^{1c}$, $R^{1a}$ is a hydrogen atom, $C_{1-6}$ alkyl, $(C_{1-4})$ alkyl optionally substituted with $R^{15}$, $C_{3-6}$ cycloalkyl, E4, E5, E10, E13, E20, $C_{2-6}$ alkenyl, $C_{2-6}$ haloalkenyl, $C_{2-6}$ alkynyl, —CH=NOR$^{10}$, phenyl substituted with $(Z^a)_{p1}$, D2, D8 or D32, $Z^a$ is a halogen atom, cyano, nitro, $C_{1-4}$ alkyl or $C_{1-4}$ alkylthio, when p1 and p2 are an integer of 2 or more, Zs are optionally the same as or different from each other, $R^{1b}$ is $C_{1-6}$ alkyl, $C_{1-6}$ haloalkyl, $C_{3-6}$ alkenyl or $C_{3-6}$ alkynyl, $R^{1c}$ is $C_{1-6}$ alkyl, $(C_{1-4})$ alkyl optionally substituted with $R^{15}$, $C_{3-6}$ cycloalkyl, $C_{3-6}$ alkenyl, $C_{3-6}$ alkynyl, $C_{1-6}$ alkoxy, $C_{1-6}$ alkylsulfonyl or —N(R$^{17}$)R$^{16}$, $R^{1d}$ is a hydrogen atom or $C_{1-6}$ alkyl, or $R^{1d}$ together with $R^{1c}$ optionally forms a $C_{4-5}$ alkylene chain to form together with a nitrogen atom to which $R^{1c}$ and $R^{1d}$ are bonded, a 5- to 6-membered ring, and in this case, the alkylene chain optionally contains one oxygen atom or sulfur atom and is optionally substituted with a methyl group or an oxo group, $R^2$ is a hydrogen atom, $C_{1-6}$ alkyl, $(C_{1-4})$ alkyl optionally substituted with $R^{15a}$, $C_{3-6}$ alkenyl, $C_{3-6}$ alkynyl or $C_{1-6}$ alkoxy, $R^3$ is $C_{1-6}$ haloalkyl or $C_{3-8}$ halocycloalkyl, $R^{3a}$ is a hydrogen atom or $C_{1-4}$ alkyl, R$^4$ is a hydrogen atom, cyano, C$_{1-4}$ alkyl, C$_{1-4}$ haloalkyl, C$_{3-4}$ cycloalkyl, C$_{2-4}$ alkynyl, —C(O)NH$_2$, —C(S)NH$_2$, phenyl, D9 or D10, R$^{4a}$ is a hydrogen atom or C$_{1-4}$ alkyl, or R$^{4a}$ together with R$^4$ optionally forms an ethylene chain to form together with a carbon atom to which R$^4$ and R$^{4a}$ are bonded, a cyclopropyl ring, R$^{4b}$ is a hydrogen atom, C$_{1-4}$ alkyl, C$_{1-4}$ alkylcarbonyl, C$_{3-6}$ cycloalkylcarbonyl or C$_{1-4}$ alkoxycarbonyl, R$^5$ is —OH, C$_{1-4}$ alkoxy, C$_{1-4}$ alkylthio, C$_{1-4}$ alkylsulfinyl or C$_{1-4}$ alkylsulfonyl, R$^6$ is C$_{1-6}$ alkyl, C$_{1-6}$ haloalkyl or C$_{1-4}$ haloalkoxy(C$_{1-4}$) haloalkyl, R$^7$ is a hydrogen atom, C$_{1-6}$ alkyl, —CHO, C$_{1-6}$ alkylcarbonyl or C$_{1-6}$ alkoxycarbonyl, R$^8$ is a hydrogen atom or C$_{1-6}$ alkyl, R$^{10}$ is C$_{1-4}$ alkyl, R$^{11a}$ is a hydrogen atom, C$_{1-4}$ alkyl, C$_{1-4}$ haloalkyl, (C$_{1-2}$) alkyl substituted with R$^{22}$, C$_{3-4}$ cycloalkyl, E4, —CH=NOR$^{10}$, —C(O)OR$^{10}$, —C(O)NH$_2$, —N(R$^{12b}$)R$^{11b}$, D34 or D35, R$^{12a}$ is a hydrogen atom, (C$_{1-2}$) alkyl substituted with R$^{22a}$, C$_{1-4}$ alkylcarbonyl, cyclopropylcarbonyl or C$_{1-4}$ alkoxycarbonyl, R$^{11b}$ is phenyl or D34, R$^{12b}$ is C$_{1-4}$ alkyl, R$^{14}$ is C$_{1-4}$ alkyl, R$^{15}$ is a halogen atom, cyano, C$_{3-4}$ cycloalkyl, C$_{1-4}$ alkoxy, C$_{1-4}$ haloalkoxy, —N(R$^{24}$)R$^{23}$, —S(O)$_r$R$^{25}$, —S(O)$_t$(R$^{25}$)=NR$^{21}$ or —C(O)N(R$^{29}$)R$^{28}$, R$^{15a}$ is a halogen atom, cyano, C$_{3-4}$ cycloalkyl, C$_{1-4}$ alkoxy, C$_{1-4}$ haloalkoxy, C$_{1-4}$ alkylthio, —N(R$^{24}$)R$^{23}$, C$_{1-4}$ alkoxycarbonyl, —C(O)N(R$^{29}$)R$^{28}$ or —C(S)NH$_2$, R$^{16}$ is a hydrogen atom, C$_{1-6}$ alkyl or C$_{1-6}$ alkoxycarbonyl, R$^{17}$ is a hydrogen atom or C$_{1-6}$ alkyl, R$^{21}$ is a hydrogen atom, cyano or C$_{1-4}$ haloalkylcarbonyl, R$^{22}$ is C$_{1-4}$ alkoxy, C$_{1-4}$ haloalkoxy, C$_{1-4}$ haloalkylaminocarbonyl, D10 or D32, R$^{22a}$ is cyano or —OR$^{23}$, R$^{23}$ is C$_{1-4}$ alkyl, cyano(C$_{1-4}$) alkyl, —C(O)R$^{31}$, —C(O)OR$^{32}$, —C(O)SR$^{32}$ or C$_{1-4}$ alkylsulfonyl, R$^{24}$ is a hydrogen atom, C$_{1-4}$ alkyl, C$_{1-4}$ haloalkylcarbonyl, C$_{1-4}$ alkoxycarbonyl or C$_{1-4}$ alkylsulfonyl, R$^{25}$ is C$_{1-4}$ alkyl, (C$_{1-4}$) alkyl optionally substituted with R$^{30}$, C$_{3-4}$ cycloalkyl, C$_{3-4}$ alkenyl, C$_{3-4}$ alkynyl, —C(O)R$^{31}$, —CO(O)R$^{32}$ or —C(O)N(R$^{34}$)R$^{33}$, R$^{28}$ is a hydrogen atom, C$_{1-4}$ alkyl, C$_{1-4}$ haloalkyl or cyclopropylmethyl, R$^{29}$ is a hydrogen atom or C$_{1-4}$ alkyl, R$^{30}$ is a halogen atom, cyano or —C(O)N(R$^{34}$)R$^{33}$, R$^{31}$ is C$_{1-4}$ alkyl, C$_{1-4}$ haloalkyl, C$_{3-4}$ cycloalkyl, D7, D11 or D22, R$^{32}$ is C$_{1-4}$ alkyl, R$^{33}$ is C$_{1-4}$ alkyl or C$_{1-4}$ haloalkyl, R$^{34}$ is a hydrogen atom or C$_{1-4}$ alkyl, m is an integer of 1 to 3, n is an integer of 0 or 1, p1 is an integer of 1 to 3, p2 is an integer of 0 to 2, p3 and p4 are an integer of 0 or 1, and q4, q6 and q8 are 0.

3. The substituted dihydroazole compound or the salt of the substituted dihydroazole compound according to claim 2, wherein A$^1$ is C—Y or N, A$^2$ and A$^3$ are C—H, A$^4$ is C—H or N, A$^5$ is —CH$_2$— or S, L is —C(R$^4$)(R$^{4a}$)—, X is a halogen atom, cyano, nitro, —SF$_5$, C$_{1-4}$ alkyl, C$_{1-4}$ haloalkyl, C$_{1-4}$ alkoxy, C$_{1-4}$ haloalkoxy, C$_{1-4}$ alkylthio or C$_{1-4}$ haloalkylthio, when m is 2 or 3, Xs are optionally the same as or different from each other, Y is a hydrogen atom, a halogen atom, cyano, nitro, C$_{1-4}$ alkyl, C$_{1-4}$ haloalkyl, C$_{2-4}$ alkynyl, C$_{1-4}$ alkoxy, C$_{1-4}$ haloalkoxy, C$_{1-4}$ alkylthio, C$_{1-4}$ haloalkylthio or —C(S)NH$_2$, Z is a halogen atom, cyano, nitro, C$_{1-4}$ alkyl, —NH$_2$, —C(O)NHR$^{11a}$ or —C(S)NHR$^{11a}$, R$^3$ is C$_{1-4}$ haloalkyl, R$^4$ is a hydrogen atom, cyano, methyl, trifluoromethyl, ethynyl, —C(S)NH$_2$ or D10, R$^{4a}$ is a hydrogen atom, or R$^{4a}$ together with R$^4$ optionally forms an ethylene chain to form together with a carbon atom to which R$^4$ and R$^{4a}$ are bonded, a cyclopropyl ring, R$^{11a}$ is a hydrogen atom, C$_{1-4}$ alkyl, C$_{1-4}$ haloalkyl, (C$_{1-2}$) alkyl substituted with R$^{22}$, cyclopropyl, E4 or —CH=NOR$^{10}$, R$^{10}$ is C$_{1-2}$ alkyl, and R$^{22}$ is C$_{1-2}$ alkoxy, C$_{1-2}$ haloalkoxy, C$_{1-2}$ haloalkylaminocarbonyl, D10 or D32.

4. The substituted dihydroazole compound or the salt of the substituted dihydroazole compound according to claim 3, wherein A$^5$ is —CH$_2$—, G$^2$ is a structure of G$^2$-1, G$^2$-6 or G$^2$-9, L is —CH(R$^4$)—, X is a halogen atom, cyano, —SF$_5$, C$_{1-2}$ haloalkyl, C$_{1-2}$ haloalkoxy or C$_{1-2}$ haloalkylthio, when m is 2 or 3, Xs are optionally the same as or different from each other, Y is a hydrogen atom, a halogen atom, cyano, nitro, C$_{1-2}$ alkyl, C$_{1-2}$ haloalkyl, C$_{2-3}$ alkynyl, C$_{1-2}$ haloalkoxy, C$_{1-2}$ haloalkylthio or —C(S)NH$_2$, Z is a halogen atom, nitro, methyl or —NH$_2$, R$^1$ is —C(O)R$^{1a}$, —C(O)SR$^{1b}$, —C(O)N(R$^{1d}$)R$^{1c}$ or —C(S)R$^{1a}$, R$^{1a}$ is C$_{1-4}$ alkyl, (C$_{1-4}$) alkyl optionally substituted with R$^{15}$, C$_{3-4}$ cycloalkyl, E4, E5, C$_{2-4}$ alkenyl, C$_{2-4}$ haloalkenyl, C$_{2-4}$ alkynyl, phenyl substituted with (Z$^a$)$_{p1}$ or D32, Z$^a$ is a halogen atom, cyano, nitro or C$_{1-4}$ alkylthio, when p1 and p2 are an integer of 2 or more, Z$^a$s are optionally the same as or different from each other, R$^{1b}$ is C$_{1-4}$ alkyl or C$_{1-4}$ haloalkyl, R$^{1c}$ is C$_{1-4}$ alkyl, C$_{1-4}$ haloalkyl, C$_{3-4}$ cycloalkyl or C$_{3-4}$ alkynyl, R$^{1d}$ is a hydrogen atom or C$_{1-4}$ alkyl, R$^2$ is a hydrogen atom, C$_{1-4}$ alkyl, (C$_{1-2}$) alkyl substituted with R$^{15a}$, C$_{3-4}$ alkenyl or C$_{3-4}$ alkynyl, R$^3$ is C$_{1-2}$ haloalkyl, R$^4$ is a hydrogen atom, cyano, methyl, ethynyl or —C(S)NH$_2$, R$^{15}$ is a halogen atom, C$_{3-4}$ cycloalkyl, C$_{1-2}$ alkoxy, C$_{1-2}$ haloalkoxy, —N(R$^{24}$)R$^{23}$, —S(O)$_r$R$^{25}$, —S(O)$_t$(R$^{25}$)=NR$^{21}$ or —C(O)N(R$^{29}$)R$^{28}$, R$^{15a}$ is cyano, C$_{3-4}$ cycloalkyl, C$_{1-2}$ alkoxy, C$_{1-2}$ haloalkoxy, —N(R$^{24}$)R$^{23}$, C$_{1-2}$ alkoxycarbonyl, —C(O)N(R$^{29}$)R$^{28}$ or —C(S)NH$_2$, R$^{21}$ is a hydrogen atom or C$_{1-2}$ haloalkylcarbonyl, R$^{23}$ is cyano(C$_{1-2}$) alkyl, —C(O)R$^{31}$ or C$_{1-2}$ alkoxycarbonyl, R$^{24}$ is a hydrogen atom or C$_{1-2}$ alkoxycarbonyl, R$^{25}$ is C$_{1-2}$ alkyl, C$_{1-2}$ haloalkyl or cyanomethyl, $R^{28}$ is a hydrogen atom or $C_{1-2}$ alkyl,
$R^{29}$ is a hydrogen atom or methyl, and
$R^{31}$ is $C_{1-2}$ alkyl, $C_{1-2}$ haloalkyl or cyclopropyl.

5. The substituted dihydroazole compound or the salt of the substituted dihydroazole compound according to claim 4, wherein $A^1$ is C—Y,
$A^4$ is C—H,
$G^2$ is a structure of $G^2$-1,
X is a halogen atom or trifluoromethyl, when m is 2 or 3, Xs are optionally the same as or different from each other,
Y is a hydrogen atom, a halogen atom, nitro or methyl,
$R^1$ is —C(O)$R^{1a}$ or —C(O)NH$R^{1e}$,
$R^{1a}$ is $C_{1-4}$ alkyl, $C_{1-4}$ haloalkyl, ($C_{1-2}$) alkyl optionally substituted with $R^{15}$, cyclopropyl, E4 or E5,
$R^{1e}$ is $C_{1-3}$ alkyl, $C_{1-3}$ haloalkyl, cyclopropyl or propargyl,
$R^2$ is a hydrogen atom, $C_{1-2}$ alkyl, cyclopropylmethyl, $C_{1-2}$ alkoxymethyl, cyanomethyl, allyl or propargyl,
$R^3$ is trifluoromethyl or chlorodifluoromethyl,
$R^4$ is a hydrogen atom, cyano or methyl,
$R^{15}$ is cyclopropyl or —S(O)$_r R^{25}$, and
$R^{25}$ is $C_{1-2}$ alkyl or $C_{1-2}$ haloalkyl.

6. The substituted dihydroazole compound or the salt of the substituted dihydroazole compound according to claim 4, wherein $A^1$ is C—Y,
$A^4$ is C—H,
$G^2$ is a structure of $G^2$-6 or $G^2$-9,
X is a halogen atom or trifluoromethyl, when m is 2 or 3, Xs are optionally the same as or different from each other,
Y is a hydrogen atom, cyano or nitro,
$R^3$ is trifluoromethyl or chlorodifluoromethyl, and
n is 0.

* * * * *